(12) United States Patent
Moisa et al.

(10) Patent No.: US 11,350,989 B2
(45) Date of Patent: Jun. 7, 2022

(54) CATHETER SYSTEM

(71) Applicant: KARDIUM INC., Burnaby (CA)

(72) Inventors: Saar Moisa, Vancouver (CA); Marius J. Postma, Coquitlam (CA)

(73) Assignee: KARDIUM INC., Burnaby (CA)

( * ) Notice: Subject to any disclaimer, the term of this patent is extended or adjusted under 35 U.S.C. 154(b) by 878 days.

(21) Appl. No.: 16/161,319

(22) Filed: Oct. 16, 2018

(65) Prior Publication Data

US 2019/0046265 A1 Feb. 14, 2019

Related U.S. Application Data

(63) Continuation of application No. 15/254,130, filed on Sep. 1, 2016, now Pat. No. 10,485,608, which is a (Continued)

(51) Int. Cl.
*A61M 3/00* (2006.01)
*A61B 5/05* (2021.01)
(Continued)

(52) U.S. Cl.
CPC .......... *A61B 18/1492* (2013.01); *A61B 5/287* (2021.01); *A61B 5/6858* (2013.01); (Continued)

(58) Field of Classification Search
CPC ....... A61B 18/1492; A61B 8/12; A61B 8/445; A61B 5/6852; A61B 2018/00214; (Continued)

(56) References Cited

U.S. PATENT DOCUMENTS 4,114,202 A 9/1978 Roy et al.
4,164,046 A 8/1979 Cooley
(Continued)

FOREIGN PATENT DOCUMENTS

CN 101797181 A 8/2010
DE 102010026210 A1 1/2012
(Continued)

OTHER PUBLICATIONS

Notice of Intention to Grant issued in EP Appln. No. 14871405.8 dated Jan. 22, 2019.
(Continued)

*Primary Examiner* — Joseph A Stoklosa
*Assistant Examiner* — Brian M Antiskay
(74) *Attorney, Agent, or Firm* — Rossi, Kimms & McDowell LLP

(57) ABSTRACT

A manipulable portion of a catheter system advances out of a lumen of a catheter sheath at a distal end of a shaft, which is also within the lumen of the catheter sheath. The catheter system causes different advancement and retraction trajectories of a manipulable portion out of and into the lumen based at least upon different relative movements between the catheter sheath and the shaft. A projection and a corresponding receiver may be used to control relative positioning of the catheter sheath and the shaft, as well as to control positioning of the manipulable portion. The catheter system may control metering rates of a control element coupled to the manipulable portion during advancement and retraction of the manipulable portion. A control element of the catheter system has varying amounts of length outside a distal end of the catheter sheath during advancement and retraction of the manipulable portion.

7 Claims, 31 Drawing Sheets

Related U.S. Application Data continuation of application No. 14/136,946, filed on Dec. 20, 2013, now Pat. No. 9,452,016, which is a continuation-in-part of application No. 13/942,354, filed on Jul. 15, 2013, now Pat. No. 9,675,401, which is a continuation of application No. PCT/US2012/022061, filed on Jan. 20, 2012.

(60) Provisional application No. 61/515,141, filed on Aug. 4, 2011, provisional application No. 61/488,639, filed on May 20, 2011, provisional application No. 61/485,987, filed on May 13, 2011, provisional application No. 61/435,213, filed on Jan. 21, 2011.

(51) Int. Cl.
*A61B 18/14* (2006.01)
*A61B 5/00* (2006.01)
*A61B 5/287* (2021.01)
*A61B 5/026* (2006.01)
*A61B 5/0538* (2021.01)
*A61B 5/06* (2006.01)
*A61M 25/00* (2006.01)
*A61B 18/00* (2006.01)

(52) U.S. Cl.
CPC ............ *A61B 5/026* (2013.01); *A61B 5/0538* (2013.01); *A61B 5/06* (2013.01); *A61B 5/6843* (2013.01); *A61B 2018/0016* (2013.01); *A61B 2018/00166* (2013.01); *A61B 2018/00172* (2013.01); *A61B 2018/00184* (2013.01); *A61B 2018/00267* (2013.01); *A61B 2018/00351* (2013.01); *A61B 2018/00357* (2013.01); *A61B 2018/00577* (2013.01); *A61B 2018/00791* (2013.01); *A61B 2018/00839* (2013.01); *A61B 2018/00863* (2013.01); *A61B 2018/00875* (2013.01); *A61B 2018/1475* (2013.01); *A61M 25/0074* (2013.01); *A61M 25/0082* (2013.01)

(58) Field of Classification Search
CPC ............ A61B 5/0084; A61B 2218/002; A61B 2017/003; A61B 2018/0022; A61B 2034/301; A61B 2217/007; A61B 2018/00744; A61B 17/3421; A61B 17/3415; A61B 2017/00243; A61B 1/015; A61M 2025/0681; A61M 25/0662; A61M 25/007; A61M 25/0068; A61M 2025/0031; A61M 25/003; A61M 25/04; A61M 2025/0034; A61M 25/0029; A61M 25/0084; A61M 25/0102; A61M 1/85; A61M 2210/125; A61M 25/00; A61M 1/84; A61M 2025/09116; A61M 2039/0205; A61M 31/00; A61M 3/0283; A61M 2025/091; A61M 2039/0276; A61N 1/0568
USPC .............. 604/43, 136, 164.01–164.13, 604/164.01–164.6, 264
See application file for complete search history.

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,576,182 A | 3/1986 | Normann |
| 4,699,147 A | 10/1987 | Chilson et al. |
| 4,770,187 A | 9/1988 | Lash et al. |
| 4,787,369 A | 11/1988 | Allred, III et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,905,667 A | 3/1990 | Foerster et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,153,151 A | 10/1992 | Aitken |
| 5,156,151 A | 10/1992 | Imran |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,195,505 A | 3/1993 | Josefsen |
| 5,201,316 A | 4/1993 | Pomeranz et al. |
| 5,228,442 A | 7/1993 | Imran |
| 5,242,386 A | 9/1993 | Holzer |
| 5,245,987 A | 9/1993 | Redmond et al. |
| 5,255,679 A | 10/1993 | Imran |
| 5,279,299 A | 1/1994 | Imran |
| 5,293,869 A | 3/1994 | Edwards et al. |
| 5,297,549 A | 3/1994 | Beatty et al. |
| 5,309,910 A | 5/1994 | Edwards et al. |
| 5,312,435 A | 5/1994 | Nash et al. |
| 5,317,952 A | 6/1994 | Immega |
| 5,324,284 A | 6/1994 | Imran |
| 5,327,889 A | 7/1994 | Imran |
| 5,341,807 A | 8/1994 | Nardella |
| 5,345,936 A | 9/1994 | Pomeranz et al. |
| 5,351,551 A | 10/1994 | Drubetsky |
| 5,351,679 A | 10/1994 | Mayzels et al. |
| 5,366,443 A | 11/1994 | Eggers et al. |
| 5,370,679 A | 12/1994 | Atlee, III |
| 5,379,773 A | 1/1995 | Hornsby |
| 5,397,321 A | 3/1995 | Houser et al. |
| 5,419,767 A | 5/1995 | Eggers et al. |
| 5,450,860 A | 9/1995 | O'Connor |
| 5,456,254 A | 10/1995 | Pietroski et al. |
| 5,462,545 A | 10/1995 | Wang |
| 5,465,717 A | 11/1995 | Imran et al. |
| 5,478,353 A | 12/1995 | Yoon |
| 5,485,849 A | 1/1996 | Panescu et al. |
| 5,496,267 A | 3/1996 | Drasler et al. |
| 5,496,330 A | 3/1996 | Bates |
| 5,499,981 A | 3/1996 | Kordis |
| 5,531,760 A | 7/1996 | Alwafaie |
| 5,545,193 A | 8/1996 | Fleischman et al. |
| 5,549,661 A | 8/1996 | Kordis et al. |
| 5,555,883 A | 9/1996 | Avitall |
| 5,557,967 A | 9/1996 | Renger |
| 5,575,810 A | 11/1996 | Swanson et al. |
| 5,593,424 A | 1/1997 | Northrup, III |
| 5,598,848 A | 2/1997 | Swanson et al. |
| 5,599,345 A | 2/1997 | Edwards et al. |
| 5,620,481 A | 4/1997 | Desai et al. |
| 5,630,813 A | 5/1997 | Kieturakis |
| 5,636,634 A * | 6/1997 | Kordis ................ A61B 5/6857 600/374 |
| 5,637,090 A | 6/1997 | McGee et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |

(56) References Cited

U.S. PATENT DOCUMENTS

| | | |
|---|---|---|
| 5,704,914 A * | 1/1998 | Stocking .......... A61M 25/0631 604/195 |
| 5,713,896 A | 2/1998 | Nardella |
| 5,713,942 A | 2/1998 | Stern et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,738,096 A | 4/1998 | Ben-Haim |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,823,189 A | 10/1998 | Kordis |
| 5,824,066 A | 10/1998 | Gross |
| 5,831,159 A | 11/1998 | Renger |
| 5,836,947 A | 11/1998 | Fleischman et al. |
| 5,836,990 A | 11/1998 | Li |
| 5,853,422 A | 12/1998 | Huebsch et al. |
| 5,868,743 A | 2/1999 | Saul |
| 5,868,755 A | 2/1999 | Kanner et al. |
| 5,876,343 A | 3/1999 | Teo |
| 5,879,295 A | 3/1999 | Li et al. |
| 5,881,727 A | 3/1999 | Edwards |
| 5,885,278 A | 3/1999 | Fleischman |
| 5,891,136 A | 4/1999 | McGee et al. |
| 5,893,847 A | 4/1999 | Kordis |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,944,715 A | 8/1999 | Goble et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,001,093 A | 12/1999 | Swanson et al. |
| 6,014,581 A | 1/2000 | Whayne et al. |
| 6,023,638 A | 2/2000 | Swanson |
| 6,030,382 A | 2/2000 | Fleischman et al. |
| 6,036,689 A | 3/2000 | Tu et al. |
| 6,063,082 A | 5/2000 | DeVore et al. |
| 6,071,282 A | 6/2000 | Fleischman |
| 6,104,944 A | 8/2000 | Martinelli |
| 6,106,460 A | 8/2000 | Panescu |
| 6,106,522 A | 8/2000 | Fleischman et al. |
| 6,119,030 A | 9/2000 | Morency |
| 6,123,702 A | 9/2000 | Swanson et al. |
| 6,138,043 A | 10/2000 | Avitall |
| 6,142,993 A | 11/2000 | Whayne et al. |
| 6,156,046 A | 12/2000 | Passafaro et al. |
| 6,210,432 B1 | 4/2001 | Solem et al. |
| 6,216,043 B1 | 4/2001 | Swanson et al. |
| 6,217,573 B1 | 4/2001 | Webster |
| 6,240,307 B1 | 5/2001 | Beatty |
| 6,241,747 B1 | 6/2001 | Ruff |
| 6,248,124 B1 | 6/2001 | Pedros et al. |
| 6,254,598 B1 | 7/2001 | Edwards |
| 6,258,258 B1 | 7/2001 | Sartori et al. |
| 6,266,550 B1 | 7/2001 | Selmon et al. |
| 6,292,695 B1 | 9/2001 | Webster, Jr. et al. |
| 6,304,769 B1 | 10/2001 | Arenson et al. |
| 6,306,135 B1 | 10/2001 | Ellman et al. |
| 6,308,091 B1 | 10/2001 | Avitall |
| 6,319,249 B1 | 11/2001 | Tollner |
| 6,322,559 B1 | 11/2001 | Daulton et al. |
| 6,325,797 B1 | 12/2001 | Stewart et al. |
| 6,330,478 B1 | 12/2001 | Lee et al. |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,428,537 B1 | 8/2002 | Swanson |
| 6,436,052 B1 | 8/2002 | Nikolic et al. |
| 6,471,700 B1 | 10/2002 | Burbank et al. |
| 6,475,223 B1 | 11/2002 | Werp et al. |
| 6,485,409 B1 | 11/2002 | Voloshin et al. |
| 6,485,482 B1 | 11/2002 | Belef |
| 6,485,489 B2 | 11/2002 | Teirstein et al. |
| 6,506,210 B1 | 1/2003 | Kanner |
| 6,514,249 B1 | 2/2003 | Maguire et al. |
| 6,517,534 B1 | 2/2003 | McGovern |
| 6,529,756 B1 | 3/2003 | Phan et al. |
| 6,537,198 B1 | 3/2003 | Mdlund et al. |
| 6,537,314 B2 | 3/2003 | Langberg et al. |
| 6,540,670 B1 | 4/2003 | Hirata et al. |
| 6,551,310 B1 | 4/2003 | Ganz et al. |
| 6,551,312 B2 | 4/2003 | Zhang et al. |
| 6,558,378 B2 | 5/2003 | Sherman et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,616,684 B1 | 9/2003 | Vidlund et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| D484,979 S | 1/2004 | Fontaine |
| 6,704,590 B2 | 3/2004 | Haldeman |
| 6,723,038 B1 | 4/2004 | Schroeder et al. |
| 6,726,716 B2 | 4/2004 | Marquez |
| 6,738,655 B1 | 5/2004 | Sen et al. |
| 6,760,616 B2 | 7/2004 | Hoey et al. |
| 6,763,836 B2 | 7/2004 | Tasto et al. |
| 6,773,433 B2 | 8/2004 | Stewart et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,899,709 B2 | 5/2005 | Lehmann et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,206 B2 | 11/2005 | Keane |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,166,127 B2 | 1/2007 | Spence et al. |
| 7,174,201 B2 | 2/2007 | Govari et al. |
| 7,177,677 B2 | 2/2007 | Kaula et al. |
| 7,186,210 B2 | 3/2007 | Feld et al. |

(56) References Cited

U.S. PATENT DOCUMENTS

| | | | |
|---|---|---|---|
| 7,187,964 B2 | 3/2007 | Khoury |
| 7,189,202 B2 | 3/2007 | Lau et al. |
| 7,198,635 B2 | 4/2007 | Danek et al. |
| 7,255,695 B2 | 8/2007 | Falwell et al. |
| 7,276,044 B2 | 10/2007 | Ferry et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,311,705 B2 | 12/2007 | Sra |
| 7,317,950 B2 | 1/2008 | Lee |
| 7,335,196 B2 | 2/2008 | Swanson et al. |
| 7,468,062 B2 | 12/2008 | Oral et al. |
| 7,481,808 B2 | 1/2009 | Koyfman et al. |
| 7,496,394 B2 | 2/2009 | Ahmed et al. |
| 7,507,252 B2 | 3/2009 | Lashinski et al. |
| 7,530,980 B2 | 5/2009 | Hooven |
| 7,660,452 B2 | 2/2010 | Zwirn et al. |
| 7,736,388 B2 | 6/2010 | Goldfarb et al. |
| 7,738,967 B2 | 6/2010 | Salo |
| 7,826,881 B1 | 11/2010 | Beatty et al. |
| 8,012,149 B2 | 9/2011 | Jackson et al. |
| 8,097,926 B2 | 1/2012 | De Graff et al. |
| 8,103,338 B2 | 1/2012 | Harlev et al. |
| D654,588 S | 2/2012 | Taube et al. |
| 8,118,853 B2 | 2/2012 | Grewe |
| 8,147,486 B2 | 4/2012 | Honour et al. |
| 8,150,499 B2 | 4/2012 | Gelbart et al. |
| D660,967 S | 5/2012 | Braido et al. |
| 8,216,228 B2 | 7/2012 | Pachon Mateos et al. |
| 8,224,432 B2 | 7/2012 | MacAdam et al. |
| 8,386,057 B2 | 2/2013 | Flach et al. |
| 8,398,623 B2 | 3/2013 | Warnking et al. |
| 8,398,631 B2 | 3/2013 | Ganz et al. |
| 8,486,063 B2 | 7/2013 | Werneth et al. |
| 8,500,731 B2 | 8/2013 | Byrd et al. |
| 8,538,501 B2 | 9/2013 | Venkatachalam et al. |
| 8,562,559 B2 * | 10/2013 | Bishop | A61M 25/104 604/509 |
| 8,617,156 B2 | 12/2013 | Werneth et al. |
| 8,617,228 B2 | 12/2013 | Wittenberger et al. |
| 8,712,550 B2 | 4/2014 | Grunewald |
| 8,771,267 B2 | 7/2014 | Kunis et al. |
| 8,864,745 B2 * | 10/2014 | Ciavarella | A61B 5/287 604/164.11 |
| D717,954 S | 11/2014 | Hjelle et al. |
| 8,939,970 B2 | 1/2015 | Stone et al. |
| 9,037,259 B2 | 5/2015 | Mathur |
| 9,044,254 B2 | 6/2015 | Ladtkow et al. |
| 9,101,365 B2 | 8/2015 | Highsmith |
| 9,108,052 B2 | 8/2015 | Jarrard |
| 9,198,713 B2 | 12/2015 | Wallace et al. |
| 9,289,606 B2 | 3/2016 | Paul |
| 9,345,540 B2 | 5/2016 | Mallin et al. |
| 9,474,486 B2 | 10/2016 | Eliason et al. |
| 9,522,035 B2 | 12/2016 | Highsmith |
| 9,526,568 B2 | 12/2016 | Ohri et al. |
| 9,713,730 B2 | 7/2017 | Mathur et al. |
| 9,730,600 B2 | 8/2017 | Thakur et al. |
| 9,737,227 B2 | 8/2017 | Thakur et al. |
| 9,855,421 B2 | 1/2018 | Garai et al. |
| 9,883,908 B2 | 2/2018 | Madjarov et al. |
| 9,907,603 B2 | 3/2018 | Sklar et al. |
| 9,907,609 B2 | 3/2018 | Cao et al. |
| 9,924,994 B2 | 3/2018 | Sklar et al. |
| 9,924,995 B2 | 3/2018 | Sklar et al. |
| 9,968,783 B2 | 5/2018 | Bullinga et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0021867 A1 | 9/2001 | Kordis et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087157 A1 | 7/2002 | Sliwa, Jr. et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0107530 A1 | 8/2002 | Saucer et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0176810 A1 | 9/2003 | Maahs et al. |
| 2003/0181819 A1 | 9/2003 | Desai |
| 2003/0229395 A1 | 12/2003 | Cox |
| 2004/0002626 A1 | 1/2004 | Feld et al. |
| 2004/0054279 A1 | 3/2004 | Hanley |
| 2004/0082915 A1 * | 4/2004 | Kadan | A61B 1/317 604/164.04 |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0181139 A1 | 9/2004 | Falwell et al. |
| 2004/0186566 A1 | 9/2004 | Hindrichs et al. |
| 2004/0193103 A1 * | 9/2004 | Kumar | A61B 17/135 602/53 |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0149159 A1 | 7/2005 | Andreas et al. |
| 2005/0154252 A1 | 7/2005 | Sharkey et al. |
| 2005/0182365 A1 | 8/2005 | Hennemann et al. |
| 2005/0187620 A1 | 8/2005 | Pai et al. |
| 2005/0197593 A1 | 9/2005 | Burbank et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0245892 A1 * | 11/2005 | Elkins | A61M 25/0043 604/264 |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |

(56) References Cited

U.S. PATENT DOCUMENTS

| | | |
|---|---|---|
| 2005/0267458 A1 | 12/2005 | Paul et al. |
| 2005/0267463 A1* | 12/2005 | Vanney ............... A61B 18/1492 606/41 |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0100618 A1 | 5/2006 | Chan et al. |
| 2006/0106298 A1 | 5/2006 | Ahmed et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0027533 A1 | 2/2007 | Douk |
| 2007/0038208 A1 | 2/2007 | Kefer |
| 2007/0083168 A1* | 4/2007 | Whiting ............... A61M 25/007 604/264 |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232858 A1 | 10/2007 | MacNamara et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0161799 A1 | 7/2008 | Stangenes et al. |
| 2008/0262337 A1 | 10/2008 | Falwell et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0024138 A1 | 1/2009 | Saleh |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0171274 A1 | 7/2009 | Harlev et al. |
| 2009/0182405 A1* | 7/2009 | Arnault De La Menardiere ........ A61F 2/856 623/1.11 |
| 2009/0192441 A1 | 7/2009 | Gelbart et al. |
| 2009/0270737 A1 | 10/2009 | Thornton |
| 2009/0287271 A1 | 11/2009 | Blum et al. |
| 2009/0287304 A1 | 11/2009 | Dahlgren et al. |
| 2010/0121147 A1 | 5/2010 | Oskin et al. |
| 2010/0204560 A1 | 8/2010 | Salahieh |
| 2010/0211052 A1 | 8/2010 | Brown et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0282491 A1 | 11/2011 | Prisco et al. |
| 2012/0071870 A1 | 3/2012 | Salahieh |
| 2012/0158016 A1 | 6/2012 | Gelbart et al. |
| 2012/0165829 A1 | 6/2012 | Chen et al. |
| 2012/0271135 A1 | 10/2012 | Burke et al. |
| 2013/0165916 A1 | 6/2013 | Mathur et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0184705 A1 | 7/2013 | Gelbart et al. |
| 2013/0184706 A1 | 7/2013 | Gelbart et al. |
| 2013/0190587 A1 | 7/2013 | Lopes et al. |
| 2013/0190741 A1 | 7/2013 | Moll et al. |
| 2013/0197513 A1 | 8/2013 | Lopes et al. |
| 2013/0241929 A1 | 9/2013 | Massarwa et al. |
| 2013/0304065 A1 | 11/2013 | Lopes et al. |
| 2013/0310828 A1 | 11/2013 | Reinders et al. |
| 2014/0114307 A1 | 4/2014 | Moisa et al. |
| 2014/0350552 A1 | 11/2014 | Highsmith |
| 2015/0032103 A1 | 1/2015 | McLawhorn et al. |
| 2015/0045660 A1 | 2/2015 | Gelbart et al. |
| 2015/0066010 A1 | 3/2015 | McLawhorn et al. |
| 2015/0126993 A1 | 5/2015 | Gelbart et al. |
| 2015/0157400 A1 | 6/2015 | Gelbart et al. |
| 2015/0245798 A1 | 9/2015 | Gelbart et al. |
| 2015/0250539 A1 | 9/2015 | Gelbart et al. |
| 2015/0351836 A1 | 12/2015 | Prutchi |
| 2015/0351837 A1 | 12/2015 | Gelbart et al. |
| 2016/0008059 A1 | 1/2016 | Prutchi |
| 2016/0008062 A1 | 1/2016 | Gelbart et al. |
| 2016/0100884 A1 | 4/2016 | Fay et al. |
| 2016/0143686 A1 | 5/2016 | Tunay et al. |
| 2016/0175009 A1 | 6/2016 | Davies et al. |
| 2016/0242667 A1 | 8/2016 | Fay et al. |
| 2016/0262647 A1 | 9/2016 | Berenfeld |
| 2016/0302858 A1 | 10/2016 | Bencini |
| 2016/0317223 A1 | 11/2016 | Avitall |
| 2016/0331259 A1 | 11/2016 | Harlev et al. |
| 2016/0361111 A1 | 12/2016 | Seidel |
| 2017/0020604 A1 | 1/2017 | Lopes et al. |
| 2017/0027465 A1 | 2/2017 | Blauer et al. |
| 2017/0035486 A1 | 2/2017 | Lopes et al. |
| 2017/0065198 A1 | 3/2017 | Ruppersberg |
| 2017/0065339 A1 | 3/2017 | Mickelsen |
| 2017/0065812 A1 | 3/2017 | Goedeke et al. |
| 2017/0071661 A1 | 3/2017 | Hoitink et al. |
| 2017/0100189 A1 | 4/2017 | Clark et al. |
| 2017/0156791 A1 | 6/2017 | Govari |
| 2017/0164858 A1 | 6/2017 | Basu |
| 2017/0215947 A1 | 8/2017 | Rioux et al. |
| 2017/0281193 A1 | 10/2017 | Asirvatham et al. |
| 2017/0296084 A1 | 10/2017 | Blauer et al. |
| 2017/0312028 A1 | 11/2017 | Harlev et al. |
| 2017/0333124 A1 | 11/2017 | Gelbart et al. |
| 2018/0008343 A1 | 1/2018 | Gelbart et al. |
| 2018/0020916 A1 | 1/2018 | Ruppersberg |
| 2018/0036074 A1 | 2/2018 | Gelbart et al. |
| 2018/0036075 A1 | 2/2018 | Gelbart et al. |
| 2018/0036076 A1 | 2/2018 | Gelbart et al. |
| 2018/0036077 A1 | 2/2018 | Gelbart et al. |
| 2018/0042667 A1 | 2/2018 | Pappone et al. |
| 2018/0042671 A1 | 2/2018 | Gelbart et al. |
| 2018/0055565 A1 | 3/2018 | Gelbart et al. |
| 2018/0056074 A1 | 3/2018 | Clark et al. |
| 2018/0071017 A1 | 3/2018 | Bar-Tal et al. |
| 2018/0092688 A1 | 4/2018 | Tegg |
| 2018/0116595 A1 | 5/2018 | Ruppersberg |
| 2018/0117304 A1 | 5/2018 | Koop et al. |
| 2018/0153437 A1 | 6/2018 | Schwartz et al. |
| 2018/0235692 A1 | 8/2018 | Efimov et al. |
| 2018/0236221 A1 | 8/2018 | Opie et al. |
| 2018/0280070 A1 | 10/2018 | Pasquino et al. |
| 2020/0375659 A1 | 12/2020 | Gelbart |

(56) References Cited

U.S. PATENT DOCUMENTS

| | | | |
|---|---|---|---|
| 2021/0000537 A1 | 1/2021 | Gelbart | |
| 2021/0059750 A1 | 3/2021 | Gelbart | |

FOREIGN PATENT DOCUMENTS

| | | | |
|---|---|---|---|
| DE | 102011085720 A1 | 5/2013 | |
| EP | 0723467 A1 | 7/1996 | |
| EP | 1169974 A1 | 1/2002 | |
| EP | 1233718 B1 | 8/2006 | |
| EP | 1923095 A2 | 5/2008 | |
| EP | 1814450 B1 | 1/2013 | |
| EP | 2101642 B1 | 7/2014 | |
| EP | 2231060 B1 | 5/2015 | |
| EP | 2395933 B1 | 5/2016 | |
| EP | 2566565 B1 | 10/2017 | |
| EP | 3318211 A2 | 5/2018 | |
| EP | 3102136 B1 | 6/2018 | |
| EP | 2765939 B1 | 9/2018 | |
| EP | 2793725 B1 | 9/2018 | |
| EP | 3375365 A2 | 9/2018 | |
| WO | 9510320 A1 | 4/1995 | |
| WO | 95/20349 A1 | 8/1995 | |
| WO | 97/17892 A1 | 5/1997 | |
| WO | 0108575 A2 | 2/2001 | |
| WO | 02/087437 A1 | 11/2002 | |
| WO | 03015611 A2 | 2/2003 | |
| WO | 03077800 A1 | 9/2003 | |
| WO | 2004012629 A1 | 2/2004 | |
| WO | 2004047679 A1 | 6/2004 | |
| WO | 2004084746 A2 | 10/2004 | |
| WO | 2004100803 A1 | 11/2004 | |
| WO | 2005070330 A1 | 8/2005 | |
| WO | 2005102181 A1 | 11/2005 | |
| WO | 2006017809 A2 | 2/2006 | |
| WO | 2006105121 A2 | 10/2006 | |
| WO | 2006135747 A2 | 12/2006 | |
| WO | 2006135749 A2 | 12/2006 | |
| WO | 2007021647 A2 | 2/2007 | |
| WO | 2007115390 A1 | 10/2007 | |
| WO | 2008002606 A2 | 1/2008 | |
| WO | 2009011721 A1 | 1/2009 | |
| WO | 2009065042 A2 | 5/2009 | |
| WO | 2012050877 A1 | 4/2012 | |
| WO | 2012/100184 A2 | 7/2012 | |
| WO | 2012/100185 A2 | 7/2012 | |
| WO | 2013064576 A1 | 5/2013 | |
| WO | 2013/173917 A1 | 11/2013 | |
| WO | 2016181316 A1 | 11/2016 | |
| WO | 2017041889 A2 | 3/2017 | |
| WO | 2017041891 A1 | 3/2017 | |
| WO | 2017042623 A1 | 3/2017 | |
| WO | 2017056056 A1 | 4/2017 | |
| WO | 2017070252 A1 | 4/2017 | |
| WO | 2017136262 A1 | 8/2017 | |
| WO | 2018067540 A1 | 4/2018 | |
| WO | 2018075396 A1 | 4/2018 | |
| WO | 2018081225 A1 | 5/2018 | |
| WO | 2018144765 A1 | 8/2018 | |
| WO | 2018146613 A2 | 8/2018 | |

OTHER PUBLICATIONS

Notice of Intention to Grant issued in EP Appln. No. 15188407.9 dated Mar. 20, 2019.
Copending U.S. Appl. No. 16/369,528, filed Mar. 29, 2019.
Copending U.S. Appl. No. 16/381,317, filed Apr. 11, 2019.
Copending U.S. Appl. No. 16/381,344, filed Apr. 11, 2019.
Preliminary Amendment filed in copending U.S. Appl. No. 16/369,528 dated Apr. 24, 2019.
Preliminary Amendment filed in copending U.S. Appl. No. 16/381,317 dated Apr. 24, 2019.
Preliminary Amendment filed in copending U.S. Appl. No. 16/381,344 dated Apr. 24, 2019.
Copending U.S. Appl. No. 16/407,379, filed May 9, 2019.
Office Action issued in copending U.S. Appl. No. 15/254,130 dated May 28, 2019.
Bard, "Mesh Ablator Catheter", Brochure, 2008, 4 pgs, Bard Electrophysiology Division, C.R. Bard Inc., 55 Technology Drive Lowell, MA 07851 USA.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
"Constellation Mapping Catheters", Brochure, Boston Scientific Corp., 2 pgs © 2007 Boston Scientific Corporation.
"Waveforms and Segments", Ensite System Instructions for use, 54-06154-001 Rev02, Chapter 7 pp. 85-90 © 2007 St. Jude Medical.
Extended European Search Report and EP search opinion for EP 12736677.1, dated Mar. 28, 2014, corresponding to PCT/US2012/022061.
Extended European Search Report and EP search opinion for EP 12736962.7, dated Mar. 28, 2014, corresponding to PCT/US2012/022062.
Extended European Search Report dated Aug. 20, 2013 issued in EP Patent Application No. 13172848.7.
Written Opinion dated Aug. 22, 2012 for PCT/US2012/022061, 6 pgs.
International Search Report and Written Opinion dated Aug. 2, 2013 issued in PCT/CA2013/050350.
International Search Report and Written Opinion dated Sep. 17, 2013 issued in PCT/US2013/039982.
International Search Report and Written Opinion dated Sep. 27, 2013 issued in PCT/US2013/039977.
International Search Report dated Jul. 30, 2012 for PCT/US2012/022062, 5 pgs.
Written Opinion dated Jul. 30, 2012 for PCT/US2012/022062, 5 pgs.
International Search Report dated Aug. 22, 2012 for PCT/US2012/022061, 5 pgs.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs , Biosense Webster, Inc. 3333 Diamond Canyon Road Diamond Bar, CA 91765, USA, © Biosense Webster, Inc. 2009 All rights reserved. 1109003.0.
Gelbart "Medical Device for Use in Bodily Lumens, for Example an Atrium", OA mailed Jul. 25, 2011 for U.S. Appl. No. 11/941,819, now published as US 2009-0131930 A1.
Gelbart et al, "Apparatus and Method for Intra-Cardiac Mapping and Ablation", Notice of Allowance dated Oct. 23, 2014 for U.S. Appl. No. 11/475,950, 10 pgs.
Gelbart et al., "Medical Device for Use in Bodily Lumens, for Example an Atrium", Notice of Allowance dated Nov. 13, 2014 for U.S. Appl. No. 13/070,215, 54 pages.
International Search Report dated Mar. 10, 2015, for International Application PCT/CA2014/051144; 10 pages.
Written Opinion dated Mar. 10, 2015, for International Application PCT/CA2014/051144; 4 pages.
Official Action issued in CN201280004400.9, dated Dec. 3, 2014.
Non-Final Office Action issued in U.S. Appl. No. 13/782,867, dated Apr. 15, 2015.
Non-Final Office Action issued in U.S. Appl. No. 13/782,903, dated Apr. 28, 2015.
Lopes et al., "Enhanced Medical Device for Use in Bodily Cavities, for Example an Atrium", Office Action dated May 22, 2015 for U.S. Appl. No. 13/782,889, 86 pages.
Lopes et al., "High-Density Electrode-Based Medical Device System", Office Action dated Jul. 10, 2015 for U.S. Appl. No. 13/793,076, 98 pages.
Lopes et al., "High-Density Electrode-Based Medical Device System", Office Action dated Jul. 9, 2015 for U.S. Appl. No. 13/793,213, 99 pages.
Gelbart et al., "Apparatus and Method for Intra-Cardiac Mapping and Ablation", Office Action dated Aug. 5, 2015 for U.S. Appl. No. 13/785,910, 79 pages.

(56) References Cited

OTHER PUBLICATIONS

Lopes et al., "Enhanced Medical Device for Use in Bodily Cavities, for Example an Atrium", Amendment filed Aug. 24, 2015 for U.S. Appl. No. 13/782,889, 21 pages.
Lopes et al., "Enhanced Medical Device for Use in Bodily Cavities, for Example an Atrium", Amendment filed Aug. 28, 2015 for U.S. Appl. No. 13/782,903, 19 pages.
Lopes et al., "Enhanced Medical Device for Use in Bodily Cavities, for Example an Atrium", Amendment filed Sep. 14, 2015 for U.S. Appl. No. 13/782,867, 25 pages.
Lopes et al., "High-Density Electrode-Based Medical Device System", Amendment filed Oct. 9, 2015 for U.S. Appl. No. 13/793,213, 26 pages.
Lopes et al., "High-Density Electrode-Based Medical Device System", Amendment filed Oct. 9, 2015 for U.S. Appl. No. 13/793,076, 14 pages.
Examination Report issuedin EP13172848.7, dated Sep. 21, 2015.
Extended European Search Report issued in EP13793216.6, dated Oct. 30, 2015.
Moisa et al., "Catheter System", Office Action dated Nov. 16, 2015 for U.S. Appl. No. 14/136,946, 92 pages.
Office Action issued in U.S. Appl. No. 13/782,889, dated Dec. 18, 2015.
Office Action issued in U.S. Appl. No. 13/782,903, dated Dec. 18, 2015.
Extended European Search Report issued in EP15188407.9, datedd Jan. 21, 2016.
Lopes et al. "Enhanced Medical Device for Use in Bodily Cavities, for Example an Atrium", Office Action dated Jan. 25, 2016 for U.S. Appl. No. 13/782,867, 49 pages.
Notice of Allowance issued in U.S. Appl. No. 13/793,076, dated Feb. 10, 2016.
Final Office Action issued in U.S. Appl. No. 13/793,213, dated Feb. 26, 2016.
Non-Final Office Action issued in U.S. Appl. No. 29/509,719, dated Feb. 25, 2016.
Quayle issued in U.S. Appl. No. 29/509,621, dated Feb. 26, 2016.
Quayle issued in U.S. Appl. No. 29/509,636, dated Feb. 26, 2016.
Non-Final Office Action issued in U.S. Appl. No. 13/785,910 dated Apr. 8, 2016.
Non-Final Office Action issued in U.S. Appl. No. 14/229,250 dated Apr. 28, 2016.
Notice of Allowance issued in U.S. Appl. No. 13/793,076 dated Jul. 7, 2016.
Office Action issued in copending U.S. Appl. No. 14/564,463 dated Feb. 28, 2017.
Notice of Allowance issued in copending U.S. Appl. No. 13/942,354 dated Feb. 10, 2017.
Gelbart et al., "Apparatus and Method for Intra-Cardiac Mapping and Ablation", Amendment filed in co-pending U.S. Appl. No. 13/785,910 dated Mar. 24, 2017, 30 pgs.
Gelbart et al., "Medical Device for Use in Bodily Lumens, for Example an Atrium", Amendment filed in co-pending U.S. Appl. No. 14/521,692 dated Mar. 31, 2017, 9 pgs.
Office Action issued in Chinese Patent Application No. 201510432392.3 dated Mar. 8, 2017. English concise Explanation of Relevance provided.
Decision to Refuse a European Patent Application issued in European Patent Application No. 13172848.7 dated Feb. 22, 2017.
Notice of Allowance issued in copending U.S. Appl. No. 14/521,692 dated May 19, 2017.
Office Action issued in copending U.S. Appl. No. 14/713,114 dated Jun. 1, 2017.
Quayle Action issued in copending U.S. Appl. No. 14/713,190 dated May 30, 2017.
Office Action issued in German Application No. 112008003108.8 dated May 8, 2017. English translation provided.
Amendment filed in copending U.S. Appl. No. 14/564,463, filed May 25, 2017.

Office Action issued in copending U.S. Appl. No. 14/564,463 dated Jul. 17, 2017.
European Search Report issued in European Appln. No. 14871405.8 dated Jul. 5, 2017.
Preliminary Amendment filed in copending U.S. Appl. No. 15/299,640 pp. 4 filed Oct. 21, 2016.
Preliminary Amendment filed in copending U.S. Appl. No. 15/299,640 pp. 11 filed Dec. 9, 2016.
Response to Quayle Office Action filed in copending U.S. Appl. No. 14/713,190, filed Jul. 24, 2017.
Preliminary Amendment filed in copending U.S. Appl. No. 14/521,692, filed Oct. 23, 2014.
Preliminary Amendment filed in U.S. Appl. No. 15/697,744 dated Sep. 21, 2017.
Preliminary Amendment filed in copending U.S. Appl. No. 15/663,077 dated Aug. 8, 2017.
Amendment filed in copending U.S. Appl. No. 14/713,114, filed Aug. 23, 2017.
Notice of Allowance issued in copending U.S. Appl. No. 14/713,190 dated Aug. 28, 2017.
Office Action issued in copending U.S. Appl. No. 13/785,910 dated Aug. 30, 2017.
Examination Report issued in Indian Application No. 9902/DELNP/2014 dated Jun. 19, 2020. English translation provided.
Office Action issued in copending U.S. Appl. No. 15/697,744 dated Jul. 8, 2020.
Amendment and Statement on the Substance of the Interview filed in copending U.S. Appl. No. 15/784,722 dated Jul. 9, 2020.
Amendment and Statement on the Substance of the Interview filed in copending U.S. Appl. No. 15/784,775 on Jul. 9, 2020.
Notice of Allowance issued in copending U.S. Appl. No. 15/784,647 dated Jul. 23, 2020.
Office Action issued in Chinese Application No. 201810941271.5 dated Jun. 3, 2021. English language Statement of Relevance provided.
Extended European Search Report issued in European Appln. No. 19172980.5 dated Aug. 21, 2019.
Notice of Allowance issued in copending U.S. Appl. No. 15/254,130 dated Sep. 12, 2019.
Notice of Allowance issued in copending U.S. Appl. No. 15/663,077 dated Sep. 24, 2019.
Office Action issued in German Patent Appln No. 112008003108.8 dated Oct. 28, 2019. English machine translation provided.
Copending U.S. Appl. No. 16/655,775, filed Oct. 17, 2019.
Copending U.S. Appl. No. 16/658,820, filed Oct. 21, 2019.
Copending U.S. Appl. No. 16/662,537, filed Oct. 24, 2019.
Preliminary Amendment filed in copending U.S. Appl. No. 16/655,775 dated Nov. 1, 2019.
Preliminary Amendment filed in copending U.S. Appl. No. 16/658,820 dated Nov. 7, 2019.
Preliminary Amendment filed in copending U.S. Appl. No. 16/662,537 dated Nov. 19, 2019.
Office Action issued in copending U.S. Appl. No. 16/658,820 dated Oct. 22, 2021.
Copending U.S. Appl. No. 17/513,070, filed Oct. 28, 2021.
Office Action issued in copending U.S. Appl. No. 16/662,537 dated Oct. 29, 2021.
Amendment filed in copending U.S. Appl. No. 16/521,712 dated Nov. 1, 2021.
Preliminary Amendment filed in copending U.S. Appl. No. 17/513,070 dated Nov. 8, 2021.
Office Action issued in copending U.S. Appl. No. 15/299,640 dated Nov. 12, 2021.
Notice of Allowance issued in copending U.S. Appl. No. 15/287,988 dated Nov. 15, 2021.
Becker R. et al, "Ablation of Atrial Fibrillation: Energy Sources and Navigation Tools: A Review", Journal of Electrocardiology, 37 (Supplement 2004): 55-62, 2004.
Calkins, Hugh, "Radiofrequency Catheter Ablation of Supraventricular Arrhythmias", Heart, 85:594-600, 2001.
De Ponti et al., "Non-Fluoroscopic Mapping Systems for Electrophysiology: The 'Tool or Toy' Dilemma After 10 Years",European Heart Journal 27:1134-1136, 2006.

(56) References Cited

OTHER PUBLICATIONS

Gelbart et al, "Apparatus and Method for Intra-Cardiac Mapping and Ablation", Office Action dated Dec. 13, 2013; Notice of Allowance dated Jul. 25, 2014 for U.S. Appl. No. 11/475,950, 19 pgs.

Gelbart et al., "Medical Device for Use in Bodily Lumens, for Example an Atrium", Office Action dated Jan. 3, 2012; Office Action dated Apr. 3, 2014; Notice of Allowance dated Aug. 26, 2014 for U.S. Appl. No. 11/941,819, 35 pgs.

Gelbart et al, "Apparatus and Method for Intra-Cardiac Mapping and Ablation", Amendment filed Apr. 10, 2014 Supplemental Amendment filed Feb. 12, 2013 for U.S. Appl. No. 11/475,950, 21 pgs.

Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,910, 10 pgs.

Gelbart et al, "Apparatus and Method for Intra-Cardiac Mapping and Ablation", Preliminary Amendment filed Aug. 22, 2014; Preliminary Amendment filed Mar. 5, 2013 for U.S. Appl. No. 13/785,931, 10 pgs.

Lopes et al, "Enhanced Medical Device for Use in Bodily Cavities, for Example an Atrium", Preliminary Amendment filed Oct. 22, 2013 for U.S. Appl. No. 13/942,354, 13 pgs.

Lopes et al, "Enhanced Medical Device for Use in Bodily Cavities, for Example an Atrium", Preliminary Amendment filed Aug. 20, 2014 for U.S. Appl. No. 13/782,889, 11 pgs.

Lopes et al, "Enhanced Medical Device for Use in Bodily Cavities, for Example an Atrium", Preliminary Amendment filed Mar. 14, 2013 for U.S. Appl. No. 13/782,867, 8 pgs.

Gelbart et al., "Medical Device for Use in Bodily Lumens, for Example an Atrium", Amendment filed Jul. 3, 2014; Amendment filed Apr. 2, 2012; Amendment filed Mar. 1, 2012; Amendment filed Nov. 23, 2011; Replacement drawings filed Feb. 13, 2008 for U.S. Appl. No. 11/941,819, 78 pgs.

Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,305, 12 pgs.

Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,250, 10 pgs.

Gelbart et al., Medical Device for Use in Bodily Lumens, for Example an Atrium, Amendment filed Sep. 22, 2014, for U.S. Patent Application SN. U.S. Appl. No. 13/070,215, 18 pgs.

Gelbart et al., "edical Device for Use in Bodily Lumens, for Example an Atrium", Office Action dated Jun. 20, 2014, for U.S. Appl. No. 13/070,215, 8 pgs.

Gelbart et al., "Medical Device for Use in Bodily Lumens, for Example an Atrium", Supplemental Notice of Allowance dated October 6, 2014 for U.S. Appl. No. 11/941,819, 4 pgs.

Notice of Allowance issued in U.S. Appl. No. 13/793,213 dated Aug. 10, 2016.

Non-Final Office Action issued in U.S. Appl. No. 13/942,354 dated Aug. 4, 2016.

Notice of Allowance issued in U.S. Appl. No. 14/136,946 dated May 12, 2016.

Notice of Allowance issued in U.S. Appl. No. 13/782,867 dated Aug. 12, 2016.

Notice of Allowance issued in U.S. Appl. No. 13/782,903 dated Jul. 6, 2016.

Corrected Notice of Allowance issued in U.S. Appl. No. 13/782,903 dated Jul. 19, 2016.

Non-Final Office Action issued in U.S. Appl. No. 14/229,305, dated Apr. 29, 2016.

Notice of Allowance issued in U.S. Appl. No. 29/509,621, dated Sep. 27, 2016.

Notice of Allowance issued in U.S. Appl. No. 29/509,636, dated Sep. 27, 2016.

Response to Examination Opinion filed Mar. 18, 2021 for Chinese Patent Application No. 201810941271.5.

Office Action issued in copending U.S. Appl. No. 15/287,988 dated May 5, 2021.

Buchbinder, Maurice MD, "Dynamic Mitral Valve Annuloplasty: A Reshapable Ring for Residual and Recurring MR," from the Foundation for Cardiovascular Medicine, La Jolla, CA. May 24, 2007.

Gabriel et al., "The Dielectric Properties of Biological Tissues: I. Literature Survey," Phys. Med. Biol. 41:2231-2249, 1996.

Konings et al., "Development of an Intravascular Impedance Catheter for Detection of Fatty Lesions in Arteries," IEEE Transactions on Medical Imaging, 16(4):439-446, 1997.

Mack, "New Techniques for Percutaneous Repair of the Mitral Valve," Heart Failure Review, 11:259-268, 2006.

Otasevic et al., "First-in-Man Implantation of Left Ventricular Partitioning Device in a Patient With Chronic Heart Failure: Twelve-Month Follow-up," Journal of Cardiac Failure 13(7):517-520, 2007.

Sharkey et al., "Left Ventricular Apex Occluder. Description of a Ventricular Partitioning Device," EuroIntervention 2:125-127, 2006.

Stiles, et al., "Simulated Characterization of Atherosclerotic Lesions in the Coronary Arteries by Measurement of Bioimpedance," IEE Transactions on Biomedical Engineering, 50(7):916-921,2003.

Tanaka et al., "Artificial SMA Valve for Treatment of Urinary Incontinence: Upgrading of Valve and Introduction of Transcutaneous Transformer," Bio-Medical Materials and Engineering 9:97-112, 1999.

Timek et al.., "Septal-Lateral Annular Cinching ('SLAC') Reduces Mitral Annular Size Without Perturbing Normal Annular Dynamics," Journal of Heart Valve Disease 11 (1):2-10, 2002.

Timek et al., "Septal-Lateral Annular Cinching Abolishes Acute Ischemic Mitral Regurgitation," Journal of Thoracic and Cardiovascular Surgery, 123(5):881-888, 2002.

Valvano et al., "Thermal Conductivity and Diffusivity of Biomaterials Measured with Self-Heated Thermistors," International Journal of Thermodynamics, 6(3):301-311, 1985.

Gelbart et al., "Automatic Atherectomy System," Office Action mailed Mar. 4, 2009 for USAN U.S. Appl. No. 11/436,584, 7 pages.

Gelbart et al., "Automatic Atherectomy System," Amendment filed Aug. 4, 2009 for U.S. Appl. No. 11/436,584, 35 pages.

Gelbart et al., "Automatic Atherectomy System," Office Action dated Dec. 1, 2009 for U.S. Appl. No. 11/436,584, 10 pages.

Gelbart et al., "Automatic Atherectomy System," Amendment filed Mar. 30, 2010 for U.S. Appl. No. 11/436,584, 20 pages.

Gelbart et al., "Automatic Atherectomy System," Amendment filed Oct. 25, 2010 for U.S. Appl. No. 11/436,584, 9 pages.

Gelbart et al., "Automatic Atherectomy System," Office Action dated Dec. 14, 2010 for U.S. Appl. No. 11/436,584, 12 pages.

Gelbart et al., "Intra-Cardiac Mapping and Ablation Method," Preliminary Amendment filed Aug. 29, 2007 for U.S. Appl. No. 11/475,950,42 pages.

Gelbart et al., "Intra-Cardiac Mapping and Ablation Method," Amendment filed Mar. 5, 2008 for U.S. Appl. No. 11/475,950, 11 pages.

Gelbart et al., "Intra-Cardiac Mapping and Ablation Method," Office Action dated Jun. 23, 2010 for U.S. Appl. No. 11/475,950, 18 pages.

Gelbart et al., "Intra-Cardiac Mapping and Ablation Method," Amendment filed Aug. 16, 2010 for U.S. Appl. No. 11/475,950, 22 pages.

Gelbart et al., "Intra-Cardiac Mapping and Ablation Method," Office Action dated Nov. 23, 2010 for U.S. Appl. No. 11/475,950, 25 pages.

Gelbart et al., "Intra-Cardiac Mapping and Ablation Method," Amendment filed Feb. 23, 2011 for U.S. Appl. No. 11/475,950, 28 pages.

Gelbart et al., "Automatic Atherectomy System," Office Action dated Jun. 15, 2011, for U.S. Appl. No. 12/950,871, 16 pages.

Gelbart et al., "Liposuction System," Office Action dated Mar. 16, 2011 for U.S. Appl. No. 12/010,458, 12 pages.

Gelbart et al., "Liposuction System," Amendment filed Jun. 10, 2011 for U.S. Appl. No. 12/010,458, 10 pages.

(56) References Cited

OTHER PUBLICATIONS

Lichtenstein "Method and Apparatus for Percutaneous Reduction of Anterior-Posterior Diameter of Mitral Valve," U.S. Appl. No. 10/690,131, filed Oct. 20, 2003, 31 pages.
International Search Report, dated Dec. 5, 2007, for PCT/US2007/014902, 5 pages.
International Preliminary Report on Patentability, dated Jan. 6, 2009, for PCT/US2007/014902, 8 pages.
International Search Report, dated Dec. 2, 2009, for PCT/US2008/083644, 5 pages.
Written Opinion, dated Dec. 5, 2007, for PCT/US2007/014902, 7 pages.
Written Opinion, dated Dec. 2, 2009, for PCT/US2008/083644, 9 pages.
Gelbart et al., "Automatic Atherectomy System," Amendment filed Sep. 15, 2011 for U.S. Appl. No. 12/950,871, 21 pages.
Gelbart et al., "Liposuction System," Amendment filed Dec. 7, 2011 for U.S. Appl. No. 12/010,458, 15 pages.
Gelbart et al., "Liposuction System," Office Action dated Sep. 14, 2011 for U.S. Appl. No. 12/010,458, 9 pages.
Notice of Allowance issued in U.S. Appl. No. 13/782,889, dated Aug. 25, 2016.
Examination Report issued in European Application No. 15188407.9 dated Dec. 11, 2017.
Office Action issued in Chinese Application No. 201510432392.3 dated Nov. 17, 2017. English translation provided.
Examination Report issued in European Application No. 13793216.6 dated Nov. 24, 2017.
Office Action issued in copending U.S. Appl. No. 14/804,810 dated Nov. 30, 2017.
Response to Office Action filed in copending U.S. Appl. No. 13/785,910 dated Nov. 30, 2017.
Office Action issued in copending U.S. Appl. No. 14/804,924 dated Nov. 17, 2017.
Preliminary Amendment filed in copending U.S. Appl. No. 15/725,662 dated Oct. 24, 2017.
Preliminary Amendment filed in copending U.S. Appl. No. 15/784,647 dated Nov. 7, 2017.
Amendment filed in copending U.S. Appl. No. 14/564,463 dated Oct. 17, 2017.
Notice of Allowance issued in copending U.S. Appl. No. 14/713,114 dated Nov. 1, 2017.
Notice of Allowance issued in copending U.S. Appl. No. 14/564,463 dated Nov. 9, 2017.
Preliminary Amendment filed in copending U.S. Appl. No. 15/784,555 dated Nov. 7, 2017.
Preliminary Amendment filed in copending U.S. Appl. No. 15/784,775 dated Nov. 7, 2017.
Preliminary Amendment filed in copending U.S. Appl. No. 15/784,722 dated Nov. 7, 2017.
Preliminary Amendment filed in copending U.S. Appl. No. 15/725,731 dated Oct. 24, 2017.
Amendment filed in copending U.S. Appl. No. 14/804,924 dated Feb. 27, 2018.
Amendment filed in copending U.S. Appl. No. 14/804,810 dated Feb. 27, 2018.
Notice of Allowance issued in copending U.S. Appl. No. 14/804,924 dated Mar. 27, 2018.
Notice of Allowance issued in copending U.S. Appl. No. 14/804,810 dated Mar. 30, 2018.
Office Action issued in Chinese Application No. 201510432392.3 dated May 18, 2018. Concise Explanation of Relevance provided.
Office Action issued in copending U.S. Appl. No. 13/785,910 dated Jan. 12, 2018.
Amendment filed in copending U.S. Appl. No. 13/785,910 on Feb. 27, 2018.
Notice of Allowance issued in U.S. Appl. No. 13/785,910 dated Jun. 15, 2018.
Examination Report issued in European Appln. No. 14871405.8 dated Jul. 6, 2018.
Lopes et al., "Intra-Cardiac Procedure Device", Amendment filed in co-pending U.S. Appl. No. 29/509,636, filed Jul. 22, 2016, 5 pgs.
Lopes et al., "Intra-Cardiac Procedure Device", Amendment filed in co-pending U.S. Appl. No. 29/509,636 dated Nov. 17, 2016, 3 pgs.
Lopes et al., "High-Density Electrode-Based Medical Device System", Preliminary Amendment filed in co-pending U.S. Appl. No. 15/287,988 dated Nov. 23, 2016, 9 pgs.
Lopes et al., "Intra-Cardiac Procedure Device", Amendment filed in co-pending U.S. Appl. No. 29/509,621 dated Jul. 22, 2016, 5 pgs.
Lopes et al., "Intra-Cardiac Procedure Device", Amendment filed in co-pending U.S. Appl. No. 29/509,621 dated Nov. 17, 2016, 3 pgs.
Lopes et al., "Enhanced Medical Device for Use in Bodily Cavities, for Example an Atrium", Amendment filed in co-pending U.S. Appl. No. 13/782,889 dated May 17, 2016, 51 pgs.
Lopes et al., "High-Density Electrode-Based Medical Device System" Amendment filed in co-pending U.S. Appl. No. 13/793,213 dated May 26, 2016, 39 pgs.
Lopes et al., "Enhanced Medical Device for Use in Bodily Cavities, for Example an Atrium", Amendment filed in co-pending U.S. Appl. No. 13/782,867 dated May 17, 2016, 39 pgs.
Gelbart et al., "Intra-Cardiac Mapping and Ablation Method", Amendment filed in co-pending U.S. Appl. No. 11/475,950 dated Feb. 12, 2013, 4 pgs.
Moisa et al., "Catheter System", Preliminary Amendment filed in co-pending U.S. Appl. No. 15/254,130 dated Sep. 19, 2016, 22 pgs.
Gelbart et al., "Apparatus and Method for Intra-Cardiac Mapping and Ablation", Preliminary Amendment filed in co-pending U.S. Appl. No. 14/804,924 dated Jul. 30, 2015, 5 pgs.
Gelbart et al., "Apparatus and Method for Intra-Cardiac Mapping and Ablation", Preliminary Amendment filed in co-pending U.S. Appl. No. 14/804,810 dated Jul. 30, 2015, 10 pgs.
Gelbart et al., "Medical Device for Use in Bodily Lumens, for Example an Atrium", Preliminary Amendment filed in co-pending U.S. Appl. No. 14/713,190 dated May 15, 2015, 3 pgs.
Gelbart et al., "Medical Device for Use in Bodily Lumens, for Example an Atrium", Preliminary Amendment filed in co-pending U.S. Appl. No. 14/713,190 dated Jun. 16, 2015, 7 pgs.
Gelbart et al., "Medical Device for Use in Bodily Lumens, for Example an Atrium", Preliminary Amendment filed in co-pending U.S. Appl. No. 14/713,114 dated Jun. 16, 2015, 8 pgs.
Office Action issued in co-pending U.S. Appl. No. 14/521,692 dated Jan. 10, 2017.
Gelbart et al., "Medical Device for Use in Bodily Lumens, for Example an Atrium", Amendment filed in co-pending U.S. Appl. No. 14/229,305 dated Sep. 27, 2016, 15 pgs.
Notice of Allowance issued in co-pending U.S. Appl. No. 14/229,305 dated Nov. 8, 2016.
Gelbart et al., "Medical Device for Use in Bodily Lumens, for Example an Atrium", Amendment filed in co-pending U.S. Appl. No. 14/229,250 dated Sep. 27, 2016, 13 pgs.
Notice of Allowance issued in co-pending U.S. Appl. No. 14/229,250 dated Dec. 7, 2016.
Moisa et al., "Catheter System", Amendment filed in co-pending U.S. Appl. No. 14/136,946 dated Apr. 18, 2016, 19 pgs.
Lopes et al., "Enhanced Medical Device for Use in Bodily Cavities, for Example an Atrium", Amendment filed in co-pending U.S. Appl. No. 13/942,354 dated Jan. 4, 2017,23 pgs.
Lopes et al., "High-Density Electrode-Based Medical Device System", Preliminary Amendment filed in co-pending U.S. Appl. No. 13/793,076 dated May 26, 2016, 15 pgs.
Lopes et al., "High-Density Electrode-Based Medical Device System", Amendment filed in co-pending U.S. Appl. No. 13/793,076 dated May 9, 2016, 15 pgs.
Gelbart et al., "Apparatus and Method for Intracardiac Mapping and Ablation", Preliminary Amendment filed in co-pending U.S. Appl. No. 13/785,931 dated Mar. 5, 2013, 2 pgs.
Gelbart et al., "Apparatus and Method for Intra-Cardiac Mapping and Ablation", Amendment filed in co-pending U.S. Appl. No. 13/785,910 dated Feb. 9, 2016, 11 pgs.
Gelbart et al., "Apparatus and Method for Intra-Cardiac Mapping and Ablation", Amendment filed in co-pending U.S. Appl. No. 13/785,910 dated Jan. 5, 2016, 15 pgs.

(56) References Cited

OTHER PUBLICATIONS

Gelbart et al., "Apparatus and Method for Intra-Cardiac Mapping and Ablation", Amendment filed in co-pending U.S. Appl. No. 13/785,910 dated Aug. 8, 2016, 18 pgs.
Office Action issued in co-pending U.S. Appl. No. 13/785,910 dated Nov. 2, 2016.
Office Action issued in copending U.S. Appl. No. 15/697,744 dated Feb. 28, 2020.
Office Action issued in copending U.S. Appl. No. 15/784,647 dated Feb. 28, 2020.
Office Action issued in copending U.S. Appl. No. 15/784,555 dated Mar. 9, 2020.
Office Action issued in copending U.S. Appl. No. 15/784,722 dated Mar. 23, 2020.
Office Action issued in copending U.S. Appl. No. 15/784,775 dated Mar. 23, 2020.
Notice of Allowance issued in copending U.S. Appl. No. 15/784,775 dated Aug. 7, 2020.
Notice of Allowance issued in copending U.S. Appl. No. 15/784,555 dated Aug. 11, 2020.
Amendment and Statement on the Substance of the Interview filed in copending U.S. Appl. No. 15/725,662 dated Aug. 13, 2020.
Amendment and Statement on the Substance of the Interview filed in copending U.S. Appl. No. 15/725,731 dated Aug. 13, 2020.
Notice of Allowance issued in copending U.S. Appl. No. 15/784,722 dated Aug. 14, 2020.
Office Action issued in copending U.S. Appl. No. 16/407,379 dated Dec. 24, 2020.
Amendment filed in copending U.S. Appl. No. 16/407,379 dated Mar. 23, 2021.
Notice of Allowance issued in copending U.S. Appl. No. 15/725,662 dated Sep. 3, 2020.
Notice of Allowance issued in copending U.S. Appl. No. 15/725,731 dated Sep. 3, 2020.
Notice of Allowance issued in copending U.S. Appl. No. 15/697,744 dated Sep. 18, 2020.
Preliminary Amendment filed in copending U.S. Appl. No. 16/995,159 dated Sep. 25, 2020.
Preliminary Amendment filed in copending U.S. Appl. No. 16/995,222 dated Sep. 25, 2020.
Preliminary Amendment filed in copending U.S. Appl. No. 17/182,732 dated Mar. 11, 2021.
Preliminary Amendment filed in copending U.S. Appl. No. 17/072,262 dated Dec. 1, 2020.
Office Action issued in Chinese Appln. No. 201810941271.5 dated Nov. 3, 2020. English translation provided.
Copending U.S. Appl. No. 17/182,732, filed Feb. 23, 2021.
Preliminary Amendment filed in copending U.S. Appl. No. 17/182,732 dated Feb. 23, 2021.
Notice of Allowance issued in copending U.S. Appl. No. 16/407,379 dated Apr. 1, 2021.
Extended European Search Report issued in European Application No. 19215957.2 dated Mar. 26, 2020.
Amendment filed in copending U.S. Appl. No. 15/287,988 dated Jul. 28, 2021.
Non-Final Office Action issued in copending U.S. Appl. No. 16/521,712 dated Sep. 30, 2021.
Copending U.S. Appl. No. 17/500,186, filed Oct. 13, 2021.
Preliminary Amendment filed in copending U.S. Appl. No. 17/500,186, filed Oct. 19, 2021.
Extended European Search Report issued in European Application No. 19189222.3 dated Nov. 29, 2019.
Office Action issued in copending U.S. Appl. No. 15/725,662 dated May 13, 2020.
Office Action issued in copending U.S. Appl. No. 15/725,731 dated May 15, 2020.
Amendment filed in copending U.S. Appl. No. 15/784,647 dated May 27, 2020.
Amendment filed in copending U.S. Appl. No. 15/697,744 dated May 27, 2020.
Amendment filed in copending U.S. Appl. No. 15/784,555 dated Jun. 3, 2020.
Preliminary Amendment filed in copending U.S. Appl. No. 16/407,379 dated Jun. 12, 2019.
Notice of Intention to Grant issued in EP Appln. No. 13793216.6 dated Jul. 15, 2019.
Copending U.S. Appl. No. 16/521,712, filed Jul. 25, 2019.
Copending U.S. Appl. No. 16/521,732, filed Jul. 25, 2019.
Copending U.S. Appl. No. 16/521,745, filed Jul. 25, 2019.
Preliminary Amendment filed in copending U.S. Appl. No. 16/521,712 dated Jul. 25, 2019.
Preliminary Amendment filed in copending U.S. Appl. No. 16/521,732 dated Jul. 25, 2019.
Preliminary Amendment filed in copending U.S. Appl. No. 16/521,745 dated Jul. 25, 2019.
Amendment filed in copending U.S. Appl. No. 15/254,130 dated Aug. 13, 2019.
Second Preliminary Amendment filed in copending U.S. Appl. No. 16/521,712 dated Aug. 15, 2019.
Second Preliminary Amendment filed in copending U.S. Appl. No. 16/521,732 dated Aug. 15, 2019.
Second Preliminary Amendment filed in copending U.S. Appl. No. 16/521,745 dated Aug. 15, 2019.
Non-Final Office Action issued in copending U.S. Appl. No. 16/369,528 dated Dec. 6, 2021.
Notice of Allowance issued in Chinese Application No. 201810941271.5 dated Dec. 22, 2021.
Non-Final Office Action issued in copending U.S. Appl. No. 16/381,317 dated Jan. 10, 2022.
Notice of Allowance issued in copending U.S. Appl. No. 16/521,712 dated Jan. 11, 2022.
Amendment filed in copending U.S. Appl. No. 16/658,820 dated Jan. 17, 2022.
Amendment filed in copending U.S. Appl. No. 16/662,537 dated Jan. 18, 2022.
Non-Final Office Action issued in copending U.S. Appl. No. 16/381,344 dated Feb. 1, 2022.
Preliminary Amendment filed in copending U.S. Appl. No. 17/584,705 dated Feb. 2, 2022.
Copending U.S. Appl. No. 17/584,705, filed Jan. 26, 2022.
Amendment filed in copending U.S. Appl. No. 15/299,640 dated Feb. 8, 2022.
Non-Final Office Action issued in copending U.S. Appl. No. 17/500,186 dated Feb. 9, 2022.

* cited by examiner

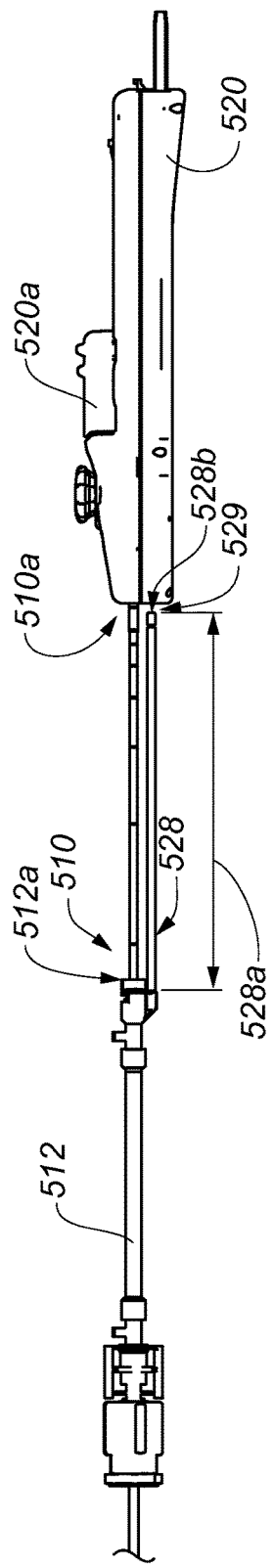
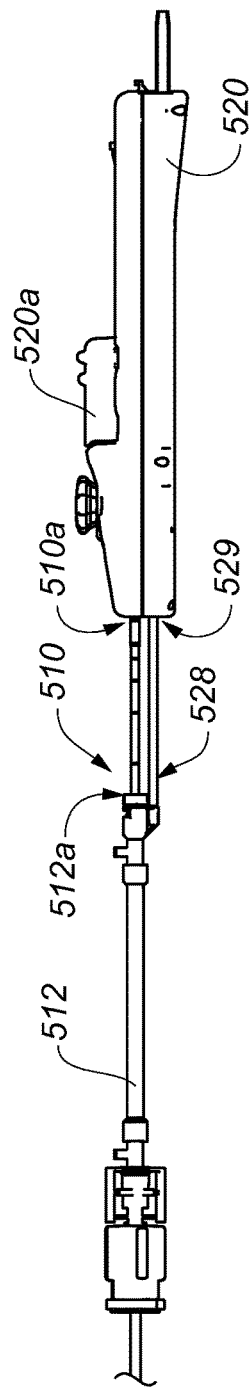
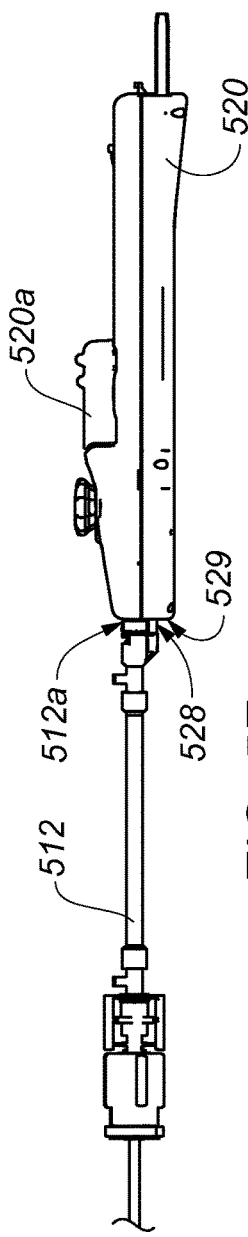
FIG. 5D
FIG. 5E
FIG. 5F

912
*TRANSITION MANIPULABLE PORTION AT LEAST PARTIALLY BETWEEN EXPANDED CONFIGURATION AND DELIVERY CONFIGURATION*

- *TRANSITION THE MANIPULABLE PORTION TOWARD THE EXPANDED CONFIGURATION AS THE MANIPULABLE PORTION IS ADVANCED OUT OF THE DISTAL END OF CATHETER SHEATH* — 912a

- *TRANSITION THE MANIPULABLE PORTION TOWARD THE DELIVERY CONFIGURATION AS THE MANIPULABLE PORTION IS RETRACTED INTO THE DISTAL END OF CATHETER SHEATH* — 912b

922 — *TRANSITION MANIPULABLE PORTION AT LEAST PARTIALLY BETWEEN EXPANDED CONFIGURATION AND DELIVERY CONFIGURATION*

924 — *CAUSE A CONTROL ELEMENT TO HAVE A FIRST AMOUNT OF LENGTH LOCATED OUTSIDE OF DISTAL END OF CATHETER SHEATH WHEN A PARTICULAR RELATIVE POSITIONING EXISTS BETWEEN THE CATHETER SHEATH AND A SHAFT RECEIVED IN THE LUMEN OF THE CATHETER SHEATH DURING THE TRANSITION TOWARD THE EXPANDED CONFIGURATION*

926 — *CAUSE A CONTROL ELEMENT TO HAVE A SECOND AMOUNT OF LENGTH LOCATED OUTSIDE OF DISTAL END OF CATHETER SHEATH WHEN THE PARTICULAR RELATIVE POSITIONING EXISTS BETWEEN THE CATHETER SHEATH AND A SHAFT RECEIVED IN THE LUMEN OF THE CATHETER SHEATH DURING THE TRANSITION TOWARD THE DELIVERY CONFIGURATION*

FIG. 9D

CATHETER SYSTEM

CROSS-REFERENCE TO RELATED APPLICATIONS

This application is a continuation of U.S. patent application Ser. No. 15/254,130, filed Sep. 1, 2016, now U.S. Pat. No. 10,485,608, issued Nov. 26, 2019, which is a continuation of U.S. patent application Ser. No. 14/136,946, filed Dec. 20, 2013, now U.S. Pat. No. 9,452,016, issued Sep. 27, 2016, which is a continuation-in-part of U.S. patent application Ser. No. 13/942,354, filed Jul. 15, 2013, now U.S. Pat. No. 9,675,401, issued Jun. 13, 2017, which is a continuation of International Patent Application PCT/US2012/022061, filed Jan. 20, 2012, which claims the benefit of U.S. Provisional Application No. 61/435,213, filed Jan. 21, 2011; U.S. Provisional Application No. 61/485,987, filed May 13, 2011; U.S. Provisional Application No. 61/488,639, filed May 20, 2011; and U.S. Provisional Application No. 61/515,141, filed Aug. 4, 2011. This application also is related to U.S. Provisional Application No. 61/919,388, filed Dec. 20, 2013, as well as International Patent Application PCT/CA2014/051144, filed Nov. 28, 2014 and its European Regional Phase Application No. 14871405.8, entered Jun. 21, 2016. The entire disclosure of each of the applications cited in this Cross-Reference to Related Applications Section is hereby incorporated herein by reference.

TECHNICAL FIELD

Aspects of this disclosure generally are related to a medical system, such as a catheter system including a catheter sheath and an elongated catheter sized for delivery through a lumen of the catheter sheath. In some embodiments, the catheter system includes a controllable manipulable portion.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During various procedures, health care providers create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality, and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature, and tissue stimulation can also complicate the operation of the employed medical device.

Conventional catheter systems have technological limitations that limit effective manipulation of a portion thereof in intra-bodily cavities and, consequently, have difficulty ensuring proper deployment, properly gathering adequate information, or performing proper lesion formation. Accordingly, a need in the art exists for catheter systems having improved manipulation capabilities.

SUMMARY

At least the above-discussed need is addressed and technical solutions are achieved by various embodiments of the present invention. In some embodiments, catheter systems and associated methods exhibit enhanced capabilities for the deployment and the activation of various transducers, which may be located within a bodily cavity, such as an intra-cardiac cavity. In some embodiments, systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Various ones of the transducers may be used to stimulate tissue within the bodily cavity. Stimulation can include pacing by way of non-limiting example. Other advantages will become apparent from the teaching herein to those of skill in the art.

In some embodiments, a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least a part of the shaft receivable in the lumen of the catheter sheath; (iii) a manipulable portion located at least proximate the distal end of the shaft, the manipulable portion including a distal end and sized for delivery through the lumen of the catheter sheath to a bodily cavity located in a body, the distal end of the manipulable portion arranged to be delivered first, with respect to other parts of the manipulable portion, through the lumen of the catheter sheath to the bodily cavity; and (iv) an actuator system operatively coupled to the manipulable portion to vary a shape thereof, the actuator system controlled at least by relative movement between the shaft and the catheter sheath. In various embodiments, the actuator system responds to a first relative movement by varying a shape of at least a part of the manipulable portion extending outside the distal end of the catheter sheath to, at least in part, cause the distal end of the manipulable portion to move along a first trajectory during the first relative movement, the first relative movement being between the catheter sheath and the part of the shaft when a distance between a location on the part of the shaft and a location on the catheter sheath decreases, and the actuator system further responds to a second relative movement by varying a shape of at least the part of the manipulable portion extending outside the distal end of the catheter sheath to, at least in part, cause the distal end of the manipulable portion to move along a second trajectory different than the first trajectory during the second relative movement, the second relative movement being between the catheter sheath and the part of the shaft when a distance between the location on the part of the shaft and the location on the catheter sheath increases.

In some embodiments, (a) the distal end of the manipulable portion follows a coiled path during the first relative movement, (b) the distal end of the manipulable portion follows a coiled path during the second relative movement, or both (a) and (b). In some embodiments, the manipulable portion includes a proximal end and an elongated part extending between the proximal and the distal ends of the manipulable portion, and at least the elongated part of the manipulable portion is coiled after the actuator system varies the shape of at least the part of the manipulable portion extending outside the distal end of the catheter sheath to at least in part cause the distal end of the manipulable portion to move along the first trajectory.

In some embodiments, the manipulable portion may be selectively moveable between a delivery configuration in which the manipulable portion is shaped to be delivered through the lumen of the catheter sheath and an expanded configuration in which the manipulable portion is sized too large for delivery through the lumen of the catheter sheath. The catheter system may further include a control element physically coupled to the manipulable portion to transmit force to the manipulable portion, the control element being receivable in the lumen of the catheter sheath. The actuator system may be operatively coupled to the control element to transition the manipulable portion, at least in part, toward the expanded configuration as the manipulable portion is advanced out of the distal end of the catheter sheath, and to transition, at least in part, the manipulable portion toward the delivery configuration as the manipulable portion is retracted into the distal end of the catheter sheath. The actuator system may be operatively coupled to the control element to cause, when a particular amount of the manipulable portion is located outside of the distal end of the catheter sheath during the transition toward the expanded configuration, at least a portion of the control element to have a first amount of length located outside of the distal end of the catheter sheath. The actuator system may be further operatively coupled to the control element to cause, when the particular amount of the manipulable portion is located outside of the distal end of the catheter sheath during the transition toward the expanded configuration, at least a portion of the control element to have a second amount of length located outside of the distal end of the catheter sheath, the second amount of length being different than the first amount of length. The particular amount of the manipulable portion may be a length of the manipulable portion extending outwardly from the distal end of the catheter sheath to the distal end of the manipulable portion in some embodiments. The control element may include a sleeve and a cable located, at least in part, in a lumen of the sleeve, each of the cable and the sleeve located, at least in part, in a lumen of the shaft. The actuator system may be operatively coupled to the control element in a configuration configured to (c) move the sleeve independently or separately from the cable to cause the sleeve to slide over the cable, and (d) move the cable independently or separately from the sleeve to cause the cable to slide through the lumen of the sleeve.

In some embodiments, the manipulable portion is selectively moveable between a delivery configuration in which the manipulable portion is shaped to be delivered through the lumen of the catheter sheath and an expanded configuration in which the manipulable portion is sized too large for delivery through the lumen of the catheter sheath. The catheter system may further include a control element physically coupled to the manipulable portion to transmit force to the manipulable portion, the control element receivable in the lumen of the catheter sheath. The actuator system may be operatively coupled to the manipulable portion to transition the manipulable portion, at least in part, toward the expanded configuration as the manipulable portion is advanced out of the distal end of the catheter sheath, and to transition, at least in part, the manipulable portion toward the delivery configuration as the manipulable portion is retracted into the distal end of the catheter sheath. The actuator system may be operatively coupled to the control element to cause, when a particular amount of the manipulable portion is located outside of the distal end of the catheter sheath during the transition toward the expanded configuration, at least a portion of the control element to be metered with a first rate, and the actuator system may be operatively coupled to the control element to cause, when the particular amount of the manipulable portion is located outside of the distal end of the catheter sheath during the transition toward the delivery configuration, at least a portion of the control element to be metered with a second rate different than the first rate. In some embodiments, the at least the portion of the control element includes a control cable, and the actuator system is operatively coupled to the control element to cause the control cable to be metered in a direction suitable to reduce an amount of the control cable located outside the distal end of the catheter sheath during one of (e) the transition toward the expanded configuration, and (f) the transition toward the delivery configuration, and to cause the control cable to be metered in a direction suitable to increase an amount of the control cable located outside the distal end of the catheter sheath during the other of (e) and (f).

In some embodiments, the manipulable portion is selectively moveable between a delivery configuration in which the manipulable portion is shaped to be delivered through the lumen of the catheter sheath and an expanded configuration in which the manipulable portion is sized too large for delivery through the lumen of the catheter sheath. The catheter system may further include a control element physically coupled to the manipulable portion to transmit force to the manipulable portion, the control element being receivable in the lumen of the catheter sheath. The actuator system may be operatively coupled to the manipulable portion to transition the manipulable portion, at least in part, toward the expanded configuration as the manipulable portion is advanced out of the distal end of the catheter sheath, and to transition, at least in part, the manipulable portion toward the delivery configuration as the manipulable portion is retracted into the distal end of the catheter sheath. The actuator system may be operatively coupled to the control element to cause, when a particular relative positioning exists between the catheter sheath and the shaft received in the lumen of the catheter sheath during the transition toward the expanded configuration, the control element to have a first amount of length located outside of the distal end of the catheter sheath. The actuator system may be further operatively coupled to the control element to cause, when the particular relative positioning exists between the catheter sheath and the shaft received in the lumen of the catheter sheath during the transition toward the delivery configuration, the control element to have a second amount of length located outside of the distal end of the catheter sheath, the second amount different than the first amount. In some embodiments, the control element includes a sleeve and a cable located, at least in part, in a lumen of the sleeve. In some embodiments, each of the cable and the sleeve may be located, at least in part, in a lumen of the shaft. In some embodiments, the actuator system is operatively coupled to the control element in a configuration configured to (e) move the sleeve independently or separately from the cable to cause the sleeve to slide over the cable, and (f) move the cable independently or separately from the sleeve to cause the cable to slide through the lumen of the sleeve. The particular relative positioning may be a relative longitudinal positioning.

In some embodiments, the elongated portion of the shaft has a length extending between the proximal and the distal ends of the shaft and is sized to position the proximal end of the shaft at a location outside the body when the manipulable portion is located in the bodily cavity. The actuator system may be located at a respective location at least proximate the proximal end of the shaft.

In some embodiments, the manipulable portion may include a plurality of elongate members, each elongate member of the plurality of elongate members including a first end, a second end, and an intermediate portion positioned between the first and the second ends, each intermediate portion including a thickness, a front surface, and a back surface opposite across the thickness from the front surface. The manipulable portion may further include a first portion and a second portion, each of the first and the second portions of the manipulable portion including a respective part of each of at least some of the plurality of elongate members. The manipulable portion may be selectively moveable between: a delivery configuration in which the manipulable portion is sized for delivery through the lumen of the catheter sheath, at least the respective intermediate portions of the elongate members of the plurality of elongate members arranged front surface-toward-back surface in a stacked array when the manipulable portion is in the delivery configuration; and a deployed configuration in which the manipulable portion is sized too large for delivery through the lumen of the catheter sheath, the first portion of the manipulable portion forming a first domed shape and the second portion of the manipulable portion forming a second domed shape when the manipulable portion is in the deployed configuration.

In some embodiments, the manipulable portion includes a first portion and a second portion, and the manipulable portion is selectively moveable between a delivery configuration in which the manipulable portion is sized for delivery through the lumen of the catheter sheath and a deployed configuration in which the manipulable portion is sized too large for delivery through the lumen of the catheter sheath. The first portion of the manipulable portion may form a first domed shape and the second portion of the manipulable portion may form a second domed shape when the manipulable portion is in the deployed configuration. The first and the second portions of the manipulable portion may be arranged in a clam shell configuration when the manipulable portion is in the deployed configuration. The manipulable portion may be arranged to be delivered second portion first through the lumen of the catheter sheath when delivered in the delivery configuration.

The manipulable portion may include a set of one or more transducers. The catheter sheath, the part of the shaft receivable in the lumen of the catheter sheath, or each of the catheter sheath and the part of the shaft receivable in the lumen of the catheter sheath may include a bendable portion that is bendable during a respective delivery to the bodily cavity. The catheter system may further include a control system operatively coupled to the actuator system, the control system operable to control activation of one or more actuators of the actuator system. The control system may be operable to control activation of the one or more actuators of the actuator system in response to the relative movement between the shaft and the catheter sheath.

In some embodiments, the distal end of the manipulable portion may be located outside of the distal end of the catheter sheath at a first location when a particular spatial relationship exists between the shaft and the catheter sheath during the first relative movement. The distal end of the manipulable portion may be located outside of the distal end of the catheter sheath at a second location when the particular spatial relationship exists between the shaft and the catheter sheath during the second relative movement. In various embodiments, the second location may be different than the first location. In various embodiments, the particular spatial relationship may be a spatial relationship between a third location on the shaft and fourth location on the catheter sheath.

In some embodiments, the first relative movement may cause an increase in an amount of the at least a part of the manipulable portion extending outside the distal end of the catheter sheath, and the second relative movement may cause a decrease in an amount of the at least a part of the manipulable portion extending outside the distal end of the catheter sheath.

In some embodiments, the catheter system may further include a control element physically coupled to the manipulable portion to transmit force to the manipulable portion, the control element receivable in the lumen of the catheter sheath. The actuator system may be operatively coupled to the control element to vary a shape of at least the part of the manipulable portion extending outside the distal end of the catheter sheath to, at least in part, cause the distal end of the manipulable portion to move along the first trajectory during the first relative movement. The first trajectory may be a modified trajectory following a respective path along which the distal end of the manipulable portion moves during the first relative movement as compared to a respective trajectory along which the distal end of the manipulable portion would move during the first relative movement absent the control element. In some embodiments, the actuator system may respond to the first relative movement by varying a radius of curvature of a surface of the at least a part of the manipulable portion extending outside the distal end of the catheter sheath to decrease and then subsequently increase during the first relative movement.

Various systems may include combinations and subsets of all the systems summarized above.

In some embodiments, a catheter system includes: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least a part of the shaft receivable in the lumen of the catheter sheath; and (iii) a manipulable portion located at least proximate the distal end of the shaft, the manipulable portion including a distal end and sized for delivery through the lumen of the catheter sheath, the distal end of the manipulable portion arranged to be delivered first, with respect to other parts of the manipulable portion, through the lumen of the catheter sheath from the proximal end of the catheter sheath toward the distal end of the catheter sheath. A method of the controlling the catheter system may be summarized as including responding to a first relative movement, which causes a distance between a location on the part of the shaft and a location on the catheter sheath to decrease, to vary a shape of at least a part of the manipulable portion extending outside the distal end of the catheter sheath to, at least in part, cause the distal end of the manipulable portion to move along a first trajectory during the first relative movement, and responding to a second relative movement, which causes a distance between the location on the part of the shaft and the location on the catheter sheath to increase, to vary a shape of at least a part of the manipulable portion extending outside the distal end of the catheter sheath to, at least in part, cause the distal end of the manipulable portion to move along a second trajectory during the second relative movement, the second trajectory being different than the first trajectory.

In some embodiments, a catheter system may be summarized as including: (i) a catheter sheath that includes a proximal end, a distal end, and a lumen extending within the catheter sheath between the proximal end of the catheter sheath and the distal end of the catheter sheath; (ii) a shaft member including a shaft that includes a proximal end, a distal end, and an elongated portion extending between the proximal end of the shaft and the distal end of the shaft, at least part of the shaft sized for delivery through the lumen of the catheter sheath to a bodily cavity located in a body, and the distal end of the shaft arranged to be delivered through the lumen of the catheter sheath toward the bodily cavity prior to at least the elongated portion of the shaft; (iii) a manipulable portion located at least proximate the distal end of the shaft, the manipulable portion sized for delivery though the lumen of the catheter sheath to the bodily cavity; (iv) a projection including a length and extending from a location at least proximate a first one of the proximal end of the catheter sheath and the proximal end of the shaft; (v) a receiver provided at a location at least proximate a second one of the proximal end of the catheter sheath and the proximal end of the shaft, the projection and the receiver configured to matingly engage at least when the part of the shaft is received in the lumen of the catheter sheath; and (vi) an actuator system operatively coupled to the manipulable portion to transmit force to the manipulable portion, the actuator system responsive to varying amounts of the length of the projection being within the receiver by varying the force transmitted to the manipulable portion.

In some embodiments, the projection may extend beyond the first one of the proximal end of the catheter sheath and the proximal end of the shaft at least when the part of the shaft is received in the lumen of the catheter sheath. In some embodiments, the projection may extend outwardly from the first one of the proximal end of the catheter sheath and the proximal end of the shaft toward one of the proximal end of the catheter sheath and the proximal end of the shaft other than the first one, at least when the part of the shaft is received in the lumen of the catheter sheath.

In some embodiments, the manipulable portion is configured to not be inserted into the receiver when the manipulable portion is delivered through the lumen of the catheter sheath to the bodily cavity.

In some embodiments, the length of the projection is a longitudinal length of the projection extending from the location at least proximate the first one of the proximal end of the catheter sheath and the proximal end of the shaft to an end of the projection, the end of the projection configured to be received first in the receiver, as compared to other parts of the projection, when the projection is inserted into the receiver. In some embodiments, the shaft includes a longitudinal length extending between the proximal and distal ends of the shaft, and the longitudinal length of the shaft is different than the longitudinal length of the projection. In some embodiments, the longitudinal length of the shaft is greater than the longitudinal length of the projection. In some embodiments, a first particular amount of the longitudinal length of the projection is located in the receiver when a second particular amount of the longitudinal length of the shaft is located inside the lumen of the catheter sheath, the first particular amount of the longitudinal length of the projection being less than the second particular amount of the longitudinal length of the shaft.

In some embodiments, the first one of the proximal end of the catheter sheath and the proximal end of the shaft is a same one as the second one of the proximal end of the catheter sheath and the proximal end of the shaft. In some embodiments, the first one of the proximal end of the catheter sheath and the proximal end of the shaft is different than the second one of the proximal end of the catheter sheath and the proximal end of the shaft. In some embodiments, the second one of the proximal end of the catheter sheath and the proximal end of the shaft is the proximal end of the shaft. In some embodiments, the first one of the proximal end of the catheter sheath and the proximal end of the shaft is the proximal end of the catheter sheath.

In some embodiments, the shaft member may further include a housing physically coupled to the shaft at a location at least proximate the second one of the proximal end of the catheter sheath and the proximal end of the shaft, and the receiver is located, at least in part, in the housing. In some embodiments, the actuator system may be located, at least in part, in the housing.

In some embodiments, the receiver may include an internal receiving mechanism sized to matingly receive at least a portion of the projection, and the actuator system may be responsive to a movement of the internal receiving mechanism within the receiver caused by a change in an amount of the length of the projection within the receiver by varying the force transmitted to the manipulable portion. The internal receiving mechanism may include a coupler that physically couples the internal receiving mechanism to at least the portion of the projection when at least the portion of the projection is matingly received in the internal receiving mechanism. In some embodiments, when at least the portion of the projection is physically coupled to the internal receiving mechanism, at least the coupler of the internal receiving mechanism may be configured to move during each of a first relative movement between the projection and the receiver that increases the amount of the length of the projection within the receiver, and a second relative movement between the projection and the receiver that decreases the amount of the length of the projection within the receiver. In some embodiments, the coupler captively couples the internal receiving mechanism to at least the portion of the projection when at least the portion of the projection is matingly received in the internal receiving mechanism. In some embodiments, the coupler may be configured to physically couple the internal receiving mechanism to at least the portion of the projection when a first relative positioning between the projection and the receiver is established, and the coupler may be further configured to physically de-couple the internal receiving mechanism from the projection when a second relative positioning between the projection and the receiver is established, the second relative positioning being different than the first relative positioning. In some embodiments, the coupler self-couples the internal receiving mechanism to at least the portion of the projection when a first relative positioning between the projection and the receiver is established, and the coupler self-decouples the internal receiving mechanism from the projection when a second relative positioning between the projection and the receiver is established, the second relative positioning being different than the first relative positioning.

In some embodiments, the catheter system includes a control cable that operatively couples the actuator system to the manipulable portion, the control cable being receivable in the lumen of the catheter sheath. The actuator system may be configured to meter the control cable to vary an amount of the control cable that extends outwardly from the distal end of the catheter sheath when the part of the shaft is received in the lumen of the catheter sheath, and the actuator system may be responsive to varying amounts of the length of the projection being within the receiver by varying a rate at which the control cable is metered. The actuator system may be configured to meter the control cable to vary an amount of the control cable that extends outwardly from the distal end of the catheter sheath when the part of the shaft is received in the lumen of the catheter sheath, and the actuator system may be responsive to a rate of change in an amount of the length of the projection being within the receiver by varying a rate at which the control cable is metered. In some embodiments, the manipulable portion is selectively moveable between a delivery configuration in which the manipulable portion is sized to be delivered though the lumen of the catheter sheath and an expanded configuration in which the manipulable portion is sized too large for delivery through the lumen of the catheter sheath. The actuator system may be operatively coupled to the manipulable portion to transition the manipulable portion, at least in part, toward the expanded configuration as the manipulable portion is advanced out of the distal end of the catheter sheath, and to transition, at least in part, the manipulable portion toward the delivery configuration as the manipulable portion is retracted into the distal end of the catheter sheath. The actuator system may be operatively coupled to the control cable to cause, when a particular amount of the length of the projection is received in the receiver during the transition toward the expanded configuration, the control cable to be metered with a first rate, and the actuator system may be operatively coupled to the control cable to cause, when the particular amount of the length of the projection is received in the receiver during the transition toward the delivery configuration, the control cable to be metered with a second rate different than the first rate.

In various embodiments, the manipulable portion may be selectively moveable between a delivery configuration in which the manipulable portion is sized to be delivered though the lumen of the catheter sheath and an expanded configuration in which the manipulable portion is sized too large for delivery through the lumen of the catheter sheath. The catheter system may further include a control element that operatively couples the actuator system to the manipulable portion, the control element receivable in the lumen of the catheter sheath. The actuator system may be operatively coupled to the manipulable portion to transition the manipulable portion, at least in part, toward the expanded configuration as the manipulable portion is advanced out of the distal end of the catheter sheath, and to transition, at least in part, the manipulable portion toward the delivery configuration as the manipulable portion is retracted into the distal end of the catheter sheath. The actuator system may be operatively coupled to the control element to cause, when a particular amount of the length of the projection is received in the receiver during the transition toward the expanded configuration, the control element to have a first amount of length located outside of the distal end of the catheter sheath, and the actuator system may be further operatively coupled to the control element to cause, when the particular amount of the length of the projection is received in the receiver during the transition toward the delivery configuration, the control element to have a second amount of length located outside of the distal end of the catheter sheath, the first amount of length different than the second amount of length. In some embodiments, the control element includes a sleeve and a cable received in a lumen of the sleeve. Each of the sleeve and the cable may be received in a lumen of the shaft. The actuator system may be operatively coupled to the control element to cause, when the particular amount of the length of the projection is received in the receiver during the transition toward the expanded configuration, the cable to have a third amount of length located outside an end of the sleeve, and the actuator system may be operatively coupled to the control element to cause, when the particular amount of the length of the projection is received in the receiver during the transition toward the delivery configuration, the cable to have a fourth amount of length located outside the end of the sleeve, the fourth amount of length different than the third amount of length.

In some embodiments, the manipulable portion includes a set of one or more transducers. In some embodiments, the catheter sheath, the part of the shaft receivable in the lumen of the catheter sheath, or each of the catheter sheath and the part of the shaft receivable in the lumen of the catheter sheath may include a bendable portion sufficiently bendable for delivery to the bodily cavity.

In some embodiments, the projection and the receiver are configured to matingly engage at least when a first amount of the part of the shaft is received in the lumen of the catheter sheath, and the projection and the receiver are configured to not matingly engage at least when a second amount of the part of the shaft is received in the lumen of the catheter sheath. The first amount of the part of the shaft may be different than the second amount of the part of the shaft. At least the second amount of the part of the shaft may be a non-zero amount. In some embodiments, the shaft includes a longitudinal length extending between the proximal and distal ends of the shaft, and each of the first amount and the second amount of the part of the shaft may be an amount of the longitudinal length of the shaft.

In some embodiments, the projection and the receiver may be configured to matingly engage at least when the shaft is not received in the lumen of the catheter sheath. In some embodiments, the projection and the receiver may form part of a plunger assembly located on one of the shaft and the catheter sheath.

In some embodiments, the manipulable portion includes a distal end, the distal end of the manipulable portion arranged to be advanced outwardly first from the distal end of the catheter sheath, as compared to other parts of the manipulable portion. The actuator system may be configured to vary the force transmitted to the manipulable portion while the distal end of the manipulable portion advances outwardly from the distal end of the catheter sheath along an arcuate path. The actuator system may be configured to vary the force transmitted to the manipulable portion while the distal end of the manipulable portion advances outwardly from the distal end of the catheter sheath along a coiled path.

Various systems may include combinations and subsets of all the systems summarized above.

In some embodiments a catheter system may be summarized as including: (i) a shaft that includes a proximal end, a distal end, and an elongated portion extending between the proximal end of the shaft and the distal end of the shaft, at least the distal end of the shaft sized for delivery through a bodily opening leading to a bodily cavity located in a body; (ii) a manipulable portion physically coupled to the shaft and located at least proximate the distal end of the shaft; (iii) an elongated control element physically coupled to the manipulable portion to transmit force to the manipulable portion; and (iv) an actuator operatively coupled to the elongated control element, at least a portion of the actuator moveable in each of a first direction and a second direction different than the first direction, the actuator operable to meter movement of at least a portion of the elongated control element. Movement of at least the portion of the actuator with a particular rate of movement in the first direction causes movement of the elongated control element by metering the portion of the elongated control element with a first rate of movement. Movement of at least the portion of the actuator with the particular rate of movement in the second direction causes movement of the elongated control element by metering the portion of the elongated control element with a second rate of movement. A first ratio of the first rate of movement to the particular rate of movement may be different than a second ratio of the second rate of movement to the particular rate of movement.

In some embodiments, the catheter system may further include a control system housing enclosing at least (a) some of the shaft, (b) some of the elongated control element, (c) some of the actuator, (a) and (b), (b) and (c), (a) and (c), or (a), (b), and (c). Movement of at least the portion of the actuator with the particular rate of movement in the first direction may be with respect to the housing. Movement of at least the portion of the actuator with the particular rate of movement in the second direction may be with respect to the housing. The control system housing may be located at least proximate the proximal end of the shaft. The control system housing may enclose at least the proximal end of the shaft.

In some embodiments, the second direction may be opposite to the first direction. The portion of the actuator may be configured to move along a linear path when moving in the first direction or in the second direction. The portion of the actuator may be configured to move along an arcuate path when moving in the first direction or in the second direction.

In some embodiments, the manipulable portion is selectively moveable between a delivery configuration in which the manipulable portion is sized to be delivered though the bodily opening and an expanded configuration in which the manipulable portion is sized too large for delivery through the bodily opening. The actuator may be operatively coupled to the elongated control element to vary movement of the elongated control element by switching a ratio of (a) a rate at which the portion of the elongated control element is metered to (b) a rate of movement of at least the portion of the actuator between each ratio of a first set of two or more different predetermined ratios when the manipulable portion transitions from the delivery configuration to the expanded configuration. The actuator may be operatively coupled to the elongated control element to vary movement of the elongated control element by switching the ratio of (a) to (b) between each ratio of a second set of two or more different predetermined ratios when the manipulable portion transitions from the expanded configuration to the delivery configuration. In some embodiments, the first ratio is a member of the first set, and the second ratio is a member of the second set. At least one of the predetermined ratios in the first set may be the same as one of the predetermined ratios in the second set. At least two of the predetermined ratios in the first set may be the same as at least two of the predetermined ratios in the second set.

In some embodiments, the manipulable portion is selectively moveable between a delivery configuration in which the manipulable portion is sized to be delivered though the bodily opening and an expanded configuration in which the manipulable portion is sized too large for delivery through the bodily opening. The actuator may be operatively coupled to the elongated control element to vary movement of the elongated control element by switching a ratio of (a) a rate at which the portion of the elongated control element is metered to (b) a rate of movement of at least the portion of the actuator between each ratio of a first set of two or more different ratios when the manipulable portion transitions from the delivery configuration to the expanded configuration, each ratio in the first set of two or more different ratios having a value corresponding to a respective one of a first set of two or more different predetermined values. The actuator may be operatively coupled to the elongated control element to vary movement of the elongated control element by switching the ratio of (a) to (b) between each ratio of a second set of two or more different ratios when the manipulable portion transitions from the expanded configuration to the delivery configuration, each ratio in the second set of two or more different ratios having a value corresponding to a respective one of a second set of two or more different predetermined values. In some embodiments, the first ratio is a member of the first set of two or more different ratios, and the second ratio is a member of the second set of two or more different ratios. At least one of the ratios in the first set of two or more different ratios may be the same as one of the ratios in the second set of two or more different ratios. At least two of the ratios in the first set of two or more different ratios may be the same as at least two of the ratios in the second set of two or more different ratios.

In some embodiments, the catheter sheath may further include a catheter sheath including a proximal end, a distal end, and a lumen extending within the catheter sheath between the proximal end of the catheter sheath and the distal end of the catheter sheath, the catheter sheath being positionable in the bodily opening. At least part of the shaft may be receivable in the lumen of the catheter sheath. In some embodiments, movement of at least the portion of the actuator in the first direction may be associated with a first relative movement between the catheter sheath and the part of the shaft, when the part of the shaft is received in the lumen of the catheter sheath, that causes a distance between a location on the part of the shaft and a location on the catheter sheath to decrease. In some embodiments, movement of at least the portion of the actuator in the second direction may be associated with a second relative movement between the catheter sheath and the part of the shaft, when the part of the shaft is received in the lumen of the catheter sheath, that causes a distance between the location on the part of the shaft and the location on the catheter sheath to increase.

In some embodiments, the catheter system may further include a projection including a length and extending from a location at least proximate a first one of the proximal end of the catheter sheath and the proximal end of the shaft and a receiver provided at a location at least proximate a second one of the proximal end of the catheter sheath and the proximal end of the shaft, the projection and the receiver configured to matingly engage at least when the part of the shaft is received in the lumen of the catheter sheath. Movement of at least the portion of the actuator in the first direction may be associated with an amount of the length of the projection within the receiver increasing in magnitude, and movement of at least the portion of the actuator in the second direction may be associated with an amount of the length of the projection within the receiver decreasing in magnitude. In some embodiments, the length of the projection is a longitudinal length of the projection extending from the location at least proximate the first one of the proximal end of the catheter sheath and the proximal end of the shaft to an end of the projection, the end of the projection configured to be received first in the receiver, as compared to other parts of the projection, when the projection is inserted into the receiver. In some embodiments, the shaft includes a longitudinal length extending between the proximal and distal ends of the shaft. The longitudinal length of the shaft may be greater than the longitudinal length of the projection in some embodiments. In some embodiments, a first particular amount of the longitudinal length of the projection may be located in the receiver when a second particular amount of the longitudinal length of the shaft is located inside the lumen of the catheter sheath. The first particular amount of the longitudinal length of the projection may be less than the second particular amount of the longitudinal length of the shaft.

In some embodiments, the manipulable portion may be selectively moveable between a delivery configuration in which the manipulable portion is sized to be delivered though the bodily opening and an expanded configuration in which the manipulable portion is sized too large for delivery through the bodily opening. Movement of at least the portion of the actuator in the first direction may transition the manipulable portion, at least in part, toward the expanded configuration, and movement of at least the portion of the actuator in the second direction may transition the manipulable portion, at least in part, toward the delivery configuration.

In some embodiments, the catheter system may further include a catheter sheath including a proximal end, a distal end, and a lumen extending within the catheter sheath between the proximal end of the catheter sheath and the distal end of the catheter sheath, the catheter sheath being positionable in the bodily opening. At least part of the shaft may be receivable in the lumen of the catheter sheath. Movement of at least the portion of the actuator in the first direction may accompany an increase in an amount of the manipulable portion extending outwardly from the distal end of the catheter sheath, and movement of at least the portion of the actuator in the second direction may accompany a decrease in an amount of the manipulable portion extending outwardly from the distal end of the catheter sheath. At least some of the elongated control element may be receivable in the lumen of the catheter sheath, and the actuator may be operatively coupled to the elongated control element to cause an increase and subsequent decrease in an amount of length of the elongated control element that is located outside of the distal end of the catheter sheath when at least the portion of the actuator moves in the first direction. The actuator may be operatively coupled to the elongated control element to cause an increase and subsequent decrease in an amount of length of the elongated control element that is located outside of the distal end of the catheter sheath when at least the portion of the actuator moves in the second direction.

In some embodiments, the elongated control element includes a sleeve and a cable located, at least in part, in a lumen of the sleeve. Each of the cable and the sleeve may be located, at least in part, in a lumen of the shaft. The portion of the elongated control element may be provided by a portion of the cable. In some embodiments, the catheter system may further include a Bowden cable that includes a sleeve and a cable located, at least in part, in a lumen of the sleeve. The portion of the elongated control element may be provided by a portion of the cable.

In some embodiments, the movement of at least the portion of the actuator with the particular rate of movement in the first direction may cause the movement of the elongated control element by metering the portion of the elongated control element with the first rate of movement when the portion of the elongated control element is positioned at a particular location, and the movement of at least the portion of the actuator with the particular rate of movement in the second direction may cause the movement of the elongated control element by metering the portion of the elongated control element with the second rate of movement when the portion of the elongated control element is positioned at the particular location.

The portion of the elongated control element may be moveable along a path during the metering of the portion of the elongated control element. The movement of at least the portion of the actuator with the particular rate of movement in the first direction may cause the portion of the elongated control element to be metered with the first rate of movement and to move in a particular direction away from a particular location along the path. The movement of at least the portion of the actuator with the particular rate of movement in the second direction may cause the portion of the elongated control element to be metered with the second rate of movement and to move in a different direction away from the particular location along the path, the different direction being different than the particular direction.

In various embodiments, the manipulable portion includes a set of one or more transducers. The shaft may be sufficiently bendable for delivery to the bodily cavity in some embodiments. The manipulable portion is physically coupled to the shaft in some embodiments.

Various systems may include combinations and subsets of all the systems summarized above.

In some embodiments, a catheter system may be summarized as including: (i) a shaft that includes a proximal end, a distal end, and an elongated portion extending between the proximal end of the shaft and the distal end of the shaft, at least the distal end of the shaft sized for delivery through a bodily opening leading to a bodily cavity located in a body; (ii) a manipulable portion located at least proximate the distal end of the shaft, the manipulable portion selectively moveable between a delivery configuration in which the manipulable portion is sized to be delivered though the bodily opening and an expanded configuration in which the manipulable portion is sized too large for delivery through the bodily opening; (iii) an elongated control element; and (iv) a control system configured to cause movement of a portion of the elongated control element along a path extending toward the manipulable portion. The control system may be configured, when a portion of the elongated control element is located at a particular position along the path, to meter movement of: (a) the portion of the elongated control element at a first rate in a first direction along the path away from the particular position at least in response to occurrence of a first state that triggers a transition of the manipulable portion toward the expanded configuration, and (b) the portion of the control element at a second rate in a second direction along the path away from the particular position at least in response to occurrence of a second state that triggers a transition of the manipulable portion toward the delivery configuration. The second direction along the path may be different than the first direction along the path, and the second rate may be different than the first rate.

In some embodiments, a catheter system may be summarized as including (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and at least the distal end of the shaft arranged to be delivered through the lumen of the catheter sheath prior to at least the elongated portion of the shaft; (iii) a manipulable portion physically coupled to the shaft and located at least proximate the distal end of the shaft, the manipulable portion configurable in a delivery configuration in which the manipulable portion is shaped for delivery through the lumen of the catheter sheath; (iv) a control element receivable in the lumen of the catheter sheath and physically coupled to the manipulable portion to transmit force to the manipulable portion; and (v) an actuator operatively coupled to the control element, at least a portion of the actuator moveable at least in one particular direction to manipulate at least a portion of the control element. Movement of at least the portion of the actuator in the one particular direction may facilitate or cause a length of a part of the control element extending outside the distal end of the catheter sheath to increase and then subsequently decrease during the movement of at least the portion of the actuator in the one particular direction. A part of the manipulable portion may extend outside the distal end of the catheter sheath and have a size too large to fit in the lumen of the catheter sheath during the movement of at least the portion of the actuator in the one particular direction.

In some embodiments, the catheter system may further include a control system housing enclosing at least (a) some of the shaft, (b) some of the control element, (c) some of the actuator, (a) and (b), (b) and (c), (a) and (c), or (a), (b), and (c). Movement of at least the portion of the actuator in the one particular direction may be with respect to the control system housing. The control system housing may be located at least proximate the proximal end of the shaft. The control system housing may enclose at least the proximal end of the shaft.

In some embodiments, the one particular direction is a first direction, and at least the portion of the actuator is selectively moveable in each of the first direction and a second direction to manipulate at least the portion of the control element, the second direction being different than the first direction. Movement of at least the portion of the actuator in the second direction may cause a length of the part of the control element extending outside the distal end of the catheter sheath to increase and then subsequently decrease during the movement of at least the portion of the actuator in the second direction. The part of the manipulable portion may have a size too large to fit in the lumen of the catheter sheath during the movement of at least the portion of the actuator in the second direction. The catheter system may further include a control system housing enclosing at least (a) some of the shaft, (b) some of the control element, (c) some of the actuator, (a) and (b), (b) and (c), (a) and (c), or (a), (b), and (c). Movement of at least the portion of the actuator in each of the first direction and the second direction may be with respect to the control system housing.

In some embodiments, the actuator may be operatively coupled to the control element to manipulate at least the portion of the control element to cause the length of the part of the control element extending outside the distal end of the catheter sheath to increase and subsequently decrease during an advancement of the manipulable portion outwardly from the distal end of the catheter sheath. In some embodiments, the actuator may be operatively coupled to the control element to manipulate at least the portion of the control element to cause the length of the part of the control element extending outside the distal end of the catheter sheath to increase and subsequently decrease during a retraction of the manipulable portion inwardly into the distal end of the catheter sheath. In some embodiments, the actuator may be operatively coupled to the control element to manipulate at least the portion of the control element to cause the length of the part of the control element extending outside the distal end of the catheter sheath to increase and subsequently decrease during a relative longitudinal movement between the shaft and the catheter sheath when the part of the shaft is located in the lumen of the catheter sheath.

In some embodiments, the manipulable portion is selectively moveable between the delivery configuration and an expanded configuration in which the manipulable portion is sized too large for delivery through the lumen of the catheter sheath. The actuator may be operatively coupled to the control element to manipulate at least the portion of the control element to cause the length of the part of the control element extending outside the distal end of the catheter sheath to increase and subsequently decrease during a transition of the manipulable portion toward the expanded configuration. The actuator may be operatively coupled to the control element to manipulate at least the portion of the control element to cause the length of the part of the control element extending outside the distal end of the catheter sheath to increase and subsequently decrease during a transition of the manipulable portion toward the delivery configuration.

In some embodiments, the movement of at least the portion of the actuator may be associated with a relative movement between the shaft and the catheter sheath, when the part of the shaft is located in the lumen of the catheter sheath.

In some embodiments, the catheter system may further include a modulation actuator operatively coupled to the manipulable portion. The manipulable portion may be selectively moveable between the delivery configuration and an expanded configuration in which the manipulable portion is sized too large for delivery through the lumen of the catheter sheath. The modulation actuator may be configured to modulate at least a size, a shape, or both a size and a shape of at least the part of the manipulable portion at least when the manipulable portion transitions between the delivery configuration and the expanded configuration in a state in which at least the part of the manipulable portion and the part of the control element extend outside the distal end of the catheter sheath. The actuator may be operatively coupled to the control element to cause, when a particular amount of the manipulable portion is located outside of the distal end of the catheter sheath during a transition toward the expanded configuration, at least a first portion of the control element to be metered with a first rate. The actuator may be further operatively coupled to the control element to cause, when the particular amount of the manipulable portion is located outside of the distal end of the catheter sheath during a transition toward the delivery configuration, at least a second portion of the control element to be metered with a second rate different than the first rate. The manipulable portion may be configured to transition, at least in part, toward the expanded configuration as the manipulable portion is advanced out of the distal end of the catheter sheath. The manipulable portion may be configured to transition, at least in part, toward the delivery configuration as the manipulable portion is retracted into the distal end of the catheter sheath.

In some embodiments, the catheter system may further include a modulation actuator operatively coupled to the manipulable portion. The manipulable portion may be selectively moveable between the delivery configuration and an expanded configuration in which the manipulable portion is sized too large for delivery through the lumen of the catheter sheath. The modulation actuator may be configured to facilitate modulation of at least a size, a shape, or both a size and a shape of at least the part of the manipulable portion at least when the manipulable portion transitions between the delivery configuration and the expanded configuration in a state in which at least the part of the manipulable portion and the part of the control element extend outside the distal end of the catheter sheath. The actuator may be operatively coupled to the control element to cause, when a particular relative positioning exists between the catheter sheath and the part of the shaft located in the lumen of the catheter sheath during a transition toward the expanded configuration, the control element to have a first amount of length located outside of the distal end of the catheter sheath. The actuator may be operatively coupled to the control element to cause, when the particular relative positioning exists between the catheter sheath and the part of the shaft located in the lumen of the catheter sheath during a transition toward the delivery configuration, the control element to have a second amount of length located outside of the distal end of the catheter sheath, the second amount of length different than the first amount of length. The manipulable portion may be configured to transition, at least in part, toward the expanded configuration as the manipulable portion is advanced out of the distal end of the catheter sheath. The manipulable portion may be configured to transition, at least in part, toward the delivery configuration as the manipulable portion is retracted into the distal end of the catheter sheath. The particular relative positioning may be a relative longitudinal positioning. In some embodiments, the control element may include a sleeve and a cable located, at least in part, in a lumen of the sleeve. The actuator may be operatively coupled to the control element to cause, when the particular relative positioning exists between the catheter sheath and the part of the shaft located in the lumen of the catheter sheath during the transition toward the expanded configuration, the cable to have a third amount of length located outside of an end of the sleeve. The actuator may be operatively coupled to the control element to cause, when the particular relative positioning exists between the catheter sheath and the part of the shaft located in the lumen of the catheter sheath during the transition toward the delivery configuration, the cable to have a fourth amount of length located outside of the end of the sleeve, the fourth amount of length different than the third amount of length.

In some embodiments, the control element may include a sleeve and a cable located, at least in part, in a lumen of the sleeve, each of the cable and the sleeve located, at least in part, in a lumen of the shaft.

In some embodiments, the elongated portion of the shaft has a length extending between the proximal and the distal ends of the shaft and is sized to position the proximal end of the shaft at a location outside a body when the manipulable portion is located in a bodily cavity within the body. The actuator may be located, at least in part, at a location at least proximate the proximal end of the shaft.

In some embodiments, the manipulable portion includes a set of one or more transducers. In some embodiments, the shaft, the catheter sheath, or each of the shaft and the catheter sheath is bendable during a respective delivery to a bodily cavity.

In some embodiments, the manipulable portion includes a distal end, the distal end of the manipulable portion arranged to be advanced first outwardly from the distal end of the catheter sheath with respect to other parts of the manipulable portion, The actuator may be operatively coupled to the control element to manipulate at least the portion of the control element to cause the length of the part of the control element extending outside the distal end of the catheter sheath to increase and then subsequently decrease during the movement of at least the portion of the actuator in the one particular direction while the distal end of the manipulable portion advances along an arcuate path extending outwardly from the distal end of the catheter sheath. The actuator may be operatively coupled to the control element to manipulate at least the portion of the control element to cause the length of the part of the control element extending outside the distal end of the catheter sheath to increase and then subsequently decrease during the movement of at least the portion of the actuator in the one particular direction while the distal end of the manipulable portion advances along a coiled path extending outwardly from the distal end of the catheter sheath.

In some embodiments, the catheter system may further include a modulation actuator operatively coupled to the manipulable portion to modulate at least a size, a shape, or both a size and a shape of at least the part of the manipulable portion at least in a state in which at least the part of the manipulable portion and the part of the control element extend outside the distal end of the catheter sheath. In some embodiments, the actuator includes the modulation actuator. In some embodiments, the actuator and the modulation actuator are distinct.

Various systems may include combinations and subsets of all the systems summarized above.

In some embodiments a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft; (iii) a manipulable portion physically coupled to the shaft and located at least proximate the distal end of the shaft, the manipulable portion selectively moveable between a delivery configuration in which the manipulable portion is shaped to be delivered though the lumen of the catheter sheath and an expanded configuration in which the manipulable portion is sized too large for delivery through the lumen of the catheter sheath; (iv) a control element physically coupled to the manipulable portion to transmit force to the manipulable portion, the control element receivable in the lumen of the catheter sheath; and (v) an actuator system. The actuator system may be operatively coupled to at least the control element to cause at least, when a particular amount of the manipulable portion is located outside the distal end of the catheter sheath, the control element to have a first amount of length located outside of the distal end of the catheter sheath, at least in response to occurrence of a first state that triggers a transition of the manipulable portion toward the expanded configuration. The actuator system may be operatively coupled to at least the control element to cause at least, when the particular amount of the manipulable portion is located outside the distal end of the catheter sheath, the control element to have a second amount of length located outside of the distal end of the catheter sheath, at least in response to occurrence of a second state that triggers a transition of the manipulable portion toward the delivery configuration. The second amount of length may be different than the first amount of length.

In some embodiments, the actuator system may be operatively coupled to the control element to transition the manipulable portion, at least in part, toward the expanded configuration as the manipulable portion is advanced out of the distal end of the catheter sheath, and to transition the manipulable portion, at least in part, toward the delivery configuration as the manipulable portion is retracted into the distal end of the catheter sheath.

In some embodiments, the control element may include a cable. In some embodiments, the control element may include a sleeve and a cable located, at least in part, in a lumen of the sleeve. Each of the cable and the sleeve may be located in a lumen of the shaft. The actuator system may be operatively coupled to the control element to cause at least, when the particular amount of the manipulable portion is located outside of the distal end of the catheter sheath during the transition toward the expanded configuration, the cable to have a third amount of length located outside an end of the sleeve. The actuator system may be operatively coupled to the control element to cause at least, when the particular amount of the manipulable portion is located outside of the distal end of the catheter sheath during the transition toward the delivery configuration, the cable to have a fourth amount of length located outside the end of the sleeve, the fourth amount of length different than the third amount of length.

In some embodiments, the actuator system may be operatively coupled to the control element to cause at least, when the particular amount of the manipulable portion is located outside of the distal end of the catheter sheath during the transition toward the expanded configuration, at least a portion of the control element to be metered with a first rate. The actuator system may be operatively coupled to the control element to cause at least, when the particular amount of the manipulable portion is located outside of the distal end of the catheter sheath during the transition toward the delivery configuration, at least the portion of the control element to be metered with a second rate different than the first rate.

The shaft, the catheter sheath, or each of the shaft and the catheter sheath may be bendable during a respective delivery to a bodily cavity. In some embodiments, the manipulable portion may include a coiled form in the expanded configuration. In some embodiments, the manipulable portion includes a distal end, the distal end of the manipulable portion arranged to be advanced first outwardly from the distal end of the catheter sheath with respect to other parts of the manipulable portion. The distal end of the manipulable portion may advance along an arcuate path as the manipulable portion is advanced outwardly from the distal end of the catheter sheath. The distal end of the manipulable portion may advance along a coiled path as the manipulable portion is advanced outwardly from the distal end of the catheter sheath.

In some embodiments, the control element includes a distal end positionable outside of the distal end of the catheter sheath when the particular amount of the manipulable portion is located outside of the distal end of the catheter sheath. The distal end of the control element may advance along a coiled path as the manipulable portion is advanced outwardly from the distal end of the catheter sheath.

In some embodiments, the actuator system may include a transition actuator operatively coupled to the manipulable portion to transition the manipulable portion at least partially between the expanded configuration and the delivery configuration.

In some embodiments, the manipulable portion includes a distal end, the distal end of the manipulable portion arranged to be advanced first outwardly from the distal end of the catheter sheath with respect to other parts of the manipulable portion. In some embodiments, the particular amount of the manipulable portion located outside the distal end of the catheter sheath may be a particular size of the manipulable portion between the distal end of the catheter sheath and the distal end of the manipulable portion. In some embodiments, the particular amount of the manipulable portion located outside the distal end of the catheter sheath may be a particular length of the manipulable portion extending from the distal end of the catheter sheath to the distal end of the manipulable portion. In some embodiments, the particular amount of the manipulable portion located outside the distal end of the catheter sheath may be a particular length of the manipulable portion extending along a surface of the manipulable portion from the distal end of the catheter sheath to the distal end of the manipulable portion. The manipulable portion may include at least one transducer located on the surface of the manipulable portion.

Various systems may include combinations and subsets of all the systems summarized above.

In some embodiments, a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft; (iii) a manipulable portion physically coupled to the shaft and located at least proximate the distal end of the shaft, the manipulable portion selectively moveable between a delivery configuration in which the manipulable portion is shaped to be delivered though the lumen of the catheter sheath and an expanded configuration in which the manipulable portion is sized too large for delivery through the lumen of the catheter sheath; (iv) a control element physically coupled to the manipulable portion to transmit force to the manipulable portion, the control element receivable in the lumen of the catheter sheath; and (v) an actuator system. The actuator system may be operatively coupled to at least the control element to cause at least, when a particular relative positioning exists between the catheter sheath and the shaft received in the lumen of the catheter sheath during a transition of the manipulable portion toward the expanded configuration, the control element to have a first amount of length located outside of the distal end of the catheter sheath, at least in response to occurrence of a first state that triggers a transition of the manipulable portion toward the expanded configuration. The actuator system may be operatively coupled to at least the control element to cause at least, when the particular relative positioning exists between the catheter sheath and the shaft received in the lumen of the catheter sheath during a transition of the manipulable portion toward the delivery configuration, the control element to have a second amount of length located outside of the distal end of the catheter sheath, at least in response to occurrence of a second state that triggers a transition of the manipulable portion toward the delivery configuration. The second amount of length may be different than the first amount of length in various embodiments.

In some embodiments, the particular relative positioning may be a relative longitudinal positioning. In some embodiments, the actuator system may be operatively coupled to the control element to transition the manipulable portion toward the expanded configuration as the manipulable portion is advanced out of the distal end of the catheter sheath, and to transition the manipulable portion toward the delivery configuration as the manipulable portion is retracted into the distal end of the catheter sheath.

In some embodiments, the control element includes a cable. In some embodiments, the control element is received in a lumen of the shaft. In some embodiments, the control element includes a sleeve and a cable located, at least in part, in a lumen of the sleeve. The actuator system may be operatively coupled to the control element to cause at least, when the particular relative positioning exists between the catheter sheath and the shaft received in the lumen of the catheter sheath during the transition toward the expanded configuration, the cable to have a third amount of length located outside of an end of the sleeve. The actuator system may be operatively coupled to the control element to cause at least, when the particular relative positioning exists between the catheter sheath and the shaft received in the lumen of the catheter sheath during the transition toward the delivery configuration, the cable to have a fourth amount of length located outside of the end of the sleeve, the fourth amount of length different than the third amount of length.

In some embodiments, the actuator system may be operatively coupled to the control element to cause at least, when the particular relative positioning exists between the catheter sheath and the shaft received in the lumen of the catheter sheath during the transition toward the expanded configuration, at least a portion of the control element to be metered with a first rate. The actuator system may be operatively coupled to the control element to cause at least, when the particular relative positioning exists between the catheter sheath and the shaft received in the lumen of the catheter sheath during the transition toward the delivery configuration, at least the portion of the control element to be metered with a second rate different than the first rate.

In some embodiments, the manipulable portion may include a set of one or more transducers. The shaft, the catheter sheath, or each of the shaft and the catheter sheath may be bendable during a respective delivery to a bodily cavity.

In some embodiments, the manipulable portion may include a coiled form in the expanded configuration. In some embodiments, the manipulable portion includes a distal end, the distal end of the manipulable portion arranged to be advanced first outwardly from the distal end of the catheter sheath with respect to other parts of the manipulable portion. In some embodiments, the distal end of the manipulable portion advances along an arcuate path as the manipulable portion is advanced outwardly from the distal end of the catheter sheath. In some embodiments, the distal end of the manipulable portion advances along a coiled path as the manipulable portion is advanced outwardly from the distal end of the catheter sheath. In some embodiments, the control element includes a distal end, the distal end of the control element advancing along a coiled path as the manipulable portion is advanced outwardly from the distal end of the catheter sheath. In some embodiments, the actuator system may include a transition actuator operatively coupled to the manipulable portion to transition the manipulable portion at least partially between the expanded configuration and the delivery configuration.

Various systems may include combinations and subsets of all the systems summarized above.

In some embodiments, a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft; (iii) a manipulable portion physically coupled to the shaft and located at least proximate the distal end of the shaft, the manipulable portion configurable in a delivery configuration in which the manipulable portion is shaped for delivery through the lumen of the catheter sheath; and (iv) a control element physically coupled to the manipulable portion to transmit force to the manipulable portion, the control element receivable in the lumen of the catheter sheath. A method for controlling the catheter system may be summarized as modulating at least a shape of at least part of the manipulable portion at least in a state in which the part of the manipulable portion and a part of the control element extends outside the distal end of the catheter sheath, and manipulating the control element to cause a length of the part of the control element extending outside the distal end of the catheter sheath to increase and subsequently decrease during the modulation of the manipulable portion. The manipulable portion may have a size during the modulation too large to fit in the lumen of the catheter sheath.

In some embodiments, a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft; (iii) a manipulable portion physically coupled to the shaft and located at least proximate the distal end of the shaft, the manipulable portion selectively moveable between a delivery configuration in which the manipulable portion is shaped to be delivered though the lumen of the catheter sheath and an expanded configuration in which the manipulable portion is sized too large for delivery through the lumen of the catheter sheath; and (iv) a control element physically coupled to the manipulable portion to transmit force to the manipulable portion, the control element receivable in the lumen of the catheter sheath. A method for controlling the catheter system may summarized as including transitioning the manipulable portion at least partially between the expanded configuration and the delivery configuration; causing the control element to have a first amount of length located outside of the distal end of the catheter sheath when a particular amount of the manipulable portion is located outside the distal end of the catheter sheath during a transition toward the expanded configuration; and causing the control element to have a second amount of length located outside of the distal end of the catheter sheath, when the particular amount of the manipulable portion is located outside the distal end of the catheter sheath during a transition toward the delivery configuration. The second amount of length may be different than the first amount of length in various embodiments.

The method may further include transitioning the manipulable portion toward the expanded configuration as the manipulable portion is advanced out of the distal end of the catheter sheath, and transitioning the manipulable portion toward the delivery configuration as the manipulable portion is retracted into the distal end of the catheter sheath.

In some embodiments, the manipulable portion includes a distal end, the distal end of the manipulable portion arranged to be advanced first outwardly from the distal end of the catheter sheath with respect to other parts of the manipulable portion. The particular amount of the manipulable portion located outside the distal end of the catheter sheath may be a particular size of the manipulable portion between the distal end of the catheter sheath and the distal end of the manipulable portion. The particular amount of the manipulable portion located outside the distal end of the catheter sheath may be a particular length of the manipulable portion extending from the distal end of the catheter sheath to the distal end of the manipulable portion. The particular amount of the manipulable portion located outside the distal end of the catheter sheath may be a particular length of the manipulable portion extending along a surface of the manipulable portion from the distal end of the catheter sheath to the distal end of the manipulable portion. The manipulable portion may include at least one transducer located on the surface of the manipulable portion.

Various methods may include combinations and subsets of all the systems summarized above.

In some embodiments, a catheter system may be summarized as including: (i) a catheter sheath that includes a proximal end, a distal end, and a lumen extending between the proximal end of the catheter sheath and the distal end of the catheter sheath; (ii) a shaft that includes a proximal end, a distal end, and an elongated portion extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft; (iii) a manipulable portion coupled to the shaft and located at least proximate the distal end of the shaft, the manipulable portion selectively moveable between a delivery configuration in which the manipulable portion is shaped to be delivered though the lumen of the catheter sheath and an expanded configuration in which the manipulable portion is sized too large for delivery through the lumen of the catheter sheath; and (iv) a control element physically coupled to the manipulable portion to transmit force to the manipulable portion, the control element receivable in the lumen of the catheter sheath. A method for controlling the catheter system may be summarized as including transitioning the manipulable portion at least partially between the expanded configuration and the delivery configuration; causing the control element to have a first amount of length located outside of the distal end of the catheter sheath when a particular relative positioning exists between the catheter sheath and the shaft received in the lumen of the catheter sheath during the transition toward the expanded configuration; and causing the control element to have a second amount of length located outside of the distal end of the catheter sheath when the particular relative positioning exists between the catheter sheath and the shaft received in the lumen of the catheter sheath during the transition toward the delivery configuration. The second amount of length may be different than the first amount of length in various embodiments.

In some embodiments, the method further includes transitioning the manipulable portion toward the expanded configuration as the manipulable portion is advanced out of the distal end of the catheter sheath, and transitioning the manipulable portion toward the delivery configuration as the manipulable portion is retracted into the distal end of the catheter sheath.

In some embodiments, a catheter system may be summarized as including (i) a shaft member that includes a shaft that includes a proximal end, a distal end, and an elongated portion extending between the proximal end and the distal end, wherein at least the distal end of the shaft is sized for delivery through a bodily opening leading to a bodily cavity located in a body; (ii) a manipulable portion physically coupled to the shaft and located at least proximate to the distal end of the shaft for delivery through the bodily opening to the bodily cavity located in the body; (iii) a plurality of Bowden cables, at least a part of one of which is operatively coupled to the manipulable portion, the plurality of Bowden cables including at least a first Bowden cable and a second Bowden cable other than the first Bowden cable, each of the plurality of Bowden cables including a respective sleeve and a respective cable located in a lumen of the respective sleeve, the lumen extending between a first end and a second end of the respective sleeve, and a first part of the respective cable of each Bowden cable extending outwardly from the first end of the respective sleeve of the Bowden cable; and (iv) an actuator system operatively coupled to each of at least some of the plurality of Bowden cables to vary an amount of length of the first part of the respective cable of each of the at least some of the plurality of Bowden cables that extends outwardly from the first end of the respective sleeve thereof during a change in a size, a shape, or both a size and a shape of the manipulable portion. The first part of the respective cable of the second Bowden cable may be operatively coupled to the first Bowden cable to cause at least the first end of the respective sleeve of the first Bowden cable to translate in response to a varying of the amount of length of the first part of the respective cable of the second Bowden cable that extends outwardly from the first end of the respective sleeve of the second Bowden cable caused by the actuator system.

In some embodiments, the actuator system may be operatively coupled to the first Bowden cable to cause a decrease in the length of the first part of the respective cable of the first Bowden cable during at least part of the varying of the length of the first part of the respective cable of the second Bowden cable. In some embodiments, the actuator system may be operatively coupled to the first Bowden cable to cause an increase in the length of the first part of the respective cable of the first Bowden cable that extends outwardly from the first end of the respective sleeve of the first Bowden cable during at least part of the varying of the length of the first part of the respective cable of the second Bowden cable that extends outwardly from the first end of the respective sleeve of the second Bowden cable. In some embodiments, the actuator system may be operatively coupled to the second Bowden cable to translate the second end of the respective sleeve of the second Bowden cable during at least part of the varying of the length of the first part of the respective cable of the second Bowden cable that extends outwardly from the first end of the respective sleeve of the second Bowden cable.

In some embodiments, a second part of the respective cable of each Bowden cable extends outwardly from the second end of the respective sleeve of the Bowden cable. In some embodiments, an amount of translation undergone by a terminus of the second part of the respective cable of the second Bowden cable at a particular time during the varying of the length of the first part of the respective cable of the second Bowden cable that extends outwardly from the first end of the respective sleeve of the second Bowden cable may have a magnitude less than an amount of translation undergone by the second end of the respective sleeve of the second Bowden cable at the particular time during the varying of the length of the first part of the respective cable of the second Bowden cable that extends outwardly from the first end of the respective sleeve of the second Bowden cable.

In some embodiments, the actuator system may be operatively coupled to the second Bowden cable to translate the second end of the respective sleeve of the first Bowden cable during at least part of the varying of the length of the first part of the respective cable of the second Bowden cable that extends outwardly from the first end of the respective sleeve of the second Bowden cable. In some embodiments, the actuator system may be operatively coupled to the second Bowden cable to translate each of the second end of the respective sleeve of the second Bowden cable and the second end of the respective sleeve of the first Bowden cable during at least part of the varying of the length of the first part of the respective cable of the second Bowden cable that extends outwardly from the first end of the respective sleeve of the second Bowden cable.

In some embodiments, the actuator system, in a state in which the first end of the respective sleeve of the first Bowden cable has translated by a predetermined amount, may cause: (v) the first Bowden cable to vary the length of the first part of the respective cable of the first Bowden cable that extends outwardly from the first end of the respective sleeve of the first Bowden cable; and (vi) the second Bowden cable to cease varying the length of the first part of the respective cable of the second Bowden cable during a varying of the length of the first part of the respective cable of the first Bowden cable that extends outwardly from the first end of the respective sleeve of the first Bowden cable after at least the first end of the respective sleeve of the first Bowden cable has translated by the predetermined amount. In some embodiments, in the state in which the first end of the respective sleeve of the first Bowden cable has translated by the predetermined amount, the actuator system may cause at least the second end of the respective sleeve of the second Bowden cable to translate during the varying of the length of the first part of the respective cable of the first Bowden cable that extends outwardly from the first end of the respective sleeve of the first Bowden cable after at least the first end of the respective sleeve of the first Bowden cable has translated by the predetermined amount.

In some embodiments, an amount of translation undergone through the lumen of the respective sleeve of the first Bowden cable by a portion of the respective cable of the first Bowden cable at a particular time during the varying of the length of the first part of the respective cable of the second Bowden cable that extends outwardly from the first end of the respective sleeve of the second Bowden cable may be at least equal in magnitude to an amount of translation undergone through the lumen of the respective sleeve of the second Bowden cable by a portion of the respective cable of the second Bowden cable at the particular time during the varying of the length of the first part of the respective cable of the second Bowden cable that extends outwardly from the first end of the respective sleeve of the second Bowden cable. In some embodiments, an amount of translation undergone through the lumen of the respective sleeve of the first Bowden cable by a portion of the respective cable of the first Bowden cable at a particular time during the varying of the length of the first part of the respective cable of the second Bowden cable that extends outwardly from the first end of the respective sleeve of the second Bowden cable may be greater in magnitude than an amount of translation undergone through the lumen of the respective sleeve of the second Bowden cable by a portion of the respective cable of the second Bowden cable at the particular time during the varying of the length of the first part of the respective cable of the second Bowden cable that extends outwardly from the first end of the respective sleeve of the second Bowden cable.

The shaft member may further include a housing located at a location at least proximate the proximal end of the shaft. In some embodiments, the elongated portion of the shaft may have a length extending between the proximal end and the distal end of the shaft sized to position the housing outside the body when the manipulable portion is located in the bodily cavity, and each of the first end and the second end of the respective sleeve member of the second Bowden cable may be located at a respective location in the housing. In some embodiments, each of the first end and the second end of the respective sleeve member of the first Bowden cable may be located at a respective location in the housing. In some embodiments, the catheter system may further include a stop positioned to restrict at least the first end of the respective sleeve of the first Bowden cable from being translated by more than a maximum amount.

In various embodiments, a second part of the respective cable of each Bowden cable extends outwardly from the second end of the respective sleeve of the Bowden cable. In some embodiments, the actuator system may include a particular actuator including a first moveable portion and a second moveable portion other than the first moveable portion. The second part of the respective cable of the second Bowden cable may be physically coupled to the first moveable portion of the particular actuator. A portion of the respective sleeve of the second Bowden cable located at least proximate to the second end of the respective sleeve of the second Bowden cable may be physically coupled to the second moveable portion of the particular actuator, and the first moveable portion of the particular actuator may include a locking device configured to restrict movement of the first moveable portion of the particular actuator at least during the varying of the length of the first part of the respective cable of the second Bowden cable that extends outwardly from the first end of the respective sleeve of the second Bowden cable. In some embodiments, the locking device may be configured to allow movement of the first moveable portion of the particular actuator after completion of the varying of the length of the first part of the respective cable of the second Bowden cable that extends outwardly from the first end of the respective sleeve of the second Bowden cable. In some embodiments, the particular actuator may restrict further varying of the length of the first part of the respective cable of the second Bowden cable that extends outwardly from the first end of the respective sleeve of the second Bowden cable during the movement of the first moveable portion of the particular actuator when the locking device is operated to cease restricting movement of the first moveable portion of the particular actuator. In some embodiments, the locking device may be configured to allow movement of the first moveable portion of the particular actuator after the second moveable portion of the particular actuator translates by a defined amount. In some embodiments, the particular actuator may further include a tether, the tether physically coupling the first moveable portion of the particular actuator to the second moveable portion of the particular actuator. The locking device may be configured to restrict movement of the first moveable portion of the particular actuator when a tension in the tether has a magnitude lower than a defined threshold, and the locking device may be configured to allow movement of the first moveable portion of the particular actuator when a tension in the tether has a magnitude greater than the defined threshold.

In some embodiments, the catheter system may further include a catheter sheath that includes a proximal end, a distal end, and a lumen extending between the proximal end of the catheter sheath and the distal end of the catheter sheath. The catheter sheath is insertable in the bodily opening and at least a part of the shaft may be receivable in the lumen of the catheter sheath to deliver the manipulable portion through the lumen of the catheter sheath to the bodily cavity. In various embodiments, the actuator system may be responsive to variances in a relative positioning between the shaft and the catheter sheath when the part of the shaft is received in the lumen of the catheter sheath to vary the length of the first part of the respective cable of at least the second Bowden cable that extends from the respective sleeve thereof.

In some embodiments, the catheter system may further include a catheter sheath that includes a proximal end, a distal end, and a lumen extending between the proximal end of the catheter sheath and the distal end of the catheter sheath. In various embodiments, the catheter sheath may be deliverable, distal end first, through the bodily opening toward the bodily cavity and at least a part of the shaft is receivable in the lumen of the catheter sheath to deliver the manipulable portion through the lumen of the catheter sheath to the bodily cavity. In various embodiments, the manipulable portion may be selectively moveable between a delivery configuration in which the manipulable portion is sized to be delivered through the lumen of the catheter sheath and an expanded configuration in which the manipulable portion is sized too large for delivery through the lumen of the catheter sheath. In some embodiments, the actuator system may cause, when the part of the shaft is received in the lumen of the catheter sheath, and when a particular relative positioning exists between the catheter sheath and the part of the shaft received in the lumen of the catheter sheath during a transition toward the expanded configuration, the first part of the respective cable of the first Bowden cable to have a first amount of length located outside of the distal end of the catheter sheath. In some embodiments, the actuator system may cause, when the part of the shaft is received in the lumen of the catheter sheath, and when the particular relative positioning exists between the catheter sheath and the part of the shaft received in the lumen of the catheter sheath during a transition toward the delivery configuration, the first part of the respective cable of the first Bowden cable to have a second amount of length located outside of the distal end of the catheter sheath, the second amount of length different than the first amount of length.

In various embodiments, the first part of the respective cable of the first Bowden cable may be physically coupled to the manipulable portion to, at least in part, change the size, the shape, or both a size and a shape of the manipulable portion. For each of at least one of the plurality of Bowden cables, the actuator system may be configured to (a) move the respective sleeve independently or separately from the respective cable to cause the respective sleeve to slide over the respective cable, and (b) move the respective cable independently or separately from the respective sleeve to cause the respective cable to slide through the lumen of the respective sleeve. For the first Bowden cable, the actuator system may be configured to (a) move the respective sleeve independently or separately from the respective cable to cause the respective sleeve to slide over the respective cable, and (b) move the respective cable independently or separately from the respective sleeve to cause the respective cable to slide through the lumen of the respective sleeve.

In some embodiments, the manipulable portion may include a set of one or more transducers. The shaft may include a bendable portion that is bendable during a respective delivery to the bodily cavity.

In some embodiments, the lumen of the respective sleeve of the Bowden cable extends longitudinally in a particular direction from the first end of the respective sleeve of the first Bowden cable, and the first part of the respective cable of the second Bowden cable may be operatively coupled to the first Bowden cable to cause at least the first end of the respective sleeve of the first Bowden cable to translate in a direction having a component parallel to the particular direction at least during part of the varying of the length of the first part of the respective cable of the second Bowden cable that extends outwardly from the first end of the respective sleeve of the second Bowden cable.

In some embodiments, the first part of the respective cable of the second Bowden cable may be operatively coupled to the first Bowden cable to cause at least the first end of the respective sleeve of the first Bowden cable to translate in a direction that causes the length of the first part of the respective cable of the first Bowden cable to vary at least during part of the varying of the length of the first part of the respective cable of the second Bowden cable that extends outwardly from the first end of the respective sleeve of the second Bowden cable.

In some embodiments, the catheter system may further include a control system operatively coupled to the actuator system and operable to control activation of one or more actuators of the actuator system to vary the amount of length of the first part of the respective cable of each of the at least some of the plurality of Bowden cables that extends outwardly from the first end of the respective sleeve thereof during the change in the size, the shape, or both a size and a shape of the manipulable portion.

Various systems may include combinations and subsets of all the systems summarized above.

In some embodiments, a catheter system may be summarized as including: (i) a shaft member that includes a shaft that includes a proximal end, a distal end, and an elongated portion extending between the proximal end and the distal end, wherein at least the distal end of the shaft is sized for delivery through a bodily opening leading to a bodily cavity located in a body; (ii) a manipulable portion physically coupled to the shaft and located at least proximate to the distal end of the shaft for delivery through the bodily opening to the bodily cavity located in the body; (iii) a Bowden cable that includes a sleeve and a cable located in a lumen of the sleeve, the lumen extending between a first end and a second end of the respective sleeve; and (iv) an actuator system operatively coupled to the Bowden cable to (a) move the sleeve independently or separately from the cable to cause the sleeve to slide over the cable during a first manipulation of the manipulable portion to change, a size, a shape or both thereof, and (b) move the cable independently or separately from the sleeve to cause the cable to slide through the lumen of the sleeve during a second manipulation of the manipulable portion to change, a size, a shape or both thereof.

Various systems may include combinations and subsets of all the systems summarized above or otherwise described herein.

Various methods may include combinations and subsets of all the methods summarized above or otherwise described herein.

In some embodiments, some or all of any of the systems or devices summarized above or otherwise described herein, or one or more combinations thereof, may be controlled by one or more control methods for executing some or all of the functionality of such systems or devices summarized above or otherwise described herein. In some embodiments, a computer program product may be provided that comprises program code portions for performing some or all of any of such control methods, when the computer program product is executed by a computing device. The computer program product may be stored on one or more computer-readable storage mediums. In some embodiments, each of the one or more computer-readable storage mediums is a non-transitory computer-readable storage medium. In some embodiments, such control methods are implemented or executed in part or in whole by at least one data processing device or system upon configuration thereof by one or more programs executable by the at least one data processing device or system and stored in one or more computer-readable storage mediums. In some embodiments, each of the one or more computer-readable storage mediums is a non-transitory computer-readable storage medium.

BRIEF DESCRIPTION OF THE DRAWINGS

It is to be understood that the attached drawings are for purposes of illustrating aspects of various embodiments and may include elements that are not to scale.

FIGS. 5D, 5E, and 5F are various side elevation views of a positioning of a shaft into a catheter sheath at three successive points in time, each of the shaft and the catheter sheath provided by the catheter system of FIG. 5A, according to some example embodiments.

FIG. 5L-1 is a perspective view of a manipulable portion of the catheter system of FIG. 5A configured in an expanded configuration known as a first fanned configuration, according to some example embodiments.

FIG. 5L-2 is a top plan view of the manipulable portion configured in the first fanned configuration of FIG. 5L-1, according to some example embodiments.

FIG. 5M-1 is a perspective view of a manipulable portion of the catheter system of FIG. 5A configured in an expanded configuration known as a second fanned configuration, according to some example embodiments.

FIG. 5M-2 is a top plan view of the manipulable portion configured in the second fanned configuration of FIG. 5M-1, according to some example embodiments.

FIGS. 5R-1 and 5R-2 are respective top and bottom perspective views of a portion of the catheter system of FIG. 5A with various external portions of a housing thereof removed, according to some example embodiments.

Figure 4:
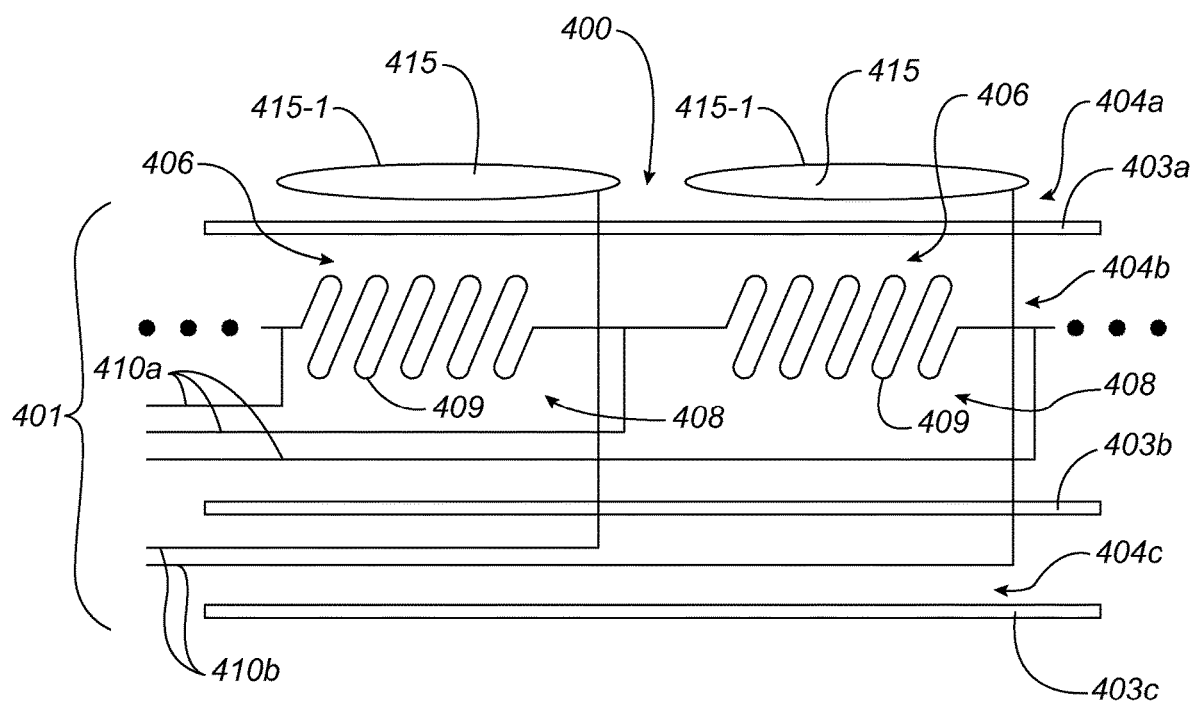
FIG. 4 is a schematic representation of a transducer-based device that includes a flexible circuit structure, according to some example embodiments.
Figure 5A:
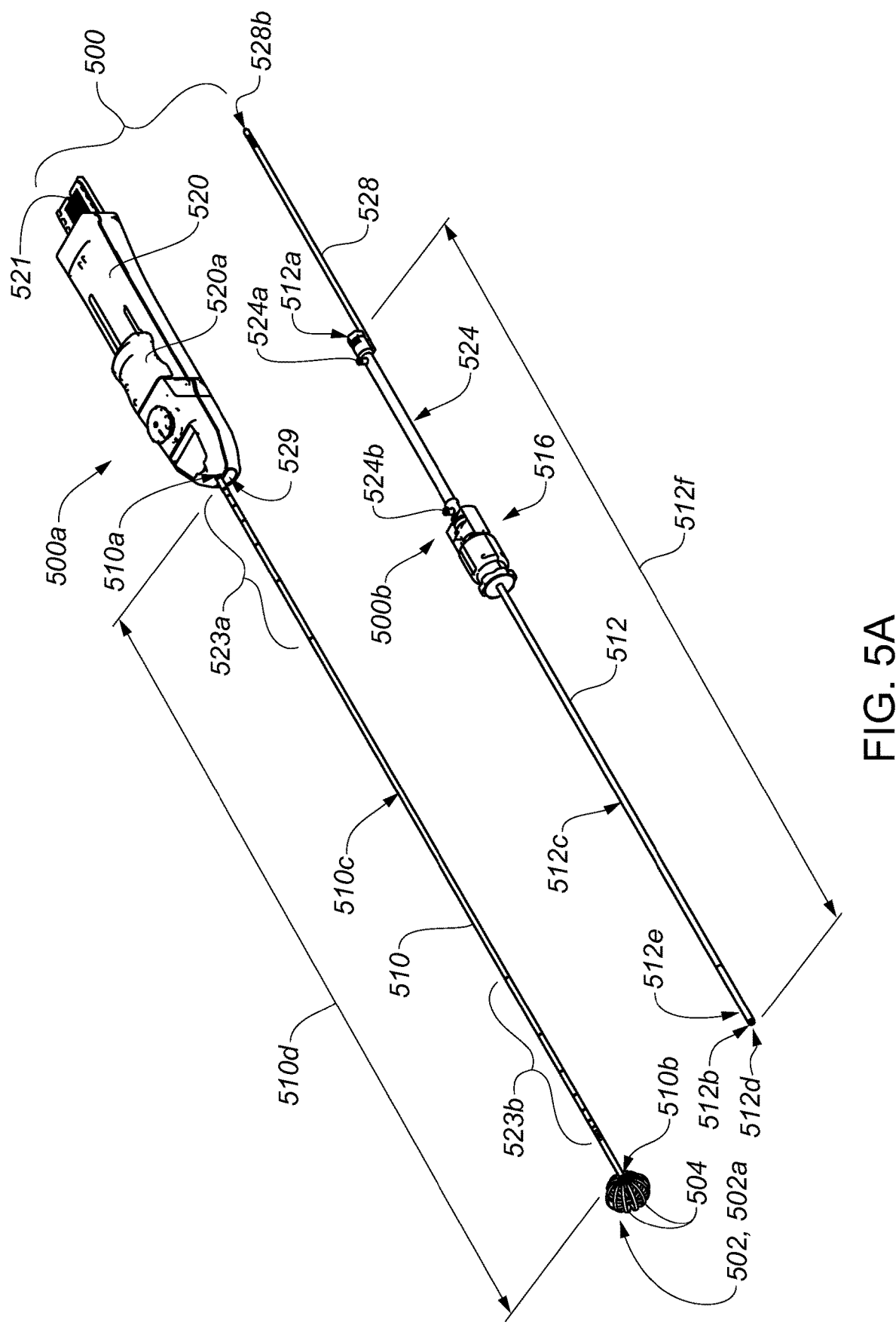
FIG. 5A is a perspective representation of a catheter system, according to some example embodiments.
Figure 5B:
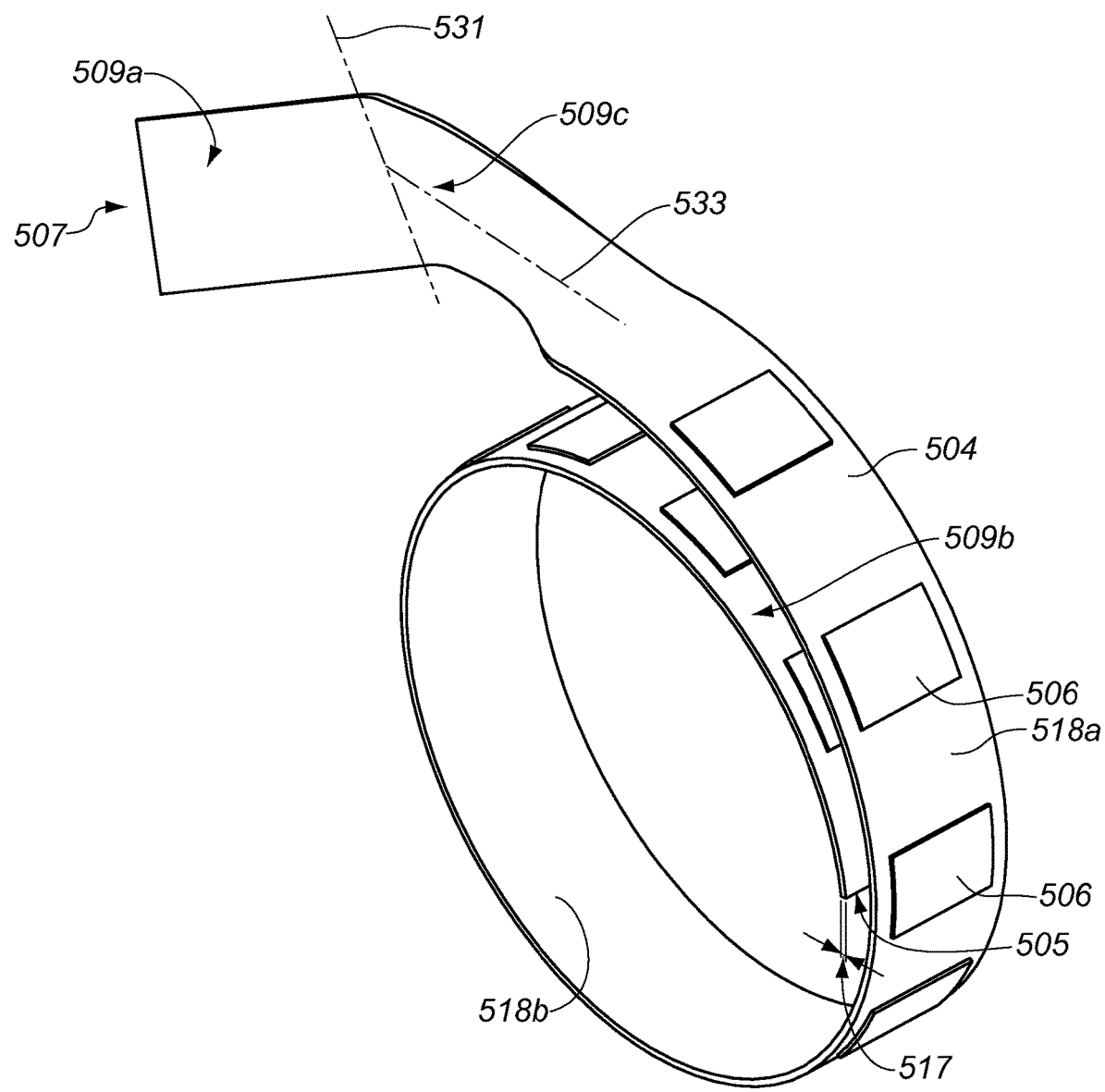
FIG. 5B is a perspective view of an elongate member of a structure provided by a manipulable portion of the catheter system of FIG. 5A, according to some example embodiments.
Figure 5C:
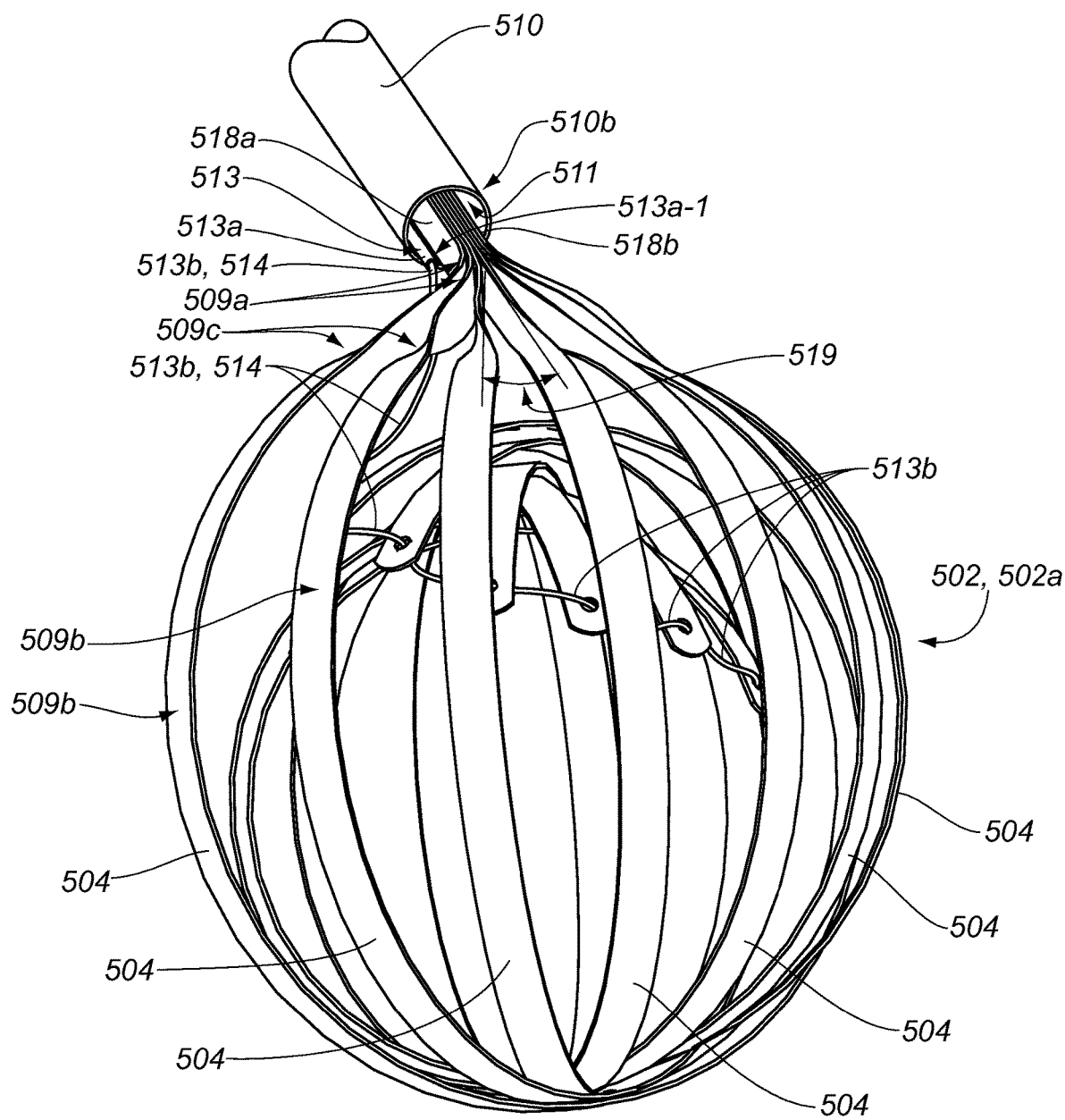
FIG. 5C is a perspective view of a manipulable portion of the catheter system of FIG. 5A, the manipulable portion in an initial or predisposed configuration, according to some example embodiments.
Figure 5G:
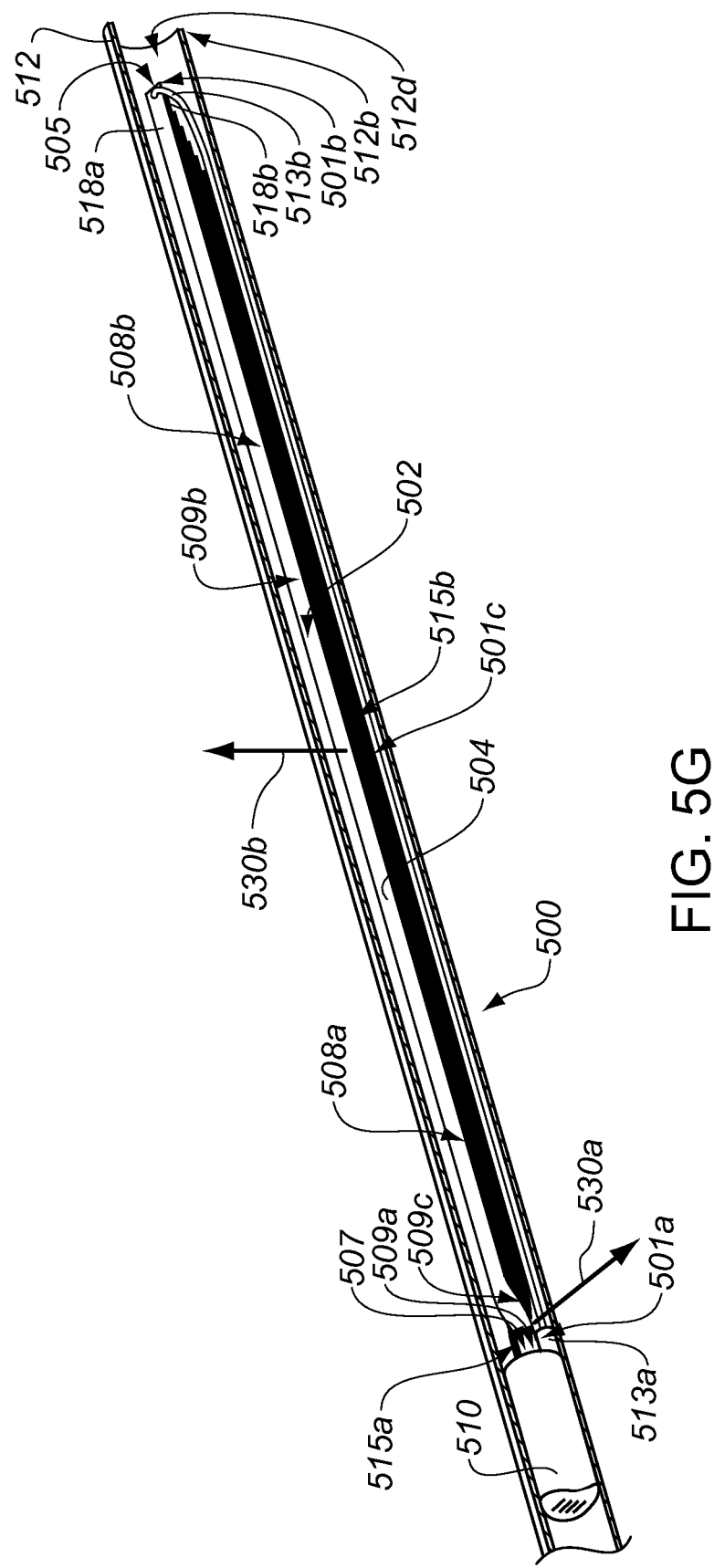
FIG. 5G is a perspective view of a manipulable portion of the catheter system of FIG. 5A, the manipulable portion in a delivery configuration, according to some example embodiments.
Figure 5H:
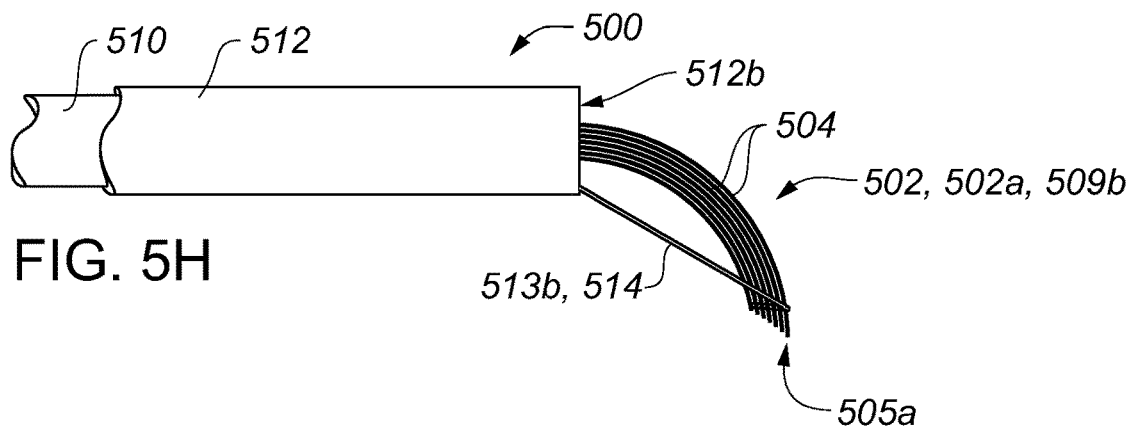
FIGS. 5H, 5I, and 5J are various side elevation views of various respective parts of a manipulable portion positioned at three successive points in time as a part of the manipulable portion is advanced outwardly from the confines of a lumen of a catheter sheath, according to some example embodiments, each of the manipulable portion and the catheter sheath provided by the catheter system of FIG. 5A, according to some example embodiments.
Figure 5I:
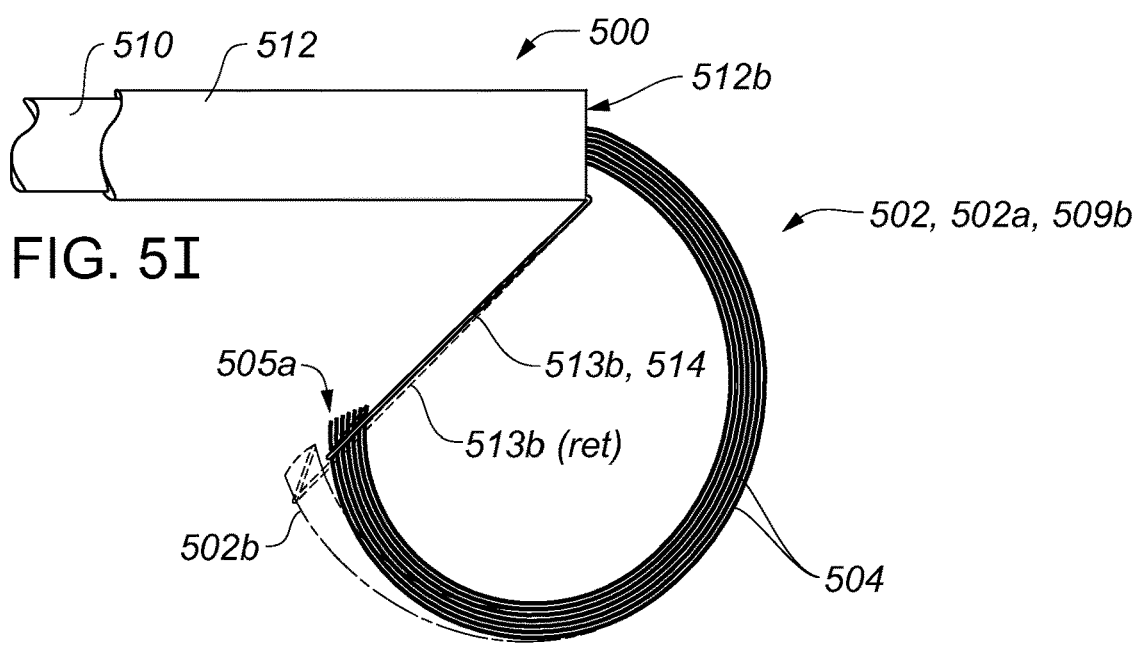
Figure 5J:
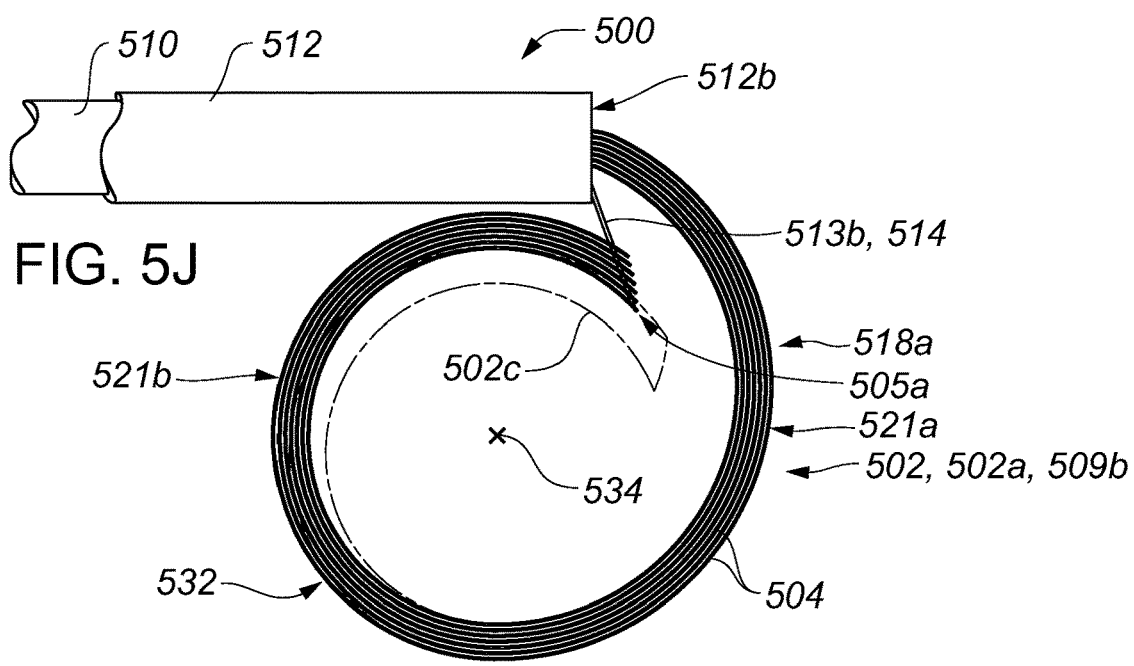
Figure 5K:
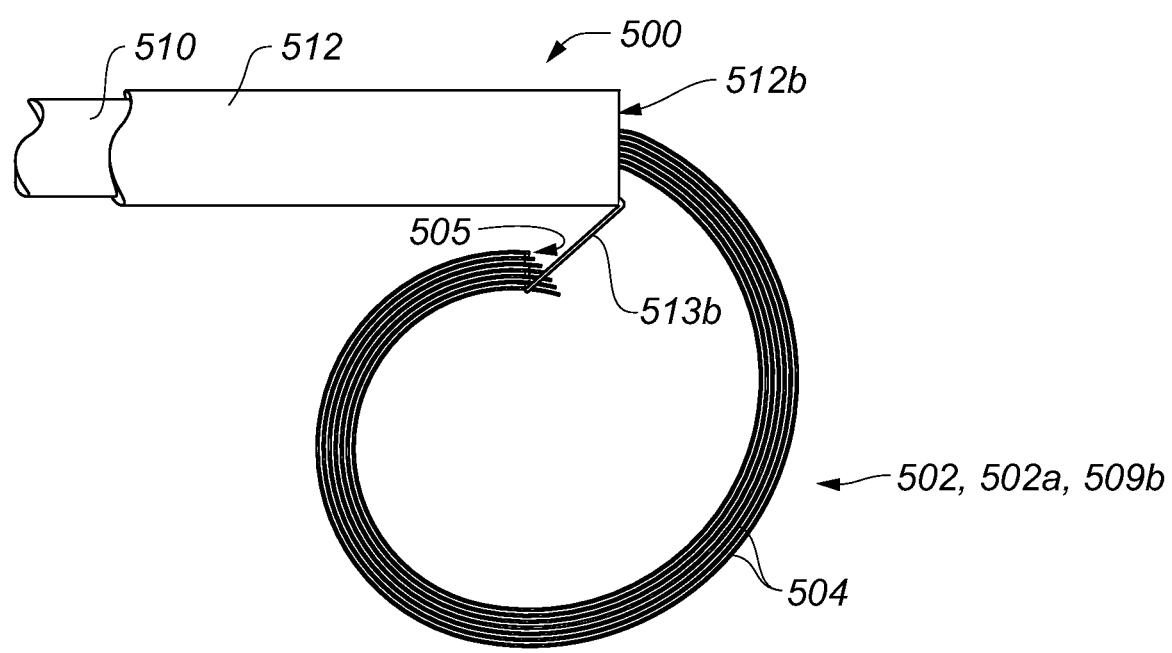
FIG. 5K is a side elevation view of a retraction of a manipulable portion to a particular location relative to a catheter sheath, each of the manipulable portion and the catheter sheath provided by the catheter system of FIG. 5A, according to some example embodiments.
Figures 1, 5L:
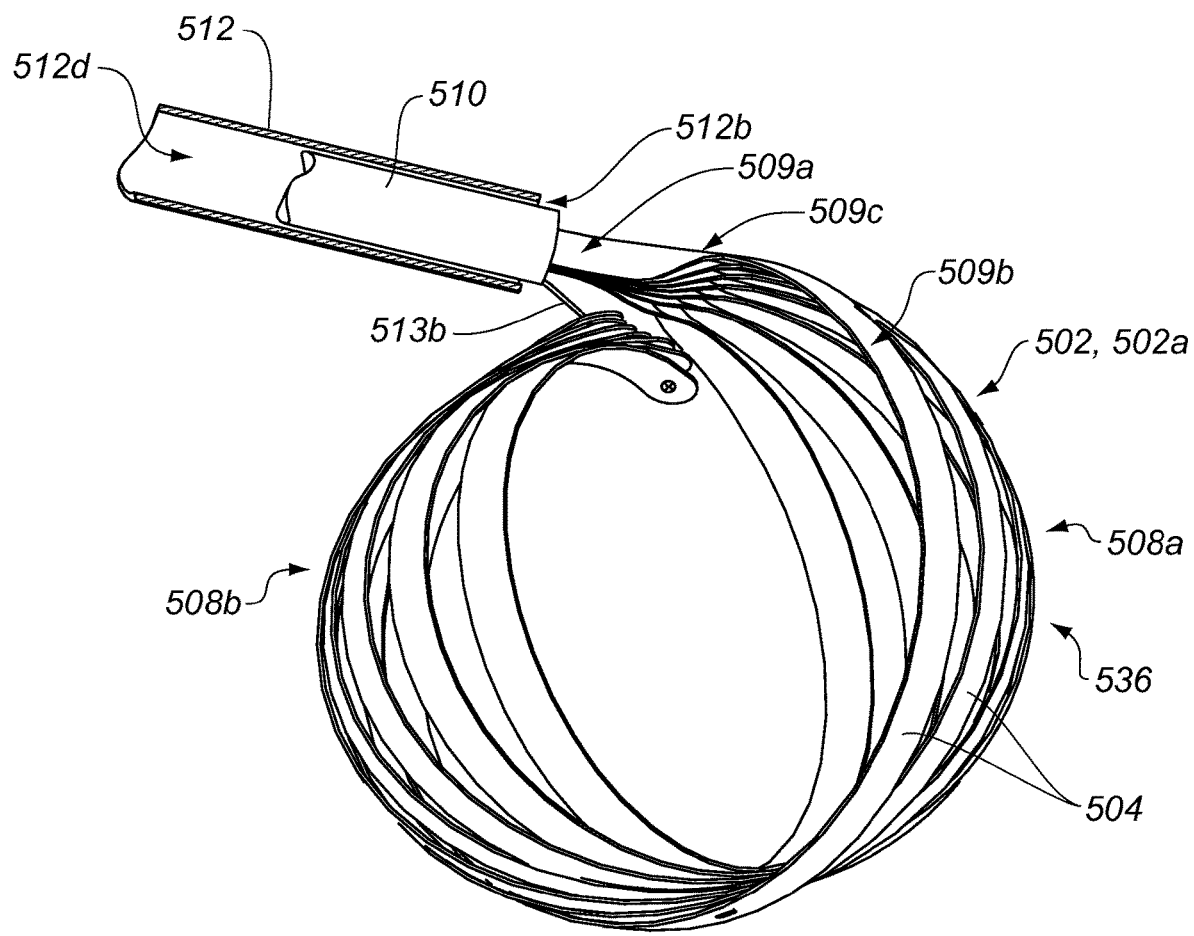
Figures 2, 5L:
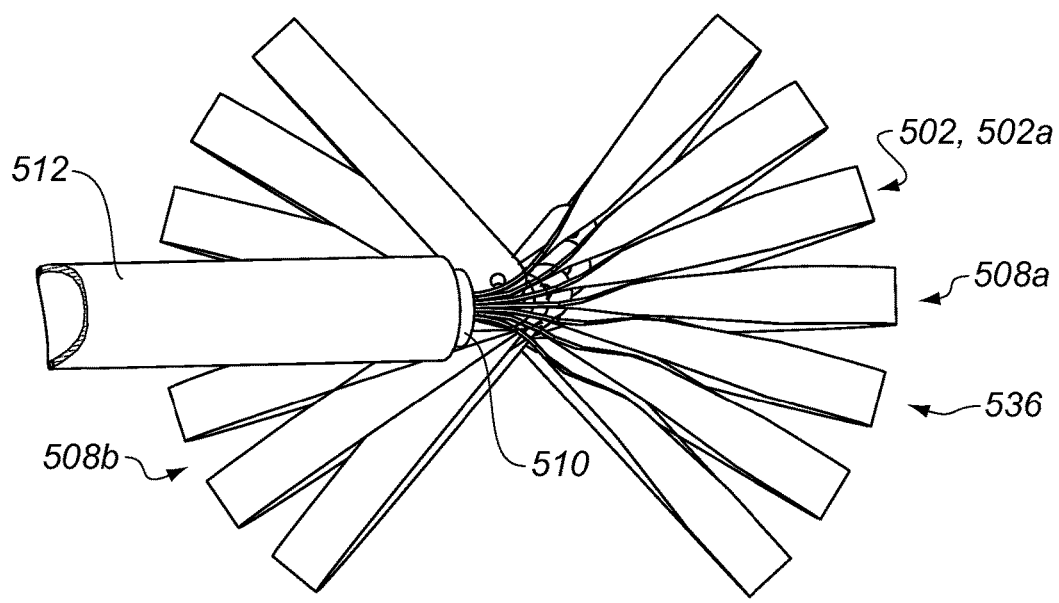
Figures 1, 5M:
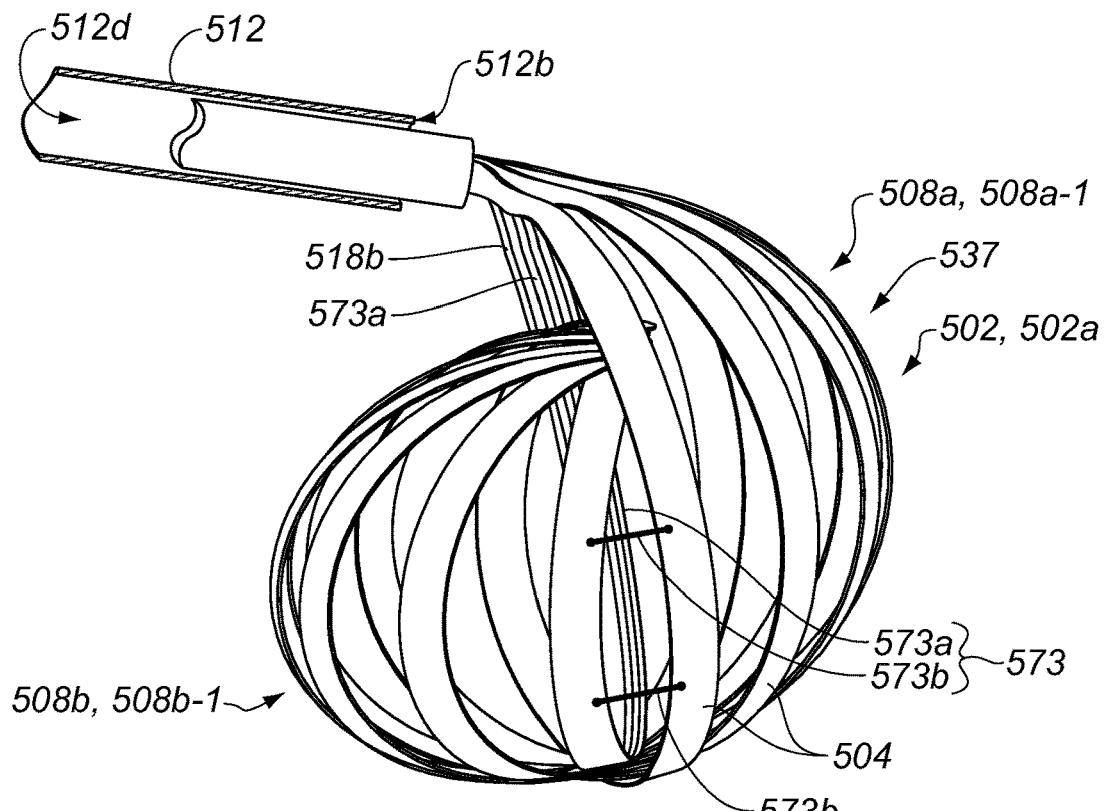
Figures 2, 5M:
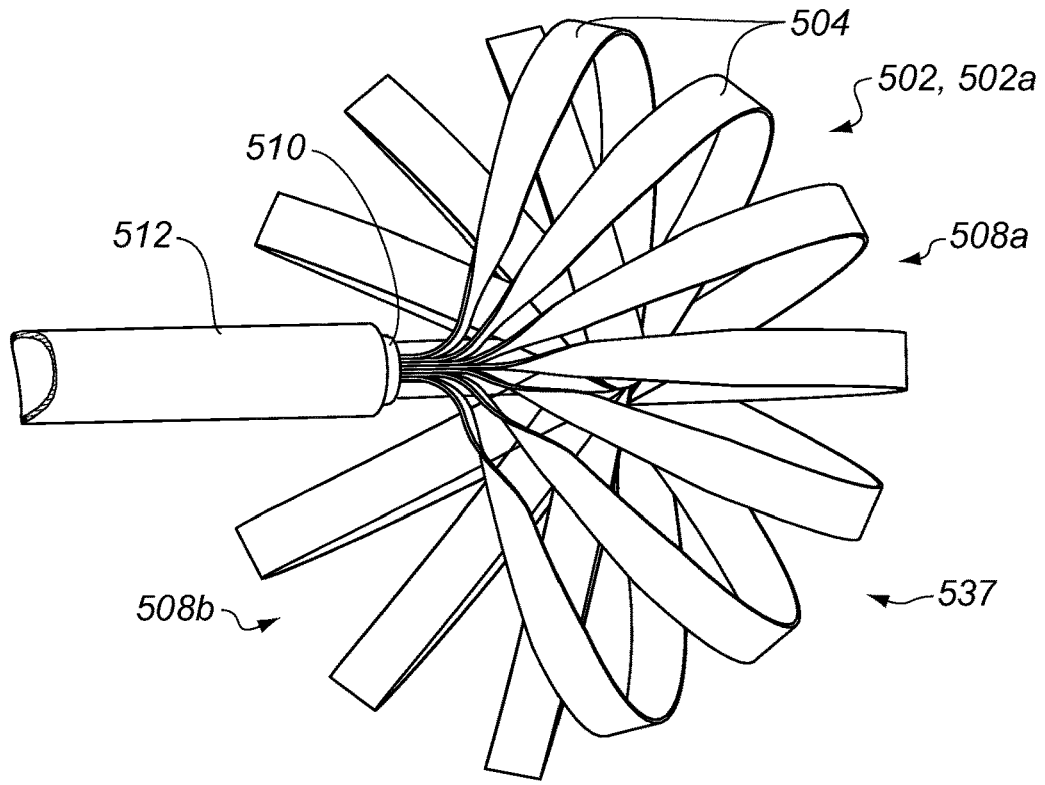
Figure 5N:
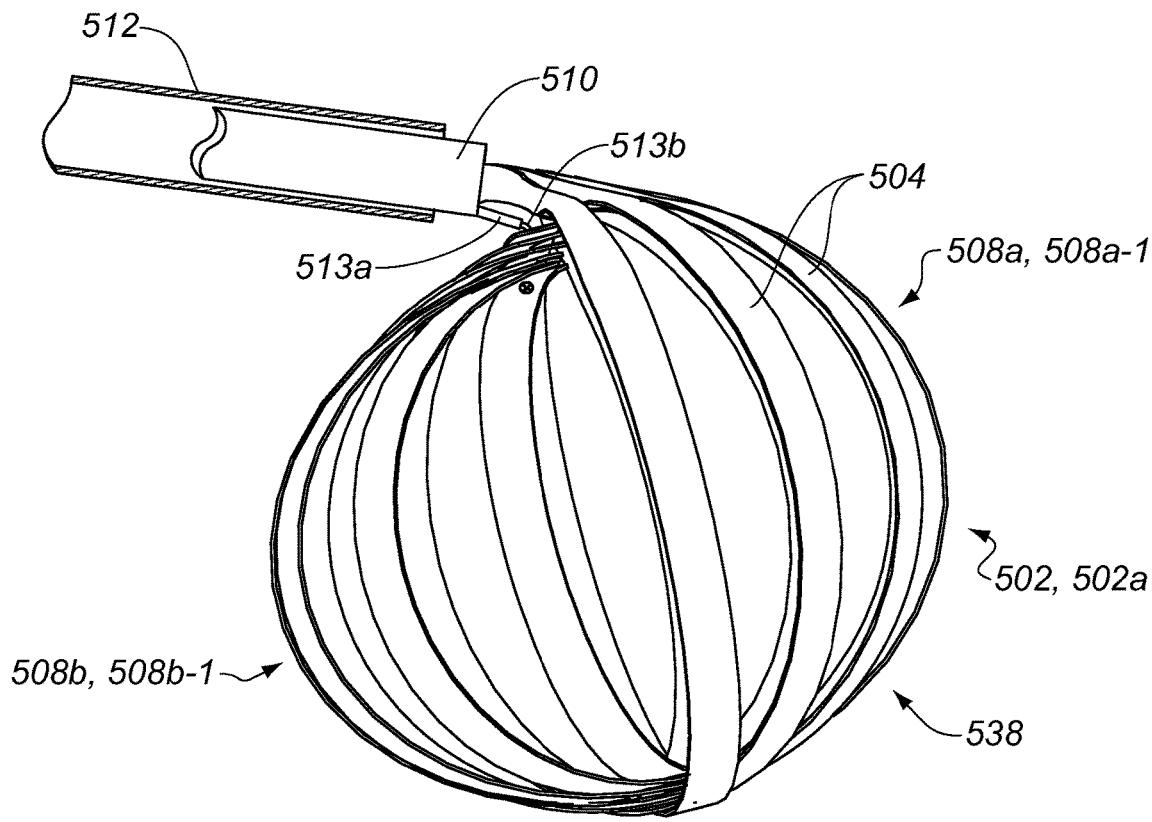
FIG. 5N is a perspective view of a manipulable portion of the catheter system of FIG. 5A configured in an expanded configuration known as enlarged expanded configuration, according to some example embodiments.
Figure 5O:
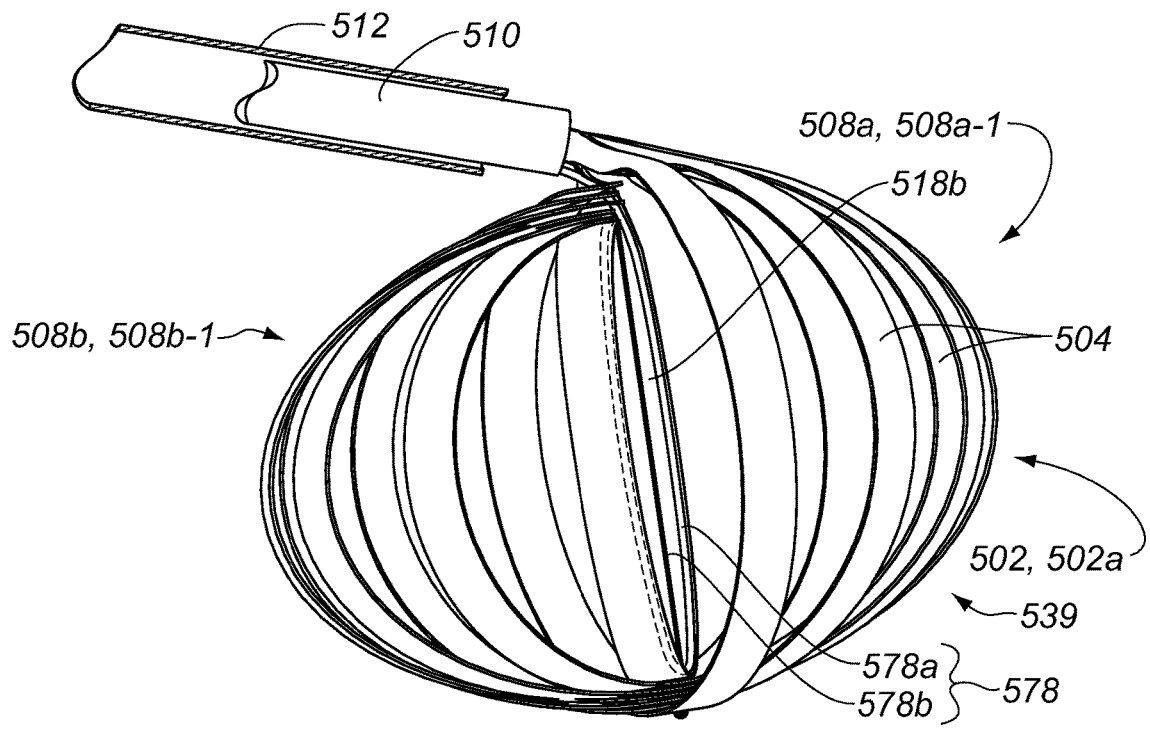
FIG. 5O is a perspective view of a manipulable portion of the catheter system of FIG. 5A configured in an expanded configuration known as a flattened expanded configuration, according to some example embodiments.
Figure 5P:
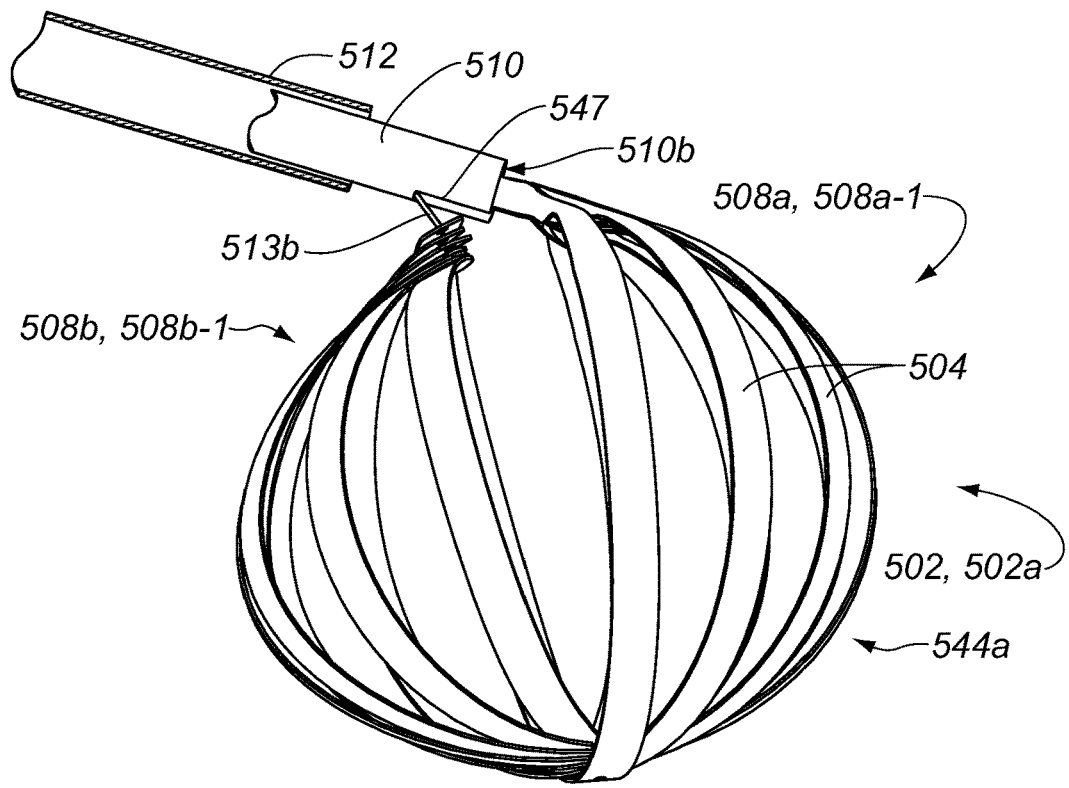
FIG. 5P is a perspective view of a manipulable portion of the catheter system of FIG. 5A configured in an expanded configuration known as an open clam shell configuration, according to some example embodiments.
Figure 5Q:
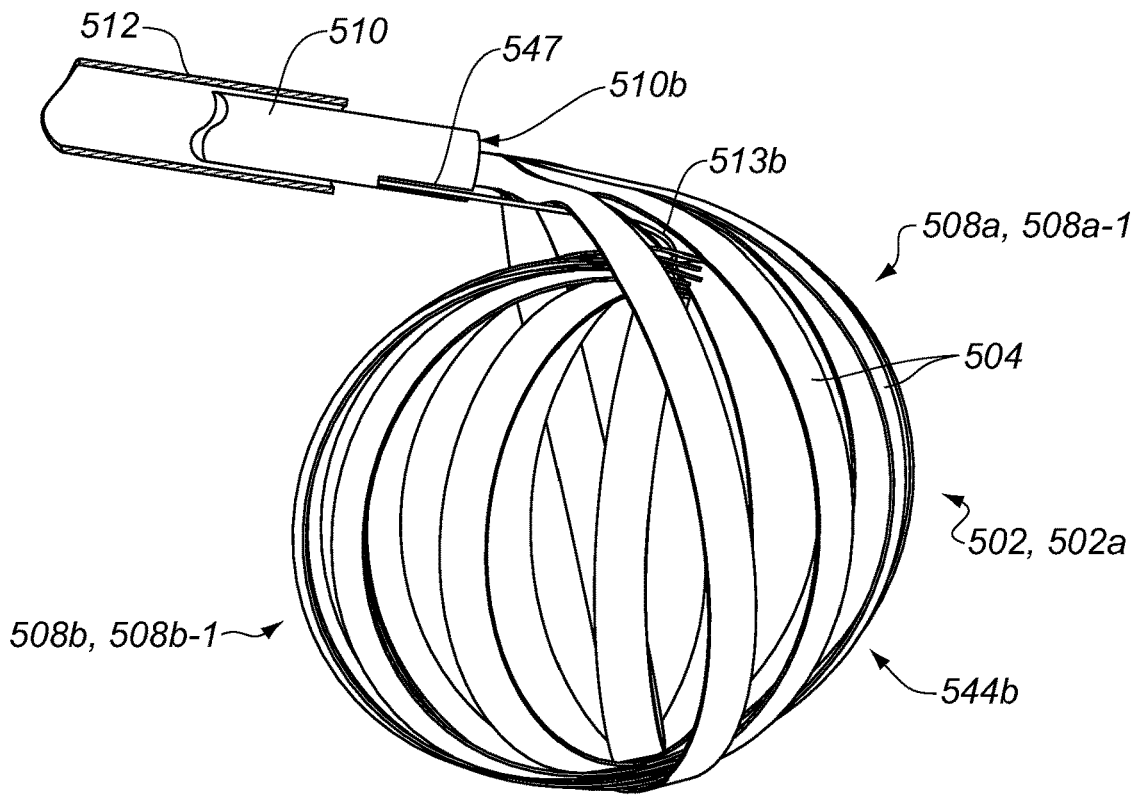
FIG. 5Q is a perspective view of a manipulable portion of the catheter system of FIG. 5A configured in an expanded configuration known as a closed clam shell configuration, according to some example embodiments.
Figures 1, 5R:
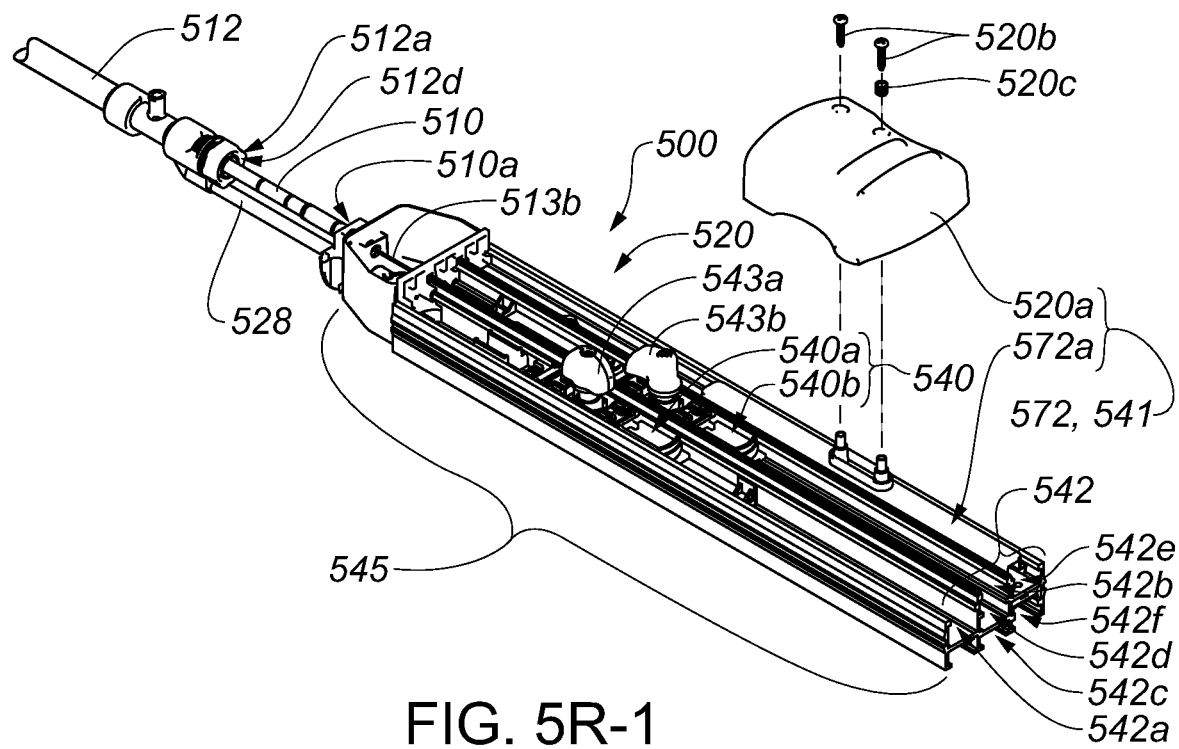
Figures 2, 5R:
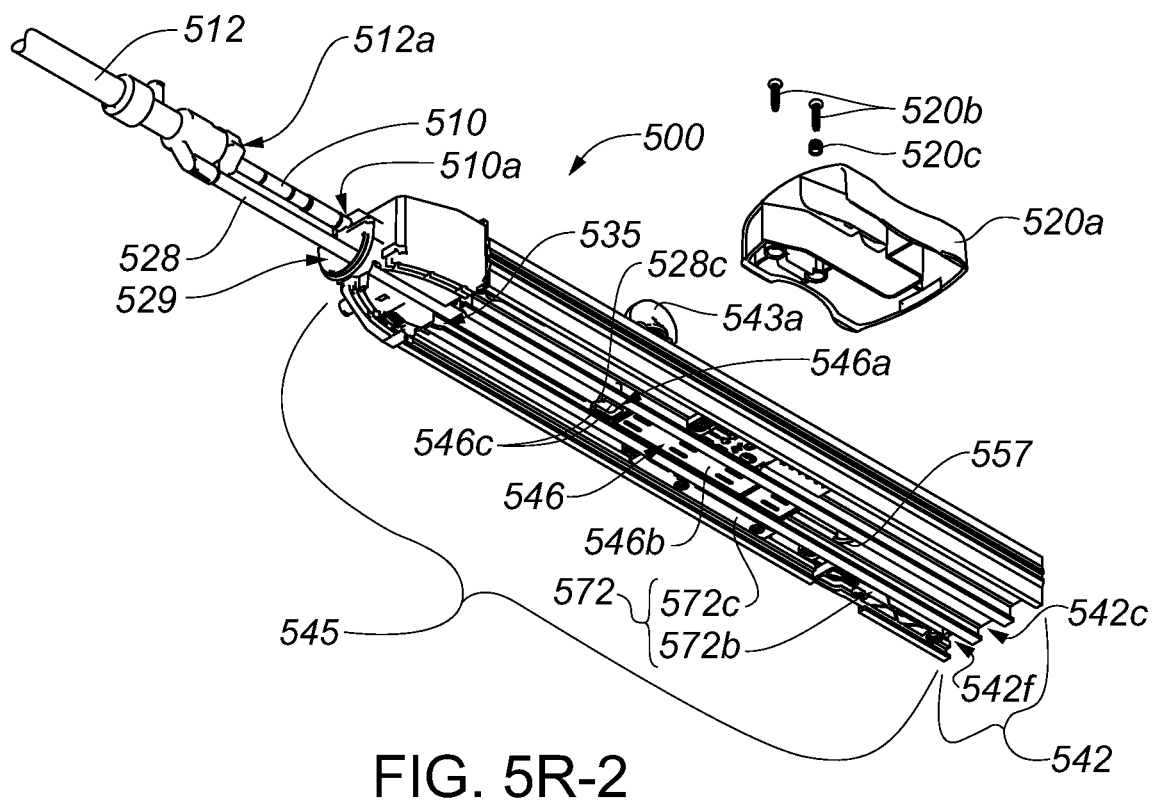
Figures 3, 5R:
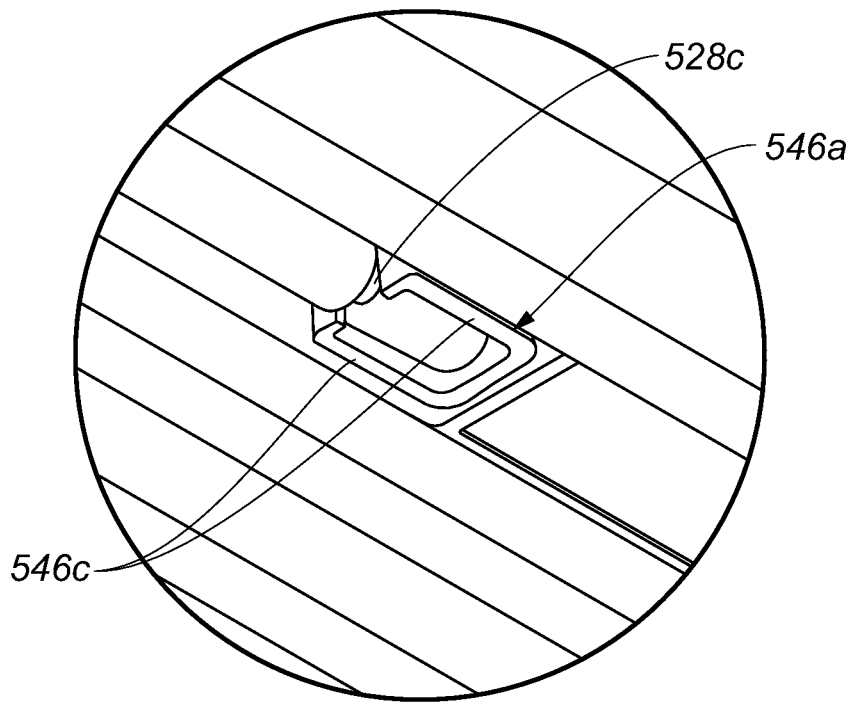
Figures 4, 5R:
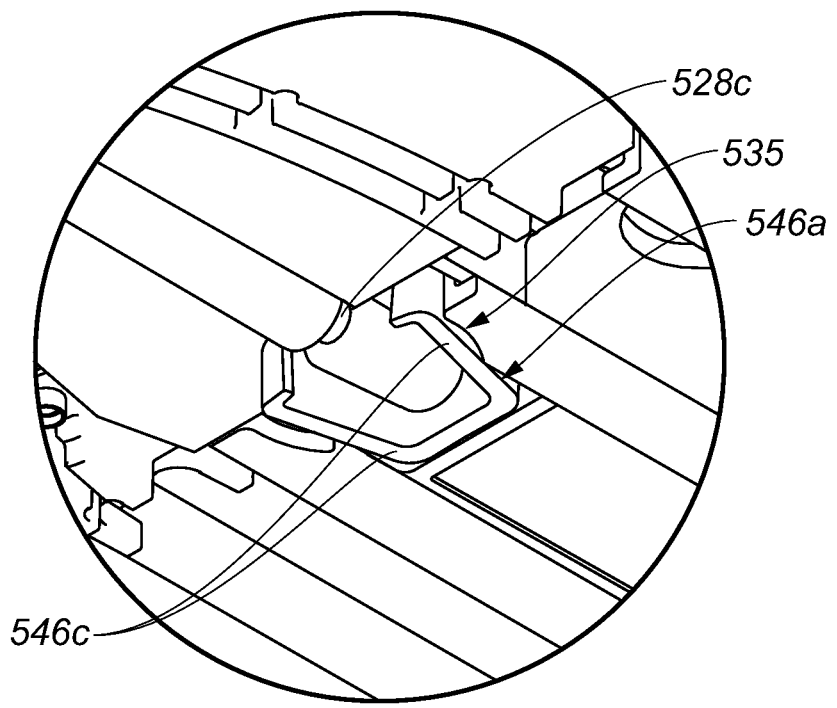

Each of FIGS. 5R-3 and 5R-4 represents a detailed view of a respective one of an engagement and disengagement between various parts of the catheter system of FIG. 5A, according to some example embodiments.

FIGS. 5S-1, 5S-2, 5S-3, 5S-4, 5S-5, and 5S-6 are top plan views of a number of actuators affiliated with a handle portion of the catheter system of FIG. 5A, various ones of the actuators positioned in respective activation positions, according to some example embodiments.

Figures 1, 5S:
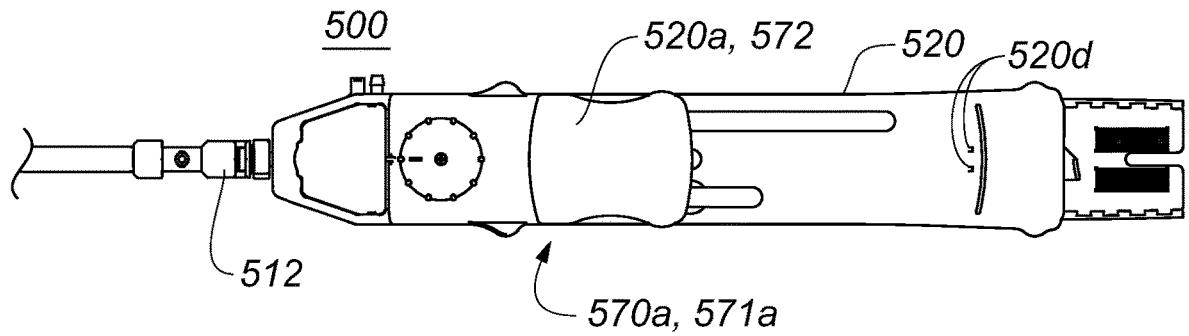
Figures 2, 5S:
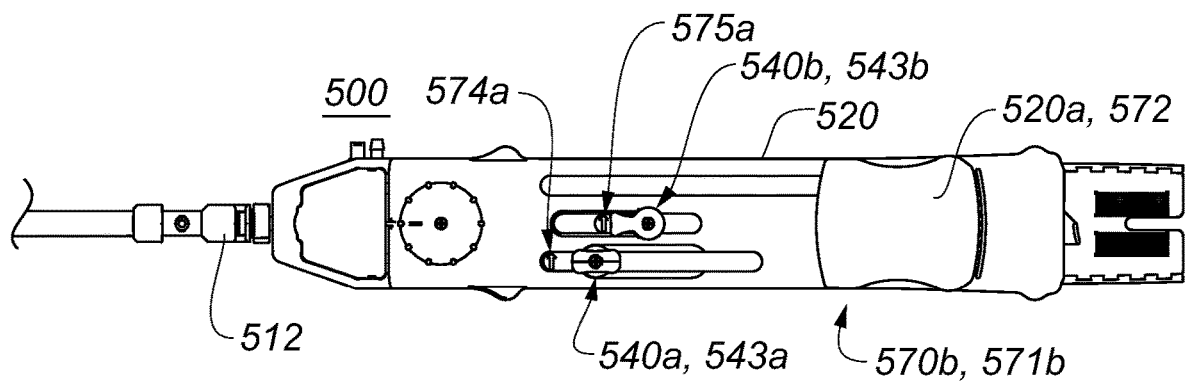
Figures 3, 5S:
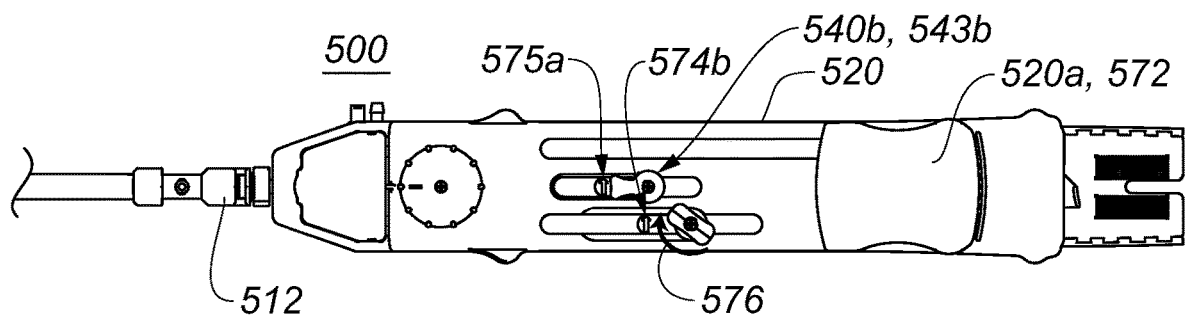
Figures 4, 5S:
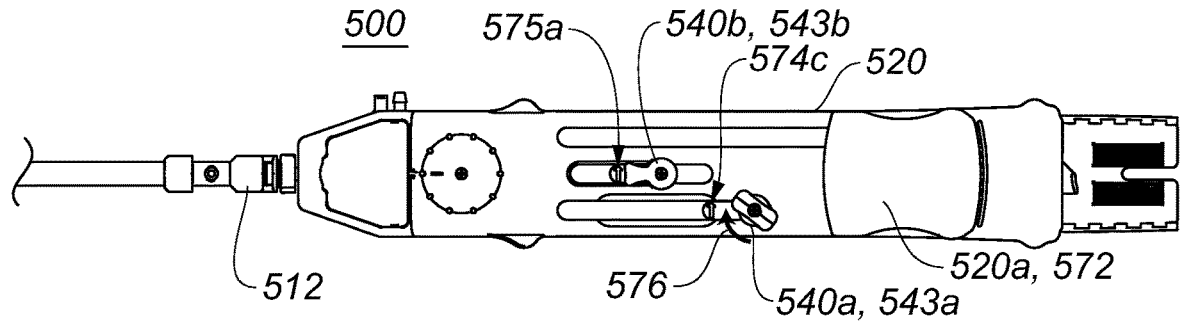
Figures 5, 5S:
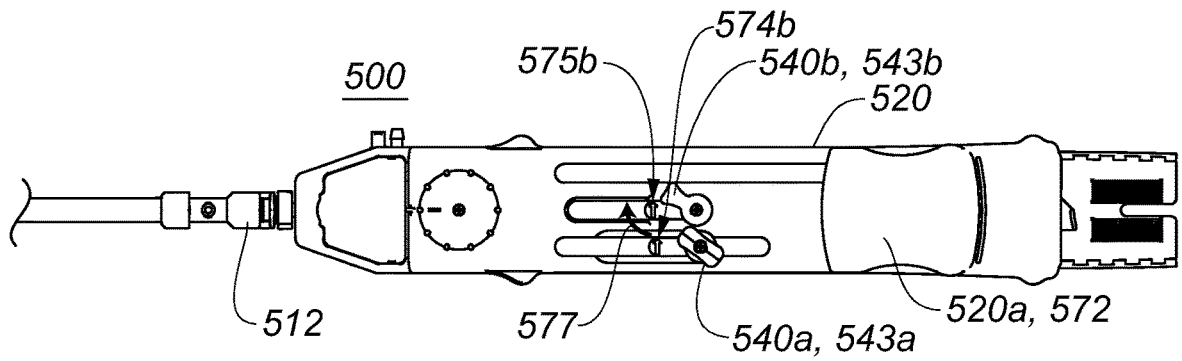
Figures 5, 5S, 6:
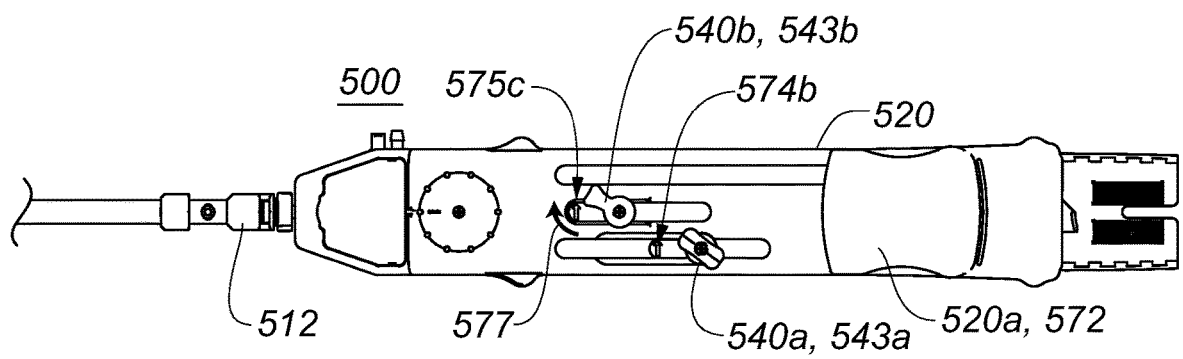
Figure 5T:
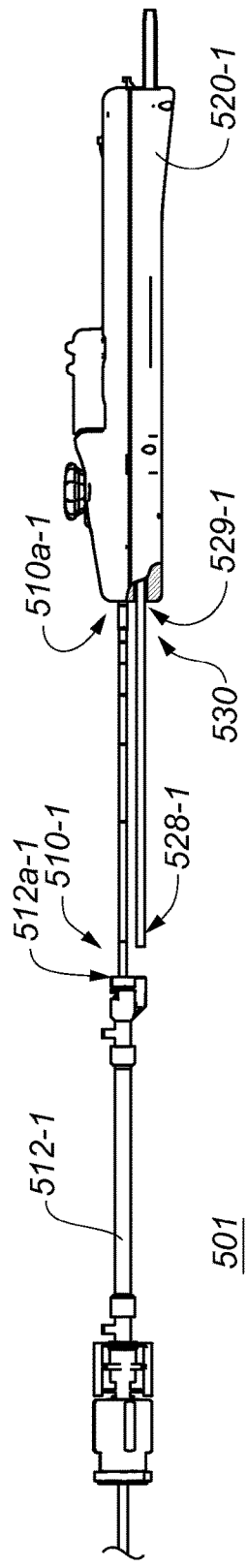
Figure 5U:
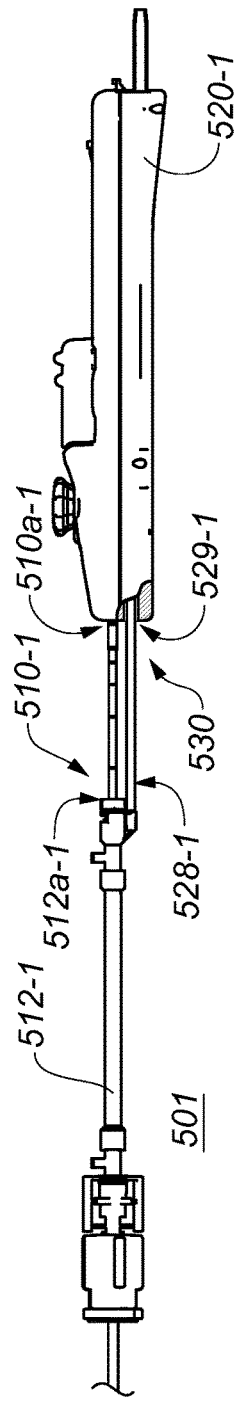
Figure 5V:
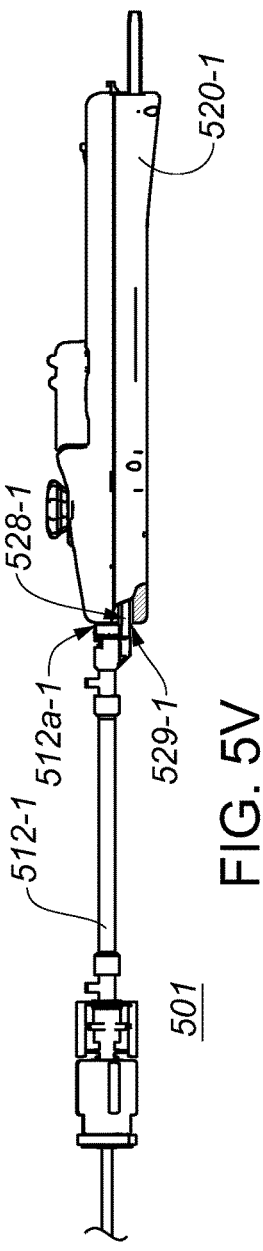

FIGS. 5T, 5U, and 5V are various side elevation views of a positioning of a shaft into a catheter sheath at three successive points in time, according to some example embodiments.

FIGS. 5W-1, 5W-2, 5W-3, and 5W-4 each respectively show plan and elevation views of a portion of a catheter system, according to some embodiments.

FIG. 6 is a graph that includes various lines representative of a metering of a control element during a take-up thereof and a play-out thereof, according to some example embodiments.

Figure 7A:
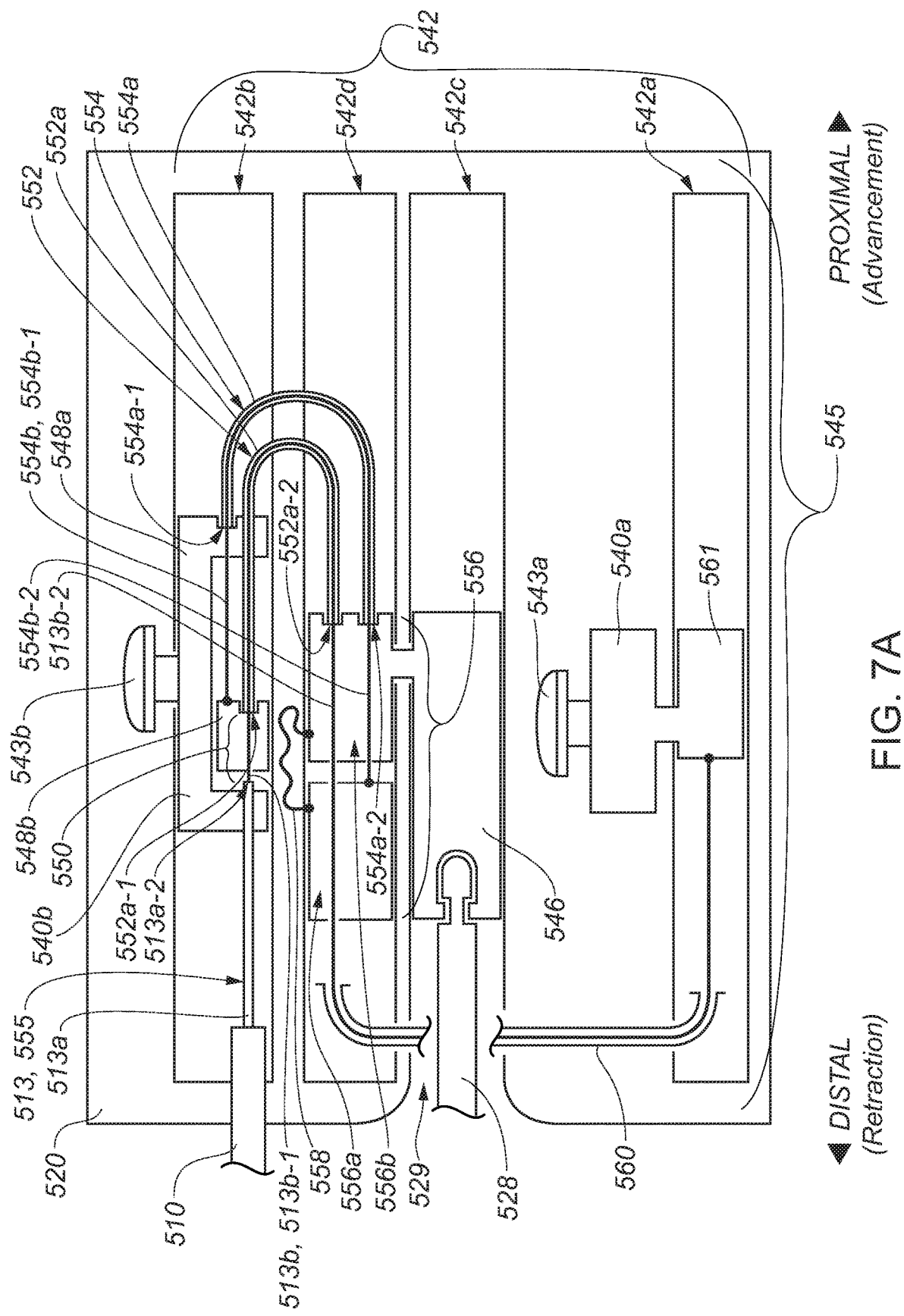
Figure 7B:
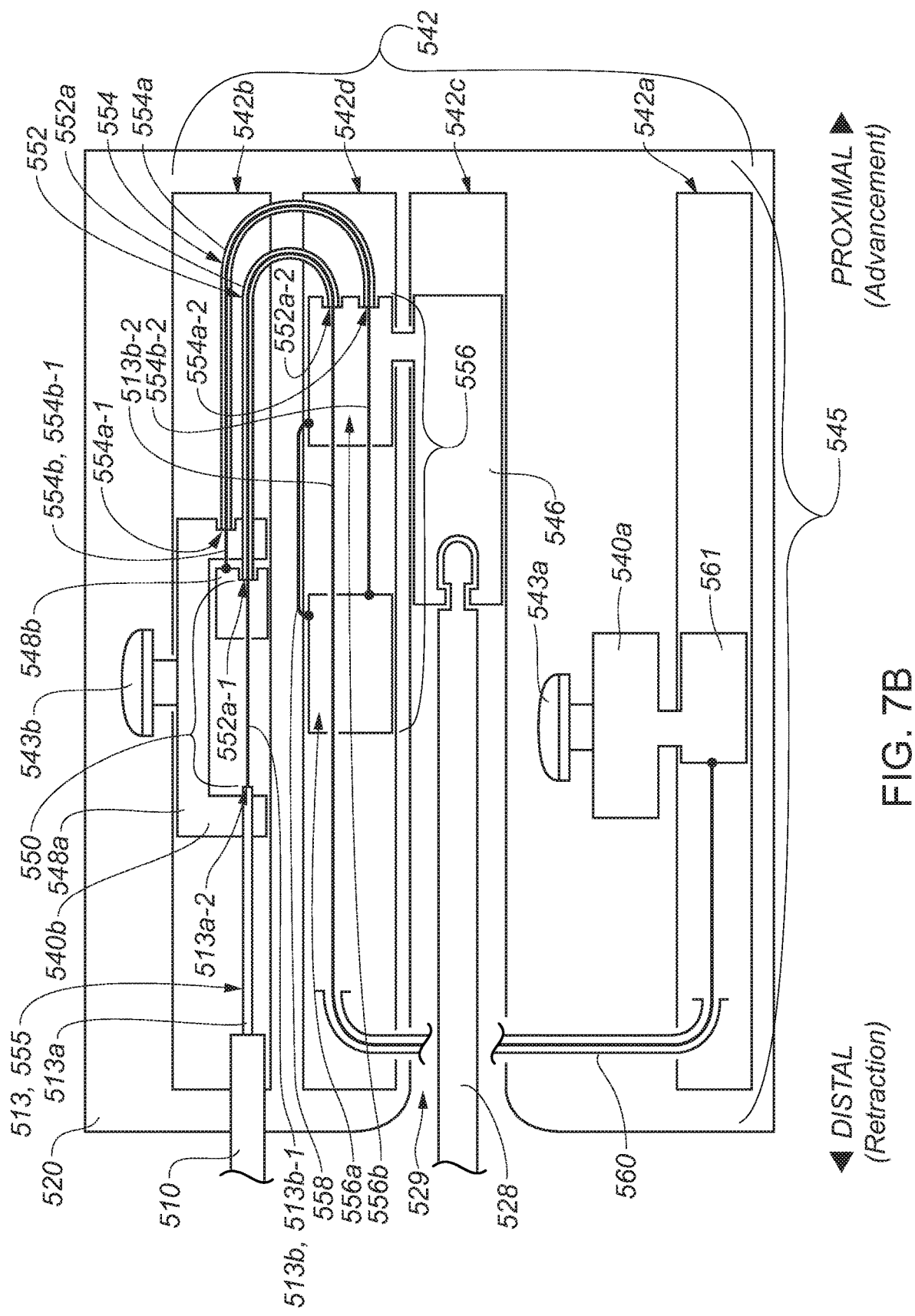

FIGS. 7A and 7B are schematic representations of least one actuator at two successive points in time as employed in some example embodiments.

Figure 8A:
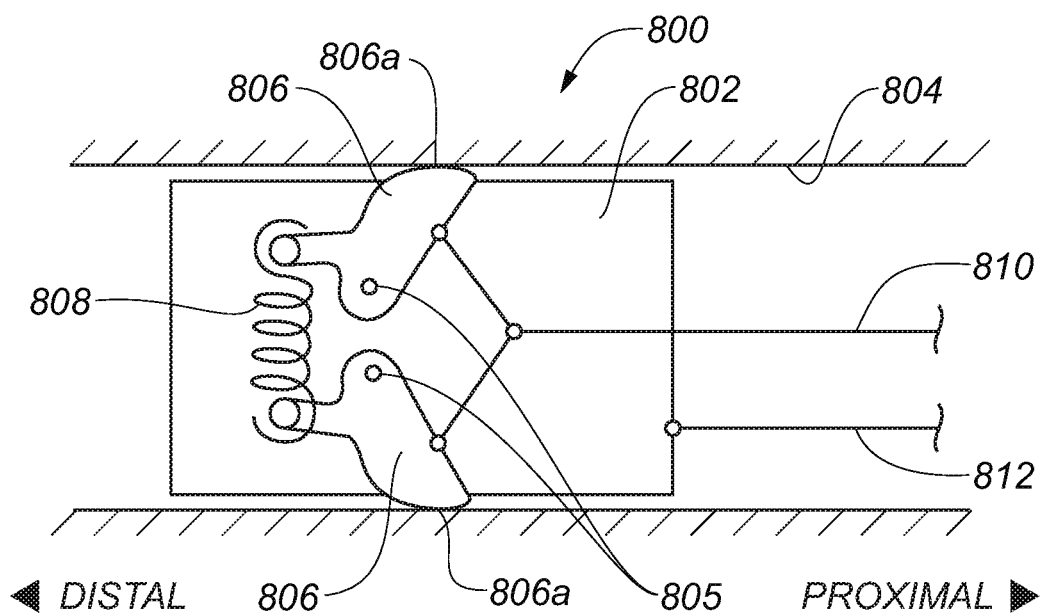
Figure 8B:
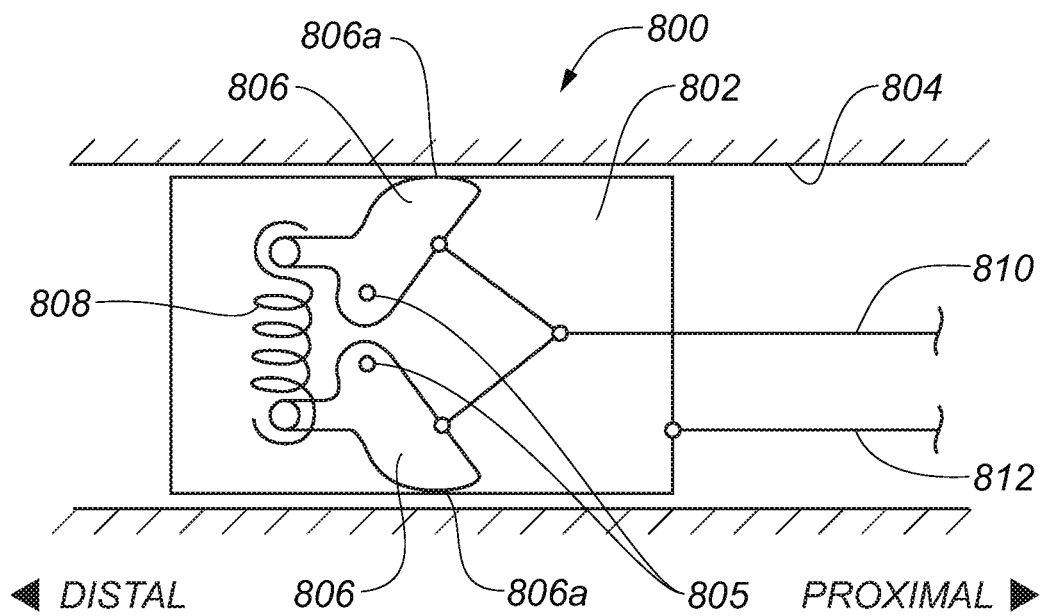

FIGS. 8A and 8B are schematic views of a locking device at two successive points in time as employed in some example embodiments.

Figure 9A:
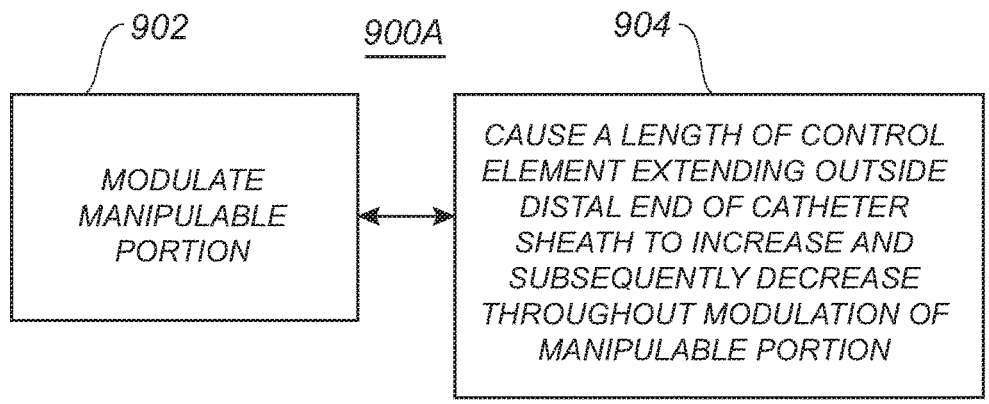

FIG. 9A is a flow chart representing a method for controlling a catheter system, according to some example embodiments.

Figure 9B:
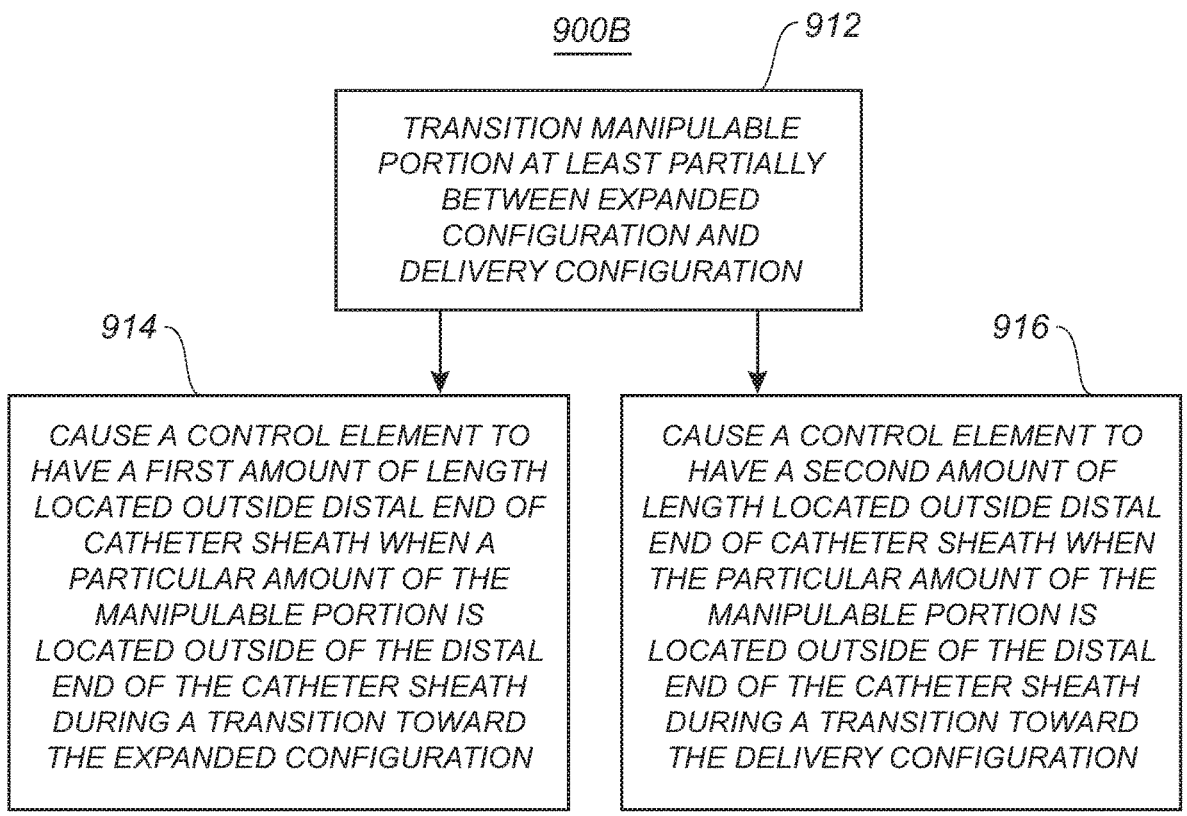

FIG. 9B is a flow chart representing a method for controlling a catheter system, according to some example embodiments.

FIG. 9C is an exploded view of one of the blocks in the flow chart of FIG. 9B, according to some example embodiments.

FIG. 9D is a flow chart representing a method for controlling a catheter system, according to some example embodiments.

Figure 9E:
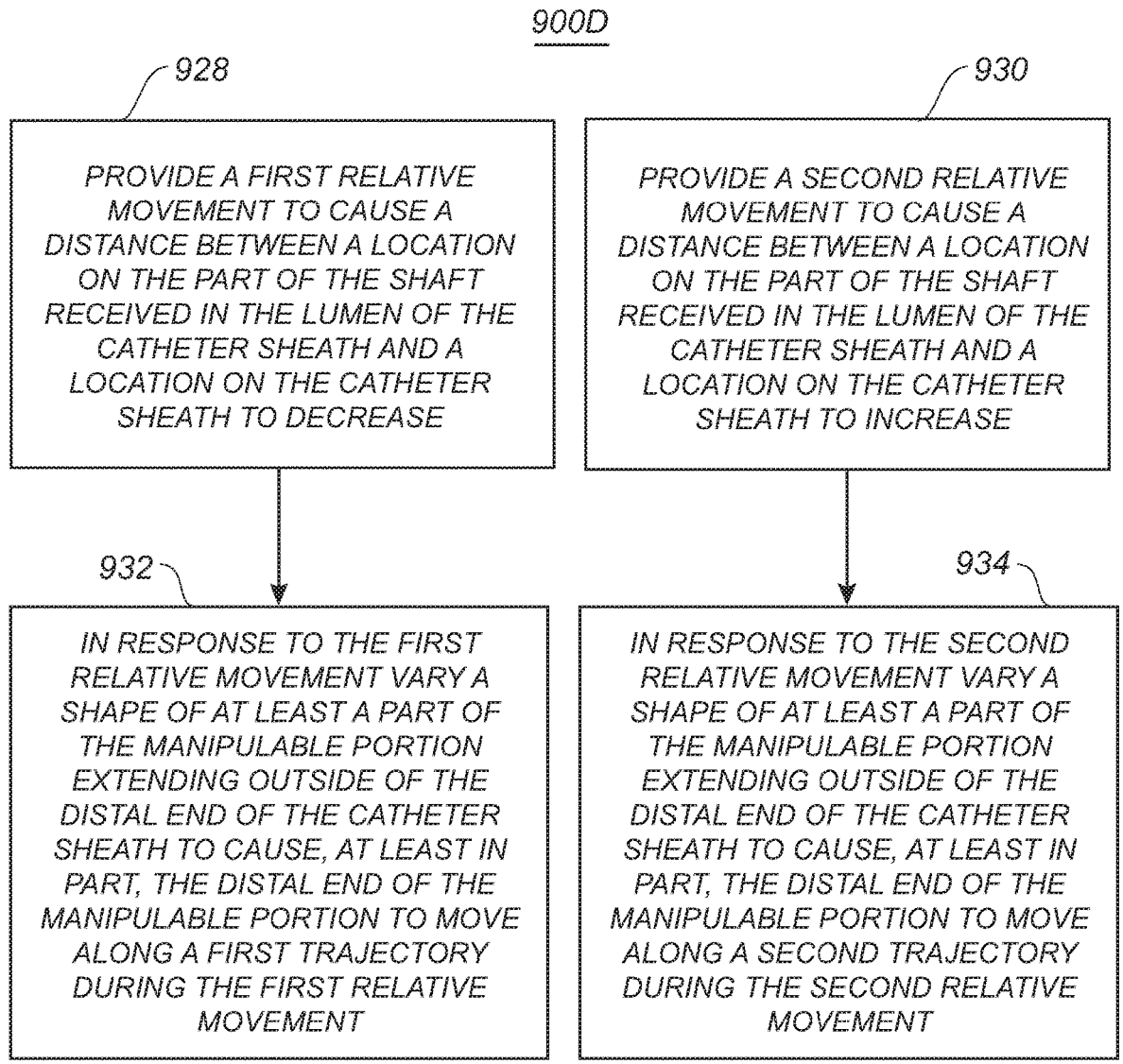

FIG. 9E is a flow chart representing a method for controlling a catheter system, according to some example embodiments.

FIGS. 10A, 10B, 10C, and 10D illustrate a slider locking device, according to some example embodiments.

DETAILED DESCRIPTION

In the following description, certain specific details are set forth in order to provide a thorough understanding of various embodiments of the invention. However, one skilled in the art will understand that the invention may be practiced without one or more of these details. In some instances, well-known structures have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to the same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least upon A' includes A as well as the possibility of one or more other additional elements or functions besides A. In the same manner, the phrase, 'based upon A' includes A, as well as the possibility of one or more other additional elements or functions besides A. However, the phrase, 'based only upon A' includes only A. For another similar example, each of the phrases 'configured at least to A' and 'configured to at least A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A', for example, means a configuration to perform only A.

The word "ablation" as used in this disclosure should be understood to include, for example, any disruption to certain properties of tissue. Most commonly, the disruption is to the electrical conductivity and is achieved by heating, which can be generated with resistive or radio-frequency (RF) techniques for example. However, any other technique for such disruption may be included when the term "ablation" is used, such as mechanical, chemical, or optical techniques.

The word "fluid" as used in this disclosure should be understood to include, for example, any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" as used in some embodiments in this disclosure should be understood to include, for example, any surface-forming tissue that is used to form a surface of a body or a surface within a bodily cavity, a surface of an anatomical feature or a surface of a feature associated with a bodily opening positioned in fluid communication with the bodily cavity. The tissue can include, for example, part or all of a tissue wall or membrane that defines a surface of the bodily cavity. In this regard, the tissue can form an interior surface of the cavity that surrounds a fluid within the cavity. In the case of cardiac applications, tissue can include, for example, tissue used to form an interior surface of an intra-cardiac cavity such as a left atrium or right atrium. In some embodiments, tissue is non-excised tissue. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The term "activation" as used in this disclosure should be interpreted broadly as making active a particular function as related to various transducers disclosed in this disclosure. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer is activated to cause a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such as a controller system or data processing device system, in order to cause the system to perform one or more operations. The set of instructions or modules can be stored by any kind of memory device, such as those described subsequently with respect to the memory device system 130 shown in FIG. 1. In addition, instructions or modules of a program may be described as being configured to cause the performance of a function or action.

The phrase "configured to" in this context is intended to include, for example, at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include, for example, one or more physical devices or sub-devices (e.g., pieces of equipment) that interact to perform one or more functions, regardless of whether such devices or sub-devices are located within a same housing or different housings. In this regard, the word "device" may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

The phrase "physically coupled" is intended to include, for example, a coupling between two objects that involves a physical contacting of the two objects. The phrase "fixedly coupled" is intended to include, for example, a secure coupling between two objects that may, in some instances, not involve a mechanism configured to release the coupling of the two objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling.

Figure 1:
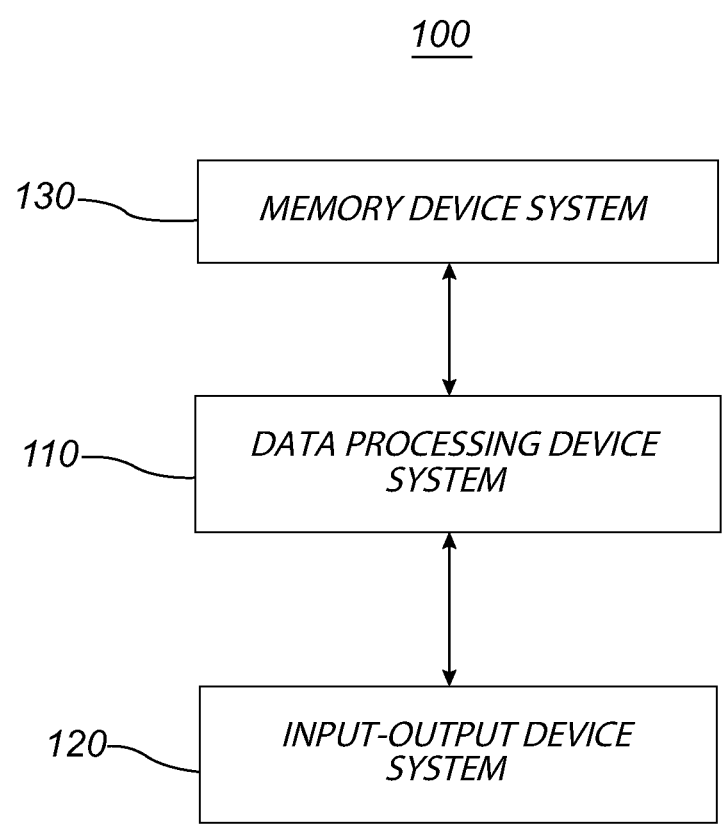
FIG. 1 is a schematic representation of a system, according to some example embodiments, the system including a data processing device system, an input-output device system, and a processor-accessible memory device system.

FIG. 1 schematically illustrates a system 100, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement methods by controlling, driving, or otherwise interacting with various structural components described herein, including, but not limited to, one or more of the various structural components illustrated in FIGS. 2-5, 7, 8, and 10. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods, including, in some embodiments, some or all of one or more of the methods of FIG. 9, implemented by the data processing device system 110. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single housing or data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the memory device system 130 may be considered to include or be a non-transitory processor-accessible (or computer-readable) data storage medium system. And, in some embodiments, the memory device system 130 may be considered to include or be a non-transitory processor-accessible (or computer-readable) data storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, a computer, a processor-accessible memory device, some or all of a catheter device system (e.g., FIGS. 3A, 3B, 4, or catheter system 500, described below), or any device or combination of devices from which a desired selection, desired information, instructions, or any other data is input to the data processing device system 110. The input-output device system 120 may include a user-activatable control system that is responsive to a user action. The input-output device system 120 may include any suitable interface for receiving a selection, information, instructions, or any other data from other devices or systems described in various ones of the embodiments. In this regard, the input-output device system 120 may include various ones or portions of other systems or devices described in various embodiments.

The input-output device system 120 also may include an image generating device system, a display device system, a processor-accessible memory device, some or all of a catheter device system (e.g., FIGS. 3A, 3B, 4, or catheter system 500, described below), or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions, or any other data to other devices or systems described in various ones of the embodiments. In this regard, the input-output device system 120 may include various other devices or systems described in various embodiments.

Various embodiments of catheter systems are described herein. It should be noted that any catheter system described herein may also be referred to as a medical system. Some of the described devices of such systems are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are moveable between a delivery or unexpanded configuration in which a portion of the device is sized, shaped, or both for passage through a bodily opening leading to a bodily cavity, and an expanded or deployed configuration in which the portion of the device has a size, shape, or both too large for passage through the bodily opening leading to the bodily cavity. An example of an expanded or deployed configuration is when the portion of the catheter system is in its intended-deployed-operational state inside the bodily cavity. Another example of the expanded or deployed configuration is when the portion of the catheter system is being changed from the delivery configuration to the intended-deployed-operational state to a point where the portion of the device now has a size, shape, or both too large for passage through the bodily opening leading to the bodily cavity.

In some example embodiments, the catheter system includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

Figure 2:
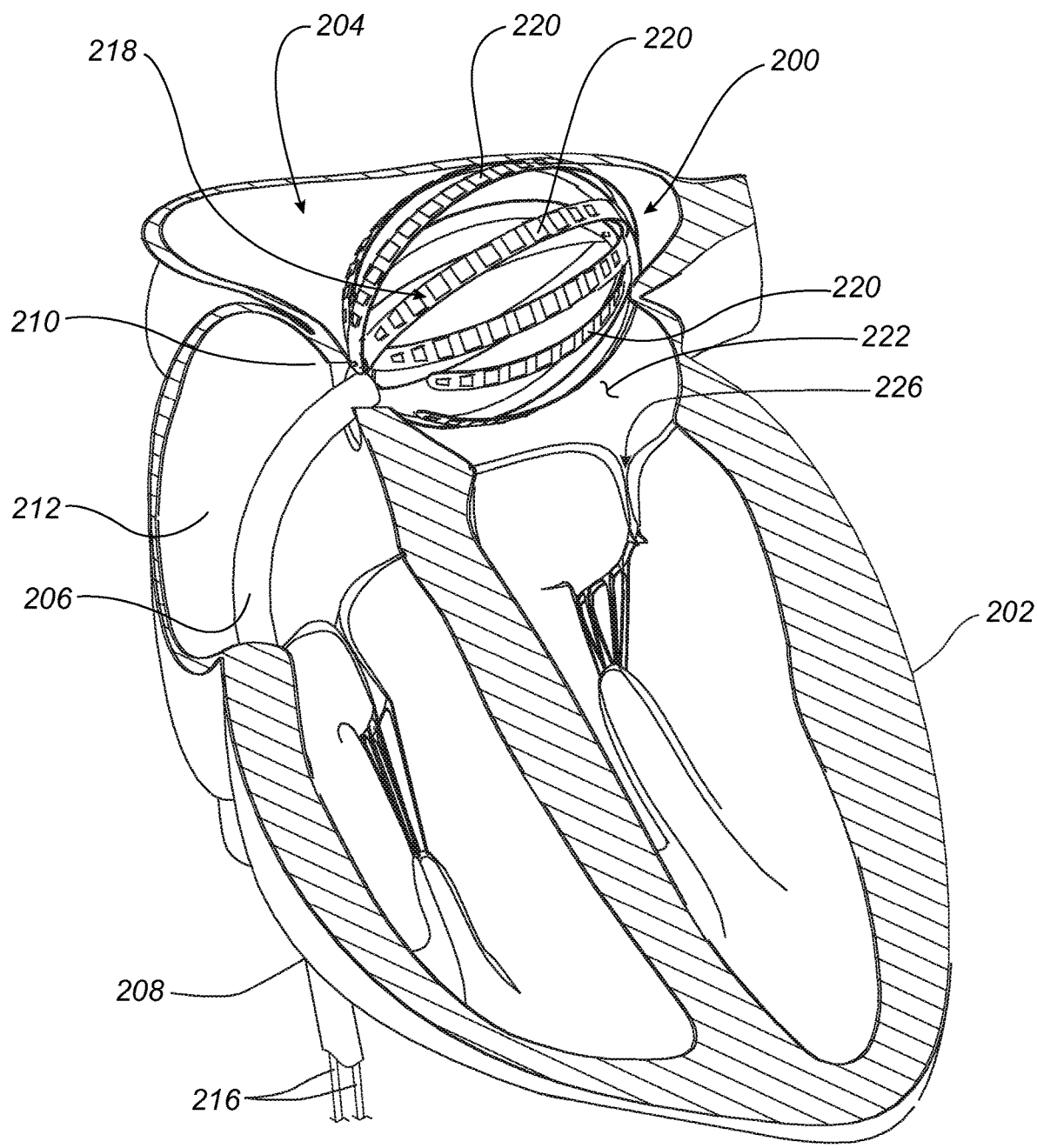
FIG. 2 is a cutaway diagram of a heart showing a transducer-based device percutaneously placed in a left atrium of the heart, according to some example embodiments.

FIG. 2 shows a portion of a catheter system, according to some embodiments, such portion including a transducer-based device 200, which may be at least part of a medical device useful in investigating or treating a bodily organ, for example a heart 202, according to some example embodiments. The transducer-based device 200 may also be referred to as a manipulable portion, due to its ability to have its size, shape, or both size and shape altered, according to some embodiments described below. Transducer-based device 200 can be percutaneously or intravascularly inserted into a portion of the heart 202, such as an intra-cardiac cavity like left atrium 204.

In the example of FIG. 2, the illustrated portion of the catheter system also includes a catheter 206, which may be inserted via the inferior vena cava 208 and may penetrate through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown in this embodiment). Electrical conductors 216 provide electrical connections to transducer-based device 200 that are accessible externally from a patient in which the transducer-based device 200 is inserted.

In various embodiments, transducer-based device, or manipulable portion, 200 includes a frame or structure 218, which assumes an unexpanded configuration for delivery to left atrium 204. Structure 218 is expanded (i.e., shown in a deployed or expanded configuration in FIG. 2) upon delivery to left atrium 204 to position a plurality of transducers 220 (three called out in FIG. 2) proximate the interior surface formed by tissue 222 of left atrium 204. In this regard, it can be stated that one or more of the transducers 220 are moveable with one or more parts of the transducer-based device, or manipulable portion, 200. In some embodiments, at least some of the transducers 220 are used to sense a physical characteristic of a fluid (i.e., blood) or tissue 222, or both, that may be used to determine a position or orientation (i.e., pose), or both, of a portion of transducer-based device 200 within, or with respect to left atrium 204.

For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

Figure 3A:
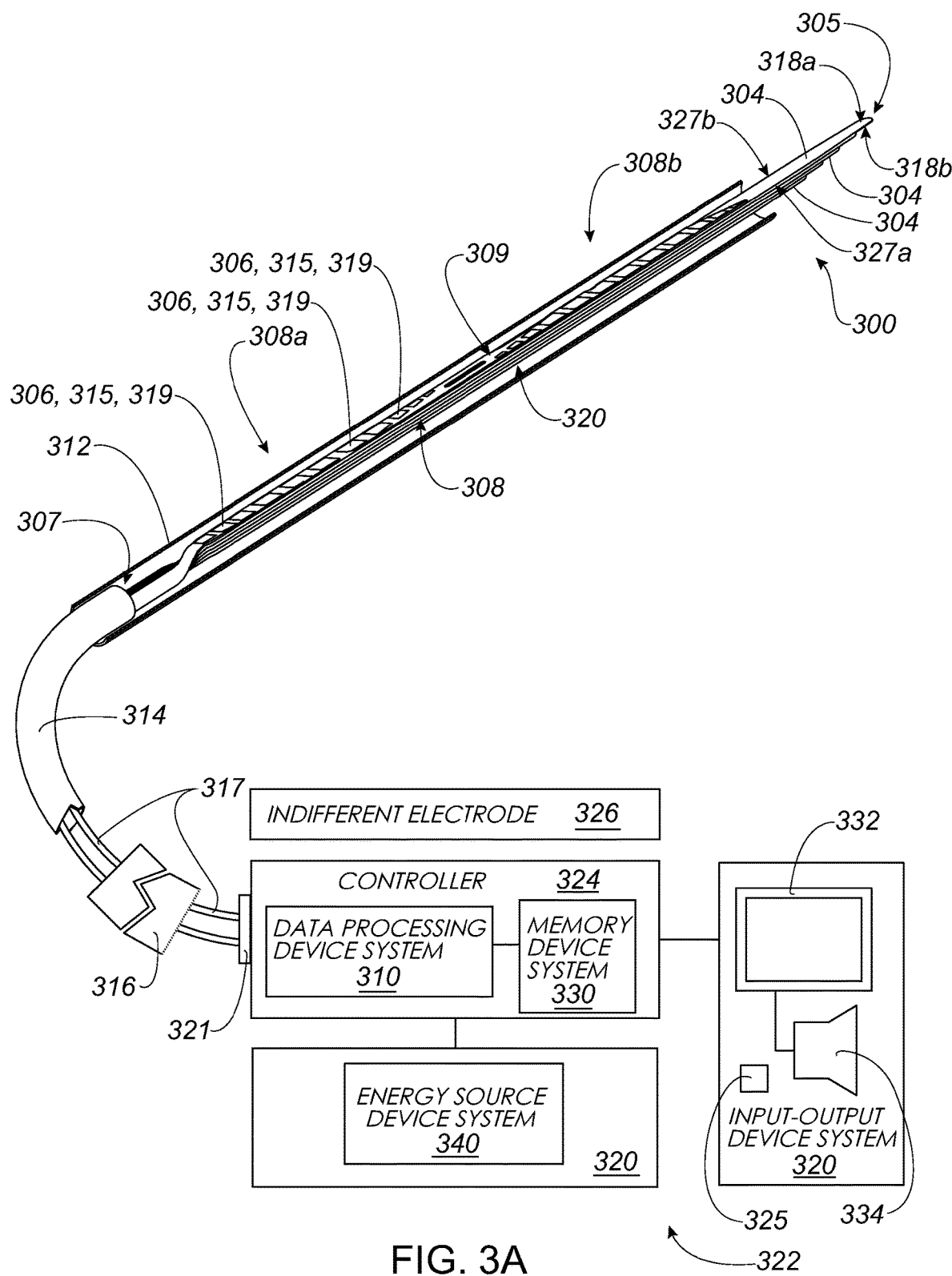
FIG. 3A is a partially schematic representation of a catheter system, according to some example embodiments, the system, which may also be referred to as a medical system, including a data processing device system, an input-output device system, a processor-accessible memory device system, and a manipulable portion shown in a delivery or unexpanded configuration.
Figure 3B:
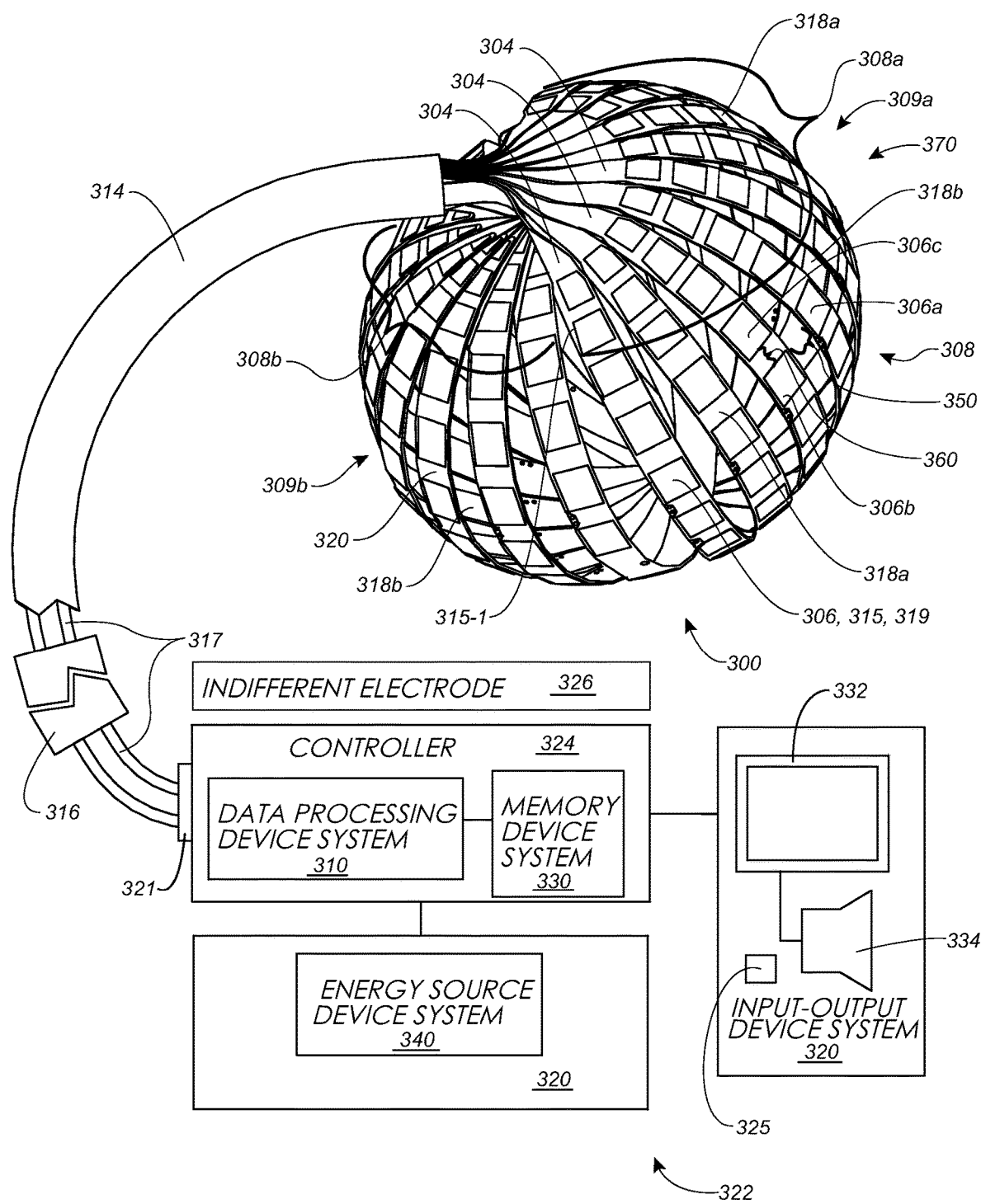
FIG. 3B is the catheter system of FIG. 3A with the manipulable portion shown in a deployed or expanded configuration, according to some example embodiments.

FIGS. 3A and 3B show a catheter system (i.e., a portion thereof shown schematically) that includes a transducer-based device 300 according to one illustrated embodiment. The transducer-based device 300 may correspond to the transducer-based device 200 and, in this regard, may also be referred to as a manipulable portion, due to its ability to have its size, shape, or both size and shape altered, according to some embodiments described below. Transducer-based device 300 may include a plurality of elongate members 304 (three called out in each of FIGS. 3A and 3B) and a plurality of transducers 306 (three called out in FIG. 3A, and three called out in FIG. 3B as 306a, 306b and 306c). As will become apparent, the plurality of transducers 306 are positionable within a bodily cavity. For example, in some embodiments, the transducers 306 are able to be positioned in a bodily cavity by movement into, within, or into and within the bodily cavity, with or without a change in a particular configuration of the plurality of transducers 306. In some embodiments, the plurality of transducers 306 are arrangeable to form a two- or three-dimensional distribution, grid or array of the transducers capable of mapping, ablating, or stimulating an inside surface of a bodily cavity or lumen without requiring mechanical scanning. As shown, for example, in FIG. 3A, the plurality of transducers 306 are arranged in a distribution receivable in a bodily cavity, as the transducer-based device 300 and its plurality of transducers 306 are located within the catheter sheath 312. Stated differently, in FIG. 3A, for example, the plurality of transducers 306 are arranged in a distribution suitable for delivery to a bodily cavity. (It should also be noted, however, that the expanded or deployed configuration (e.g., FIGS. 2, 3B) may also be considered to have the transducers 306 arranged in a distribution receivable in a bodily cavity, as the transducer-based device 300 and its transducers 306 may be returned to the delivery configuration of FIG. 3A, for example.) In some embodiments, each of the transducers 306 includes an electrode 315 (one called out in FIG. 3B) having an energy transmission surface 319 (one called out in FIG. 3B) suitable for transmitting energy in various directions. In some embodiments, tissue-ablating energy is transmitted toward or away from an electrode 315. In some embodiments, tissue-based electrophysiological energy is transmitted toward an electrode 315.

The elongate members 304 form part of a manipulable portion, and in various embodiments, are arranged in a frame or structure 308 that is selectively moveable between an unexpanded or delivery configuration (i.e., as shown in FIG. 3A) and an expanded or deployed configuration (i.e., as shown in FIG. 3B) that may be used to position elongate members 304 against a tissue surface within the bodily cavity or position the elongate members 304 in the vicinity of or in contact with the tissue surface. In this regard, it may also be stated that the transducer-based device, or manipulable portion, 300 is selectively moveable between an unexpanded or delivery configuration (i.e., as shown in FIG. 3A) and an expanded or deployed configuration (i.e., as shown in FIG. 3B). In some embodiments, the transducer-based device, or manipulable portion, 300, (e.g., the structure 308 thereof) has a size, shape, or both a size and a shape in the unexpanded or delivery configuration suitable for percutaneous delivery through a bodily opening (for example, via catheter sheath 312, not shown in FIG. 3B) to the bodily cavity. In some embodiments, structure 308 has a size, shape, or both a size and a shape in the expanded or deployed configuration too large for percutaneous delivery through a bodily opening (i.e., via catheter sheath 312) to the bodily cavity. The elongate members 304 may form part of a flexible circuit structure (i.e., also known as a flexible printed circuit board (PCB) circuit). The elongate members 304 can include a plurality of different material layers, and each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. The number of elongate members depicted in FIG. 3B is non-limiting.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively moveable between a delivery configuration sized for percutaneous delivery and an expanded or deployed configuration sized too large for percutaneous delivery. In some embodiments, the flexible circuit structure 401 may be located on, or form at least part of, of a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415. FIG. 3B shows another example of electrode edges 315-1 and illustrates that the electrode edges can define electrically-conductive-surface-peripheries of various shapes.

Returning to FIG. 4, electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example.

Energy that is sufficient for tissue ablation may be dependent upon factors including tissue characteristics, transducer location, size, shape, relationship with respect to another transducer or a bodily cavity, material or lack thereof between transducers, et cetera.

In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form at least part of a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). In some embodiments in which the transducer-based device is deployed in a bodily cavity (e.g., when the transducer-based device 300 is part of a catheter system and may be arranged to be percutaneously or intravascularly delivered to a bodily cavity via a catheter), it may be desirable to perform various mapping procedures in the bodily cavity. For example, when the bodily cavity is an intra-cardiac cavity, a desired mapping procedure can include mapping electro-physiological activity in the intra-cardiac cavity. Other desired mapping procedures can include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

Referring to FIGS. 3A, 3B, transducer-based device or manipulable portion 300 may communicate with, receive power from, or be controlled by a control system 322. In some embodiments, elongate members 304 can form a portion of an elongated cable 316 of control leads 317, for example by stacking multiple layers, and terminating at a connector 321 or other interface with control system 322. The control leads 317 may correspond to the electrical connectors 216 in FIG. 2 in some embodiments. The control system 322 may include a controller 324 that may include a data processing device system 310 (e.g., data processing device system 110 from FIG. 1) and a memory device system 330 (e.g., memory device system 130 from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

In some embodiments, the controller 324 may be configured to control deployment, expansion, retraction, or other manipulations of the shape, positioning, or both shape and positioning of the transducer-based device (e.g., manipulable portion) 300 at least by driving (e.g., by an electric or other motor) movement of various actuators or other catheter system components described below, with respect to, e.g., FIGS. 5 and 7.

In this regard, in some embodiments, some of which are described later in this disclosure, the controller 324 is at least part of a control system, which may include one or more actuators, configured to advance at least part of the transducer-based device (e.g., 200, 300, 400, or 502), at least a portion of which may be considered a manipulable portion, out of the catheter sheath 312, retract at least part of the transducer-based device back into the catheter sheath 312, expand, contract, or otherwise change at least part of the shape of the transducer-based device.

Control system 322 may include an input-output device system 320 (e.g., an example of 120 from FIG. 1) communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a health care provider or technician. For example, output from a mapping process may be displayed on a display device system 332.

Control system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 may be fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 3A, the indifferent electrode 326 may be communicatively connected to the energy source device system 340 via one or more communication lines in some embodiments. In addition, although shown separately in FIG. 3A, indifferent electrode 326 may be considered part of the energy source device system 340 in some embodiments. In some embodiments, the indifferent electrode 326 is provided outside the body or at least the bodily cavity in which the transducer-based device (e.g., 200, 300, or 400) or catheter system 500 is, at least in part, located.

In some embodiments, the energy source device system 340 may include one or more driving motors configured to drive movement, in response to instructions from the controller 324, of various actuators or other catheter system components described, below, with respect to, e.g., FIGS. 5 and 7 to control deployment, expansion, retraction, or other manipulations of the shape, positioning, or both shape and positioning of the transducer-based device (e.g., manipulable portion) 300.

It is understood that input-output device system 320 may include other systems. In some embodiments, input-output device system 320 may optionally include energy source device system 340, transducer-based device 300 or both energy source device system 340 and transducer-based device 300 by way of non-limiting example.

Structure 308 of transducer-based device 300 can be delivered and retrieved through a catheter member, for example, a catheter sheath 312. In some embodiments, the structure 308 provides expansion and contraction capabilities for a portion of a medical device (e.g., an arrangement, distribution or array of transducers 306). The transducers 306 can form part of, be positioned or located on, mounted or otherwise carried on the structure and the structure may be configurable to be appropriately sized to slide within a lumen of catheter sheath 312 in order to be deployed percutaneously or intravascularly. FIG. 3A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 3A) and a second side edge 327b (only one called out in FIG. 3A). In some embodiments, each of the elongate members 304, including each respective intermediate portion 309, is arranged front surface 318a-toward-back surface 318b in a stacked array during an unexpanded or delivery configuration (e.g., FIG. 3A, 5G). In many cases, a stacked array allows the structure 308 to have a suitable size for percutaneous or intravascular delivery. A stacked array can allow structure 308 to have a spatially efficient size for delivery through a lumen of catheter sheath 312. In some embodiments, the elongate members 304 are arranged to be introduced into a bodily cavity distal end 305 first. For clarity, not all of the elongate members 304 of structure 308 are shown in FIG. 3A. A flexible catheter body or shaft 314 is used to deliver structure 308 through catheter sheath 312. In some embodiments, each elongate member includes a twisted portion proximate proximal end 307 (e.g., also FIG. 5B, discussed below).

In some embodiments, each of the elongate members 304 is arranged in a fanned arrangement 370 in FIG. 3B. In some embodiments, the fanned arrangement 370 is formed during the expanded or deployed configuration in which the transducer-based device (e.g., manipulable portion) 300 or structure 308 thereof is manipulated to have a size, shape, or both size and shape too large for percutaneous or intravascular delivery, for example a size, shape, or both size and shape too large for percutaneous or intravascular delivery toward a bodily cavity, or a size, shape, or both size and shape too large for percutaneous or intravascular delivery away from a bodily cavity. In some embodiments, the fanned arrangement 370 is formed during the expanded or deployed configuration in which the transducer-based device (e.g., manipulable portion) 300 or structure 308 thereof is manipulated to have a size, shape, or both size and shape too large for delivery through a lumen of catheter sheath 312, for example, a size, shape, or both size and shape too large for delivery through a lumen of catheter sheath 312 toward a bodily cavity, or a size, shape, or both size and shape too large for delivery through a lumen of catheter sheath 312 away from a bodily cavity.

In some embodiments, the transducer-based device (e.g., manipulable portion) 300 or structure 308 thereof includes a proximal portion 308a having a first domed shape 309a and a distal portion 308b having a second domed shape 309b when the transducer-based device (e.g., manipulable portion) 300 or structure 308 thereof is in the expanded or deployed configuration. In some embodiments, the proximal and the distal portions 308a, 308b include respective portions of elongate members 304. In some embodiments, the transducer-based device (e.g., manipulable portion) 300 or structure 308 thereof is arranged to be delivered or advanced distal portion 308b first into a bodily cavity when the transducer-based device (e.g., manipulable portion) 300 or structure 308 thereof is in the unexpanded or delivery configuration as shown in FIG. 3A. In some embodiments, the proximal and the distal portions 308a, 308b are arranged in a clam shell configuration in the expanded or deployed configuration shown in FIG. 3B. In various example embodiments, each of the front surfaces 318a (two called out in FIG. 3B) of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positioned adjacent an interior tissue surface of a bodily cavity in which the structure 308 (i.e., in the deployed configuration) is located. In various example embodiments, each of the back surfaces 318b (two called out in FIG. 3B) of the intermediate portions 309 of the plurality of elongate members 304 face an inward direction when the structure 308 is in the deployed configuration.

The transducers 306 can be arranged in various distributions or arrangements in various embodiments. In some embodiments, various ones of the transducers 306 are spaced apart from one another in a spaced apart distribution in the delivery configuration shown in FIG. 3A. In some embodiments, various ones of the transducers 306 are arranged in a spaced apart distribution in the deployed configuration shown in FIG. 3B. In some embodiments, various pairs of transducers 306 are spaced apart with respect to one another. In some embodiments, various regions of space are located between various pairs of the transducers 306. For example, in FIG. 3B the transducer-based device 300 includes at least a first transducer 306a, a second transducer 306b and a third transducer 306c (all collectively referred to as transducers 306). In some embodiments each of the first, the second, and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device 300 (i.e., a portion of an elongate member 304) is between the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter device. For example, an elongated catheter member may be used to distribute the transducers in a linear or curvilinear array. Basket catheters or balloon catheters may be used to distribute the transducers in a two-dimensional or three-dimensional array.

In some embodiments, a manipulable portion, such as, but not limited to, a transducer-based device (e.g., 200 or 300) is manipulated to transition between a delivery configuration (e.g., FIG. 3A) and an expanded or deployed configuration (e.g., FIG. 3B) manually (e.g., by a user's manual operation) or at least in part by way of motor-based driving (e.g., from the energy source device system 340) of one or more actuators or other catheter system components described, below, with respect to, e.g., FIGS. 5 and 7. Motor-based driving may augment or otherwise be in response to manual actions, may be responsive to automated control of a data processing device system (e.g., 110 in FIG. 1 or 310 in FIGS. 3A and 3B), or may use a hybrid manual-automated approach.

In this regard, each of the individual figures of FIG. 5 and FIG. 7 shows some or all of a catheter system 500, which includes a manipulable portion 502, according to various embodiments. In this regard, it should be noted that any of the catheter systems described herein may also be referred to as a medical system and, consequently, that catheter system 500 may be referred to as a medical system 500. In some embodiments, the manipulable portion 502 corresponds to the transducer-based device 200 or 300, although the manipulable portion 502 need not be a transducer-based device and may be some other form of catheter-based manipulable portion (e.g., a stent or other implant).

According to some embodiments, the catheter system 500 includes several different types of motions to control the deployment, retraction, positioning, size, and shape of the manipulable portion 502. These different types of motions may include coiling, uncoiling, fanning, un-fanning, bifurcated doming, flattening, clam shelling, or a combination of some or all of these motions. In some embodiments, these motions facilitate accommodation of different bodily cavity sizes (e.g., different atrium sizes), as well as proper positioning of the manipulable-portion within the bodily cavity (e.g., atrium) and contact with one or more tissue walls of the bodily cavity.

With respect to these types of motions, for example, deployment of the manipulable portion 502 may involve a coiling of the manipulable portion 502 by way of a built-in predisposition of the manipulable portion 502 to autonomously coil when released from the confines of a catheter sheath 512 or some other confining member, by way of a control element 513 (e.g., a cable 513b), or by way of both autonomous coiling and a control element. See, e.g., the sequence of FIGS. 5H, 5I, and 5J, discussed in detail below. In some embodiments, the control element (e.g., cable 513b) is physically coupled to the manipulable portion 502 (e.g., at least proximate to a distal end 505a thereof) to transmit force to the manipulable portion and to control a positioning of at least part of the manipulable portion 502 during coiling. Uncoiling of the manipulable portion 502 during retraction is described in more detail below, with respect to at least the sequence of Figures of 5J, 5I, and 5H. Such uncoiling may occur by way of a control element 513 (e.g., a cable 513b), by way of a containment force applied by the catheter sheath 512 or some other confining member as the manipulable portion 502 is retracted into the catheter sheath 512 or other confining member, or by way of both a control element and a containment force of a confining member into which the manipulable portion 502 is retracted.

In some embodiments, the coiling/uncoiling motion during deployment/retraction of the manipulable portion 502 is caused and controlled, at least in part, by activation or movement of a second particular actuator 540b and an internal receiving mechanism 546 with respect to a first particular actuator 540a, which may act as an anchor in some configurations. In some embodiments, the coiling/uncoiling motion during deployment/retraction involves a metering of a portion of the control element 513 (e.g., a cable 513b) with different rates under the control of a master slider 556a, a sleeve slider 556b, and the second particular actuator 540b, which are described in more detail, below, with respect to at least FIGS. 7A and 7B.

In some embodiments, once the manipulable portion 502 is extended outside of the distal end 512b of the catheter sheath 512, as shown, for example, at least in FIGS. 5L-1 and 5L-2, the manipulable portion 502 may be fanned, or additionally fanned, as shown in FIGS. 5M-1 and 5M-2 by action of a sliding actuator 572, of which a cover 520a is a part, which are described in more detail, below, with respect to at least FIGS. 5S-1 and 5S-2. Un-fanning of the manipulable portion 502 to return the manipulable portion 502 back into a retraction-ready shape may also be controlled by the sliding actuator 572, as described in more detail, below.

In some embodiments, at least when the manipulable portion 502 is fanned, different portions 508a, 508b (e.g., hemispheres in some embodiments) of the manipulable portion 502 may be controlled to have different domed shapes. This type of motion may be referred to as bifurcated doming and is described in more detail, below, with respect to FIGS. 5M-1 and 5M-2, for example. This type of motion may be controlled by positioning of cover 520a, described in more detail, below, with respect to FIGS. 5S-1 and 5S-2, for example. FIGS. 5N-5Q, discussed below, also illustrate different domed shapes to which the manipulable portion 502 may be controlled to have, according to some embodiments.

In some embodiments, at least when the manipulable portion 502 is fanned, the manipulable portion 502 may be flattened, as described in more detail, below, with respect to FIGS. 5N and 5O. In some embodiments, this flattening motion may be caused and controlled by activation or action of the first particular actuator 540a, which is described in more detail, below, with respect to FIGS. 5S, 7A, and 7B.

In some embodiments, at least when the manipulable portion 502 is fanned, the manipulable portion 502 may be subjected to clam shelling as described in more detail, below, with respect to FIGS. 5P and 5Q. In some embodiments, this clam shelling may be caused and controlled by activation or action of the second particular actuator 540b, which is described in more detail, below, with respect to FIGS. 5S, 7A, and 7B.

Now, each of the figures of FIG. 5 (collectively referred to as "FIGS. 5") will be described. FIG. 5 illustrate various views of various aspects of medical systems or catheter systems, according to various embodiments. In this regard, the systems of FIG. 5 (as well as the other remaining figures) may be particular implementations of the systems of FIGS. 2 and 3, according to some embodiments. Accordingly, descriptions herein regarding the systems of FIGS. 2 and 3 apply to the systems of FIG. 5 (as well as the other remaining figures), according to some embodiments.

As shown in FIG. 5A, catheter system 500 includes various devices including a catheter shaft member 500a (also referred to as shaft member 500a) and, in some embodiments, a catheter sheath member 500b (also referred to as sheath member 500b). Shaft member 500a includes a shaft 510 (e.g., the same or similar to catheter body 314) that includes a proximal end 510a, a distal end 510b, and an intermediate or elongated portion 510c extending between the proximal end 510a and the distal end 510b (e.g., extending along a path that connects proximal end 510a and distal end 510b). In some embodiments associated with various ones of FIG. 5, the manipulable portion 502 is located at least proximate the distal end 510b.

Catheter sheath member 500b includes a catheter sheath 512 (e.g., the same or similar to sheath 312) that includes proximal end 512a, a distal end 512b and a body portion 512c between the proximal end 512a and the distal end 512b. In various embodiments, catheter sheath 512 includes one or more lumens, each of at least some of the one or more lumens extending between proximal end 512a and distal end 512b (e.g., extending along a path that connects proximal end 512a and distal end 512b). In various embodiments associated with various ones of FIG. 5, catheter sheath 512 includes a first lumen 512d extending between (or connecting, in some embodiments) proximal end 512a and distal end 512b. Catheter sheath member 500b is provided in various embodiments to provide a passageway for at least a portion of shaft member 500a (e.g., a part of shaft 510) to be delivered therethrough to a location within a body during a medical procedure. In some embodiments, catheter sheath member 500b is deployed percutaneously or intravascularly into a body. In this regard, it may be stated that at least part of the shaft 510 is sized for percutaneous delivery to the bodily cavity. In various embodiments, at least a portion of catheter sheath member 500b (e.g., at least a portion of the catheter sheath 512) is delivered distal end 512b first through a naturally occurring bodily opening toward a bodily cavity. For instance, the catheter sheath 512 may be receivable in, insertable into, or positionable in a bodily opening. In some of these various embodiments, the bodily opening is accessed by a natural orifice or port provided by the body. In some of these embodiments, the bodily opening is accessed by a perforation made in bodily tissue. In various embodiments, a portion or part of shaft member 500a (e.g., at least part of the shaft 510) is received in, receivable in, or sized for delivery through the first lumen 512d of the catheter sheath 512 to a bodily cavity or to deliver the manipulable portion 502 through the first lumen 512d of the catheter sheath 512 to a bodily cavity (e.g., a bodily vessel, chamber or cavity within a bodily organ). In this regard, in some embodiments, at least the distal end 510b of the shaft 510 is sized for delivery through a bodily opening leading to a bodily cavity located in a body. It is understood that, although each of shaft 510 and catheter sheath 512 is depicted in FIG. 5A in an essentially straight configuration, each of shaft 510 (or at least part of the shaft 510 receivable in the lumen 512d of the catheter sheath 512) and catheter sheath 512 may be flexible or bendable or may include one or more flexible or bendable portions that that allow bending or deflection or the assumption of a bent or curved (e.g., arcuate) form, e.g., during or for delivery to a bodily cavity. In various embodiments, shaft member 500a is arranged with respect to catheter sheath member 500b such that the distal end 510b of shaft 510 is configured, arranged, or sized to be delivered through the first lumen 512d of the catheter sheath 512 prior to at least the elongated portion 510c of the shaft 510, when the distal end 510b of shaft 510 is delivered toward or to the bodily cavity. In various embodiments, shaft member 500a is arranged with respect to catheter sheath member 500b such that the distal end 510b of shaft 510 is configured, arranged, or sized to be delivered through the first lumen 512d of the catheter sheath 512 in a direction extending from the proximal end 512a of catheter sheath 512 toward the distal end 512b of catheter sheath 512 when the distal end 510b of shaft 510 is delivered toward or to the bodily cavity.

In various embodiments, the manipulable portion 502 includes a proximal end 501a (e.g., in the vicinity of elongate member proximal ends 507 in FIG. 5G), a distal end 501b (e.g., in the vicinity of elongate member distal ends 505 in FIG. 5G), and an elongated part 501c (e.g., FIG. 5G) extending between the proximal end 501a and the distal end 501b of the manipulable portion 502. In some embodiments, the manipulable portion is delivered and advanced outwardly, e.g., distal end 501b first with respect to or as compared to other parts of the manipulable portion 502, through the first lumen 512d of the catheter sheath 512 toward or to the bodily cavity as the shaft 510 is advanced accordingly through first lumen 512d. It is noted that each of shaft 510 and catheter sheath 512 has a respective elongated portion that can have longitudinal or axial components. For example, the shaft 510 has a longitudinal length 510d extending between the respective proximal end 510a and distal end 510b, according to some embodiments. Similarly, the sheath 512 has a longitudinal length 512f extending between the respective proximal end 512a and distal end 512b, according to some embodiments. As used in this disclosure, words such as "longitudinal" or "axial" are not limited to various members having generally straight forms but can include members that have bent or arcuate forms or forms that have been bent from a generally straight form into a generally non-straight form.

In various embodiments, manipulable portion 502 is selectively configurable or moveable, e.g., based at least upon user (e.g., a health care provider, technician, or other user) input (e.g., by way of actuators 540a, 540b, or 546 described with respect to FIG. 7, below, by way of actuator 572 described with respect to FIG. 5S, below, or by relative movement of the shaft 510 and catheter sheath 512) or other sensory input (e.g., from sensors in the input-output device system 120 of FIG. 1), into various configurations. For example, in some embodiments, the manipulable portion 502 may form at least part of a steerable portion of shaft member 500a. Catheter devices employing steerable portions may be used to better negotiate tortuous paths sometimes encountered during delivery to a bodily cavity. Catheter devices employing steerable portions may be employed to better achieve a desired positioning of various devices (e.g., implants or transducer systems). In some embodiments, the manipulable portion 502 may be selectively detachable from the shaft member 500a. For example, the manipulable portion 502 may, in some embodiments, form part of an implant (e.g., a stent). In some of these embodiments, an implant provided at least in part by the manipulable portion 502 may be selectively configurable or moveable (e.g., by way of a modulation or other actuator described in this disclosure) between a delivery configuration in which the implant is appropriately sized for delivery through the first lumen 512d toward or to a particular location in the bodily opening or bodily cavity and a deployed configuration in which the implant is sized too large for delivery through the first lumen 512d toward or to the particular location in the bodily opening or bodily cavity. In some of these embodiments, the implant may be positioned in the deployed configuration when implanted or otherwise brought into engagement with tissue (e.g., a stent that is selective expanded to grip or to otherwise be secured within a bodily vessel).

In some embodiments associated with various ones of FIG. 5, manipulable portion 502 forms a part of a transducer-based device (e.g., 200, 300) with various sets of one or more transducers located on, or forming part of the manipulable portion 502. For example, in some embodiments, manipulable portion 502 includes a structure 502a (e.g., the same or similar to structure or frame 308) and various transducers 506 (not shown for clarity in FIG. 5A, but may be the same or similar to transducers 220, 306, 406) that are located on or carried by a surface of the manipulable portion 502 or the structure 502a thereof. In a manner that is the same or similar to other embodiments described above in this disclosure, manipulable portion 502 or structure 502a is selectively configurable or moveable (e.g., by way of a modulation or other actuator described in this disclosure) between a delivery configuration in which at least the structure 502a is appropriately sized, shaped, or both sized and shaped for delivery through the first lumen 512d of the catheter sheath 512 at least toward or to a bodily cavity located in a body and an expanded or deployed configuration in which at least the structure 502a is sized, shaped, or both sized and shaped too large for delivery through the first lumen 512d of the catheter sheath 512 at least toward or to the bodily cavity. In various embodiments, the manipulable portion 502 or structure 502a thereof is physically coupled to the shaft 510 at a location at least proximate the distal end 510b of the shaft 510. In this regard, the manipulable portion 502 or structure 502a thereof may include a plurality of elongate members 504 (two called out in FIG. 5A) that are physically coupled to shaft 510, which is employed to transport the elongate members 504 through first lumen 512d when the structure 502a is in a delivery configuration. The number of elongate members 504 shown in various ones of FIG. 5 is non-limiting. An enlarged view of the manipulable portion 502 illustrated in FIG. 5A is shown in FIG. 5C, which is described in more detail below.

FIG. 5B is an isometric view of a representative one of the elongate members 504 in an initial or predisposed configuration as employed in some embodiments. Various dimensions of the representative one of the elongate member 504 have been exaggerated for clarity in FIG. 5B. Each of the elongate members 504 includes a respective first or distal end 505 and a respective second or proximal end 507. Each intermediate portion includes a respective length between the respective proximal and distal ends 507, 505 of the elongate member 504. Each elongate member 504 includes a respective length between the respective proximal and distal ends 507, 505 of the elongate member 504. In various embodiments, two or more of the elongate members 504 may have substantially equal lengths or substantially unequal lengths. In various example embodiments, a respective portion of each of the elongate members 504 has a length that is at least approximately equal to or greater than a circumference of a portion of an interior tissue surface of a bodily cavity into which the elongate member 504 is to be positioned at least proximate to when the manipulable portion 502 is in an expanded or deployed configuration. The circumference of the portion of the interior tissue surface may have a measured or anticipated value. In a manner that is the same or similar to other described embodiments, a set of transducer elements 506 (two called out) are distributed along a surface (e.g., surface 518a) of each of various ones of the elongate members 504. In some example embodiments, each elongate member 504 includes at least a portion of a flexible circuit structure (e.g., the same or similar to that employed by embodiments of FIG. 4) that at least provides an electrically communicative path to various ones of the transducer elements 506.

In various embodiments, each of the elongate members 504 includes a plurality of various portions including first portion 509a, second portion 509b, and third portion 509c (collectively portions 509) arranged between the respective proximal and distal ends 507, 505 of the elongate member 504. The second portion 509b, which may be considered an intermediate portion of the respective elongate member 504, may be positioned between the first (e.g., distal) end 505 and the second (e.g., proximal) end 507 of the respective elongate member 504. In some embodiments, each intermediate portion 509b includes a set of two opposing major faces or surfaces 518 denominated as a front surface 518a and a back surface 518b in FIG. 5B. The two opposing surfaces 518 may be separated from one another by a thickness 517 of the elongate member 504, such that the back surface 518b is opposite across the thickness 517 from the front surface 518a. In some embodiments, each of one or more of portions 509 may be considered an intermediate portion of the respective elongate member 504. In FIG. 5B, the third portion 509c, positioned between the first and the second portions 509a, 509b, and first portion 509a is located along the elongate member 504 relatively closer to proximal end 507 than to distal end 505, and the second portion 509b is located along the elongate member 504 relatively closer to distal end 505 than to proximal end 507. In various embodiments, the various portions 509 are combined in a unitary structure. In various embodiments, a number of the respective portions 509 of various ones of the elongate members 504 include various distortions or deformations. As used in reference to this context, the words "distortion" or "deformation" are used interchangeably herein to mean modification in shape away from an elongated strip-like form that, prior to any distortion or deformation, was predominately a body with a relatively small thickness as compared to a length or width, although major faces of the body may not necessarily have smooth planar surfaces. For example, the respective second portion 509b of the representative elongate member 504 shown in FIG. 5B has a coiled profile (e.g., a profile that curves or curls back on itself). In this particular embodiment, the respective second portion 509b includes a volute shaped profile in the initial or predisposed configuration. Also for example, the respective third portion 509c of the representative elongate member 504 shown in FIG. 5B includes a twisted profile about a respective twist axis 533 extending across at least part of the third portion 509c of the elongate member 504, the twist in the third portion 509c arranged to rotationally offset (e.g., angularly rotated or twisted out of plane about an axis that may extend generally along a length of the elongate member prior to any distortion of deformation thereof) the respective second portion 509b of the elongate member 504 from the respective first portion 509a of the elongate member 504 along a portion of the length of the elongate member 504. In this example embodiment of FIG. 5B, the respective first portion 509a of the representative elongate member 504 includes a bent profile about a respective bending axis 531. It is understood that the number of elongate members 504 employed by the various embodiments of manipulable portion 502 associated with various ones of FIG. 5 is non-limiting.

In FIGS. 5A, 5B, and 5C, each of the elongate members 504 is arranged in an arrangement having an initial or predisposed configuration in which each elongate member 504 is provided essentially in its distorted form. In various embodiments, the initial or predisposed configuration is associated with an initial, low, or lowest (potential) energy state. In various embodiments, each elongate member 504 is a resilient member and further distortion of various portions 509 of the elongate member 504 can increase spring or potential energy of the elongate member 504 and thereby bring it into a higher energy state. The (a) bent profiles of the respective first portions 509a, (b) the twisted profiles of the respective third portion 509c, or both (a) and (b) of various ones of the elongate members 504 in the initial or predisposed configuration may be arranged to fan or partially fan at least the respective second portions 509b of various ones of elongate members 504 into a fanned array as shown, for example, in FIG. 5C. It is noted, however, that various fanning angles 519 (only one called out in FIG. 5C) may be achieved between a respective pair of the first and the second portions 509a, 509b by positional adjustments of the twist axis 533, according to some embodiments.

In some embodiments, various ones of the elongate members 504 are physically or operatively coupled with at least one other elongate member 504 by at least one coupler. In FIG. 5C, at least one coupler is arranged to couple at least the respective first portions 509a of the elongate members 504 together in the initial configuration. Various couplers may be employed in these embodiments. For example, in embodiments where each of various ones of the elongate members 504 includes a flexible printed structure having a relatively large number of electrically conductive traces, a coupler that couples at least the side edges of the first portions 509a may be well suited to avoid imposing undesired space constraints on the placement of the electrically conductive traces. In various example embodiments, additional couplers may also be employed to couple various other portions (e.g., portions 509) of various ones of the elongate members 504 together. In this regard, as shown in FIG. 5C, a control cable 513b passes through openings at distal end portions of the elongate members 504 to operatively couple such distal end portions of elongate members 504 in some embodiments. A coupling system like that illustrated by control cable 513b in FIG. 5C may be used to couple other portions (e.g., various portions 509) of elongate members 504 in some embodiments.

Referring back to FIG. 5A, in various embodiments, the intermediate or elongated portion 510c of the shaft 510 has a length 510d extending between the proximal end 510a and the distal end 510b of shaft 510. The length 510d may be sized to position the proximal end 510a at a location outside of a body when the distal end 510b (or the manipulable portion 502) is located in a bodily cavity within the body. In various embodiments associated with FIG. 5, a housing 520 of the shaft member 500a is physically or operatively coupled to shaft 510 at a location at least proximate the proximal end 510a of the shaft 510, the proximal end 512a of the catheter sheath 512, or both (e.g., at a location outside a body when the manipulable portion 502 is positioned at a desired location within a bodily cavity located in the body).

One or more control systems (e.g., one or more components of control system 322, control system 545, or both control system 322 and control system 545 described in this disclosure) may be provided by housing 520 (e.g., in, on, or both in and on housing 520). In this regard, the housing 520 may be referred to as a control system housing. Such housing 520 may be located at least proximate the proximal end 510a of the shaft 510.

Various actuator sets described in this disclosure may be provided by housing 520 (e.g., in, on, or both in and on housing 520). For example, in some embodiments, at least (a) some of the shaft 510 (e.g., at least part of the proximal end 510a of the shaft 510), (b) some of the control element 513, (c) some of one or more of the actuators described herein with respect to FIGS. 5R, 5S, 5W, 7, 8, and 10, (a) and (b), (a) and (c), (b) and (c), or (a), (b), and (c) may be enclosed within the housing 520. The various actuator sets may, by way of non-limiting example, be part or all of such control system(s) and be configured to control or modulate, in response to user or other input, a size, shape, or both size and shape of various configurations of manipulable portion 502 (e.g., delivery and expanded or deployed configurations). One or more of the various actuator sets may be referred to as an actuator system, such that, for example, the actuator system is located, at least in part, in the housing 520. An actuator system may, by way of non-limiting example, be operatively coupled to the manipulable portion 502 and configured to move or transition, in response to or under the control of user or other input, manipulable portion 502 between various configurations (e.g., delivery and expanded or deployed configurations). The actuator system may, by way of non-limiting example, be configured to control, in response to or under the control of user or other input (e.g., from a control system such as controller 324 or data processing device system 110), various control elements employed by catheter system 500. For example, at least some of these control elements may be controlled, e.g., by user or otherwise (e.g., from a control system such as controller 324 or data processing device system 110) to selectively provide (a) a desired amount of force outputted by an actuator in the actuator system, (b) a desired duration of a force outputted by an actuator in the actuator system, or both (a) and (b) to manipulable portion 502.

Control elements may include, by non-limiting example, control rods, control lines, control cables, Bowden cables, other force transmission components configured or arranged to selectively deliver force or energy outputted by an actuator to a particular device or structure (e.g., manipulable portion 502). In some embodiments, a control element forms part of a bending system that operates on the manipulable portion 502 to bend at least some of the manipulable portion 502. For example, the control element may be employed to transmit a bending force to the manipulable portion 502 to bend at least a part thereof.

In some embodiments, an actuator system includes at least a portion of one or more of the various actuators described herein (e.g., with respect to at least any one of the figures in FIGS. 5R, 5S, 5W, 7, 8, and 10). In this regard, in embodiments where the actuator system is controlled by a control system (e.g., from a control system such as controller 324 or data processing device system 110), such control system is operatively coupled to the actuator system, for example, to control motion or other activation of at least a portion of the one or more of the actuators in the actuator system.

In various embodiments, housing 520 includes a cover 520a that is moveable along a surface of housing 520 to provide access to an interior portion of housing 520. In some of these various embodiments, cover 520a is moveable to provide access (e.g., user access) to various actuators associated with housing 520. In various embodiments, housing 520 may be directly handled by a user during a medical procedure in which catheter system 500 is employed. As shown in FIG. 5A, housing 520 may include at least part of an electrical coupling 521 which may in some embodiments allow for data, power, or both data and power communication with various transducers (e.g., transducers 506). Electrical coupling 521 may allow for electrical communication with (a) a controller (e.g., controller 324 or data processing device system 110) or (b) an energy source device system (e.g., energy source device system 340) or both (a) and (b).

As best shown in FIG. 5C, shaft 510 can include, in various embodiments, one or more lumens extending between the proximal end 510a (not shown in this figure) and the distal end 510b of shaft 510, the one or more lumens including at least a second lumen 511 (to be distinguished from the first lumen 512d of the catheter sheath 512). In various embodiments at least one control element is provided in the second lumen 511. For example, an elongated control element 513 is provided in second lumen 511 in FIG. 5C. In embodiments where the shaft 510 is within the first lumen 512d of the catheter sheath 512, the control element 513 within the second lumen 511 of the shaft 510 may also be considered to be within the first lumen 512d of the catheter sheath 512, because the shaft 510 is within the catheter sheath 512 in these embodiments. It is understood that additional or alternate control elements may be received in the second lumen 511 in other embodiments.

In various embodiments, control element 513 is physically coupled to the manipulable portion 502 to transmit force to the manipulable portion and includes multiple components or portions. For example, in FIG. 5C, control element 513 includes a sleeve 513a and a control cable 513b located, at least in part, in a lumen of the sleeve 513a. The control cable 513b may be physically coupled to the manipulable portion 502 to transmit force to the manipulable portion. Each of the cable 513b and the sleeve 513a may be located, at least in part, in the lumen 511 of the shaft 510. In some embodiments, sleeve 513a and cable 513b (and any sleeve and cable of a Bowden cable described herein) are moveable independently or separately with respect to one another to allow (a) the sleeve 513a to move independently or separately from the cable 513b to cause the sleeve 513a to slide over the cable 513b (e.g., during a first manipulation of the manipulable portion 502 to change a size, shape, or both thereof), and to allow (b) the cable 513b to move independently or separately from the sleeve 513a to cause the cable 513b to slide through the lumen of the sleeve 513a (e.g., during a second manipulation of the manipulable portion to change a size, a shape, or both thereof). This can occur, for example, when the at least a portion of the cable 513b received in the lumen of the sleeve 513a is translated in a direction that the lumen of the sleeve 513a extends along. In some embodiments, a portion of cable 513b and a portion of sleeve 513a are each translated concurrently (for example, in a direction that a portion of the lumen of the sleeve 513a extends along). In some embodiments, cable 513b is provided by a flexible control line (e.g., a flexible control line having a polymeric, metallic, or composite composition). In this regard, the control element 513 may be considered a flexible control element in some embodiments. In some embodiments, sleeve 513a is also flexible and can be bent (i.e., elastically or plastically) to have an arcuate form. In various embodiments, sleeve 513a comprises sufficient axial stiffness to withstand a particular compressive force, for example created by a tensioning of cable 513b. In various embodiments, sleeve 513a has a polymeric, metallic or composite composition. For example, the present inventors have employed thin-walled stainless steel tubing in some embodiments.

In some embodiments, sleeve 513a and cable 513b form part of a Bowden cable. A Bowden cable is a generally flexible cable used to transmit force by the movement of an inner cable relative to a hollow outer cable housing (also sometimes referred to as a sleeve or sheath). The housing may be generally of composite construction, for example a tightly helically wound metallic wire sometimes lined with a friction reducing polymer. Typically, a first part of the cable extends outwardly from a first end of the sleeved housing, and a second part of the cable extends outwardly from a second end of the sleeved housing. The translational movement of the inner cable is most often used to transmit a pulling force, although push/pull cables are also employed. The cable housing provides the Bowden cable with compressive strength to resist buckling during a tensioning of the inner cable. The cable housing maintains a fixed separation with respect to the length of the inner cable so that displacing the inner cable relative to one end of the cable housing results in an equal displacement at the other end, regardless of the cable's path in-between. In FIG. 5C a portion 514 of cable 513b (i.e., also called part 514 in some embodiments) of elongated control element 513 extends or is located outwardly from an end 513a-1 of sleeve 513a and is physically coupled to the manipulable portion 502 at least by being physically coupled to one or more of the elongate members 504. In this regard, cable 513b (an example of a control element or an elongated control element) includes a distal end positionable outside of the distal end 512b of the catheter sheath 512 when a particular amount of the manipulable portion 502 is located outside of the distal end 512b of the catheter sheath 512. In embodiments such as those illustrated by FIG. 5C, cable 513b extends through a respective opening provided near the distal end 505 (not called out in FIG. 5C) of each of a majority of the elongate members 504 and terminates near the distal end 505 of another of the elongate members 504. In some embodiments, this arrangement couples distal end portions of the elongate members 504 and allows the distal ends 505 of the elongate members 504 to be drawn together in a purse string-like manner. In various embodiments, both the sleeve 513a and the cable 513b extend through the second lumen 511 to housing 520 (not shown in FIG. 5C). In various embodiments, (e.g., as described later in this disclosure) each of the sleeve 513a and the cable 513b extends through the second lumen 511 to a respective actuator provided by housing 520, which, in some embodiments, couples at least one of the respective actuators to the manipulable portion 502. In some embodiments, each of these respective actuators is operable to move a respective one of the sleeve 513a and the cable 513b independently or separately of the other of the sleeve 513a and the cable 513b. In some embodiments, each of these respective actuators is operable to move a respective one of the sleeve 513a and the cable 513b independently or separately of the other of the sleeve 513a and the cable 513b to cause translational movement of a portion of the cable 513b through a portion of the sleeve 513a or to cause translational movement of a portion of the sleeve 513a over a portion of the cable 513b. In FIG. 5C, cable 513b may be in a slackened configuration or a configuration having limited tension imposed on the cable 513b when the manipulable portion 502 is in the initial configuration.

In various embodiments, the body portion 512c of catheter sheath 512 has a length 512f (e.g., FIG. 5A) extending between the proximal end 512a and the distal end 512b and sized and dimensioned to position manipulable portion 502 at a desired location outwardly from the distal end 512b, when the shaft 510 has delivered the manipulable portion 502 through the first lumen 512d (i.e., along a path extending from the proximal end 512a toward the distal end 512b of catheter sheath 512), such that the proximal end 510a of the shaft 510 is positioned at a desired location with respect to the proximal end 512a of the catheter sheath 512. Positioning indicia set 523a may be provided on a visible surface of the elongated portion 510c of shaft 510 proximate the proximal end 510a, to provide a user with a visual indication of a distance between a location on the shaft 510 (e.g., proximal end 510a) and a location on the sheath 512 (e.g., the proximal end 512a) as the two locations are advanced with respect to one another to reduce a distance therebetween (for example, during an advancement of manipulable portion 502 toward a bodily cavity as the manipulable portion 502 is moved through first lumen 512d). Positioning indicia set 523b may be provided on a visible surface of the elongated portion 510c of shaft 510 proximate the distal end 510b, to provide a user a visual indication of a distance between a location on the shaft 510 (e.g., the distal end 510b) and a location on the sheath 512 (e.g., the proximal end 512a) as the two locations are advanced with respect to one another to increase a distance therebetween (for example during a retraction of manipulable portion 502 away from a bodily cavity as the manipulable portion 502 is moved through first lumen 512d).

The positioning indicia sets 523a and 523b can visually indicate a magnitude of their respective shaft 510-to-catheter sheath 512 spacing in various ways. For example, in some embodiments associated with FIG. 5A, the spacing between successive pairs of indicia in each one of the respective sets 523a, 523b is reduced (i.e., as compared to the pair of indicia immediately preceding the successive pair) to indicate a reduction in the magnitude of the respective shaft 510-to-catheter sheath 512 distance. The positioning indicia sets 523a, 523b can be employed by a user to determine an approach of an end-of-travel condition between the shaft 510 and the catheter sheath 512.

In some embodiments, catheter sheath 512 includes a steerable portion 512e. In FIG. 5A, steerable portion 512e is located at least proximate to distal end 512b but may be located at other locations in other embodiments. The steerable portion can be caused to bend or deflect in a desired manner by user or other (e.g., data processing device system) operation of a catheter sheath actuator 516. Steering of the steerable portion 512e may be motivated by various reasons including assisting delivery of the catheter sheath 512 through a bodily opening extending along a tortuous path to the bodily cavity. Various suitable catheter sheath steering mechanisms are known in the art and are not elaborated in further detail in this disclosure. In some embodiments, catheter sheath 512 includes a flushing portion 524 that includes various ports 524a, 524b configured to provide an inlet or outlet, or both an inlet and outlet for a fluid (e.g., saline) to be introduced to reduce occurrences of gas (e.g., air) that may be present or sometimes entrapped within first lumen 512d. In some embodiments, flushing portion 524 is detachable from catheter sheath 512. In various embodiments, an extension or projection 528 extends from a location proximate a first one of the proximal end 512a of catheter sheath 512 and the proximal end 510a of shaft 510. In some embodiments, projection 528 extends beyond the first one of the proximal end 512a of catheter sheath 512 and the proximal end 510a of shaft 510 at least when a part of the shaft 510 is received in first lumen 512d.

In some embodiments, projection 528 extends outwardly from the first one of the proximal end 512a of catheter sheath 512 and the proximal end 510a of shaft 510 toward one of the proximal end 512a of catheter sheath 512 and the proximal end 510a of shaft 510 other than the first one, at least when part of the shaft 510 is received in first lumen 512d. In some embodiments, a receiver 529 located, at least in part, in the housing 520, and sized to matingly receive at least a portion of the projection 528, is provided at a location proximate a second one of the proximal end 512a of catheter sheath 512 and the proximal end 510a of shaft 510. In some of these various embodiments, the projection 528 and the receiver 529 are configured to matingly engage at least when a first amount of part of the shaft 510 is received in the first lumen 512d of the catheter sheath 512, but to not matingly engage at least when a second amount of the part of the shaft is received in the lumen of the catheter sheath, the second amount being a non-zero amount in some embodiments. For example, projection 528 may form part of a male component while receiver 529 forms part of a female component sized to mate with the male component. In some embodiments, the projection 528 and the receiver 529 are configured or arranged to additionally matingly engage the catheter member 512 to the shaft 510 at least when part of the shaft 510 is matingly received in the first lumen 512d of the sheath 512. In various embodiments, the projection 528 includes a length (e.g., a longitudinal length) that extends from a location at least proximate the first one of the proximal end 512a of the catheter sheath 512 and the proximal end 510a of the shaft 510 to an end 528b of the projection 528, the end 528b of the projection 528 configured to be received first in the receiver 529, as compared to other parts of the projection 528 when the projection 528 is inserted into receiver 529. In various embodiments, projection 528 has a length 528a (called out in FIG. 5D) that is different than the longitudinal length 510d of the shaft 510. In this regard, in some embodiments, the longitudinal length 510d of the shaft 510 is greater than the longitudinal length 528a of the projection 528.

It is noted that in some embodiments, the first one of the proximal end 512a of catheter sheath 512 and the proximal end 510a of shaft 510 is a same one as the second one of the proximal end 512a of catheter sheath 512 and the proximal end 510a of shaft 510 (for example, when projection 528 and receiver 529 are integrated into or form part of a plunger assembly located on one of the shaft 510 (or shaft member 500a) and the catheter sheath 512 (or catheter sheath member 500b). FIGS. 5T, 5U, and 5V are various side elevation views of a catheter system 501 comprising a shaft 510-1 physically coupled to a housing 520-1, the shaft 510-1 sized and dimensioned for insertion into a lumen of a catheter sheath 512-1 according to some embodiments. In particular, FIGS. 5T, 5U, and 5V show a positioning of shaft 510-1 into the lumen of catheter sheath 512-1 at three successive points in time (from FIG. 5T to FIG. 5V, or vice versa). Catheter system 501 includes a plunger assembly 530 that includes a projection 528-1 received in a receiver 529-1, each of the projection 528-1 and receiver 529-1 provided at least in part in housing 520-1 (i.e., shown partially sectioned) at a location proximate a proximal end 510a-1 of the shaft 510-1. In FIG. 5T, shaft 510-1 has been inserted into the lumen of catheter sheath 512-1 by an amount insufficient to cause an end of projection 528-1 to engage with the catheter sheath 512-1 (e.g., at a location proximate a proximal end 512a-1 of the catheter sheath 512). As the amount of the shaft 510-1 inserted into the lumen of catheter sheath 512 increases, the distance between the proximal end 512a-1 of catheter sheath 512-1 and the proximal end 510a-1 of the shaft 510-1 decreases and causes engagement between the projection 528-1 and the catheter sheath 512-1 to occur. As the amount of the shaft 510-1 inserted into the lumen of catheter sheath 512 increases, the distance between the proximal end of catheter sheath 512-1 and the proximal end 510a-1 of the shaft 510-1 decreases and causes increasing amounts of projection 528-1 to be received in receiver 529-1 as shown in FIGS. 5U and 5V. In some embodiments, a biasing device such as a spring provides a restoring force sufficient to move projection 528-1 to its extended configuration as the distance between the proximal end of catheter sheath 512-1 and the proximal end 510a-1 of the shaft 510-1 increases.

In other embodiments, the first one of the proximal end 512a of catheter sheath 512 and the proximal end 510a of shaft 510 (i.e., the "first one" being the end proximate the location from which the extension or projection 528 extends) is different than the second one of the proximal end 512a of catheter sheath 512 and the proximal end 510a of shaft 510 (i.e., the "second one" being the end proximate the location at which the receiver 529 is provided). For example, in some embodiments associated with FIG. 5A, the projection 528 is located at least proximate the proximal end 512a of catheter sheath 512, the projection 528 sized and dimensioned to be matingly received in at least a receiver 529 provided, in some embodiments, at a location at least proximate the proximal end 510a of shaft 510 (e.g., in the housing 520 in FIG. 5A) at least when a part of shaft 510 is received in first lumen 512d. In some of the embodiments associated with FIG. 5A, a longitudinal axis of the first lumen 512d (e.g., when catheter sheath 512 assumes a straightened form) is not coaxial with a longitudinal axis of first projection 528. In some of the embodiments associated with FIG. 5A, a longitudinal axis of the first lumen 512d (e.g., when catheter sheath 512 assumes a straightened form) is not coaxial with a longitudinal axis along which projection 528 is moveable within receiver 529. In some of the embodiments associated with FIG. 5A, the manipulable portion 502 is arranged to not be inserted into the receiver 529 when the manipulable portion 502 is delivered though first lumen 512d of the catheter sheath 512, e.g., to a bodily cavity. In some embodiments, the receiver 529 and first lumen 512d may be coaxially arranged when the manipulable portion 502 is delivered outwardly from the distal end 512b of catheter sheath 512. In some embodiments, the projection 528 is coupled to, or forms part of, shaft member 500a. In some embodiments, the receiver 529 is coupled to, or forms part of, sheath member 500b. In some embodiments, the projection 528 is distinct from shaft member 500a.

FIGS. 5D, 5E, and 5F are various side elevation views of a positioning of shaft 510 into the first lumen 512d (not called out in these figures) of catheter sheath 512 at three successive points in time (from FIG. 5D to FIG. 5F, or vice versa). At least one portion of the catheter system 500 (e.g., manipulable portion 502, not shown in FIGS. 5D, 5E and 5F) is selectively reconfigured according to various embodiments during at least some of these points in time. It is understood that in each of FIGS. 5D, 5E and 5F, the distal end 510b (not shown in FIGS. 5D-5F) of shaft 510 has been introduced into the first lumen 512d (not shown in FIGS. 5D-5F) of catheter sheath 512 and is advanced from the proximal end 512a of the catheter sheath 512 toward the distal end 512b (not shown in FIGS. 5D-5F) of catheter sheath 512. As best shown in FIG. 5A, in some embodiments, shaft 510 includes a longitudinal length 510d extending between the proximal and distal ends 510a, 510b of shaft 510, the longitudinal length 510d of the shaft being different (e.g., greater in FIG. 5A) than the longitudinal length 528a of projection 528.

In some embodiments associated with various ones of FIG. 5, a first particular amount of the longitudinal length 528a of the first projection 528 is located in receiver 529 when a second particular amount of the longitudinal length 510d of shaft 510 is located inside first lumen 512d of the catheter sheath 512, the first particular amount of the longitudinal length 528a of the first projection 528 being less than the second particular amount of the longitudinal length 510d of shaft 510. In various embodiments, the projection 528 and receiver 529 are configured to matingly engage at least when a first amount of part of the shaft 510 is received in the first lumen 512d (e.g., as shown respectively by each of FIGS. 5E and 5F), and the projection 528 and receiver 529 are configured not to matingly engage at least when a second amount of the part of the shaft 510 is received in the first lumen 512d (e.g., as shown in FIG. 5D). In some of these various embodiments, the first amount is different (e.g., greater) than the second amount, and in some embodiments, the first amount and the second amount are each an amount of the longitudinal length 510d of the shaft 510.

In some embodiments, projection 528 and receiver 529 are configured to matingly engage when shaft 510 is not received in first lumen 512d. This circumstance can occur in some embodiments, when projection 528 and receiver 529 form part of a plunger assembly (e.g., plunger assembly 530) provided on one of shaft 510 and catheter sheath 512. This circumstance can occur in some embodiments that are the same or similar to that shown in FIG. 5A where a particular positioning and orientation between shaft 510 and catheter sheath 512 allow for a mating between projection 528 and receiver 529 without the shaft 510 being received in first lumen 512d.

In FIG. 5D, projection 528 extending from the proximal end 512a of catheter sheath 512 has not been received in the first receiver 529 provided in the housing 520, while various amounts of the projection 528 have been received in receiver 529 in FIGS. 5E and 5F, the amounts varying (e.g., increasing) with the advancement of shaft 510 through first lumen 512d. In the configuration evolution from FIG. 5D, to FIG. 5E, and to FIG. 5F, manipulable portion 502 (not shown in FIGS. 5D, 5E and 5F) is advanced through the first lumen 512d from the proximal end 512a of the catheter sheath 512 toward the distal end 512b of catheter sheath 512. A control system or actuator system (e.g., one or more components of control system 322 or system 545, possibly including one or more of the components of at least FIG. 5R, 5S, 5W, 7, 8, or 10) may respond to or be controlled by varying amounts of the length 528a of the projection 528 being within the receiver 529 and alter aspects of the manipulable portion 502 in response to or under the control of these varying amounts. For example, the control system or actuator system physically or operatively coupled to the manipulable portion 502 may respond to or be controlled by varying amounts of the length 528a of projection of 528 being within receiver 529 by varying force transmitted to the manipulable portion 502 in accordance with the varying amounts of the length 528a of projection of 528 being within receiver 529, e.g., while the distal end of the manipulable portion 502 advances outwardly from the distal end 512b of the catheter sheath 512 along an arcuate or coiled path (for instance, FIGS. 5H, 5I, 5J).

As shown in FIG. 5G, the respective first portions 509a (only one called out) of the elongate members 504 (only one called out) are arranged with respect to one another front surface 518a-toward-back surface 518b in a first direction represented by arrow 530a in a first stacked array 515a (see, e.g., proximal end 307 in FIG. 3A for a closer look at such a first stacked array) sized and shaped to be delivered through first lumen 512d of catheter sheath 512 when a portion of the catheter system 500 (e.g., manipulable portion 502) is in a delivery configuration also known as a first or unexpanded configuration in some embodiments. In various embodiments, manipulable portion 502 is in the delivery configuration as it is delivered through the first lumen 512d as described above, for example, in regards to FIGS. 5D, 5E, and 5F. As shown in FIG. 5G, the respective second (intermediate) portions 509b (only one called out) of the elongate members 504 are arranged with respect to one another front surface 518a-toward-back surface 518b in a second direction as represented by arrow 530b in a second stacked array 515b sized to be delivered through the first lumen 512d when the portion of the catheter system 500 is in the delivery configuration. In various embodiments, the first direction (i.e., arrow 530a) and the second direction (i.e., arrow 530b) are non-parallel directions at least when the arrayed elongate members 504 assume a straightened form.

In various embodiments, the elongate members 504 of the manipulable portion 502 are arranged within catheter sheath 512 such that each elongate member 504 is to be advanced distal end 505 first into a bodily cavity. In various embodiments, the elongate members 504 are arranged within catheter sheath 512 such that each elongate member 504 is to be advanced out distal end 505 first from the distal end 512b of catheter sheath 512. In some embodiments, manipulable portion 502 includes a first or proximal portion 508a and a second or distal portion 508b, each of these portions comprising a respective part of each of at least some of the elongate members 504. In some embodiments, the proximal and the distal portions 508a, 508b include respective portions of elongate members 504. In some embodiments, the manipulable portion 502 is arranged to be delivered second or distal portion 508b first through the lumen 512d of the catheter sheath 512 into a bodily cavity when the manipulable portion 502 is delivered in the unexpanded or delivery configuration as shown, e.g., in FIG. 5G.

Notably, as used herein, the term "stacked" does not necessarily require the elongate members 504 rest directly or even indirectly upon one another, but rather refers to an ordered arrangement which may include spaces or gaps between immediately adjacent or most immediate neighboring pairs of elongate members 504. It is also noted that while illustrated in FIG. 5G as a plurality of substantially parallel stacked plates or strips, the elongate members 504 need not be perfectly rigid, so there may be some flex, sag, or curvature even when the catheter sheath 512 is essentially straight. It is further noted that in use, the catheter sheath 512 may curve or even twist to follow a bodily lumen. The elongate members 504 may adopt or conform to such curvatures or twists as the elongate members 504 are advanced through catheter sheath 512. In either of these situations, the elongate members 504 generally maintain the relative positions to one another as a stacked arrangement.

In various embodiments, the respective first, second, and third portions 509a, 509b and 509c (only one of each called out in FIG. 5G) of various ones of the elongate members 504 have been stressed into a higher energy state illustrated in FIG. 5G, as compared to a lower energy state shown, e.g., in FIGS. 5A, 5B, and 5C. In various embodiments, the respective second portions 509b of various ones of the elongate members 504 in the initial or predisposed configuration (e.g., as shown in FIGS. 5A, 5B, and 5C) have been stressed into a higher energy state suitable for unbending or uncoiling them sufficiently enough to allow the elongate members 504 to be delivered through catheter sheath 512 in the delivery configuration as shown in FIG. 5G. In various embodiments, at least one of the respective first portions 509a and the third portions 509c of each of various ones of the elongate members 504 has been stressed into a higher energy state by un-fanning at least the second portions 509b of the elongate members 504 sufficiently to allow the elongate members 504 to be introduced into, and delivered though catheter sheath 512. In some of these embodiments, potential energy is imparted to the various elongate members 504 in the delivery configuration by the higher energy state, the potential energy sufficient to return the arrangement of elongate members 504 generally back toward a lower energy state when released from the confines of catheter sheath 512.

In some example embodiments, the arrangement of elongate members 504 is stressed into a higher energy state by retracting the arrangement of elongate members 504 into at least a portion of catheter sheath 512 prior to inserting catheter sheath 512 into a body. For example, in various embodiments the arrangement of elongate members 504 is stressed into a higher energy state by retracting the arrangement of elongate members 504 at least into the flushing portion 524 of catheter sheath 512. In some of these various embodiments, the flushing portion 524 is detached from the remainder of the catheter sheath 512 when the arrangement of elongate members 504 is retracted into the flushing portion 524 with the flushing portion 524 subsequently attached or reattached to the remainder of the catheter sheath 512 after the retraction. This technique may advantageously allow for a more efficient operation as the arrangement of elongate members 504 need not be retracted through the entirety of the catheter sheath 512.

In some embodiments, the arrangement of elongate members 504 is stressed into a higher energy state by uncoiling the elongate members 504 and inserting the arrangement of elongate members 504 into catheter sheath 512. In some embodiments, the arrangement of elongate members 504 is reconfigured from the initial or predisposed configuration shown in FIGS. 5A, 5B, 5C, which is typically provided or calibrated at the time of manufacturing, to the delivery configuration shown in FIG. 5G at a point of use. In some embodiments, the arrangement of elongate members 504 is reconfigured from the initial or predisposed configuration shown in FIGS. 5A, 5C to the delivery configuration shown in FIG. 5G at a place of manufacture, assembly, or distribution. In various embodiments, various devices including various guides or manipulators may be employed to reconfigure the arrangement of elongate members 504 from the initial or predisposed configuration shown in FIGS. 5A, 5C to the delivery configuration shown in FIG. 5G. In some of these various embodiments, these devices form part of catheter system 500 (e.g., flushing portion 524). In some embodiments, the devices are extraneous to catheter system 500. The higher energy states may be controlled to not cause damage to portions of catheter system 500 during delivery through catheter sheath 512. In FIG. 5G, cable 513b is extended along the elongate members 504 in the delivery configuration. In various embodiments, cable 513b is delivered through first lumen 512d when the elongate members 504 are advanced in a delivery configuration toward a bodily cavity. In various embodiments, cable 513b is drawn through first lumen 512d by the manipulable portion 502 as the manipulable portion 502 is advanced in a delivery configuration toward a bodily cavity.

FIGS. 5H, 5I, and 5J are various side elevation views of various respective parts of manipulable portion 502 positioned at three successive points in time as each respective part of the manipulable portion 502 or structure 502a thereof is advanced outwardly from the confines of the first lumen 512d (not called out in these figures) of catheter sheath 512 (i.e., from the distal end 512b). These figures illustrate coiling and uncoiling of the manipulable portion 502 during deployment and retraction, respectively, of the manipulable portion.

FIG. 5J shows a portion of the catheter system 500 including the plurality of elongate members 504 (two called out) positioned in an expanded configuration also referred to as a second or bent configuration. In Figured 5J, the manipulable portion 502 (or at least an elongated part thereof) has a volute or coiled shape, e.g., after a control system or actuator system (e.g., as described herein) that is operatively or physically coupled to the manipulable portion 502 varies a size, shape, or both size and shape of at least part of the manipulable portion extending outside of the distal end 512b of the catheter sheath 512 to, at least in part, cause the distal end of the manipulable portion to move along a first trajectory. In FIG. 5J, the respective second portions 509b (only one called out) of various ones of the elongate members 504 have cleared the confines of first lumen 512d (not called out) while other portions of the elongate members 504 remain within the confines of first lumen 512d. In various embodiments, each of at least the respective second portions 509b of each elongate member 504 is curved about a respective bending axis 534 (i.e., one represented by symbol "X") into an arcuate stacked array 532. Each bending axis 534 extends in a direction having a directional component transversely oriented to the respective longitudinal length of the respective elongate members 504. In various embodiments, each of the respective second portions 509b of various ones of the elongate members 504 in the arcuate stacked array 532 is coiled about a respective bending axis 534 into a coiled stacked array. In various embodiments, each respective second portion 509b is bent to have a scroll or volute shaped profile. In various embodiments, each second portion 509b is arranged to have a curvature that varies at least once along the respective length of the elongate member 504. In some embodiments, when positioned in the second or bent configuration, a first portion 521a of the front surface 518a (only one called out) of the respective second portion 509b of each elongate member 504 is positioned diametrically opposite to a second portion 521b of the front surface 518a in the volute shaped structure 502a. When positioned in the second or bent configuration, the coiled arrangement of elongate members 504 is sized, shaped, or both sized and shaped too large for delivery through the first lumen 512d, at least in a direction toward the bodily cavity. In this regard, it can be said that when the coiled arrangement of elongate members 504 is in the second or bent configuration (e.g., FIG. 5J), the manipulable portion 502 comprises a coiled form in an expanded configuration.

In various embodiments, the respective second portions 509b of various ones of the elongate members 504 are pre-formed to autonomously bend when the second portions 509b are advanced outwardly from the confines of first lumen 512d. As the respective second portions 509b are advanced from the confines of first lumen 512d, they are urged or biased to seek their low energy state (e.g., their initial coiled configuration). In various embodiments, the respective distal ends 505 of various ones of the elongate members 504 (only one called out in each of FIGS. 5H, 5I, and 5J) move along a trajectory that follows a coiled path (e.g., a path that curves back on itself) during the advancement of various parts of manipulable portion 502 outwardly from the confines of first lumen 512d. In various embodiments, the coiled path makes at least one full turn. In some embodiments, at least part of the coiled path may extend along a volute path. In some embodiments, manipulable portion 502 or structure 502a thereof has a distal end (i.e., the same or different than a distal end 505 of an elongate member 504) configured to be delivered first, with respect to other parts of the manipulable portion 502 through the first lumen 512d or outwardly from the distal end 512b of catheter sheath 512.

In various embodiments, the respective second portions 509b of various ones of the elongate members 504 are pre-formed to autonomously coil as they are advanced into a bodily cavity in a manner that may advantageously reduce physical interactions between at least the distal end 505 of the elongate members 504 and an interior tissue surface within the bodily cavity (not shown in FIG. 5 but may be exemplified by left atrium 204 of FIG. 2) into which they are deployed. In various embodiments, the elongate members 504 are arranged to continuously bend or curl to move at least the respective distal ends 505 of the elongate members away from an interior tissue surface within a bodily cavity into which they are advanced. A reduction of contact and other physical interaction of the elongate members 504 with an interior tissue surface within a bodily cavity during the advancement may reduce occurrences of, or the severity of, damage inflicted to various tissue structures (i.e., especially damage caused by the distal end 505 of an elongate member 504 which may catch on various tissue structures during the advancement). In some embodiments, the arcuate stacked array 532 is arranged to have a predetermined size that will allow the arcuate stacked array 532 to be positioned within a bodily cavity with at most relatively minor amounts of contact with an interior tissue surface within the bodily cavity.

FIGS. 5H, 5I, and 5J show various interactions between a portion of control element 513 (e.g., cable 513b) and the manipulable portion 502 (e.g., structure 502a) as various respective parts of the manipulable portion 502 or structure 502a thereof are advanced outwardly from the confines of first lumen 512d. For example, FIGS. 5H, 5I, and 5J show various interactions between the part or portion 514 (FIG. 5C) of cable 513b located outside the distal end 512b of catheter sheath 512 and the manipulable portion 502 (e.g., structure 502a) as various respective parts of the manipulable portion 502 or structure 502a thereof are advanced outwardly from the confines of first lumen 512d. In some embodiments, a control system or actuator system (e.g., as described herein) responds to or is controlled by relative movement between shaft 510 and catheter sheath 512, and may control one or more actuators to cause these interactions. In some embodiments, a control system (e.g., from a control system such as controller 324 or data processing device system 110) is operatively coupled to an actuator system and is operable to control activation of one or more actuators of the actuator system in response to the relative movement between shaft 510 and catheter sheath 512. For example, in some embodiments, at least a portion of at least one actuator or modulation actuator (e.g., actuator 546, some other actuator or actuator set, or a portion of at least one of these actuators) physically or operatively coupled to a control element (e.g., 513) is moveable in each of a first direction and a second direction different than the first direction. In some embodiments, movement of at least the portion of the actuator (e.g., modulation actuator) in the first direction may accompany an increase in an amount of manipulable portion 502 extending outwardly from the distal end 512b of catheter sheath 512 (e.g., as shown by the sequence of FIGS. 5H, 5I, and 5J), e.g., as the shaft 510 is moved distally through the catheter sheath 512. In some embodiments, movement of at least the portion of the actuator (e.g., modulation actuator) in the second direction may accompany a decrease in an amount of manipulable portion 502 extending outwardly from the distal end 512b of catheter sheath 512 (e.g., as shown by the sequence of FIGS. 5J, 5I, and 5H), e.g., as the shaft 510 is moved proximally through the catheter sheath 512.

In various embodiments, it may be important to prevent tension levels in various control elements (e.g., cable 513b) from reducing below certain threshold levels during the outward advancement of the various respective parts of the manipulable portion 502 or structure 502a thereof from the confines of first lumen 512d. For example, reduction of tension in the cable 513b to a level where slack develops in the cable member 513b as parts of the manipulable portion 502 or structure 502a are advanced outwardly from the confines of the first lumen 512d of catheter sheath 512 may lead to various undesired conditions. In some cases, if sufficient slack in cable 513b results, portions of cable 513b may become wrapped, or otherwise entangled with the manipulable portion 502 and interfere with, or restrict a current or subsequent manipulation or deployment of the manipulable portion 502 (e.g., a subsequent manipulation or deployment as shown in FIGS. 5L-1, 5L-2, 5M-1, 5M-2, 5N, 5O, 5P and 5Q). Maintaining a desired tension on cable 513b can be complicated when the elongate members 504 are advanced outwardly from the confines of first lumen 512d along a path that requires both an advancement of portions of the cable 513b from the first lumen 512d and a subsequent retraction of portions of the cable 513b into the first lumen 512d during the movement along the path. For example, the coiled path that a distal end of the manipulable portion 502 follows as the manipulable portion 502 is advanced outwardly from the confines of first lumen 512d of the catheter sheath 512 (e.g., as shown in FIGS. 5H, 5I and 5J) may require an advancement of various portions of the cable 513b from the first lumen 512d and a subsequent retraction of various portions of the cable 513b into the first lumen 512d when some desired level of tension is required in cable 513b (e.g., a level of tension sufficient to reduce occurrences of slackness in the cable 513b). In various embodiments, modulation of a size, a shape, or both, of the manipulable portion 502 or structure 502a thereof occurs at least in a state where at least a part of the manipulable portion 502 or structure 502a thereof and a part of the control element 513 (e.g., cable 513b) extends outside the distal end 512b of the catheter sheath 512. In some of these embodiments, a length of the part of the control element 513 is required to increase and then subsequently decrease during or throughout the modulation of the manipulable portion 502 or structure 502a. In some of these various embodiments, the manipulable portion 502 or structure 502a is sized or shaped during or throughout the modulation to have a size or shape sufficient to limit or restrict movement of at least the part of the manipulable portion 502 or structure 502a through the first lumen 512d.

FIG. 6 is a graph that includes a data set (i.e., represented by plot 600) measured by some of the present inventors using a device that is the same or similar in construction to the manipulable portion 502 shown in FIG. 5. The device includes a structure comprised of a stacked array of resilient elongate members approximately 240 millimeters in length and pre-shaped to autonomously coil as the elongate members are advanced outwardly from the confines of a catheter lumen along which the device has been advanced (e.g., in a manner the same or similar to embodiments previously described with respect to FIGS. 5H, 5I, and 5J). Plot 600 represents a required movement of a control line physically coupled to the distal ends of the device elongate members (i.e., the same or similar to cable 513b) as the elongate members are positioned at different locations outwardly from the distal end of the catheter sheath as the elongate members autonomously bend to follow a coiled path upon advancement from the confines of the catheter sheath. The horizontal axis of the FIG. 6 graph is associated with an amount that a distal end of the structure (e.g., a distal end of at least one of the elongate members, such as distal end 505) travels along a path that extends outwardly from a distal end of the catheter sheath while the vertical axis is associated with an amount of the control line that is metered during the movement along the path in accordance with various embodiments.

As used in this disclosure, the word "meter" means to supply or provide in a measured or regulated amount. In this regard, the metering of a control line (e.g., control cable 513b or other elongated control element or portion thereof) can occur in different directions. For example in some embodiments, the control line can be caused (e.g., by one or more of the actuators 540a, 540b, 546 in FIG. 7) to be metered or to move along a path with a controlled or regulated rate in a first direction (e.g., an action associated with "take-up" of the control line) suitable to reduce or decrease an amount of at least a portion of the control line (e.g., control cable 513b) located outside a distal end (e.g., distal end 512b) of the catheter sheath (e.g., catheter sheath 512) during one of (a) a transition toward or to an expanded configuration of a manipulable portion (e.g., manipulable portion 502) and (b) a transition toward or to a delivery configuration of the manipulable portion (e.g., manipulable portion 502). In some embodiments, the control line can be caused (e.g., by one or more of the actuators 540a, 540b, 546 in FIG. 7) to be metered or to move along a path with a controlled or regulated rate in a second direction (e.g., an action associated with "play-out" of the control line) suitable to increase an amount of at least a portion of the control line (e.g., control cable 513b) located outside a distal end (e.g., distal end 512b) of the catheter sheath (e.g., catheter sheath 512) during the other of (a) and (b), or which can result in a relatively larger portion of the control line being available for extension outwardly from a distal end of the sheath.

In various embodiments, metering during play-out can reduce tension in the control line, sometimes to the point of imparting slackness in the control line. In some of these various embodiments, metering during play-out may allow increased amounts of the control line to be pulled outwardly from the distal end of the catheter sheath (for example by a release of stored potential energy in manipulable portion 502). In some embodiments, metering during take-up can increase tension in the control line. It is noted that, in some circumstances, slack in the control line can exist during some part of a take-up procedure. For example, slack in cable 513b may arise if the metering rate during take-up is insufficient to take up a portion of the cable 513b that extends outwardly from the distal end 512b of sheath 512 with a rate appropriate for the advancement of manipulable portion 502 from the distal end 512b of sheath 512 along a coiled trajectory as shown in FIGS. 5H, 5I and 5J. In various embodiments, the control line is metered with a rate that is dependent on a rate in which the distal end of the structure (e.g., structure 502a) advances outwardly from the distal end of the catheter sheath or advances inwardly into the distal end of the catheter sheath.

A portion 600a of plot 600 shows that the control line is advanced outwardly from the distal end of the catheter sheath up to about a point where the stacked elongate members have been initially advanced outwardly from the distal end of the catheter sheath by approximately 50 mm along the path (e.g., in a manner that is the same or similar to that shown in FIG. 5H). In various embodiments, the control line is not actively metered and the control line may be advanced outwardly from the catheter sheath as the stacked array of elongate members pulls the control line outwardly during this initial advancement. Any slack in the control line may be taken up at least in part during this initial advancement. Further advancement along the path (i.e., from 50 mm up to about 170 mm) of the stacked elongate members outwardly from the distal end of the catheter sheath requires, in these embodiments, that the control line be taken-up to cause a portion of the control line to be retracted back into the distal end of the catheter sheath. In particular, portion 600b of plot 600 is associated with an amount of the control line, in these embodiments, to be taken up without imparting particular force on the advanced portion of the elongate members extending outwardly from the distal end of the catheter sheath, the particular force sufficient to noticeably move the advanced portion of the elongate members away from their low potential energy state. It is noted that force transmitted to the elongate members by the control line can cause bending of the elongate members that in turn can impart potential or spring energy to the elongate members. It is understood that if an amount of control line taken-up between the 50 mm and 170 mm points on the horizontal axis is less than that required by plot 600 (i.e., below portion 600b), then slack in the control line may exist, which may in turn, lead to various undesired results.

In part 600c of plot 600, the control line is controlled in accordance with a further movement of the coiled structure outwardly from the distal end of the catheter sheath according to various embodiments (for example as shown in FIGS. 5C, 5L-1, 5L-2). It is understood that different plots will result for other devices having different dimensions or different configurations, and the plot 600 is only presented by way of non-limiting example.

Ideally, in some embodiments, the take-up of the control line of the device described above in conjunction with FIG. 6 should occur above the "minimal" take-up amount specified by the portion 600b of plot 600 to increase the likelihood that the control line does not slacken during the advancement of the device outwardly from the confines of the catheter sheath.

FIG. 6 includes a line 602 associated with a particular control line metering action employed according to some embodiments. Portion 602a of line 602 is associated with a condition in which the control line is not taken up as the stacked elongate members are initially advanced outwardly from the distal end of the catheter sheath about 40 mm along a deployment path. During an additional or subsequent advancement of the stacked elongate members outwardly from the distal end of the catheter sheath along the deployment path, the control line is taken up or metered with a first rate (i.e., associated with the portion 602b of line 602) to cause a portion of the control line to be retracted inwardly into the distal end of the catheter sheath during a first part of the take-up. In FIG. 6, this first part of the control line take-up occurs when the stacked elongate members have been advanced between 40 mm and 90 mm along the deployment path outwardly from the distal end of the catheter sheath. During further advancement of the stacked arrangement of the elongate members outwardly from the distal end of the catheter sheath, the control line is taken up or metered with a second rate (i.e., associated with the portion 602c of line 602) during a second part of the take-up. In FIG. 6, this second part of the control line take-up occurs when the stacked elongate members have been advanced between 90 mm and 200 mm along the deployment path outwardly from the distal end of the catheter sheath. In various embodiments, the first metering rate is different than the second metering rate. For example, in FIG. 6, the first metering rate is twice the second metering rate as indicated by the difference in the slopes of line portions 602b and 602c. In this regard, in some embodiments, the first metering rate may be referred to as a "2× rate", and the second metering rate may be referred to as a "1× rate". Different rates may be employed in other embodiments. In various embodiments, metering of the control line, with the first rate, the second rate or each of the first and second rates occurs along a particular direction that is relative to, or respective with, a reference frame that is provided by a portion of the catheter device (e.g., the catheter shaft to which the manipulable portion is coupled) that is moveable with respect to the catheter sheath. In various embodiments, metering of the control line, with the first rate, the second rate or each of the first and second rates, may lead to different respective rates of movement of the control line with respect to a reference point on the catheter sheath (e.g., a distal end of the catheter sheath).

A large portion of the control line take-up represented by portion 602b of line 602 is above the "minimum" threshold provided by the portion 600b of plot 600 and occurrences of slack in the control line are reduced when the control line is metered in accordance with line 602. The different metering rates represented by portions 602b, 602c of line 600 may be motivated by different reasons. For example, with reference to FIG. 5I, a first (e.g., a relatively higher) take-up rate similar to the first rate represented by the slope of portion 602b in FIG. 6 may be employed to ensure proper retraction of control cable 513b since the manipulable portion 502 is being further advanced along a portion of its trajectory outwardly from the distal end 512b of the catheter sheath 512 (i.e., as compared between FIGS. 5H and 5I) along a path that coils or curls back on itself and may thus benefit from a relatively rapid take-up of the cable 513b. It is noted that in various embodiments associated with FIG. 5, the manipulable portion 502 autonomously coils as the manipulable portion 502 is advanced outwardly from the confines of the first lumen 512d. As previously described above in this disclosure, the autonomous coiling may be motivated by different reasons including reducing occurrences of undesired contact between a distal end 505a (e.g., provided by at least one of the distal ends 505 in some embodiments) of the manipulable portion 502 and a tissue surface defining a bodily cavity into which the manipulable portion 502 is advanced. The first take-up rate can be defined or predetermined to cause the take-up of the cable 513b to be sufficient to additionally bend the manipulable portion 502 or structure 502a thereof to cause portions thereof to assume a smaller radius of curvature than they would normally have from their autonomously formed shapes. This situation can in turn result in an advancement trajectory of the distal end of the manipulable portion 502 outwardly from the distal end 512b of the catheter sheath 512 that has a "tighter" curvature than an un-modified respective trajectory that the distal end of the manipulable portion 502 undergoes solely on the basis of its autonomous coiling during the advancement. In some embodiments, this situation can in turn result in a coiled advancement trajectory of the distal end of the manipulable portion 502 outwardly from the distal end 512b of the catheter sheath 512 that is "tighter" or more closely wound than an un-modified respective trajectory that the distal end of the manipulable portion 502 undergoes solely on the basis of its autonomous bending during the advancement. A tighter, more compact or more closely wound advancement path may, in some cases, further reduce occurrences of undesired contact between the distal end of the manipulable portion 502 and the tissue surface during the advancement of the distal end of the manipulable portion 502 into the bodily cavity. It is noted that this additional bending of the structure 502a during the take-up of the cable 513b with the first rate imparts additional potential or spring energy in the structure. However, unlike various embodiments described in co-assigned International Patent Application No. PCT/US2012/022061 in which similar structures are bent into an arcuate or coiled configuration from a low energy configuration in which the similar structures are generally straight in form, lower amounts of potential energy are imparted onto structure 502a by the take-up of cable 513b since structure 502a is being bent from a pre-formed coiled shape having a low energy state. Nonetheless, additional deflection imparted on manipulable portion 502 by cable 513b may be limited to reduce the amount of spring-back that would occur in manipulable portion 502 should a failure in cable 513b occur. A phantom line 502b is representative of a portion of structure 502 in its initial or predisposed configuration (i.e., a low energy state) in FIG. 5I.

In various embodiments, further advancement of the manipulable portion 502 outwardly from the confines of first lumen 512d further advances the distal end of manipulable portion 502 along the coiled path and coils manipulable portion 502 from a state shown in a FIG. 5I to a state as shown in FIG. 5J. In these embodiments, a second (e.g., a relatively lower) take-up rate similar to the second rate represented by the slope of portion 602c in FIG. 6 may be employed to take up control cable 513b since the manipulable portion 502 is being further advanced along a portion of its trajectory back generally toward the distal end 512b of the catheter sheath 512 along a portion of the coiled path where a relatively slower take-up of the cable 513b may be required. The slower second take-up rate may be motivated for various reasons including providing a better match for the profile of plot 600. In some embodiments, the distal portions of the elongate members 504 in the structure 502a may be pre-formed with a tight curvature in their initial or predisposed configuration to promote a rapid transition away from a tissue surface of the bodily cavity as the structure is advanced outwardly from the distal end 512b of the catheter sheath 512. Although these relatively tightly coiled distal portions of the elongate members 504 may enhance advancement of the manipulable portion 502 into the bodily cavity, they may hinder or restrict other required functions of the manipulable portion 502. For example, fanning of the various curved portions of the coiled elongate members 504 as described later in this disclosure may be required, and various factors such as the widths of the curved portions the elongate members 504 as well as the amount of curvature along the coiled form may restrict or hinder the required fanning.

In some embodiments associated with FIG. 5J, the second take-up rate can be defined or predetermined to cause the take-up of the cable 513b to be sufficient to additionally bend the manipulable portion 502 to cause portions thereof to assume a larger radius of curvature than they would normally have from their autonomously formed shapes. The larger radius of curvature is contrasted with a phantom line 502c, which is representative of a part of manipulable portion 502 in its initial or predisposed configuration (i.e., a low energy state). It is noted that the take-up of cable 513b associated with FIG. 5J has imparted larger dimensions to manipulable portion 502 or structure 502a thereof as compared with the initial or predisposed configuration of manipulable portion 502 or structure 502a thereof. In some embodiments, this may advantageously simplify or reduce complexity for additional actions to manipulate manipulable portion 502 to cause manipulable portion 502 or structure 502a thereof to better conform (e.g., to further expand to conform) with a tissue surface of a bodily cavity into which the manipulable portion 502 has been deployed. It is noted that a failure of cable 513b in FIG. 5J would cause manipulable portion 502 to contract inwardly onto itself from any release of stored potential energy caused by such a failure. This can, in some embodiments, reduce occurrences of tissue damage that may be possibly associated with a failure of cable 513b. In the sequence depicted by FIGS. 5H, 5I and 5J, an end or terminus of cable 513b (an example of at least part of a control element) advances along a coiled path as the manipulable portion 502 is advanced outwardly from the distal end 512b of the catheter sheath 512.

FIG. 5L-1 shows an expanded configuration in which the manipulable portion 502 has been advanced outwardly from the confines of the first lumen 512d sufficiently to allow potential energy from at least the respective first portions 509a of the elongate members to be released and cause the first portions 509a to be urged or biased to assume a lower energy state (i.e., the same or similar to their initial or predisposed configuration shown in FIG. 5A). This situation in turn causes at least the respective second portions 509b of various ones of the elongate members 504 to autonomously fan at least in part, with respect to one another into an expanded configuration also known as a first fanned configuration 536. In some example embodiments, as the respective third portions 509c are advanced from the confines of catheter sheath 512, stored potential energy is released and the respective third portions 509c are urged or biased into a lower energy state to cause at least the respective second portions 509b of various ones of the elongate members 504 to autonomously fan, at least in part, with respect to one another into the first fanned configuration 536. In some example embodiments, as both the respective third portions 509c and the respective first portions 509a of various ones of the elongate members 504 are advanced from the confines of catheter sheath 512, stored potential energy is released and the respective first and third portions 509a, 509c are urged or biased into respective lower energy states to cause at least the respective second portions 509b of various ones of the elongate members 504 to autonomously fan at least in part, with respect to one another into the first fanned configuration 536. In various embodiments, the manipulable portion 502 is sized too large for delivery through the first lumen 512d at least in a direction toward the distal end portion 512b of the catheter sheath 512 when the manipulable portion 502 is positioned in the first fanned configuration 536. A crossing location between various elongate members 504 in the first fanned configuration 536 is positioned between the proximal and distal portions 508a and 508b of manipulable portion 502 in FIG. 5L-1.

In various embodiments, additional fanning mechanisms or actuators (for example, as described later in this disclosure, such as with respect to FIG. 5S) may be employed to assist in the fanning of, or to promote an additional fanning of various ones of the elongate members 504 as the elongate members 504 are moved into various additional expanded configurations. Additional manipulations of manipulable portion 502 (for example, as described later in this disclosure) may be employed to further modify the expanded configuration shown in FIG. 5L-1. In various embodiments, various manipulations of manipulable portion 502 may be employed to transition the expanded configuration of the manipulable portion 502 between various particular states.

A discussion will now be made on the interplay between the metering of cable 513b and a retraction of manipulable portion 502 into the confines of first lumen 512d that occurs in some embodiments. In the state of FIG. 5J, if effort was made to retract manipulable portion 502 back into the confines of the first lumen 512d (for example by a relative movement between shaft 510 and catheter sheath 512), the tensioned cable 513b would likely impede or resist these efforts. In some cases, cable 513b would be subjected to significant forces in response to these attempts to urge the manipulable portion 502 into the first lumen 512d. In some cases, these forces may be sufficient to raise concerns about damage to or failure of the cable 513b or manipulable portion 502.

In some embodiments, the cable 513b is controlled to develop reduced tension in various portions of the cable 513b to a level or levels sufficient to reduce resistance (e.g., tension) that would impede the retraction of manipulable portion 502 into the first lumen 512d. For example, in some embodiments, cable 513b is so controlled by clutching or decoupling a take-up mechanism coupled to the cable 513b to "free-wheel" so as to allow the cable 513b to be freely pulled outwardly from the distal end 512b of the catheter sheath 512 to allow various portions of manipulable portion 502 to be retracted into the first lumen 512d with reduced levels of resistance. In some embodiments, cable 513b is played out with a metered rate to allow a portion of the cable 513b to be moved outwardly from the distal end 512b of the catheter sheath 512 in a regulated manner during the retraction of the manipulable portion 502 into the first lumen 512d. In some embodiments, cable 513b is metered to regulate reduced tension levels (e.g., slack) formed in the cable 513b. In FIG. 6, line 604 represents a particular control line metering action employed according to some embodiments. Portion 604b of line 604 is associated with a condition in which the control line (e.g., control line previously described in conjunction with FIG. 6) is played-out or metered with a third rate (e.g., represented by the slope of portion 604b of line 604) to cause a portion of the control line to have a reduced tension level (e.g., slackened). A slackened portion of the control line in some embodiments is sufficient to allow a portion of the array of elongate members protruding outwardly from the catheter sheath to autonomously bend toward (e.g., inwardly to) a lower energy position (for example, an inward location the same or similar to that represented by phantom line 502c in FIG. 5J) as the arrayed elongate members undergo retraction back into the catheter sheath. In FIG. 6, this part of the control line play-out occurs when the stacked elongate members have been retracted from a point approximately 200 mm along the coiled retraction path (i.e., as measured outwardly from the distal end of the catheter sheath) to a point approximately 180 mm along the coiled retraction path. At the point approximately 180 mm along the horizontal axis in FIG. 6, portion 604b of line 604 crosses plot 600 indicating that the arrayed structure is in a low energy state (for example as represented by a retraction of manipulable portion 502 to a particular location shown in FIG. 5K). In various embodiments, further play-out of the control line in accordance with the remaining part of portion 604b of line 604 and the subsequent portion 604c of line 604 essentially maintains a portion of the arrayed structure protruding outside the catheter sheath in a low energy state as the arrayed structure is retracted back into the lumen of the catheter sheath. For example, phantom line 502b in FIG. 5I may be used to envision a position of manipulable portion 502 in a low energy state during the further play-out of the cable 513b that occurs during the retraction of the manipulable portion 502 back into first lumen 512d. It is understood that portions of the structure (e.g., structure 502a) entering the catheter sheath are brought into a higher energy state due to the shape restrictions imposed by the lumen of the catheter sheath.

During further retraction of the stacked arrangement of the elongate members into the distal end of the catheter sheath, the control line is played out or metered with a fourth rate (i.e., as represented by the slope of portion 604c of line 604) during a second part of the play-out to cause a portion of the control line to have a reduced tension level (e.g., slackened level). A slackened portion of cable 513b in some embodiments is sufficient to allow a portion of the arrangement of elongate members protruding outwardly from the catheter sheath to autonomously continue to bend toward (e.g., outwardly to) a lower energy configuration or generally maintain the lower energy configuration as the arrangement of elongate members continues to undergo retraction into the catheter sheath. In FIG. 6, this second part of the control line play-out occurs when the arrangement of elongate members has been retracted from a point of 150 mm along the retraction path to a point about 40 mm along the retraction path (i.e., again as measured outwardly from the distal end of the catheter sheath). In various embodiments, the third metering rate (e.g., as represented by the slope of portion 604b of line 604) is different than the fourth metering rate (e.g., as represented by the slope of portion 604c of line 604). For example, in FIG. 6, the third metering rate associated with the slope of portion 604b of line 604 is twice the fourth metering rate associated with the slope of portion 604c of line 604. In some embodiments, the third metering rate associated with the slope of portion 604b of line 604 is generally equal to the first metering rate associated with the slope of portion 602b of line 602. In some embodiments, the fourth metering rate associated with the slope of portion 604c of line 604 is generally equal to the second metering rate associated with the slope of portion 602c of line 602. In this regard, in some embodiments, the third metering rate may be referred to as a "2× rate", like the first metering rate, and the fourth metering rate may be referred to as a "1× rate" like the second metering rate. Different rates may be employed in other embodiments. It is noted in various embodiments associated with FIG. 6 that a large part of line 604 remains below the data of plot 600 indicating that slack in the control line is present during or throughout the metering of the control line in conjunction with line 604.

In various embodiments, advancement of various parts of manipulable portion 502 outwardly from the confines of first lumen 512d (i.e., outwardly from the distal end 512b of catheter sheath 512) accompanies a first relative movement between the shaft 510 and catheter sheath 512 that results in a reduction or decrease in a distance between the proximal end 510a of the shaft 510 and the proximal end 512a of the catheter sheath 512 (e.g., as shown by the sequence depicted in FIGS. 5D, 5E and 5F), and also results in an increase in an amount of at least a part of the manipulable portion 502 extending outside the distal end of the catheter sheath 512. In this regard, in some embodiments, the distal end of the manipulable portion 502 is located outside of the distal end 512b of the catheter sheath 512 at a first location when a particular spatial relationship exists between the shaft 510 and the catheter sheath 512 during the first relative movement. See, e.g., the non-phantom lined first location of the distal end of the manipulable portion 502 in FIG. 5I. A reduction in a distance between the proximal end 510a of shaft 510 and the proximal end 512a of catheter sheath 512 may correspond to a reduction in a distance between a location on shaft 510 and a location on catheter sheath 512 during the first relative movement. In various embodiments, this reduction in distance may be accomplished by (a) a forward advancement of shaft 510 (e.g., away from housing 520 in FIG. 5A), (b) a rearward retraction of catheter sheath 512 (e.g., toward housing 520), or both (a) and (b).

In various embodiments, retraction of various parts of manipulable portion 502 inwardly into the confines of first lumen 512d (i.e., inwardly into the distal end 512b of catheter sheath 512) accompanies a second relative movement between the shaft 510 and catheter sheath 512 that results in an increase in a distance between the proximal end 510a of the shaft 510 and the proximal end 512a of the catheter sheath 512 (i.e., for example, as may occur in a sequence reverse to the sequence depicted in FIGS. 5D, 5E and 5F), and also results in a decrease in an amount of at least a part of the manipulable portion 502 extending outside the distal end of the catheter sheath 512. In this regard, in some embodiments, the distal end of the manipulable portion 502 is located outside of the distal end 512b of the catheter sheath 512 at a second location (different than, e.g., the non-phantom lined first location of the distal end of the manipulable portion 502 in FIG. 5I) when the same particular spatial relationship exists (as compared to advancement of various parts of manipulable portion 502 outwardly from the confines of first lumen 512d, discussed above) between the shaft 510 and the catheter sheath 512 during the second relative movement, the particular spatial relationship being a spatial relationship between a third location on the shaft 510 and a fourth location on the catheter sheath 512. See, e.g., the phantom lined second location of the distal end of the manipulable portion 502 in FIG. 5I. An increase in a distance between the proximal end 510a of shaft 510 and the proximal end 512a of catheter sheath 512 may correspond to an increase in a distance between a (third) location on shaft 510 and a (fourth) location on catheter sheath 512 during the second relative movement. In various embodiments, this may be accomplished by (a) a rearward retraction of shaft 510 (e.g., in a direction toward the housing 520 in FIG. 5A), (b) a forward advancement of catheter sheath 512b (e.g., in a direction away from the housing 520), or both (a) and (b).

In some embodiments, a control system or actuator system (e.g., as described herein) that is operatively or physically coupled to the manipulable portion 502 varies a size, a shape, or both, of the manipulable portion 502. In some embodiments, the control system or actuator system may respond to or be controlled by the first relative movement by causing at least one actuator to vary a size, a shape, or both, of at least part of the manipulable portion 502 extending outside (or located outside) the distal end 512b of catheter sheath 512 to, at least in part, cause the distal end of the manipulable portion 502 to move along a first trajectory during the first relative movement (for example as described above with respect to line 602 in FIG. 6). As discussed above, the first relative movement may be a relative movement between the catheter sheath 512 and a part of the shaft 510 when a distance between a location on the part of the shaft 510 and a location on the catheter sheath 512 decreases (e.g., as shown by the sequence depicted in FIGS. 5D, 5E and 5F)

The control system or actuator system may additionally respond to or be controlled by the second relative movement by varying a size, a shape, or both of at least the part of the manipulable portion 502 extending outside (or located outside) the distal end 512b of catheter sheath 512 to, at least in part, cause the distal end of the manipulable portion 502 to move along a second trajectory during the second relative movement (for example as described above with respect to line 604 in FIG. 6). In some of these embodiments, the first trajectory and the second trajectory are different trajectories. As discussed above, the second relative movement may be a relative movement between the catheter sheath 512 and a part of the shaft 510 when a distance between a location on the part of the shaft 510 and a location on the catheter sheath 512 increases (e.g., as may occur in a sequence reverse to the sequence depicted in FIGS. 5D, 5E and 5F). As used in this disclosure, the word trajectory means a path described by an object moving in space (e.g., a gaseous or fluidic space) under the influence of various forces. It is understood that the word trajectory refers to the path of movement and not the particular direction of travel along the path of movement. That is, travel along a particular trajectory from either direction is considered to be travel along the same trajectory in either case.

With respect to FIGS. 5H, 5I and 5J, a distal end 505a of the manipulable portion 502 moves along a first trajectory under the influence of a control element (e.g., the metered cable 513b), according to some embodiments. The control element (e.g., metered cable 513b), in some embodiments, is operatively or physically coupled to a control system or actuator system to, at least in part, cause the distal end of the manipulable portion to move along the first trajectory. In this regard, in some embodiments, the first trajectory is a modified trajectory following a respective path along which the distal end of the manipulable portion 502 moves during the first relative movement as compared to a respective trajectory along which the distal end of the manipulable portion 502 would move during the first relative movement absent the control element (e.g., the metered cable 513b). For example, in some embodiments, the first trajectory is modified from a trajectory that the distal end 505a of the manipulable portion 502 would follow solely from the autonomous coiling of the manipulable portion during the advancement of the manipulable portion 502 outwardly from the distal end 512b of the catheter sheath 512.

In some embodiments, (a) the distal end of the manipulable portion 502 follows a coiled path during the first relative movement, (b) the distal end of the manipulable portion 502 follows a coiled path during the second relative movement, or both (a) and (b). In some embodiments, the control system or actuator system responds to or is controlled by, the first relative movement by varying a radius of curvature of a surface of at least part of the manipulable portion 502 extending outside the distal end 512b of catheter sheath 512 to decrease during the first relative movement (for example, as shown in FIG. 5I) and then subsequently increase (for example as shown in FIG. 5J) during the first relative movement.

In various embodiments, the manipulable portion 502 is selectively moveable between a delivery configuration in which the manipulable portion 502 is sized, shaped, or both sized and shaped to be delivered through the first lumen 512d of catheter sheath 512 and an expanded configuration in which the manipulable portion 502 is sized, shaped or both sized and shaped too large for delivery through the first lumen 512d. In some of these various embodiments, an actuator system (e.g., one or more of the components of at least FIG. 5R, 5S, 5W, 7, 8, or 10) is physically or operatively coupled to at least a control element (e.g., cable 513b), and may be controlled by a control system (e.g., one or more components of at least control system 322 or control system 545) to transition the manipulable portion 502, at least in part, toward or to the expanded configuration as the manipulable portion is advanced out of the distal end 512b of the catheter sheath 512, and to transition, at least in part, the manipulable portion 502 toward or to the delivery configuration as the manipulable portion is retracted into the distal end 512b of the catheter sheath 512. In some embodiments, the control system or actuator system is operatively or physically coupled to the control element (e.g., cable 513b) to cause, when a particular amount of the manipulable portion 502 is located outside of the distal end 512b of the catheter sheath 512 during the transition toward or to the expanded configuration, at least a portion of the control element (e.g., cable 513b) to have a first amount of length located outside the distal end 512b of the catheter sheath 512 (for example, cable 513b in FIG. 5I is shown with a first amount of length during the outward advancement of manipulable portion 502).

The control system or actuator system may be operatively or physically coupled to the control element (e.g., cable 513b) to cause, when the same particular amount of the manipulable portion 502 is located outside of the distal end 512b of the catheter sheath 512 during the transition toward or to the delivery configuration, at least the portion of control element (e.g., cable 513b) to have a second amount of length located outside of the distal end 512b of the catheter sheath 512, the second amount of length being different than the first amount of length. For example, although FIG. 5I is associated with the outward advancement of manipulable portion 502 from catheter sheath 512, phantom line 502b can be envisioned to reflect a same particular amount (e.g., a length or other dimension) of the manipulable portion 502 extending outwardly from the distal end 512b of catheter sheath 512 to the distal end of the manipulable portion 502 during a retraction of the manipulable portion 502 as compared to advancement thereof. Cable 513b is represented as cable 513b(ret) (i.e., shown in broken lines) for the case of retraction. When the same particular amount of the manipulable portion 502 is located outside the distal end 512b of catheter sheath 512 during the retraction of manipulable portion 502 as compared with the advancement of manipulable portion 502, the amount of length of cable 513b, 513b(ret) located outside of the distal end 512b of catheter sheath 512 is greater during the retraction of manipulable portion 502 than during the advancement of manipulable portion 502 (e.g., length of cable 513b(ret) outside the distal end 512b is greater than length of cable 513b outside the distal end 512b).

In some embodiments, the particular amount of the manipulable portion located outside the distal end 512b of the catheter sheath 512 is a particular size of the manipulable portion between the distal end 512b of the catheter sheath 512 and the distal end of the manipulable portion 502. In some embodiments, the particular amount of the manipulable portion located outside the distal end 512b of the catheter sheath 512 is a particular length of the manipulable portion 502 extending from the distal end 512b of the catheter sheath 512 to the distal end of the manipulable portion 502. In some embodiments, the particular amount of the manipulable portion located outside the distal end 512b of the catheter sheath 512 is a particular length of the manipulable portion 502 extending along a surface of the manipulable portion 502 from the distal end 512b of the catheter sheath 512 to the distal end of the manipulable portion 502.

In some embodiments, the control system or actuator system is physically or operatively coupled to the control element (e.g., cable 513b) to cause, when a particular relative positioning (e.g., a relative longitudinal positioning) exists between the catheter sheath 512 and the shaft 510 received in the first lumen 512d of the catheter sheath 512 during the transition toward or to the expanded configuration, at least part of the control element to have a first amount of length located outside of the distal end 512b of the catheter sheath 512. The control system or actuator system may be physically or operatively coupled to the control element (e.g., cable 513b) to cause, when the same particular relative positioning exists between the catheter sheath 512 and the shaft 510 received in the first lumen 512d during the transition toward or to the delivery configuration, at least part of the control element (e.g., cable 513b) to have a second amount of length located outside of the distal end 512b of the catheter sheath 512, the second amount of length being different than the first amount of length. In some embodiments, the control system or actuator system is physically or operatively coupled to the control element (e.g., cable 513b) to cause, when the particular relative positioning (e.g., a relative longitudinal positioning) exists between the catheter sheath 512 and the shaft 510 received in the first lumen 512d of the catheter sheath 512 during the transition toward or to the expanded configuration, the control element (e.g., cable 513b) to have a third amount of length located outside of end 513a-1 (i.e., shown in FIG. 5C) of sleeve 513a. In addition, the control system or actuator system may be physically or operatively coupled to the control element (e.g., cable 513b) to cause, when the same particular relative positioning exists between the catheter sheath 512 and the shaft 510 received in the first lumen 512d during the transition toward or to the delivery configuration, the control element to have a fourth amount of length located outside of the end 513a-1 of sleeve 513a, the fourth amount of length being different than the third amount of length. In some embodiments, cable 513b and sleeve 513a form part of a Bowden cable (e.g., third Bowden cable 555, called out in FIG. 7).

An actuator system (e.g., part or all of system 545, in some embodiments), which may be controlled at least in part by a control system (e.g., one or more components of control system 322, control system 545, or both control system 322 and control system 545 described in this disclosure), may employ one or more various actuators to manipulate or control various portions of a control element (e.g., control element 513) in accordance with various embodiments. For example, in some embodiments the use of projection 528 and receiver 529 may be employed to control a portion of control element 513. For instance, existence of a particular state (e.g., location, amount of tension, or both) of the control of control element 513 may be based, at least in part, on a particular amount of the length 528a received in receiver 529. It is noted that, in some embodiments, a particular aspect of the control of control element 513 based on a particular positioning between catheter sheath 512 and shaft 510 in the first lumen 512d of catheter sheath 512 may be analogous to a particular aspect of the control of control element 513 that is based, at least in part, on a particular amount of the length 528a of projection 528 received in receiver 529.

In some embodiments, the use of projection 528 and receiver 529 may be employed to meter cable 513b in a manner that is the same or similar to that described with respect to FIG. 6. In some embodiments, an actuator system (e.g., one or more of the components of at least FIG. 7 or others, in some embodiments) is operatively or physically coupled to the manipulable portion 502 (e.g., via each of at least one of a plurality of Bowden cables, for example, first Bowden cable 552 (an example of at least part of a control element) or cable 513b thereof) to transmit force to the manipulable portion. This operative coupling between the actuator system and the manipulable portion 502 may be configured to meter, e.g., control cable 513b to vary an amount of the cable 513b that extends outwardly (or is located outwardly) from the distal end 512b of catheter sheath 512 when part of shaft 510 is received in the first lumen 512d of catheter sheath 512 and, e.g., during a change in a size, a shape, or both, of the manipulable portion 502. In some embodiments, the actuator system may be configured to respond to, or be controlled by, varying amounts of the length 528a of projection 528 being within the receiver 529 by varying a rate in which the cable 513b is metered. In some embodiments, the actuator system responds to or is controlled by a rate of change in an amount of the length 528a of the projection 528 being within the receiver 529 by varying a rate in which the cable 513b is metered.

Turning now to FIGS. 5R-1 and 5R-2, respective top and bottom perspective views are illustrated of a part of catheter system 500 with various external portions of housing 520 removed for viewing of various internal mechanisms and actuators contained, at least in part, in housing 520. In each of FIGS. 5R-1 and 5R-2, at least part of projection 528 is shown received in receiver 529, while a portion of shaft 510 is received in first lumen 512d (not called out in FIG. 5R-2). For clarity, various portions of catheter system 500 (e.g., manipulable portion 502) are not shown in FIGS. 5R-1 and 5R-2. As best seen in FIG. 5R-1, a first actuator set 540, which may comprise some or all of an actuator system, includes a first particular actuator 540a and a second particular actuator 540b, the operation of each of which is described later in this disclosure. In this regard, the first actuator set 540 is located at least proximate the proximal end 510a of the shaft 510, according to some embodiments. As best seen in FIG. 5R-1, cable 513b (e.g., a portion of control element 513) extends along a particular path toward or to the second particular actuator 540b. In some embodiments, each actuator in the first actuator set 540 is operatively coupled to the manipulable portion by at least one respective flexible control element (e.g., at least the control cable 513b) arranged to selectively transmit force provided by the respective actuator in at least the first actuator set 540 to the manipulable portion 502.

Each of the actuators in the first actuator set 540 may be independently, separately, or selectively moveable from the other actuators in the first actuator set 540 from a respective first activation position toward or to a respective second activation position to vary a size, shape, or both a size and a shape of a deployed or expanded configuration of the manipulable portion 502 into a particular state. Each of the actuators in the first actuator set 540 may include various passive and active components suitable for causing force to be transmitted to manipulable portion 502 to change a size or shape thereof according to various embodiments. Different types of actuators may be employed in various embodiments. By way of non-limiting example, various ones of the first actuator set 540 can include a rotary actuator, a portion of which is rotatable from a first activation position toward or to a second activation position to cause a size, shape, or both a size and a shape of manipulable portion or structure 502a thereof to be varied.

In some embodiments, a third particular actuator 572 (described in detail later in this disclosure) is employed. In some embodiments, actuator 572 may be independently, separately, or selectively moveable from the other actuators (e.g., actuators in the first actuator set 540) from a respective first activation position toward or to a respective second activation position to vary a size, shape, or both a size and a shape of a deployed or expanded configuration of the manipulable portion 502 into a particular state. In some embodiments, actuator 572 is a particular actuator in a second actuator set 541, in which actuator 572 is moveable between two activation positions to cause one or more actuators (or sometimes two or more actuators in some embodiments) in the first actuator set 540 that are positioned in their respective second activation positions to move away from their respective activation positions as described later in this disclosure. The second actuator set 541 may comprise some or all of an actuator system. In some embodiments, the second actuator set 541 is located at least proximate the proximal end 510a of the shaft 510.

In FIGS. 5R-1 and 5R-2, each of actuators 540a, 540b, and 572 is a linear actuator, a portion of each translatable from a respective first activation position toward or to a respective second activation position to cause a size, shape, or both a size and a shape of manipulable portion 502 or structure 502a thereof to be varied. In FIGS. 5R-1 and 5R-2, each of actuators 540a, 540b, 572 is a linear actuator, a portion of each translatable from a respective first activation position toward or to a respective second activation position (for example, as described later in this disclosure) to cause a size, shape, or both a size and a shape of an expanded configuration of the manipulable portion 502 or structure 502a thereof to be varied into a particular state. In FIGS. 5R-1 and 5R-2, a portion of each of actuators 540a and 540b is guided by a respective one of guides 542a, 542b of guide system 542. In FIG. 5R-1, a portion of actuator 572 is guided by a guide 542e. In various embodiments, guide system 542 is configured to capture various portions (e.g., slider portions) of each of actuators 540a, 540b and 572 while allowing the portions of each of actuators 540a, 540b, and 572 to slide along a respective one of guides 542a, 542b, 542e. In some embodiments, guide system 542 is provided at least in part by an extrusion (e.g., an aluminum extrusion) while various portions of each of actuators 540a, 540b, and 572 can include a combination of metallic and non-metallic components. In various embodiments, each of various ones of the guides of guide system 542 includes a guide channel. In various embodiments, each of various ones of the guides of guide system 542 includes a guide rail.

In various embodiments illustrated in FIGS. 5R-1 and 5R-2, each of various ones of the guides (e.g., guides 542a, 542b) includes a channel-like member configured to at least partially enclose respective ones of at least some of the actuators in the first and second actuator sets 540, 541. In various embodiments, each of actuators 542a and 542b includes a respective one of handles 543a and 543b, each of the handles 543a, 543b manipulable by a user (e.g., a health care provider or technician) to move the respective one of actuators 540a, 540b at least toward or away from its respective second activation position. In various embodiments, each of the handles 543a, 543b is engageable to move the respective one of actuators 540*a*, 540*b* toward or away from (a) its respective first activation position, (b) its respective second activation position, or both (a) and (b). In various embodiments, each of one or more of actuators 540*a*, 540*b* is selectively lockable to maintain one or more desired positions (e.g., the second activation position) along respective ones of the guides 542*a*, 542*b*. For example, in some embodiments, each or one or more of handles 543*a*, 543*b* is rotatable (for example, in a clockwise direction) to lock a respective one of actuators 540*a*, 540*b* so as to maintain a desired positioning along a respective one of guides 542*a*, 542*b*. In some embodiments, each of one or more of handles 543*a*, 543*b* is rotatable (for example, in a counter-clockwise direction) to unlock a respective one of actuators 540*a*, 540*b* so as to allow the respective one of actuators 540*a*, 540*b* to move away from a particular positioning along a respective one of guides 542*a*, 542*b*. The locking of a particular actuator of the first set actuators 540 may be accomplished by various mechanisms that can cause the particular actuator to grip or otherwise become secured to a guide 542.

Figure 10A:
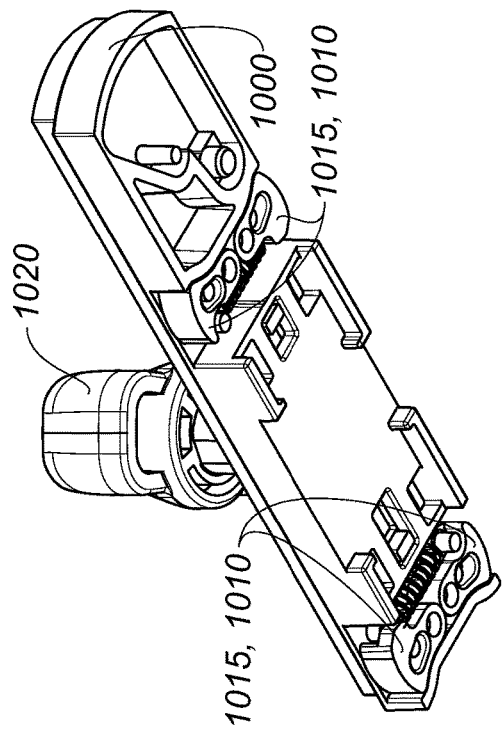
Figure 10C:
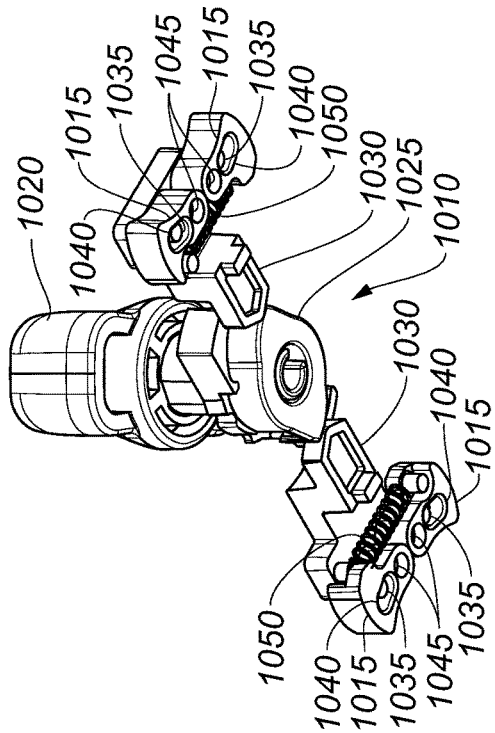
Figure 10B:
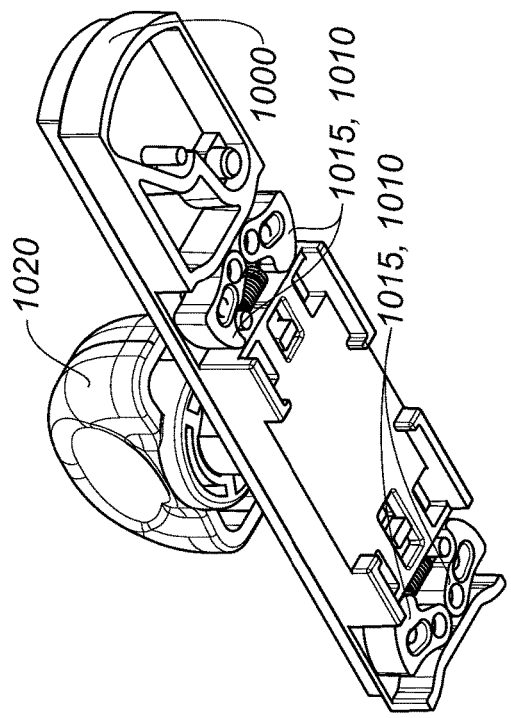

In some embodiments, various ones of handles 543*a*, 543*b* may be physically or operatively coupled to one or more cams that can be selectively brought into and out of frictional engagement with a guide of the guide system 542. For example, FIGS. 10A and 10B show respective perspective views of a locking device 1010 employed by a slider 1000 which may function in a similar or same manner to one or both of actuators 540*a*, 540*b* according to some embodiments. In this regard, in some embodiments, each respective actuator in the first actuator set 540 may include a respective locking device like that shown in FIG. 10).

Figure 10D:
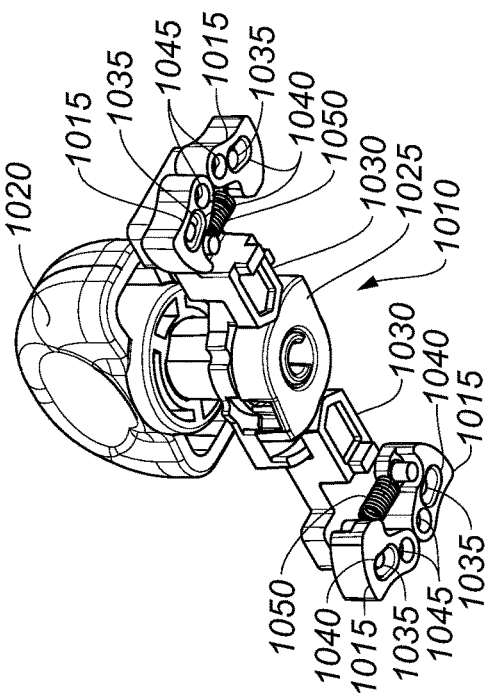

In some embodiments, the locking device 1010 is selectively moveable between or operable in an unlocked configuration (e.g., FIGS. 10A and 10C) and a locked configuration (e.g., FIGS. 10B and 10D). In embodiments where the locking device 1010 is part of an actuator (e.g., each of one or more actuators in the first set of actuators 540), the unlocked configuration permits or allows the actuator to move (e.g., at least in a direction toward or away from a respective activation position). In embodiments where the locking device 1010 is part of an actuator (e.g., each of one or more actuators in the first set of actuators 540), the locked configuration restricts or prevents the actuator from moving (e.g., at least in the direction toward or away from a respective activation position).

In FIG. 10A, locking device 1010 is in an unlocked configuration which allows slider 1000 to move with respect to a guide element (not shown for clarity but similar to, or the same as one or both of guides 542*a*, 542*b* in some embodiments), while in FIG. 10B, locking device 1010 is in a locked configuration which restricts slider 1000 from moving with respect to the guide element. Detailed perspective views of locking device 1010 are provided in FIG. 10C (i.e., unlocked configuration) and FIG. 10D (i.e., locked configuration). Various parts of slider 1000 are not shown in FIGS. 10C and 10D to better show parts of locking device 1010 not visible in FIGS. 10A and 10B. In some embodiments, locking device 1010 employs a plurality of locking cams 1015 (i.e., four in this illustrated embodiment) that may be selectively moved between the unlocked configuration and the locked configuration. In some embodiments, the locking cams 1015 are moved between the unlocked and the locked configuration by rotation of handle 1020 (which may correspond to handle 543*a*, 543*b*, or each of 543*a* and 543*b* in some embodiments). For example, in some embodiments, handle 1020 is physically coupled to a drive cam 1025 of locking device 1010 in a manner suitable for rotating the drive cam 1025 in each of a clockwise or counter clockwise direction. In some embodiments, drive cam 1025 is engageable with one or more (two in this illustrated embodiment) cam followers 1030. Each of the cam followers 1030 may include a drive pin 1035 received in a respective channel 1040 provided in each of the locking cams 1015. Rotation of handle 1020 in a manner that rotates drive cam 1025 such that it forces the cam followers 1030 relatively further apart from one another causes the locking device 1010 to move from the unlocked configuration (e.g., FIGS. 10A, 10C) toward or to the locked configuration (e.g., FIGS. 10B, 10D) by causing the drive pins 1035 to rotate the locking cams 1015 (i.e., about pivots 1045) outwardly into frictional engagement with the guide element (not shown for clarity but similar to, or the same as one or both of guides 542*a*, 542*b* in some embodiments). Rotation of the drive cam 1025 in an opposite direction may be employed to restore the locking device 1010 back to its unlocked configuration. In some embodiments, biasing members 1050 employ a biasing action that biases the locking device 1010 toward or to the unlocked configuration. Other locking/unlocking mechanisms may be employed in other embodiments.

Returning to FIGS. 5R-1 and 5R-2, actuator 572 includes cover 520*a* in various embodiments. For example, in FIGS. 5R-1 and 5R-2 cover 520*a* is operatively coupled to a first fanning slider 572*a* that makes up at least part of actuator 572 and which is guided by guide system 542. In this illustrated embodiment, the cover 520*a* is physically coupled to first fanning slider 572*a* via fasteners 520*b* and biasing element 520*c*. Biasing element 520*c* may include a compression spring in some embodiments. In some embodiments, cover 520*a* forms a handle of actuator 572. Other operations or functions associated with cover 520*a* are described later in this disclosure. The interaction of cover 520*a* with respect to actuator 572 is shown in exploded view in each of FIGS. 5R-1 and 5R-2 for clarity of illustration.

In various embodiments, catheter system 500 includes a control system 545 (which also may be referred to as an actuator system in some embodiments) comprising a set of devices or a device system that manages, controls, directs, or regulates the behavior of other device(s) or sub-system(s) that make up system 500. For example, control system 545 can, in some embodiments, control or include a transition actuator (e.g., actuator 540*a*, 540*b*, 546, 572, some other actuator or actuator set, or a portion of at least one of these actuators) physically or operatively coupled to the manipulable portion 502 to transition or modulate manipulable portion 502 or structure 502*a* thereof at least partially between various states or configurations (e.g., between a delivery configuration and an expanded or deployed configuration, or vice versa). In some embodiments, control system 545 is configured to control or include a modulation actuator (e.g., an actuator in FIG. 7, some other actuator or actuator set, or a portion of at least one of these actuators) physically or operatively coupled to the manipulable portion 502 (e.g., via at least the elongated control element 513) to modulate at least a size, a shape, or both a size and a shape of manipulable portion 502, for example, at least in a state where at least a part of the manipulable portion 502 and a part of the control element 513 extend outside the distal end of the catheter sheath 512 (e.g., FIG. 5C). In some embodiments, control system 545 can control or include a control element manipulation actuator (e.g., an actuator in FIG. 5S or 7, some other actuator or actuator set, or a portion of at least one of these actuators) to manipulate various control elements (e.g., control element 513) in system 500. In some embodiments, various ones of the transition, modulation, and control element manipulation actuators may be the same or separate devices or may be combined into a single device or system. For example, one of the actuators in FIG. 5S or 7 may be deemed a transition actuator, another one of these actuators may be deemed a modulation actuator, and yet another one of these actuators may be deemed a control element manipulation actuator. Or, in some embodiments, some or all of the transition actuator, modulation actuator, and control element manipulation actuator may be the same actuator. The points made in this discussion also apply to other actuators described herein. In various embodiments, various actuators (e.g., modulation, transition, and control element manipulation actuators) controlled by control system 545 may form part of control system 545 or may be distinct from control system 545. In some embodiments, the control system 545 may include one or more components of system 100 or control system 322, such as controller 324, that control one or more of the actuators described in this paragraph or otherwise herein.

Control system (which may also be referred to as an actuator system) 545 may trigger, be triggered, or cause an operation of a series of mechanical actuators in the correct sequence to perform a task associated with catheter system 500. Control system 545 may, in some embodiments, include a feedback system responsive to various inputs (e.g., user actions, machine action, or a combination of both) to initiate a particular function or transition between particular functions of system 500. In some embodiments, control system 545 is provided at least in part by at least one data processor, for example, as provided by one or more components of system 100 or control system 322, such as controller 324, and as such may be responsive to or controlled by various transducer data, machine data, or data input by a user. In various embodiments, control system 545 includes or takes the form of a mechanical system that includes a receiving mechanism configured to receive input force or input movement and a conversion mechanism that converts the input force or input movement to achieve a particular application of output force or output movement. In some of these various embodiments, the mechanical system may include various sensors, force limiters, or movement limiters that compare the output to a desired value and then directs the input or the conversion of the input. In some embodiments, control system 545 is entirely provided by a mechanical system. In some embodiments, input force or input movement is provided manually. Manual application of force or movement may be preferred for some medical device systems to avoid undesired outcomes that may accompany a misapplication of power-based (e.g., electrical, hydraulic or pneumatic) force or movement. Some example operations associated with control system 545 are schematically represented, according to some embodiments, in FIGS. 7A and 7B, which are described in more detail later in this disclosure.

In various embodiments, control system (which also may be referred to as an actuator system in some embodiments) 545 is responsive to or is controlled by relative movement between shaft 510 and catheter sheath 512 (e.g., at least when a portion of shaft 510 is received in the first lumen 512d of catheter sheath 512) to (a) modulate or control a particular configuration or state of manipulable portion 502 (e.g., by varying a force applied to the manipulable portion 502), (b) control a transition between various particular configurations or states of manipulable portion 502, (c) manipulate a control element (e.g., control element 513) or some particular combination of some or all of (a), (b), and (c). In some embodiments, control system 545 is responsive to or controlled by varying amounts of the length 528a of projection 528 being received within receiver 529 to (a) modulate or control a particular configuration or state of manipulable portion 502 (e.g., by varying a force applied to the manipulable portion 502), (b) control a transition between various particular configurations or states of manipulable portion 502, (c) manipulate a control element (e.g., control element 513), or some particular combination of some or all of (a), (b), and (c). In this regard, in some embodiments, the control system 545 responds to or is controlled by movement of the internal receiving mechanism 546 within the receiver 529 caused by a change in an amount of the length of the projection 528 within the receiver 529 by varying the force transmitted to the manipulable portion 502. In some embodiments, the control system 545 responds to or is controlled by a rate of change in an amount of the length of the projection 528 within the receiver 529 by varying a rate at which a control cable (e.g., cable 513b) is metered, e.g., as described with respect to FIG. 6 in this disclosure.

In some embodiments, at least a portion of at least one actuator (e.g., 546, described later in this disclosure, which may include a modulation actuator) is moveable in each of a first direction and a second direction different than the first direction. In some embodiments, the control system 545 may be configured to cause at least the portion of the actuator (e.g., modulation actuator) to move in the first direction to cause or accompany an increase in an amount of manipulable portion 502 extending outwardly from the distal end 512b of catheter sheath 512 and may be configured to cause at least the portion of the actuator (e.g., modulation actuator) to move in the second direction to cause or accompany a decrease in an amount of manipulable portion 502 extending outwardly from the distal end 512b of catheter sheath 512. In other words, at least the actuator (e.g., modulation actuator) may be operable to cause or accompany an increase or decrease in the amount of manipulable portion 502 extending outwardly from the distal end 512b of catheter sheath 512, depending upon when at least a portion of the actuator moves in the first direction or second direction, respectively.

In some embodiments associated with FIGS. 5R-1 and 5R-2, the receiver 529 includes an internal receiving mechanism 546 (which may be an example of an actuator or a particular actuator) configured to engage with a part of projection 528 received in receiver 529. In some embodiments, the internal receiving mechanism 546 is sized to matingly receive at least a portion of the projection 528. As best seen in FIG. 5R-2, the internal receiving mechanism 546 includes a coupler portion 546a (also referred to as coupler 546a) and a slider portion 546b (also referred to as receiver slider 546b) physically coupled to the coupler 546a. Receiver slider 546b is configured to move along guide 542c of guide system 542. In various embodiments, coupler 546a captively or otherwise physically couples the internal receiving mechanism 546 to at least the portion of the projection 528 matingly received in the internal receiving mechanism 546. The captive coupling allows at least the coupler 546a of internal receiving mechanism 546 to move along guide 542c during each of a first relative movement between projection 528 and receiver 529 that increases the amount of length 528a of projection 528 within receiver 529, and a second relative movement between projection 528 and receiver 529 that decreases the amount of length 528a of projection 538 within receiver 529. In various embodiments, coupler 546a includes a set of gripper arms 546c configured to engage or otherwise physically couple with a recess 528c of first projection 528 as best shown in FIG. 5R-3 which is a detailed view of part of FIG. 5R-2. In some of these various embodiments, the gripper arms 546c are biased to move apart (for example by means of a flexure) to disengage from recess 528c when the coupler 546a is positioned at a particular location along guide 542c (e.g., at location 535) where the gripper arms 546c are not constrained by a channel associated with guide system 542. This arrangement advantageously allows at least a portion of the projection 528 to self-couple (e.g., physically couple) to the coupler 546a (and internal receiving mechanism 546) when a first relative positioning between projection 528 and receiver 529 positions the gripper arms 546c within a confining structure of guide 542c, the positioning of the gripper arms 546c in the confining structure causing the gripper arms 546c to move together in a pinching or gripping manner that securely couples the gripper arms 546c to projection 528. Additionally, this arrangement advantageously allows at least a portion of the projection 528 to self-decouple (e.g., physically de-couple) from coupler 546a (and internal receiving mechanism 546) when a second relative positioning (different than the first relative positioning) between projection 528 and receiver 529 positions the gripper arms 546c at a location (e.g., location 535) where the gripper arms 546c are not confined but are allowed to move or flex apart to release the projection 528 from the gripper arms 546c, thereby allowing the shaft 510 and catheter sheath 512 to be pulled apart and become fully separated, if desired.

FIGS. 7A and 7B schematically show an operation of at least one actuator of a control system (which may also be referred to as an actuator system in some embodiments) 545 associated with housing 520 at two successive points in time. In various embodiments, operation of various actuators and control elements associated with FIGS. 7A and 7B may be employed during a change in a size, a shape, or both a size and a shape of manipulable portion 502 (not shown in FIGS. 7A and 7B). In various embodiments, operation of various actuators and control elements associated with FIGS. 7A and 7B may be employed to cause, at least in part, a change in a size, a shape, or both a size and a shape of manipulable portion 502 (for example as depicted in the sequence shown in FIGS. 5H, 5I and 5J). In FIGS. 7A and 7B, schematic representations are employed for ease of discussion. Additionally, for the ease of discussion, the movement proximally or distally of various elements in FIG. 7A, 7B as discussed herein is made in accordance with the "◄DISTAL" and "PROXIMAL►" indicators provided at the bottom of each of the FIGS. 7A and 7B. In this regard, in some embodiments, each of the control system 545 and at least one actuator or modulation actuator (e.g., 540a, 540b, 546, 572, some other actuator or actuator set, or a portion of at least one of these actuators) thereof are located, at least in part, at respective locations at least proximate the proximal end of the shaft 510.

In some embodiments, the coiling/uncoiling motion during deployment/retraction of the manipulable portion 502 (e.g., FIGS. 5H, 5I, and 5J) is caused and controlled, at least in part, by activation or movement of a second particular actuator 540b and an internal receiving mechanism 546 with respect to a first particular actuator 540a, which may act as an anchor in some configurations. In some embodiments, the coiling/uncoiling motion during deployment/retraction involves a metering of a portion of the control element 513 (e.g., a cable 513b) with different rates under the control of a master slider 556a, a sleeve slider 556b, and the second particular actuator 540b. In some embodiments, movement of the first particular actuator 540a causes or controls flattening of the manipulable portion 502 (e.g., FIGS. 5N and 5O). In some embodiments, clam shelling of the manipulable portion (e.g., FIGS. 5P and 5Q) may be caused and controlled by activation or action of the second particular actuator 540b.

With this context in mind, a portion of control element 513 may be operatively coupled to second particular actuator 540b to at least in part control coiling/uncoiling of the manipulable portion 502 during deployment/retraction. In some embodiments, the second particular actuator 540b includes various portions including a first slider portion 548a (also referred to in some embodiments as sleeve slider 548a) configured to slide along guide 542b, and a second slider portion 548b (also referred to in some embodiments as slave slider 548b) configured to slide within or with respect to, sleeve slider 548a. In some of these various embodiments, a portion of sleeve 513a proximate a proximal end 513a-2 of sleeve 513a (i.e., an end of sleeve 513a located relatively closer to the proximal end 510a of shaft 510 than the distal end 510b of shaft 510) is physically coupled (or, in some embodiments, fixedly coupled) to sleeve slider 548a. In this regard, axial or longitudinal movement of sleeve slider 548a along guide 542b can also cause longitudinal or axial movement of a portion of sleeve 513a in second lumen 511 within shaft 510. A particular location of sleeve slider 548a along guide 542b can be maintained by operating handle 543b to operate an associated lock as described herein.

As shown in FIGS. 7A and 7B, a first part 513b-1 of cable 513b extends outwardly from a first end 552a-1 of sleeve 552a at least across a region of space 550, the region of space 550 extending between first end 552a-1 and end 513a-2 of sleeve 513a. Cable 513b further extends through a lumen of a sleeve 552a and is physically or operatively coupled to first particular actuator 540a. In particular, a second part 513b-2 of cable 513b extends outwardly from a second end 552a-2 of sleeve 552a along a path that extends to first particular actuator 540a. In FIGS. 7A and 7B, sleeve 552a is physically coupled (or, in some embodiments, fixedly coupled) to slave slider 548b to accompany or move in tandem with slave slider 548b. In some embodiments, sleeve 552a and cable 513b form part of a Bowden cable (e.g., first Bowden cable 552). In various embodiments, the first part 513b-1 of cable 513b includes at least the portion 514 of cable 513b (not shown in FIGS. 7A and 7B, but shown at least in FIGS. 5H, 5I and 5J). In some embodiments, the part 513b-1 of cable 513b is physically coupled to manipulable portion 502 to, at least in part change the size, shape, or both, of the manipulable portion 502. A size of the region of space 550 varies when the slave slider 548b moves relative to the sleeve slider 548a. When the slave slider 548b is distally positioned as shown in FIG. 7A, the region of space 550 has a relatively smaller size than when the slave slider 548b is proximally positioned (e.g., as shown in FIG. 7B). The varying size of region of space 550 will result in different distances between the end 513a-2 of the sleeve 513a and first end 552a-1 of sleeve 552a in various embodiments. It is noted that various levels of tension on the cable 513b can lead to shortening of a distance between the end 513a-2 of the sleeve 513a and first end 552a-1 of sleeve 552a. In some embodiments, tension on the cable 513b may urge the slave slider 548b to move distally.

In various embodiments, a first part 554b-1 of a second cable 554 extends outwardly from the first end 554a-1 of a second sleeve 554a. In some embodiments, the second cable 554b is located at least in part of a lumen of second sleeve 554a, and second cable 554b and second sleeve 554a form part of a Bowden cable (e.g., second Bowden cable 554). In various embodiments, the first part 554b-1 of second cable 554b is physically coupled (or, in some embodiments, fixedly coupled) to the slave slider 548b. In some of these various embodiments, second cable 554b is operable to allow for a movement of the slave slider 548b in at least one of the proximal and distal directions. In some embodiments associated with FIGS. 7A and 7B, second sleeve 554a is physically coupled (or, in some embodiments, fixedly coupled) to sleeve slider 548a. It is noted in various embodiments that when the sleeve slider 548a is moved along guide 542b, sleeve 513a, slave slider 548b, and at least the respective first ends 552a-1, 554a-1 of sleeve 552a and second sleeve 554a also move with sleeve slider 548a. It is also noted in some embodiments that little or no relative movement between the sleeve 513a and the cable 513b occurs due to an adjustment in a positioning of the sleeve slider 548a, for example, as described later in this disclosure.

In various embodiments, the first part 554b-1 of cable 554b of the second Bowden cable 554 is physically or operatively coupled to the first Bowden cable 552 to cause at least the first end 552a-1 of the respective sleeve 552a of the first Bowden cable 552 to translate in response to, or during, at least part of a varying, caused by at least one actuator (e.g., 540b, 546, some other actuator or actuator set, or a portion of at least one of these actuators), of the amount of length of the first part 554b-1 of the cable 554b of the second Bowden cable 554 that extends outwardly from the first end 554a-1 of the respective sleeve 554a of the second Bowden cable 554. In some embodiments, the control (or actuator) system 545 or an actuator or other portion thereof is responsive to or controlled by variances in a relative positioning between the shaft 510 and the catheter sheath 512 (i.e., when part of the shaft 510 is received in the lumen 512d of the catheter sheath 512) to vary the length of at least part of cable 554b of the second Bowden cable 554 that extends from the first end 554a-1 of the sleeve 554a of the second Bowden cable. In this regard, in some embodiments, a control system (e.g., one or more components of system 100 or control system 322, such as controller 324) may be operatively coupled to an actuator system and operable to control activation of one or more actuators of the actuator system to vary the amount of length of a first part of the respective cable of each of the at least some of a plurality of Bowden cables that extends outwardly from the first end of the respective sleeve thereof during a change in a size, a shape, or both a size and a shape of the manipulable portion 502.

In some embodiments, the lumen of the sleeve 552a of the first Bowden cable 552 extends longitudinally in a particular direction from the first end 552a-1 of the sleeve 552a of the first Bowden cable 552, and the first part 554b-1 of cable 554b of the second Bowden cable 554 is physically or operatively coupled to the first Bowden cable 552 to cause at least the first end 552a-1 of the respective sleeve 552a of the first Bowden cable 552 to translate in a direction having a component parallel to this particular (longitudinal) direction (of the first Bowden cable 552) in response to, or at least during part of, the varying, caused by at least one actuator, of the amount of length of the first part 554b-1 of the cable 554b that extends outwardly from the first end 554a-1 of the respective sleeve 554a of the second Bowden cable 554. In some embodiments, at least one actuator (e.g., 556a, 556b, some other actuator or actuator set, or a portion of at least one of these actuators) is physically or operatively coupled to the first Bowden cable 552 to cause the length of the first part 513b-1 of cable 513b that extends from the first end 552a-1 of the respective sleeve 552a of the first Bowden cable 552 to vary during at least part of the varying of the amount of length of the first part 554b-1 of the cable 554b of the second Bowden cable 554 that extends outwardly from the first end 554a-1 of the respective sleeve 554a of the second Bowden cable 554 caused by at least one actuator (e.g., 540b, 546, some other actuator or actuator set, or a portion of at least one of these actuators) in housing 520.

In FIGS. 7A and 7B, various portions of the receiver 529 (e.g., internal receiving mechanism 546) can be moved (e.g., pushed) proximally or moved (e.g., pulled) distally by the projection 528. For example, in some embodiments, internal receiving mechanism 546 is moved proximally by projection 528 when a first relative movement between catheter sheath 512 and a part of the shaft 510 received in the first lumen 512d causes a distance between a location on the part of the shaft 510 and a location on the catheter sheath 512 to decrease (for example, as the shaft 510 and sheath 512 are drawn together as shown in a sequence depicted consecutively by FIGS. 5D, 5E, and 5F). In some embodiments, internal receiving mechanism 546 is moved distally by projection 528 when a second relative movement between catheter sheath 512 and a part of the shaft 510 received in the first lumen 512d causes a distance between a location on the part of the shaft 510 and a location on the catheter sheath 512 to increase (for example, as the shaft 510 and sheath 512 are drawn apart as shown in a sequence depicted consecutively by FIGS. 5F, 5E, and 5D).

As shown in FIGS. 7A and 7B, internal receiving mechanism 546 may include a physically coupled slider mechanism 556 (which may be an example of an actuator or a particular actuator), portions of which are configured to move along guide 542d (also called out in FIG. 5R-1). In FIG. 5R-2, an aperture 557 in guide system 542 allows for a physical coupling between internal receiving mechanism 546 and slider mechanism 556. In some embodiments, internal receiving mechanism 546 is fixedly coupled to slider mechanism 556. In some embodiments, internal receiving mechanism 546 is releasably coupled to slider mechanism 556. In some embodiments, internal receiving mechanism 546 is configured to selectively couple to, or decouple from, slider mechanism 556 at one or more particular locations along a path of travel along guide 542c. For example, various mechanisms activatable at different locations along guide 542c can be employed to selectively couple or decouple internal receiving mechanism 556 respectively to or from slider mechanism 556 at the different positions or at other positions having a defined relationship to the different positions. In some embodiments, slider mechanism 556 includes various moveable portions including a first portion 556a (also referred to as master slider 556a in some embodiments) and a second portion 556b (also referred to as second sleeve slider 556b in some embodiments).

As shown in FIGS. 7A and 7B, the two sleeves 552a and 554a may be physically coupled (or, in some embodiments, fixedly coupled) to the second sleeve slider 556b. In various embodiments, second sleeve slider 556b is physically coupled to master slider 556a with a mechanism, such as with a tether 558, that delays a movement of master slider 556a until second sleeve slider 556b has been moved by a predetermined or defined amount or has moved to a predetermined or defined position.

In some embodiments associated with FIGS. 7A and 7B, the second sleeve slider 556b (an example of a second moveable portion) is physically coupled to master slider 556a (an example of a first moveable portion) by the tether 558. In various embodiments, second sleeve slider 556b can be moved proximally or distally by the projection 528 when the projection 528 repositions internal receiving mechanism 546 as described above in this disclosure.

In FIGS. 7A and 7B, master slider 556a is located distally of second sleeve slider 556b. In various embodiments, master slider 556a and second sleeve slider 556b are located on or guided by a same guide of guide system 542 (e.g., guide 542d). In various embodiments, master slider 556a is physically coupled to slave slider 548b by second cable 554b. In particular, a second part 554b-2 of cable 554b of second Bowden cable 554 extending outwardly from a second end 554a-2 of second sleeve 554a is physically coupled to master slider 556a (which is an example of a first moveable portion of a particular actuator (e.g., slider mechanism 556, internal receiving mechanism 546, some other actuator or actuator set, or a portion of at least one of these actuators)). In some embodiments, a portion of the sleeve 554a of the second Bowden cable 554 located at least proximate to the second end 554a-2 of the sleeve 554a of the second Bowden cable 554 is physically coupled to the second sleeve slider 556b (an example of a second moveable portion of a particular actuator (e.g., slider mechanism 556, internal receiving mechanism 546, some other actuator or actuator set, or a portion of at least one of these actuators)). In various embodiments associated with FIGS. 7A and 7B, each of the respective ends (represented by dots in FIGS. 7A and 7B) of second cable 554b and each of the respective ends 554a-1 and 554a-2 of second sleeve 554a are located at respective locations in housing 520. In various embodiments associated with FIGS. 7A and 7B, each of the respective ends of cable 554b and each of the respective ends 554a-1 and 554a-2 of second sleeve 554a are located at respective locations outside a body when the manipulable portion 502 is located at a desired location within a bodily cavity in the body.

In various embodiments, master slider 556a (which is an example of a first moveable portion of a particular actuator (e.g., slider mechanism 556, internal receiving mechanism 546, some other actuator or actuator set, or a portion of at least one of these actuators)) includes a locking device (not shown in FIGS. 5 and 7, but an example is illustrated in FIGS. 8A and 8B, which is described in more detail in this disclosure below) configured to restrict movement of master slider 556a (e.g., along guide 542d) when various forces suitable for translating master slider 556a along guide 542d are not applied to master slider 556a. In some embodiments, this restricting of movement occurs during a varying of the length of the first part 554b-1 of the cable 554b of the second Bowden cable 554 that extends outwardly from the first end 554a-1 of the sleeve 554a of the second Bowden cable 554. In some embodiments, the locking device (e.g., FIGS. 8A and 8B) is configured to allow movement of the master slider 556a (an example of a first moveable portion) of the internal receiving mechanism 546 (an example of a particular actuator) after completion of a varying of a length of a part of cable 554b of the second Bowden cable 554 that extends outwardly from the first end 554a-1 of the sleeve 554a of the second Bowden cable 554.

In various embodiments, the locking device remains normally locked or fixedly coupled to a structure (e.g., guide 542d) when various forces suitable for translating master slider 556a along guide 542d are not applied to master slider 556a. In various embodiments, master slider 556a remains normally locked or secured to guide 542d but is configured to move more freely when moved in one, but not both of the proximal and distal directions. For example, in various embodiments associated with FIGS. 7A and 7B, master slider 556a is configured to move more freely when master slider 556a is urged to move distally than when the master slider 556a is urged to move proximally. In various embodiments, when master slider 556a is subjected to an applied force that is directed distally, master slider 556a will move relatively freely in the distal direction. When the applied force is removed, master slider 556a will once again secure itself to the guide 542d. In various embodiments, associated with FIGS. 7A and 7B, when a force (i.e., not applied by tether 558) is applied to master slider 556a in a proximal direction, master slider 556a remains relatively fixed or secured to guide 542d. That is, in these embodiments, while there is slack (or a tension level magnitude lower than a defined threshold) on the tether 558, the master slider 556a is restricted from being moved proximally (for example, under the influence of tension exerted by second cable 554b). However, when there is a suitable tension (i.e., a tension level or magnitude at least equal to the defined threshold) on the tether 558, the master slider 556a unlocks from the guide 542d and can be moved proximally in these embodiments. In other words, the locking device (e.g., FIGS. 8A and 8B) is configured to allow movement of the master slider 556a (an example of a first moveable portion) of the internal receiving mechanism 546 (an example of a particular actuator) after the sleeve slider 556b (an example of a second moveable portion) of the internal receiving mechanism 546 translates by a defined amount (e.g., a length of the tether 558). If a magnitude or level of tension on tether 558 subsequently falls below the defined threshold, the master slider 556a once again locks to guide 542d. It is noted that although selective locking of master slider 556a to guide 542d has been described in these embodiments, master slider 556a may be selectively locked to other structures (e.g., other guides of guide system 542) in other embodiments.

Various mechanisms may be employed to provide the locking device(s) described above with respect to master slider 556a. For example, a slider assembly 800 is schematically represented in FIGS. 8A and 8B. The slider assembly 800 includes a slider body 802 that is selectively moveable in a guide channel 804 (which, in some embodiments, may correspond to guide 542d). In some embodiments, the slider body 802 may correspond to the master slider 556a or be coupled to the master slider 556a. A set of locking cams 806 (i.e., two cams in this illustrated embodiment) is provided in slider body 802. Each of locking cams 806 may be pivotable about a respective pin 805. A biasing member 808 (e.g., shown as a tension spring in FIG. 8A. 8B) may be coupled to the locking cams 806 to urge each of the locking cams 806 to pivot about its respective pin 805 and cause a respective engagement surface 806a of each locking cam 802 to engage with guide channel 804 as shown in FIG. 8A.

In various embodiments, the engagement surfaces 806a are shaped to provide unidirectional self-locking characteristics. For example, in FIG. 8A, the engagement surfaces 806a are shaped to cause the locking cams 806 to pivot inwardly and thereby reduce their locking or holding capability when a particular force is applied to move the slider body 802 distally (i.e., in the direction indicated as "◀DISTAL" in FIG. 8A). Conversely, the shape of each of the engagement surfaces 806a is configured to urge the locking cams 806 to pivot outwardly and thereby increase locking or holding capability when a particular force is applied to move the slider body 802 proximally (i.e., in the direction indicated as "PROXIMAL▶" in FIG. 8A).

A tether 810 (which, in some embodiments, may correspond to the tether 558) may be coupled to the set of locking cams 806 to selectively cause the locking cams 806 to pivot inwardly and unlock when a particular tension having a suitable magnitude to overcome the biasing action of biasing member 808 is applied to tether 810. When the particular tension is applied to tether 810, the slider body 802 can be moved proximally (i.e., in the direction indicated as "PROXIMAL▶" for example, under the influence of tension provided by a cable member 812 (which, in some embodiments, may correspond to the cable 554b) physically coupled to slider body 802 as shown in FIG. 8B.

Returning to FIGS. 7A and 7B, as projection 528 is inserted into the housing 520 and is received by receiver 529, projection 528 may engage internal receiving mechanism 546 to cause internal receiving mechanism 546 to move (e.g., proximally in various embodiments) during the insertion. This movement in turn causes second sleeve slider 556b to move (i.e., proximally in various embodiments). During the movement of second sleeve slider 556b, an increasing distance develops between the moving second sleeve slider 556b and the stationary master slider 556a. It is noted that in various embodiments, master slider 556a remains stationary at this time because master slider 556a is locked in position, e.g., due to the locking mechanisms of FIG. 8. In various embodiments, an amount of length of the second part 554b-2 of second cable 554b that extends from second end 554a-2 of second sleeve 554a to master slider 556a increases with the increasing distance between second sleeve slider 556b and the stationary master slider 556a. That is, increasing amounts of length of the second part 554b-2 of the second cable 554b coupled to master slider 556a are pulled out of sleeve 554a with the increasing distance between second sleeve slider 556b and the stationary master slider 556a. This in turn, causes a varying of a length (e.g., a decrease in a length) of the first part 554b-1 of the cable 554b of the second Bowden cable 554 that extends outwardly from the first end 554a-1 of the sleeve 554a of the second Bowden cable 554.

It is noted that, in some embodiments such as those illustrated by FIGS. 7A and 7B, the second sleeve slider 556b (an example of at least part of an actuator) is at least operatively coupled to the second Bowden cable 554 to translate the second end 554a-2 of sleeve 554a of the second Bowden cable 554, the second end 552a-2 of the sleeve 552a of the first Bowden cable 552, or each of the second end 554a-2 and the second end 552a-2 of the sleeve 552a during at least part of a varying of the length of the first part 554b-1 of the cable 554b of the second Bowden cable 554 that extends outwardly from the first end 554a-1 of the sleeve 554a of the second Bowden cable 554 (e.g., due to the increasing distance between second sleeve slider 556b and the stationary master slider 556a).

It is also noted in various embodiments associated with FIGS. 7A and 7B, that an amount of translation undergone by an end or terminus of the second part 554b-2 of the cable 554b of the second Bowden cable 554 at a particular time during a varying of the length of the first part 554b-1 of the cable 554b of the second Bowden cable 554 that extends outwardly from the first end 554a-1 of the sleeve 554a of the second Bowden cable 554 (e.g., due to an increase in distance between second sleeve slider 556b and the stationary master slider 556a) has a magnitude less than an amount of translation undergone by the second end 554a-2 of sleeve 554a of the second Bowden cable 554 at the particular time during the varying of the length of the first part 554b-1 of the cable 554b of the second Bowden cable 554 that extends outwardly from the first end 554a-1 of the sleeve 554a of the second Bowden cable 554 (e.g., due to the increase in distance between second sleeve slider 556b and the stationary master slider 556a).

It is also noted in various embodiments associated with FIGS. 7A and 7B, that an amount of translation undergone through the lumen of the sleeve 552a of the first Bowden cable 552 by a portion of the cable 513 of the first Bowden cable 552 at a particular time during a varying of the length of the first part 554b-1 of the cable 554b of the second Bowden cable 554 that extends outwardly from the first end 554a-1 of the sleeve 554a of the second Bowden cable 554 (e.g., due to an increase in distance between second sleeve slider 556b and the stationary master slider 556a) is at least substantially equal in magnitude to an amount of translation undergone through the lumen of the sleeve 554a of the second Bowden cable 554 by a portion of the cable 554b of the second Bowden cable 554 at the particular time during the varying of the length of the first part 554b-1 of the cable 554b of the second Bowden cable 554 that extends outwardly from the first end 554a-1 of the sleeve 554a of the second Bowden cable 554 (e.g., due to the increase in distance between second sleeve slider 556b and the stationary master slider 556a).

A third Bowden cable may be employed in some embodiments. For example, a third Bowden cable 555 other than at least the second Bowden cable 554 may be employed in various embodiments. For example, control element 513 may, in some embodiments, provide a third Bowden cable 555 made up of sleeve 513a and cable 513b. It is also noted in various embodiments associated with FIGS. 7A and 7B, (and described in greater detail later in this disclosure) that an amount of translation undergone through the lumen of the sleeve 513a of the third Bowden cable 555 by a portion of the cable 513b of the third Bowden cable 555 at a particular time during a varying of the length of the first part 554b-1 of the cable 554b of the second Bowden cable 554 that extends outwardly from the first end 554a-1 of the sleeve 554a of the second Bowden cable 554 (e.g., due to an increase in distance between second sleeve slider 556b and the stationary master slider 556a) is greater in magnitude than an amount of translation undergone through the lumen of the sleeve 554a of the second Bowden cable 554 by a portion of the cable 554b of the second Bowden cable 554 at the particular time during the varying of the length of the first part 554b-1 of the cable 554b of the second Bowden cable 554 that extends outwardly from the first end 554a-1 of the sleeve 554a of the second Bowden cable 554 (e.g., due to the increase in distance between second sleeve slider 556b and the stationary master slider 556a). In this illustrated embodiment, the first Bowden cable 552 and the third Bowden cable 555 provided by control element 513 have different respective sleeves but share a common or same cable (i.e., cable 513b). In other embodiments, a third Bowden cable may be distinct from control element 513.

In some embodiments, such as those illustrated by FIGS. 7A and 7B, the second sleeve slider 556b (an example of an actuator) is at least operatively coupled to the first Bowden cable 552 to cause a change (e.g., an increase or decrease) in an amount of the length (e.g., due to the relative movement between the second sleeve slider 556b and the stationary master slider 556a) of the first part 513b-1 of the cable 513 of the first Bowden cable 552 that extends outwardly from the first end 552a-1 of sleeve 552a during at least part of a varying (e.g., due to the relative movement between the second sleeve slider 556b and the stationary master slider 556a) of the length of the first part 554b-1 of the respective cable 554b of the second Bowden cable 554 that extends outwardly from the first end 554a-1 of sleeve 554.

In some embodiments associated with FIGS. 7A and 7B, each of the second end 554a-2 of the second sleeve 554 and the second end 552a-2 of the sleeve 552a translates during at least part of the varying of the length of the first part 554b-1 of the respective cable 554b that extends outwardly from the first end 554a-1 of second sleeve 554a.

Since the second cable 554b is physically coupled to slave slider 548b (i.e., via the first part 554b-1 of cable 554b), the slave slider 548b is also moved (i.e., proximally in this illustrated embodiment) relative to sleeve slider 548a during the relative movement between second sleeve slider 556b and the stationary master slider 556a.

While the second sleeve slider 556b moves proximally, away from the stationary master slider 556a with a particular rate (e.g., under the pushing influence from the projection 528), the control element 513 is metered with a relatively faster rate (e.g., the 2× rate in some embodiments) discussed herein with respect to FIG. 6, according to some embodiments. Typically, in various embodiments, this movement of the second sleeve slider 556b away from the stationary master slider 556a, and its accompanying control element faster metering rate, occurs while the manipulable portion 502 is being advanced outwardly from the distal end 512b of the catheter sheath 512 due to a relative movement between the shaft 510 and the catheter sheath 512. In some embodiments, this faster metering rate is due to the occurrence of two concurrent movements. The first of the two concurrent movements is a movement of a portion of the first Bowden cable 552 (e.g., at least the first end 552a-1 of its sleeve 552a together with its cable 513b) proximally due to the proximal movement of the slave slider 548b. The second of the two concurrent movements is a relative movement between the cable 513b of the first Bowden cable 552 and the sleeve 552a of the first Bowden cable 552 due to a proximal movement of at least the second end 552a-2 of sleeve 552 (e.g., due to proximal movement of the second sleeve slider 556b). The combination of the first and second of the two concurrent movements causes the faster control cable metering rate (e.g., the 2× rate in some embodiments).

However, as the second sleeve slider 556b continues to translate proximally under the influence of the pushing from the projection 528, in some embodiments, the distance between the master slider 556a and the second sleeve slider 556b reaches a defined amount sufficient to remove slack in tether 558 (or 810) and allow tether 558 (or 810) to be sufficiently tensioned to cause the master slider 556a to unlock (e.g., by way of a locking/unlocking device of FIG. 8) and move along guide channel 542d (or 804). Upon unlocking, master slider 556a is moveable (i.e., proximally in this illustrated embodiment) by further movement of second sleeve slider 556b (i.e., proximally in this illustrated embodiment), and, since there is no more relative movement between the master slider 556a and the second sleeve slider 556b (i.e., the master slider 556a is in an unlocked state), the cable 554b of the second Bowden cable 554 no longer moves relative to its sleeve 554a (e.g., FIG. 7B). Consequently, the first of the above-discussed two concurrent movements no longer exists, thereby leaving only the movement of the cable 513b through sleeve 552a as the second sleeve slider 556b continues to move proximally while pulling the master slider 556a with it. Without the movement of the first end 552a-1 of the sleeve 552a of the first Bowden cable 552 in this tensioned-tether state, the control element metering rate drops to a relatively slower rate (e.g., the 1× rate in some embodiments) discussed herein with respect to FIG. 6, according to some embodiments. In various embodiments of FIGS. 7A and 7B, sleeve slider 548a remains stationary during the associated movements.

In some embodiments, the tensioned-tether state (e.g., FIG. 7B) causes the slave slider 548b to cease moving relative to the sleeve slider 548a. In some embodiments, tether 558 acts as a stop configured to restrict at least the slave slider 548b from being translated by more than a maximum amount. In some embodiments, tether 558 acts as a stop configured to restrict at least the first end 552a-1 of sleeve 552a from being translated by more than a predetermined or defined amount. In various embodiments, the control system (which also may be referred to as an actuator system in some embodiments) 545, in a particular state in which the first end 552a-1 of sleeve 552a of the first Bowden cable 552 has been translated by a predetermined amount, causes the first Bowden cable 552 to vary the length of the first part 513b-1 of cable 513b of the first Bowden cable 552 that extends outwardly from the first end 552a-1 of sleeve 552a of the first Bowden cable 552, and causes the second Bowden cable 554 to cease varying the length of the first part 554b-1 of the cable 554b of the second Bowden cable 554 during a varying of the length of the first part 513b-1 of cable 513b of the first Bowden cable 552 that extends outwardly from the first end 552a-1 of sleeve 552a of the first Bowden cable 552 after at least the first end 552a-1 of sleeve 552a of the first Bowden cable 552 has translated by the predetermined amount. The predetermined amount may be an amount of or related to a distance between the master slider 556a and second sleeve slider 556b in which tension in the tether 558 reaches a predetermined threshold. In addition, in some embodiments, in the particular state in which the first end 552a-1 of sleeve 552a of the first Bowden cable 552 has been translated by the predetermined amount, the control system (which also may be referred to as an actuator system in some embodiments) 545 causes at least the second end 554a-2 of the sleeve 554a of the second Bowden cable 554 to translate during the varying of the length of the first part 513b-1 of cable 513b of the first Bowden cable 552 that extends outwardly from the first end 552a-1 of sleeve 552a of the first Bowden cable 552 after at least the first end 552a-1 of sleeve 552a of the first Bowden cable 552 has translated by the predetermined amount.

In FIGS. 7 and 8 tethers 558, 810 may be provided by a flexible element (e.g., a flexible cable or line) according to various embodiments. In other embodiments other forms of tethers may be employed including by way of non-limiting example, telescoping members that can telescope between predetermined minimum and maximum extents. In other embodiments, other tethers may be provided by a pin-in-channel type coupling in which a pin is physically coupled to a first member and the channel is coupled to a second member, and relative movement between the first and second members is controlled by various stop features that limit movement of the channel.

In some embodiments, the particular state is a state in which the second end 554a-2 of sleeve 554a of the second Bowden cable 554 has been translated by a predetermined amount (e.g., with respect to the master slider 556a). In some embodiments, the particular state is a state in which the length of the first part 554b-1 of the respective cable 554*b* of the second Bowden cable 554 that extends outwardly from the first end 554*a*-1 of the respective sleeve 554*a* of the second Bowden cable 554 has been varied by a predetermined amount.

It is noted in various embodiments, when the relative movement of the projection 528 relative to the housing 520 changes direction, the movement of the second sleeve slider 556*b* also changes direction. For example, when the movement of the projection 528 is changed from moving proximally to moving distally, the second sleeve slider 556*b* is also changed to move distally, thereby reducing tension on the tether 558 (or 810) and causing master slider 556*a* to lock (e.g., by the locking mechanism of FIG. 8) and thereby restrict movement thereof along guide 542*d* (or 804) in the proximal direction. In this case, the relative movement between the second sleeve slider 556*b* and the now stationary master slider 556*a* can cause a reduction of an amount of length of the second part 554*b*-2 of the cable 554*b* as the distance between the second end 554*a*-2 of sleeve 554*a* and the master slider 556*a* reduces. The reduction in the amount of length of the second part 554*b*-2 of the cable 554*b* causes an increase in an amount of length of the first part 554*b*-1 of cable 554*b* (e.g., an increase in length thereof which reduces tension in the first part 554*b*-1 of cable 554*b*), which in turn allows the slave slider 548*b* to move distally under the influence of a reactive force provided by sleeve 552*a* due to tension in control cable 513*b*. In various embodiments, distal movement of a portion of cable 513*b* outwardly from housing 520 accompanies distal movement of the slave slider 548*b*. In various embodiments, play-out of a portion of cable 513*b* outwardly from housing 520 accompanies distal movement of the slave slider 548*b*.

In various embodiments, the distal movement of slave slider 548*b* continues until the second sleeve slider 556*b* and the master slider 556*a* come into contact. At that point, further distal movement of the second sleeve slider 556*b* pushes the master slider 556*a* distally. A lack of relative movement between the master slider 556*a* and the second sleeve slider 556*b* results in no movement of the slave slider 548*b* relative to sleeve slider 548*a*. In some embodiments, as the second sleeve slider 556*b* pushes the master slider 556*a* distally, a reduction in the amount of length of the second part 513*b*-2 of control cable 513*b* occurs, which in turn, allows for a distal movement of a portion of cable 513*b* outwardly from housing 520. In some embodiments, as the second sleeve slider 556*b* pushes the master slider 556*a* distally, a reduction in the amount of length of the second part 513*b*-2 of control cable 513*b* occurs, which in turn, allows for a play-out of a portion of cable 513*b* outwardly from housing 520.

Withdrawal of the projection 528 from the housing 520 accompanies a distal movement of the internal receiving mechanism 556, according to some embodiments. In this state, in some embodiments, the second sleeve slider 556*b* moves toward the master slider 556*a*, releasing tension in the tether 558 and causing both of the above-discussed two concurrent movements (albeit distally, not proximally), and a relatively faster control element metering rate (e.g., the 2× rate in some embodiments). When the distal movement of the second sleeve slider 556*b* causes second sleeve slider 556*b* to come into contact with the master slider 556*a*, master slider 556*a* is pushed distally. In this state, both the second sleeve slider 556*b* and the master slider 556*a* move together distally, so that little or no relative movement occurs between the cable 554*b* and sleeve 554*a* of the second Bowden cable 554, leaving only or primarily, the movement of cable 513*b* relative to sleeve 552*a*. Without the relative movement occurring between the cable 554*b* and sleeve 554*a* of the second Bowden cable 554, the control element metering rate drops to a relatively slower rate (e.g., the 1× rate in some embodiments) discussed herein with respect to FIG. 6, according to some embodiments. In various embodiments, sleeve slider 548*a* remains stationary during these movements.

It is noted in various embodiments that when the second sleeve slider 556*b* moves distally or proximally in a manner where a relative positioning between the second sleeve slider 556*b* and the master slider 556*a* is changing, the slave slider 548*b* is caused to move in the same direction of travel as the second sleeve slider 556*b*. When the second sleeve slider 556*b* moves distally or proximally in a manner where a relative positioning between the second sleeve slider 556*b* and the master slider 556*a* is not changing (e.g., when the master slider 556*a* moves along with the second sleeve slider 556*b*), the slave slider 548*b* does not move relative to sleeve slider 548*a*.

In various embodiments described above, the movement of the projection 528 relative to the housing 520 moves at least a portion of an actuator (e.g., internal receiving mechanism 546, some other actuator or actuator set, or a portion of at least one of these actuators) in a first direction (e.g., proximally along a linear path as defined in FIGS. 7A and 7B) and may be employed during manipulation or metering movement of at least a portion of cable 513*b* (an example of an elongated control element in some embodiments) in a manner that is the same or similar to that described with the take-up of the control line associated with line 602 in FIG. 6. When the relative movement of the projection 528 relative to the housing member 520 changes direction, the portion of the actuator (e.g., internal receiving mechanism 546, some other actuator or actuator set, or a portion of at least one of these actuators) moves in a second direction different than (e.g., opposite) the first direction (e.g., distally along a linear path as defined in FIGS. 7A and 7B) and may be employed during manipulation or metering movement of cable 513*b* in a manner that is the same or similar to that described with the play-out of the control line associated with line 604 in FIG. 6. In various embodiments, movement of the portion of the actuator in the first direction is associated with an amount of the length 528*a* of projection 528 within receiver 529 increasing in magnitude, while movement of the portion of the actuator in the second direction is associated with an amount of the length 528*a* of projection 528 within receiver 529 decreasing in magnitude. In some embodiments, movement of the portion of the actuator (e.g., internal receiving mechanism 546, some other actuator or actuator set, or a portion of at least one of these actuators) in the first direction is associated with a transition of the manipulable portion 502, at least in part, toward or to an expanded configuration, while movement of the portion of the actuator in the second direction is associated with a transition of the manipulable portion 502, at least in part, toward or to a delivery configuration.

In various embodiments, the actuator (e.g., internal receiving mechanism 546, some other actuator or actuator set, or a portion of at least one of these actuators) is operatively coupled to the cable 513*b* (an example of at least a portion of an elongated control element) to cause an increase and a subsequent decrease in an amount of the length of the cable 513*b* located outside of the distal end 512*b* of catheter sheath 512 when at least the portion of the actuator moves in the first direction (e.g., proximally as defined in FIGS. 7A and 7B), which may, in some embodiments, accompany or be required by an advancement of manipulable portion 502 outwardly from the distal end 512*b* of the catheter sheath 512, as shown by the sequence represented consecutively in FIGS. 5H, 5I and 5J. In this regard, in some embodiments, at least a portion of the actuator (e.g., internal receiving mechanism 546, some other actuator or actuator set, or a portion of at least one of these actuators) is moveable (and, in some embodiments, is selectively moveable, e.g., by way of the projection 528, or by relative movement between shaft 510 and catheter sheath 512) in each of one particular direction (e.g., the first direction) and a second direction different than the one particular direction (e.g., the first direction) to manipulate at least the portion of the cable 513*b* (an example of at least part of a control element). This movement of at least the portion of the actuator in each of the first direction and the second direction may be with respect to the housing 520.

In various embodiments, the actuator (e.g., internal receiving mechanism 546, some other actuator or actuator set, or a portion of at least one of these actuators) is operatively coupled (to the cable 513*b* (an example of at least part of an elongated control element) to cause an increase and a subsequent decrease in an amount of the length of the cable 513*b* located outside of the distal end 512*b* of catheter sheath 512 when at least the portion of the actuator moves in the second direction (e.g., distally as defined in FIGS. 7A and 7B), which may, in some embodiments, accompany or be required by a retraction of manipulable portion 502 into the distal end 512*b* of the catheter sheath 512, as shown by the sequence represented consecutively in FIGS. 5J, 5I and 5H.

In some embodiments, a modulation actuator (e.g., second particular actuator 540*b*, some other actuator or actuator set, or a portion of at least one of these actuators) may be physically or operatively coupled to the manipulable portion 502 to modulate at least a size, a shape, or both a size and a shape of the manipulable portion 502, e.g., at least in a state where at least a part of the manipulable portion 502 and a part of the cable 513*b* (an example of at least part of a control element) extends outside of the distal end 512*b* of the catheter sheath 512 (e.g., FIG. 5C). In some embodiments, the modulation actuator is operable to selectively move at least in part (e.g., by way of the projection 528, or relative movement between shaft 510 and catheter sheath 512) the manipulable portion 502 between a delivery configuration in which the manipulable portion 502 is sized, shaped, or both sized and shaped to be delivered through the first lumen 512*d* of the catheter sheath 512 and an expanded configuration in which the manipulable portion 502 is sized, shaped, or both sized and shaped too large for delivery through the first lumen 512*d* of the catheter sheath 512.

In some embodiments, the control system (e.g., an actuator system in some embodiments) 545, or one or more components of system 100 or control system 322, such as controller 324) may be physically or operatively coupled to or include the actuator (e.g., the internal receiving mechanism 546, some other actuator or actuator set, or a portion of at least one of these actuators), and may be configured to cause the actuator (e.g., the internal receiving mechanism 546, some other actuator or actuator set, or a portion of at least one of these actuators) to manipulate at least the portion of the cable 513*b* (e.g., at least part of a control element) to cause a length of the part of the cable 513*b* extending outside the distal end 512*b* of the catheter sheath 512 to increase and then subsequently decrease during or throughout a movement of at least the portion of the actuator in the one particular direction (e.g., in the first direction, proximal direction causing the advancement sequence of FIGS. 5H, 5I, 5J or in the second, distal direction causing the retraction sequence of FIGS. 5J, 5I, 5H). The movement of at least a portion of the actuator (e.g., the internal receiving mechanism 546, some other actuator or actuator set, or a portion of at least one of these actuators) in the one particular direction may be associated with a relative movement between the shaft 510 and the catheter sheath 512, when part of the shaft 510 is located in the lumen 512*d* of the catheter sheath 512. In some of these embodiments, a part of the manipulable portion 502 extends outside the distal end 512*b* of the catheter sheath 512 and has a size, a shape, or both a size and a shape too large to fit in the lumen of the catheter sheath (for example, as shown in FIGS. 5I and 5J) during or throughout the movement of at least the portion of the actuator in the one particular direction. In some of these embodiments, cable 513*b* is located, at least in part, in the lumen 512*d* of catheter sheath 512 during the movement of at least the portion of the actuator in the one particular direction. In some of these embodiments, shaft 510 is located at least in part, in the lumen 512*d* of catheter sheath 512 during the movement of at least the portion of the actuator in the one particular direction. In some embodiments, such control system 545 may be configured to cause the modulation actuator to modulate the manipulable portion 502, such that a part of the manipulable portion 502 extending outside the distal end 512*b* of the catheter sheath 512 has a size, a shape, or both a size and a shape too large to fit in the lumen 512*d* of the catheter sheath 512 (for example, as shown in FIGS. 5I and 5J) during or throughout the movement of at least a portion of the actuator (e.g., the internal receiving mechanism 546, some other actuator or actuator set, or a portion of at least one of these actuators) in the one particular direction.

In some embodiments, the actuator and the modulation actuator are the same device, or the actuator includes the modulation actuator. For example, the actuator may be the internal receiving mechanism 546, and the modulation actuator may be the master slider 556*a* or the sleeve slider 556*b* of the internal receiving mechanism 546. In this regard, it should be noted that the present invention is not limited to any particular actuator configuration. For example, although the internal receiving mechanism 546 is identified in some examples above as an actuator, any other component of catheter system 500 that achieves a desired function or result may alternatively be considered an actuator. For instance, although the internal receiving mechanism 546 may be deemed an actuator configured to move along a linear path when moving in the first direction (e.g., proximal direction in FIG. 7) or in the second direction (e.g., distal direction in FIG. 7), a portion of cable 554*b*, sleeve 554*a*, or each of the cable 554*b* and sleeve 554*a* may be considered a portion of such actuator (e.g., internal receiving mechanism 546, some other actuator or actuator set, or a portion of at least one of these actuators) due to their operative coupling, such that the portion of cable 554*b*, sleeve 554*a*, or each of the cable 554*b* and sleeve 554*a* follows an arcuate or coiled path (e.g., FIGS. 7A and 7B) when the internal receiving mechanism 546 is moving in the first direction (e.g., proximal direction in FIG. 7) or in the second direction (e.g., distal direction in FIG. 7).

In various embodiments, the amount of cable 513*b* within the housing 520 will vary in accordance with the movement of projection 528 when received by receiver 529. It is further noted that the amount of the portion 514 of cable 513*b* extending outwardly from the distal end 512*b* of the catheter sheath 512 will vary inversely (e.g., linearly or non-linearly) with an increase or decrease in an amount of the cable 513 located within the housing 520. In various embodiments, when movement of the projection 528 causes the second sleeve slider 556*b* to move distally or proximally in a manner where a relative positioning between the second sleeve slider 556*b* and the master slider 556*a* is changing, take-up of cable 513*b* (e.g., occurring during insertion of projection 528 inwardly into receiver 529) or play-out (e.g., occurring during retraction of projection 528 outwardly from receiver 529) occurs at a 2:1 ratio with the movement of the projection 528. This occurs because the slave slider 548*b* moves concurrently with the movement of the second sleeve slider 556*b* relative to the stationary master slider 556*a*. When movement of the projection 528 causes the second sleeve slider 556*b* to move distally or proximally in a manner where a relative positioning between the second sleeve slider 556*b* and the master slider 556*a* is not changing, take-up of cable 513*b* (e.g., occurring during insertion of projection 528 inwardly into receiver 529) or play-out of cable 513*b* (e.g., occurring during retraction of projection 528 outwardly from receiver 529) occurs at a 1:1 ratio with the movement of the projection 528. This occurs because the slave slider 548*b* does not move relatively to sleeve slider 548*a* during this movement.

It is understood that in various embodiments, the actual rate that cable 513*b* is metered during take-up or play-out is dependent on the actual rate of relative movement between projection 528 and receiver 529. That is, in various embodiments a defined speed ratio between the metering rate of cable 513*b* and the rate of relative movement between projection 528 and receiver 529 controls the actual metering rate of control cable 513*b*. The speed ratio specifies an output speed associated with an output portion of a particular device as a function of an input speed associated with an input portion of the particular device. It is noted in FIGS. 7A and 7B, that although a portion of a control element manipulation actuator (e.g., internal receiving mechanism 546, some other actuator or actuator set, or a portion of at least one of these actuators) moves along an essentially linear path during the take-up or play-out of cable 513*b*, the invention is not so limited, and the portion of the actuator may move along an arcuate path during the take-up or play-out of cable 513*b* in other embodiments.

In some embodiments, control system 545 is physically or operatively coupled to at least one control element manipulation actuator (e.g., internal receiving mechanism 546, some other actuator or actuator set, or a portion of at least one of these actuators) to control at least the actuator to cause movement of at least a portion of an elongated control element (e.g., cable 513*b*), e.g., along a path extending toward the manipulable portion 502, by metering the portion of the elongated control element with (a) a first rate of movement in response to at least a portion of the control element manipulation actuator (e.g., internal receiving mechanism 546, some other actuator or actuator set, or a portion of at least one of these actuators) moving (e.g., with respect to the housing 520) with a particular rate of movement in a first direction (e.g., proximally as defined in FIGS. 7A and 7B), and (b) a second rate of movement in response to the at least a portion of the control element manipulation actuator (e.g., internal receiving mechanism 546, some other actuator or actuator set, or a portion of at least one of these actuators) moving (e.g., with respect to the housing 520) with the same particular rate of movement in a second direction different than the first direction (e.g., distally as defined in FIGS. 7A and 7B), such that a first ratio of the first rate of movement to the particular rate of movement is different than a second ratio of the second rate of movement to the particular rate of movement, e.g., when a portion of cable 513*b* (an example of an elongated control element in some embodiments) is positioned at a particular location.

In various embodiments, a modulation actuator is operable to selectively move manipulable portion 502 or structure 502*a* thereof between a delivery configuration in which manipulable portion 502 or structure 502*a* thereof is sized or shaped to be delivered through a bodily opening leading to a bodily cavity and an expanded configuration in which the manipulable portion 502 or structure 502*a* thereof is sized or shaped too large for delivery through the bodily opening. In some of these various embodiments, such as those described above with respect to FIG. 6, control system 545 controls at least one control element manipulation actuator by switching a ratio of (a) a rate at which the portion of the elongated control element (e.g., cable 513*b*) is metered to (b) a rate of movement of at least the portion of the control element manipulation actuator (e.g., internal receiving mechanism 546, some other actuator or actuator set, or a portion of at least one of these actuators) between each ratio of a first set of two or more different predetermined ratios when the modulation actuator transitions the manipulable portion 502 from the delivery configuration to the expanded configuration. On the other hand, in some embodiments, the control system 545 controls the control element manipulation actuator to vary movement of the control element by switching the ratio of (a) to (b) between each ratio of a second set of two or more different predetermined ratios when the modulation actuator transitions the manipulable portion 502 from the expanded configuration to the delivery configuration. In some of these various embodiments, the first ratio is a member of the first set and the second ratio is member of the second set. In some embodiments, at least one of the predetermined ratios in the first set is the same as one of the predetermined ratios in the second set. In some embodiments, at least two of the predetermined ratios in the first set are the same as at least two of the predetermined ratios in the second set.

For example, in FIG. 6, the control line is metered with a first set of two different predetermined rates (i.e., line 602) during take-up of the control line and is metered with a second set of two different predetermined rates (i.e., line 604) during play-out of the control line. When a particular amount of the associated structure is located outside the distal end of the catheter sheath (e.g., a particular amount represented by 70 mm on the horizontal axis), the control line is metered with a first rate of the first set during control line take-up (i.e., portion 602*b* of line 602) that is different (e.g., twice the rate) than a second rate of the second set that the control line is metered with during control line play-out (i.e., portion 604*c* of line 604). When the metering rate of the control element is dependent on a given rate of movement of the portion of the control line manipulation actuator in each of the metering directions (for example, as described with respect to FIGS. 7A and 7B), each of the predetermined rates in each of the first and second sets can be expressed as a ratio of the predetermined rate to the rate of movement of the portion of the control line manipulation actuator when the portion of the control line manipulation actuator is moved in each of different directions with the same rate of movement.

Stated another way, in various embodiments, a modulation actuator is operable to selectively move manipulable portion 502 or structure 502*a* thereof between a delivery configuration in which manipulable portion 502 or structure 502*a* thereof is sized or shaped to be delivered through a bodily opening leading to a bodily cavity and an expanded configuration in which the manipulable portion 502 or structure 502*a* thereof is sized or shaped too large for delivery through the bodily opening. In some of these various embodiments, such as those described above with respect to FIG. 6, control system 545 controls at least one control element manipulation actuator by switching a ratio of (a) a rate at which the portion of the elongated control element (e.g., cable 513b) is metered to (b) a rate of movement of at least the portion of the control element manipulation actuator (e.g., internal receiving mechanism 546, some other actuator or actuator set, or a portion of at least one of these actuators) between each ratio of a first set of two or more different ratios when the modulation actuator transitions the manipulable portion 502 from the delivery configuration to the expanded configuration. In some embodiments, each ratio in the first set of two or more different ratios has a value corresponding to a respective one of a first set of two or more different predetermined values. On the other hand, in some embodiments, the control system 545 controls the control element manipulation actuator to vary movement of the control element by switching the ratio of (a) to (b) between each ratio of a second set of two or more different ratios when the modulation actuator transitions the manipulable portion 502 from the expanded configuration to the delivery configuration. In some embodiments, each ratio in the second set of two or more different ratios has a value corresponding to a respective one of a second set of two or more different predetermined values. In some embodiments, the first ratio is a member of the first set of two or more different ratios and the second ratio is member of the second set of two or more different ratios. In some embodiments, at least one of the predetermined ratios in the first set is the same as one of the predetermined ratios in the second set. In some embodiments, at least two of the predetermined ratios in the first set are the same as at least two of the predetermined ratios in the second set.

In some embodiments, the particular amount of the associated structure (e.g., the structure 502a of the manipulable portion 502) located outside the distal end 512b of the catheter sheath 512 is a particular size of the manipulable portion 502 or structure 502a thereof between the distal end 512b and the distal end of the manipulable portion 502. In some embodiments, the particular amount of the manipulable portion 502 or structure 502a thereof located outside the distal end 512b of the catheter sheath 512 is a particular length of the manipulable portion 502 or structure 502a thereof extending from the distal end 512b to the distal end of the manipulable portion 502 or structure 502a thereof. In some embodiments, the particular amount of the manipulable portion 502 or structure 502a thereof located outside the distal end 512b of the catheter sheath 512 is a particular length of the manipulable portion 502 or structure 502a thereof extending along a surface of the manipulable portion 502 or structure 502a thereof from the distal end 512b to the distal end of the manipulable portion 502 or structure 502a thereof. In some embodiments, the particular amount of the manipulable portion 502 or structure 502a thereof located outside the distal end 512b of the catheter sheath 512 is a surface area or volume of a part of the manipulable portion 502 or structure 502a thereof located outside the distal end 512b of the catheter sheath 512. In some embodiments, a particular amount of the manipulable portion 502 or structure 502a thereof extending outwardly from the distal end 512b of catheter sheath 512 corresponds to a particular amount of the length 528b of projection 528 being received in receiver 529 (for example as shown in FIGS. 7A and 7B). In some embodiments where the control line metering scheme depicted in FIG. 6 is employed, a control system (e.g., control system 545, or one or more components of system 100 or control system 322, such as controller 324) may be configured to control at least a control line manipulation actuator that is the same or similar to that represented in FIGS. 7A and 7B, when a particular amount of length 528b of projection 528 is received within receiver 529 during a transition of the manipulable portion 502 toward or to an expanded configuration, to cause cable 513b (an example of at least part of a control element or cable) to be metered with a first rate. On the other hand, in some embodiments, the control system may be configured to control at least the control line manipulation actuator, when the same particular amount of length 528b of projection 528 is received within receiver 529 during a transition of the manipulable portion 520 toward or to a delivery configuration, to cause control cable 513b to be metered with a second rate different than the first rate.

When the control line metering scheme depicted in FIG. 6 is employed by a control line manipulation actuator that is the same or similar to that represented in FIGS. 7A and 7B, each of portion 602b of line 602 and portion 604b of line 604 may be associated with a condition in which a relative positioning between the second sleeve slider 556b and the master slider 556a is changing, while each of portion of 602c of line 602 and portion 604c of line 604 may be associated with a condition in which a relative positioning between the second sleeve slider 556b and the master slider 556a is not changing. Accordingly a control loop that is the same or similar to that created by portions 602b, 602c, 604b and 604c may be established by the control system 545 for the metering of cable 513b as the manipulable portion 502 is advanced outwardly from the distal end 512b of catheter sheath 512 into an expanded configuration that is the same or similar to that shown in FIG. 5J and then subsequently retracted back into the confines of first lumen 512d (e.g., into a delivery configuration). It is noted in some embodiments, that metering action of the control line manipulation actuator represented in FIGS. 7A and 7B may in some cases be interrupted at various points along the control loop prior to a completion of an advancement of the manipulable portion 502 into the expanded configuration or prior to a completion of a retraction of the manipulable portion 502 back into the confines of first lumen 512d. The interruption may be motivated, for example, by a user decision to reverse a movement of manipulable portion 502 to (a) retract the manipulable portion 502 rather than proceeding with the advancement of the manipulable portion 502 toward or to the expanded configuration, or (b) advance the manipulable portion rather than proceeding with the retraction of the manipulable portion 502 into the confines of the first lumen 512d. In either case, a change in a metering direction of cable 513b is typically required during the reversal of movement of manipulable portion 502 caused by the interruption.

A required change in the metering direction of cable 513b may be motivated for various reasons including occurrences of slack or undesired level of tension in the cable 513b as described above in this disclosure. In various embodiments, an employed control element metering system (e.g., such as that represented in FIGS. 7A and 7B) is configured to, when interrupted from metering a portion of a control element (e.g., cable 513b) in a first particular metering direction to metering the portion of the control element in a second particular metering direction different than the first particular metering direction, cause a defined or predetermined change in metering rate to accompany the change in metering direction. That is, when the portion of the control element is interrupted from being metered with a first rate in a first metering direction to being metered in a second metering direction different than the first metering direction, the control element metering system can cause the portion of the control element to be metered with a second rate in the second metering direction, the second rate being different than the first rate. This mode of operation can occur at various points along the control loop. For example in FIG. 6, the control line is being metered with a first rate in a first metering direction (e.g., a take-up direction) associated with a portion 602c of line 602. If the metering of the control line along portion 602c in the first metering direction is interrupted and metered in a second different metering direction (e.g., a play-out direction) before less than an intended amount of the device has been advanced outwardly from the distal end of the catheter sheath (for example, when only approximately 150 mm of the device has been advanced outwardly from the catheter sheath), the control line is not metered in the second metering direction with the first rate, but rather a second rate represented by line 606. In various embodiments, the second rate is the same as the metering rate associated with portion 604b of line 604. Advantageously, these various embodiments allow for the device to be manipulated in a particular desired manner that may be required by the change in the metering direction during the interrupted cycle.

In various embodiments associated with FIGS. 5 and 7, control system 545 is configured to cause movement of a portion of control element 513 (e.g., cable 513b) along a path extending toward manipulable portion 502. Control system 545 may be further configured to, when a portion of the control element 513 is located at a particular position along the path, (a) meter movement of the portion of the control element 513 at a first rate in a first direction along the path away from the particular position at least in response to occurrence of a first state that triggers a transition of the manipulable portion 502 toward or to the expanded configuration, and (b) meter movement of the portion of the control element 513 at a second rate in a second direction along the path away from the particular position at least in response to occurrence of a second state that triggers a transition of the manipulable portion 502 toward or to the delivery configuration. In some embodiments, the second direction along the path is different than the first direction along the path and the second rate is different than the first rate.

In some embodiments, control system 545 is configured, when a particular amount of the manipulable portion 502 is located outside the distal end 512b of the catheter sheath 512 during a transition of the manipulable portion 502 toward or to the expanded configuration, to control an actuator to cause (a) control element 513 to have a first amount of length located outside the distal end 512b of the catheter sheath 512, at least in response to occurrence of a first state that triggers a transition of the manipulable portion 502 toward or to the expanded configuration, and when the same particular amount of the manipulable portion 502 is located outside the distal end 512b of the catheter sheath 512 during a transition of the manipulable portion 502 toward or to the delivery configuration, to control the actuator to cause (b) control element 513 to have a second amount of length located outside the distal end 512b of the catheter sheath 512, at least in response to occurrence of a second state that triggers a transition of the manipulable portion 502 toward or to the delivery configuration. In various ones of these embodiments, the first amount of length is different than the second amount of length.

In some embodiments, control system 545 is configured, when a particular relative positioning exists between the catheter sheath 512 and the shaft 510 received in the first lumen 512d of the catheter sheath 512 during a transition of the manipulable portion 502 toward or to the expanded configuration, to control an actuator to cause (a) control element 513 to have a first amount of length located outside the distal end 512b of the catheter sheath 512, at least in response to occurrence of a first state that triggers a transition of the manipulable portion 502 toward or to the expanded configuration, and when the same particular relative positioning exists between the catheter sheath 512 and the shaft 510 received in the first lumen 512d of the catheter sheath 512 during a transition of the manipulable portion 502 toward or to the delivery configuration, to control the actuator to cause (b) control element 513 to have a second amount of length located outside the distal end 512b of the catheter sheath 512, at least in response to occurrence of a second state that triggers a transition of the manipulable portion 502 toward or to the delivery configuration. In various ones of these embodiments, the first amount of length is different than the second amount of length. The particular relative positioning may be a relative longitudinal positioning in some embodiments.

The first and the second states described above can take different forms in various embodiments. For example, the first state may be associated with a direction of relative moment between catheter shaft 512 and a portion of shaft 510 in first lumen 512d that decreases a distance between a location on catheter sheath 512 and a location on shaft 510 and the second state may be associated with a direction of relative moment between catheter shaft 512 and a portion of shaft 510 in first lumen 512d that increases a distance between a location on catheter sheath 512 and a location on shaft 510.

In some embodiments associated with FIGS. 7A and 7B, after leaving the confines of the sleeve 552a, the second part 513b-2 of cable 513b is subjected to a bend (e.g., a 180 degree bend) in a guide 560 before coupling to the forming slider 561 associated with first particular actuator 540a. In various embodiments, guide 560 is relatively rigid in form and does not flex like sleeves 552 and 554. The use of guide 560 may be motivated by various reasons including imparting a serpentine path to the cable 513b to reduce an overall size of housing 520 or additionally or alternatively, guiding cable 513b to another guide in guide system 542 or additionally or alternatively, changing an activation direction of forming slider 561. Forming slider 561 may be configured to move along guide 542a. The operation of forming slider 561 is described later in this disclosure.

FIGS. 5S-1, 5S-2, 5S-3, 5S-4, 5S-5, and 5S-6 (collectively FIG. 5S) are top plan views of various actuator sets associated with catheter system 500, various ones of the actuators in the sets positioned in particular activation positions associated with different particular states of the expanded configuration of manipulable portion 502 according to various embodiments. In some embodiments, various ones of the actuator sets may include one or more actuators selectively moveable between at least two different activation positions. For example, an actuator may be selectively moveable from a respective first activation position into a second activation position to change a size, a shape, or both a size and a shape of an expanded configuration of manipulable portion 502 from one particular state to another particular state. In various embodiments, an actuator set (e.g., first actuator set 540) may include two or more actuators, each of the actuators in the actuator set independently or separately moveable from the other actuators in the actuator set from a respective first activation position into a respective second activation position to independently change a size, a shape, or both a size and a shape of an expanded configuration of manipulable portion 502 from one particular state into another particular state. It is noted in at least some of the embodiments of FIG. 5S that shaft 510 (not called out) is inserted into the first lumen 512d of catheter sheath 512 and that projection 528 (not called out) is received in receiver 529 (not called out in these figures).

In various embodiments, various components or devices associated with housing 520 have respective positionings depicted in FIG. 5S-1 that correspond to an expanded configuration of manipulable portion 502 having a state that is the same or similar to the first fanned configuration 536 exemplified in FIG. 5L-1. It is understood that other configurations or configuration states of manipulable portion 502 may correspond to the configuration of housing 520 in FIG. 5S-1 in other embodiments. Cover 520a is shown in a first position 570a in FIG. 5S-1. In various embodiments, first position 570a is also referred to as a closed position that may restrict user access to some other portion of housing 520 or some particular device or devices accommodated by housing 520. In various embodiments, user access to various actuators in an actuator set is restricted when cover 520a is in the first position 570a. For example, user access to a first actuator set (e.g., first actuator set 540) that includes first particular actuator 540a and second particular actuator 540b (or at least part of each of first particular actuator 540a and second particular actuator 540b) is restricted when cover 520a is in the first position 570a in some embodiments. In various embodiments, cover 520a is selectively moveable between first position 570a and a second position 570b (shown in FIG. 5S-2) located to allow or permit user access to first particular actuator 540a and second particular actuator 540b. In some embodiments, second position 570b is also referred to as an open position. In some embodiments, cover 520a forms part of an interlock whose operation prevents an operation of another device. For example, when the cover 520a is moved into the first position 570a from another position, access to, or operation of, first particular actuator 540a and second particular actuator 540b is prevented.

In various embodiments cover 520a forms part of, or is physically or operatively coupled to, an actuator that is selectively moveable between at least two different activation positions. In some embodiments, cover 520a forms part of, or is physically coupled to, an actuator that is selectively moveable between at least two activation positions to vary a size, a shape, or both a size and a shape of manipulable portion 502 or an expanded configuration of the manipulable portion 502. For example, in some embodiments, cover 520a forms a part of an actuator set comprising an actuator 572 configured to vary a size, shape, or both size and shape of an expanded configuration of manipulable portion 502 from the first fanned configuration 536 exemplified in FIGS. 5L-1, 5L-2 to a second fanned configuration 537 (also referred to as a bifurcated doming configuration) exemplified in FIGS. 5M-1, 5M-2 when a movement of cover 520a causes actuator 572 (e.g., at least first fanning slider 572a shown in FIG. 5R-1) to move from a first activation position (e.g., position 571a shown in FIG. 5S-1) into a second activation position (e.g., position 571b shown in FIG. 5S-2). In this regard, the actuator 572 (also referred to herein as a third particular actuator in some embodiments) is selectively moveable into a respective activation position (e.g., 571b) to fan at least some of the plurality of elongate members 504 with respect to one another to create a fanned arrangement radiating from a location between the proximal portion 508a and the distal portion 508b of the manipulable portion 502 when the manipulable portion 502 is in the expanded configuration. It is understood that although first position 570a and position 571a are shown as being the same position in FIG. 5S-1 and second position 570b and position 571b are shown as being the same position in FIG. 5S-2, (a) first position 570a and the first activation position may be different, (b) second position 570b and the second activation position may be different, or both (a) and (b) in other embodiments. In FIG. 5M-1, at least some of the elongate members 504 are additionally fanned by actuator 572 to reconfigure an expanded configuration of manipulable portion 502 from the first fanned configuration or state 536 to the second fanned configuration or state 537. In various embodiments, at least some of the elongate members 504 are additionally fanned (e.g., fanned in addition to the autonomous fanning described above in this disclosure) to more fully or more evenly increase a circumferential distribution of the elongate members 504. For example, FIGS. 5L-2 and 5M-2 respectively show top plan views of the expanded manipulable portion 502 in the first fanned configuration 536 and the second fanned configuration 537. As compared with FIG. 5L-2, various portions of the elongate members 504 are more fully or more completely circumferentially distributed in FIG. 5M-2.

A fuller or more complete circumferential distribution of the elongate members 504 may be motivated by various reasons. For example, such a distribution may be better suited for distributing an array of transducers (e.g., transducers 506) over a greater interior surface region of bodily cavity into which manipulable portion 502 is introduced. In various embodiments associated with FIG. 5M-1, the proximal portion 508a of manipulable portion 502 forms a first domed shape 508a-1, and the distal portion 508b of manipulable portion 502 forms a second domed shape 508b-1, when the manipulable portion is in a deployed configuration.

Different actuators may be implemented as actuator 572 in various embodiments. In some embodiments associated with FIG. 5M-1, actuator 572 may work in a same or similar fashion to the separator 2852 described in co-assigned International Application No.: PCT/US2012/022061, which is incorporated herein by reference. For example, actuator 572 may include a mechanism that converts an input movement (e.g., an input movement of cover 520a) into an output movement of various control elements 573 (shown in FIG. 5M-1) in a manner suitable for additionally fanning of the elongate members 504. In FIG. 5M-1, each control element 573 includes a control cable 573b received in a lumen of sleeve 573a (e.g., the same or similar to flexible lines 2853 and tubular members 2854 in co-assigned International Application No.: PCT/US2012/022061, which is incorporated herein by reference). In FIG. 5M-1 sleeves 573a are physically coupled (or, in some embodiments, fixedly coupled) to surface 518b of an elongate member 504 (e.g., an elongate member 504 positioned at the bottom of the stacked arrangement), each of the sleeves 573a sized to terminate at a respective location along a length of the elongate member 504. In various embodiments, each of at least some of the sleeves 573a is sized to terminate at different longitudinal locations along the length of elongate member 504. Each of the termination locations is a selected position where exiting portions of the respective cables 573b may be positioned at a desired location along the length of the elongate member 504. Each termination location may be chosen to advantageously allow the respective exiting cable 573b to apply force with sufficient mechanical advantage to move the expanded configuration of the manipulable portion 502 between the two fanned states. From each termination location, the respective exiting cable 573b is physically coupled to an adjacent elongate member 504. In FIG. 5M-1 two sets of exiting cables 573b couple the two portions 508a and 508b to additionally fan the elongate members (i.e., one set of the exiting cables 573b being on a far side of manipulable portion 502 depicted in FIG. 5M-1 and thereby not visible). In various embodiments, movement of the actuator 572 from the first activation position (e.g., position 571a) into the second activation position (e.g., position 571b) (for example, as a consequence of movement of cover 520a) increases tension levels in various cables 573b sufficiently to draw the associated coupled adjacent elongate members 504 toward each other to move the manipulable portion 502 from the first fanned configuration or state 536 into the second fanned configuration or state 537. For example, with reference to FIGS. 5R-1 and 5R-2, actuator 572 includes a first fanning slider 572a moveable along guide 542e and a pair of second fanning sliders 572b, 572c, each moveable along guide 542f. In various embodiments, various ones of the cables 573b (not shown in FIGS. 5R-1, 5R-2 for clarity) are physically coupled to respective ones of the second fanning sliders 572b, 572c. First fanning slider 572a is physically coupled (for example via passageway or channel between guides 542e and 542f) to at least one of the second fanning sliders 572b, 572c to move the connected at least one of the second fanning sliders 572b, 572c to increase tension levels in the various ones of the cables 573b when first fanning slider 572a is moved, for example, between the first activation position (e.g., position 571a) and the second activation position (e.g., position 571b) (e.g., as a consequence of movement of cover 520a). In some embodiments, various devices may be employed to delay a movement of one of the second fanning sliders 572b, 572c until another of the second fanning sliders 572b, 572c has moved by a desired amount or has moved to a desired location under the influence of a movement of first sleeve slider 572a. Such delays may be used to move the expanded configuration of the manipulable portion 502 between the two fanned states in a series of staged movements. In some embodiments, a movement of one of the second fanning sliders 572b, 572c may stop before another of the second fanning sliders 572b, 572c does. In various embodiments, the respective sleeve 573a associated with each respective cable 573b maintains the respective cable 513b in a position suitable for applying the fanning force in a suitable direction during the tensioning of the cable 573b (e.g., which may be or may not be similar to a Bowden cable). Various ones of the elongate members 504 may be additionally physically coupled together by coupling members (similar to or the same as coupling members 2858 in co-assigned International Application No.: PCT/US2012/022061, which is incorporated herein by reference). In various example embodiments, each coupling member may allow movement of one of the elongate members 504 coupled by the coupling member to also cause movement of another of the elongate members 504 coupled by the coupling member. In some example embodiments, the coupling members are arranged to restrict or limit an amount of movement that an elongate member 504 undergoes as the portion of the device is moved into the second fanned configuration 537. For clarity, control element 513 is not shown in FIGS. 5M-1 and 5M-2. For clarity, the various control elements 573 are only shown in FIG. 5M-1. In some embodiments, actuator 572 forms part of the first actuator set 540.

In some embodiments, a locking device is selectively operable in a locked configuration which restricts cover 520a from moving at least in a direction away from the second position 570b (or, in some embodiments in which cover 520a forms part of actuator 572, from the second activation position 571b) and an unlocked configuration which permits cover 520a to move at least in the direction away from the second position 570b (or from the second activation position 571b). For example, in some embodiments, biasing member 520c (i.e., FIG. 5R-1) is arranged to provide a force on cover 520a that biases cover 520a downward or toward an upper surface of housing 520. When the cover 520a is moved from the first position 570a (i.e., FIG. 5S-1) to the second position 570b (i.e., FIG. 5S-2) (or from first activation position 571a to second activation position 571b), biasing member 520c forces the cover 520a downward to entrap a portion of the cover 520a against stop elements 520d (i.e., shown in FIG. 5S-1) and thereby locking cover 520a at second position 570b. In some embodiments, cover 520a is released from its locked state when a pulling force (for example as applied by a user) is applied upwardly to the cover 520a against the biasing action of biasing member 520c and out of unlocked engagement with stop elements 520d. When the cover 520a is released from it locked state, movement away from second position 570b or second activation position 571b is permitted. In some embodiments, the ability to lock actuator 572 (for example via cover 520a) advantageously enables the second fanned configuration 537 to be maintained.

The expanded configuration may be moved into other, different states in some embodiments. It is noted in various embodiments that, in any of the various states of the expanded configuration, the manipulable portion 502 may be sized too large for delivery through the lumen 512d of catheter sheath 512 (e.g., during percutaneous delivery of manipulable portion 502) or at least a part of the manipulable portion 502 may be too large to fit in the lumen 512d of catheter sheath 512. As compared between FIGS. 5S-2 and 5S-3, first particular actuator 540a is moved from a first activation position (e.g., position 574a shown in FIG. 5S-2) into a second activation position 574b shown in FIG. 5S-3) to vary a size, shape, or both size and shape of the expanded configuration of manipulable portion 502 from the second fanned configuration 537 exemplified in FIGS. 5M-1, 5M-2 into an enlarged expanded configuration 538 exemplified in FIG. 5N. In various embodiments, movement into the enlarged expanded configuration 538 may be caused by an increase in a radial spacing between various elongate members 504 in the circumferential distribution of the elongate members 504 associated with the second fanned configuration 537 (e.g., an increase in a radial distance of various ones of the elongate members 504 from a central axis of the circumferential distribution). In various embodiments, movement into the enlarged expanded configuration 538 may be caused by an increase in an overall size or dimension of the manipulable portion 502. In various embodiments, movement into the enlarged expanded configuration 538 may be caused by an increase in a distance between respective apexes of the two domed shaped portions 508a-1 and 508b-1. Changing the expanded configuration of the manipulable portion 502 into the enlarged expanded configuration 538 may be motivated for various reasons. For example, manipulable portion 502 may be manipulated into the enlarged expanded configuration 538 to create a conformance, or increase a level of conformance with a tissue surface within a bodily cavity into which the manipulable portion 502 is deployed. In some example embodiments, manipulable portion 502 may be further manipulated into the enlarged expanded configuration 538 to position various transducer elements 506 in closer proximity to an interior tissue surface within a bodily cavity.

In various example embodiments, first particular actuator 540a is moved from its respective first activation position 574a into its second activation position 574b to manipulate cable 513b to reduce a length of the portion 514 (not called out in FIG. 5N) of cable 513b that extends outwardly from sleeve 513a to manipulate the distal end of manipulable portion 502 into closer proximity to the sleeve 513a. This movement of cable 513b draws the domed distal portion 508b in closer proximity to sleeve 513a and increases or enlarges an overall size of the manipulable portion 502. With reference to FIG. 7, movement of the expanded configuration of manipulable portion 502 into the enlarged expanded configuration 538 accompanies a movement of forming slider 561 proximally along guide 542a to take up cable 513b. In FIG. 5S-3, handle 543a of first particular actuator 540a has been rotated (e.g., by a user manipulation) in rotational direction 576 to cause a locking device (e.g., locking device of FIG. 10) of first particular actuator 540a to move from an unlocked configuration to a locked configuration suitable for maintaining the first particular actuator 540a in the second activation position 574b. In this regard, first Bowden cable 552 (i.e., which includes sleeve 552a and cable 513b) is operable in various different configurations. For example, in various embodiments, at least one actuator is physically or operatively coupled to the first Bowden cable 552 to (a) move the sleeve 552a independently or separately from the cable 513b to cause the sleeve 552a to slide over the cable 513b during a first manipulation of the manipulable portion 502 to change, a size, a shape, or both thereof (e.g., as described above with respect to the manipulation of manipulable portion 502 in FIGS. 5H, 5I and 5J), and (b) move the cable 513b independently or separately from the sleeve 552a to cause the cable 513b to slide through the lumen of the sleeve 552a during a second manipulation of the manipulable portion 502 to change a size, a shape, or both thereof (e.g., as described above with respect to the manipulable portion 502 in FIG. 5N).

In some embodiments, the expanded configuration of manipulable portion 502 is manipulated into other states. For example, as compared between FIGS. 5S-3 and 5S-4, first particular actuator 540a is unlocked and moved from a first activation position (e.g., position 574b shown in FIG. 5S-3 and previously referred above in this disclosure as a second activation position associated with a transition into the enlarged expanded configuration 538) into a second activation position (e.g., position 574c shown in FIG. 5S-4) to vary a size, shape, or both size and shape of the expanded configuration of manipulable portion 502 from the enlarged expanded configuration 538 exemplified in FIG. 5N into a flattened expanded configuration 539 exemplified in FIG. 5O. As shown in FIG. 5O, at least some of the elongate members 504 are further manipulated (e.g., at least by the first particular actuator 540a in FIG. 7, among others) to distort at least one of the domed shapes 508a-1, 508b-1 of a respective one of the proximal and the distal portion 508a, 508b of manipulable portion 502. In this regard, in some embodiments, the first particular actuator 540a is selectively moveable into a respective activation position (e.g., 574b or 574c) to (a) act on the proximal portion 508a of the manipulable portion 502 when the manipulable portion 502 is in the expanded configuration to distort the first domed shape 508a-1, (b) act on the distal portion 508b of the manipulable portion 502 when the manipulable portion 502 is in the expanded configuration to distort the second domed shape 508b-1, or both (a) and (b). In some embodiments, manipulable portion 502 is manipulated to have a more oblate shape. Changing the expanded configuration of the manipulable portion 502 into the flattened expanded configuration 539 may be motivated for various reasons. For example, manipulable portion 502 may be manipulated into the flattened expanded configuration 539 to better fit within a particular shape of a bodily cavity into which the manipulable portion 502 is deployed.

In FIG. 5O, a control element 578 is provided to convert an input movement (e.g., an input movement of first particular actuator 540a) into an output movement suitable for manipulating the expanded configuration of manipulable portion 502 into the flattened expanded configuration 539. In FIG. 5O, the control element 578 includes a control cable 578b received in a lumen of sleeve 578a that is physically coupled to surface 518b of an elongate member 504. In various embodiments, sleeve 578a is sized to extend generally circumferentially along the manipulable portion 502 and terminate at a location proximate the distal ends 505 of the elongate members 504. From this termination location, the exiting cable 578b extends outwardly from the sleeve 578a and is physically coupled to the manipulable portion 502 at a location proximate a crossing location of various ones of the elongate members 504. In various embodiments, a first particular actuator 540a causes an amount of length of the cable 578b exiting sleeve 578a to decrease as the first particular actuator 540a is moved between the activation positions 574b and 574c. A reduction in the amount of length of the exiting portion of the cable 578b in turn flexes the expanded configuration of the manipulable portion 502 into the flattened expanded configuration 539. As noted above in this disclosure, first particular actuator 540a may be physically or operatively coupled to cable 513b in various embodiments. In some of these various embodiments, first particular actuator 540a includes a mechanism configured to decouple from or cease manipulating control element 513b as the first particular actuator 540a is moved between activation positions 574b and 574c. For clarity, control element 513 is not shown in FIG. 5O. For clarity, control element 578 is only shown in FIG. 5O.

In FIG. 5S-4, handle 543a of first particular actuator 540a has been rotated (e.g., by a user manipulation) in rotational direction 576 to cause a locking device (e.g., locking device of FIG. 10) of first particular actuator 540a to move from an unlocked configuration to a locked configuration suitable for maintaining the first particular actuator 540a in the second activation position 574c. It is noted that, in some embodiments, the first particular actuator 540a may be moved from some other first activation position (for example position 574a in FIG. 5S-2) as it is moved directly or continuously toward or to the second activation position (e.g., position 574c) to move into the flattened expanded configuration 539 without pausing or stopping at position 574b. That is, pausing or stopping at the enlarged expanded configuration 538 need not be required in some embodiments during a transition toward or to the flattened expanded configuration 539.

In some embodiments, the expanded configuration of manipulable portion 502 may be manipulated into yet other states. For example, as compared between FIGS. 5S-3 and 5S-5, second particular actuator 540b may be moved from a first activation position (e.g., position 575a shown in FIG. 5S-3) into a second activation position (e.g., position 575b shown in FIG. 5S-5) to vary a size, shape, or both size and shape of the expanded configuration of manipulable portion 502 from the enlarged expanded configuration 538 exemplified in FIG. 5N into an open clam shell configuration 544*a* exemplified in FIG. 5P. To arrive at the open clam shell configuration 544*a*, in some embodiments, the distal portion 508*b* of the manipulable portion 502 is pivoted, by selective movement of the second particular actuator 540*b* into a respective activation position (e.g., 575*b*), away from the proximal portion 508*a* of manipulable portion 502 to orient the respective domed shapes 508*b*-1, 508*a*-1 apart from one another.

For another example, as compared between FIGS. 5S-3 and 5S-6, second particular actuator 540*b* may additionally or alternatively be moved from a first activation position (e.g., position 575*a* shown in FIG. 5S-3) into a second activation position (e.g., position 575*c* shown in FIG. 5S-6) to vary a size, shape, or both size and shape of the expanded configuration of manipulable portion 502 from the enlarged expanded configuration 538 exemplified in FIG. 5N into a closed clam shell configuration 544*b* exemplified in FIG. 5Q as by way of another example. To arrive at the closed clam shell configuration 544*b*, the distal portion 508*b* of the manipulable portion 502 is pivoted by selective movement of the second particular actuator 540*b* into a respective activation position (e.g., 575*c*) toward or into the proximal portion 508*a* of manipulable portion 502, which may, in some embodiments, enclose the respective domed shapes 508*b*-1, 508*a*-1 at least partially within one another. In this regard, in some embodiments, the second particular actuator 540*b* is selectively moveable into a respective activation position (e.g., 575*b* or 575*c*) to pivot the proximal portion 508*a* and the distal portion 508*b* of the manipulable portion 502 with respect to one another when the manipulable portion 502 is in the expanded or deployed configuration.

Each of the open and closed clam shell configurations may be motivated for different reasons. For example, the open clam shell configuration 544*a* may be desired to increase an overall size of the manipulable portion 502, while the closed clam shell configuration 544*b* may be desired to decrease an overall size of the manipulable portion 502, thereby allowing the manipulable portion 502 to be accommodated in a various bodily cavities having a range of different sizes.

In various embodiments, a portion of control element 513 is manipulated by second particular actuator 540*b* to selectively transition the expanded configuration of the manipulable portion 502 into at least one of the open or closed clam shell configurations 544*a*, 544*b*. For example, with reference to FIG. 7, movement of the expanded configuration of manipulable portion 502 into the closed clam shell configuration 544*b* of FIG. 5Q accompanies a movement of the second particular actuator 540*b*'s sleeve slider 548*a* distally along guide 542*b* to manipulate control element 513 to cause an amount of length of at least the sleeve 513*a* extending outwardly from the distal end 510*b* of shaft 510 to increase and apply a "push" force on the distal portion 508*b* to move at least toward the proximal portion 508*a* in various embodiments. In some embodiments, an amount of length of the cable 513*b* extending outwardly from the distal end 510*b* of shaft 510 also increases as sleeve slider 548*a* is moved distally. In some embodiments, both sleeve 513*a* and cable 513*b* are moved concurrently. In some embodiments, both sleeve 513*a* and a portion of cable 513*b* within the lumen of sleeve 513*a* are moved with little or no relative movement therebetween.

In some embodiments, movement of the expanded configuration of manipulable portion 502 into the open clam shell configuration 544*a* of FIG. 5P accompanies a movement of sleeve slider 548*a* proximally along guide 542*b* to manipulate control element 513 to cause an amount of length of at least the cable 513*b* extending outwardly from the distal end 510*b* of shaft 510 to decrease and apply a "pull" force on the distal portion 508*b* to move away from the proximal portion 508*a*. In various embodiments, the extending portion of cable 513*b* is retracted into a notch or channel 547 positioned to allow for greater separation between the distal and proximal portions 508*a* and 508*b* in the open clam shell configuration. In some embodiments, sleeve 513*a* is additionally retracted proximally as sleeve slider 548*a* is moved proximally. In some embodiments, both sleeve 513*a* and cable 513*b* are moved concurrently. In some embodiments, both sleeve 513*a* and a portion of cable 513*b* within the lumen of sleeve 513*a* are moved with little or no relative movement therebetween. Channel 547 is shown only in FIGS. 5P and 5Q for clarity.

In each of FIGS. 5S-5 and 5S-6, handle 543*b* of second particular actuator 540*b* has been rotated (e.g., by a user manipulation) in rotational direction 577 to cause a locking device (e.g., locking device of FIG. 10) of second particular actuator 540*b* to move from an unlocked configuration to a locked configuration suitable for maintaining the second particular actuator 540*b* in respective ones of the second activation positions 575*b* and 575*c*.

As can be seen from FIG. 5S, in some embodiments, each of the respective actuators (e.g., 540*a*, 540*b*) in the first actuator set 540 comprises a handle (e.g., 543*a*, 543*b*) operatively coupled to a respective locking device (e.g., locking device of FIG. 10) to selectively move the respective locking device between an unlocked configuration and a locked configuration.

It is understood that in various embodiments, at least two of the actuators in the actuator set may be moved from their respective first activation positions into their second respective second activation positions to collectively change the size, the shape, or both a size and a shape of an expanded configuration of the manipulable portion 502 into a particular state. For example, both the first and second particular actuators 540*a* and 540*b* may be moved into various associated second activation positions to collectively change a size, a shape, or both a size and a shape of an expanded configuration of the manipulable portion 502 into combinations of the various states described above in this disclosure. In some embodiments, a user may chose the locations of the second activation positions and they need not occur at the end-of-travel. In some embodiments, the particular state includes, at least in part, a combination of the various states described above in this disclosure. The manipulable portion 502 has a size too large to be delivered percutaneously to the bodily cavity when the manipulable portion 502 is in the particular state, in some embodiments.

Multiple actuator sets may be associated with catheter system 500. In some embodiments, a first actuator set includes one or more actuators at least operatively coupled to manipulable portion 502 to change or vary a size, a shape, or both a size and a shape of an expanded configuration of the manipulable portion 502. In some embodiments, a first actuator set includes two or more actuators at least operatively coupled to the manipulable portion 502, each of the actuators in the first actuator set independently or separately moveable from the other actuators in the first actuator set from a respective first activation position into a respective second activation position to independently change a size, a shape, or both a size and a shape of an expanded configuration of the manipulable portion 502. As described above in this disclosure, at least two actuators in the first actuator set 540 may be moveable from their respective first activation positions into their respective second activation positions to collectively change the size, the shape, or both a size and a shape of the expanded configuration of the manipulable portion 502 into a particular state. In this regard, in some embodiments, the manipulable portion 502 is in the expanded configuration when the at least two actuators in the first actuator set 540 are in their respective first activation positions and when the at least two actuators in the first actuator set 540 are in their respective second activation positions. In some embodiments, the manipulable portion 502 has a size too large to be delivered percutaneously to the bodily cavity when the manipulable portion 502 is in the particular state.

Figures 1, 5W:
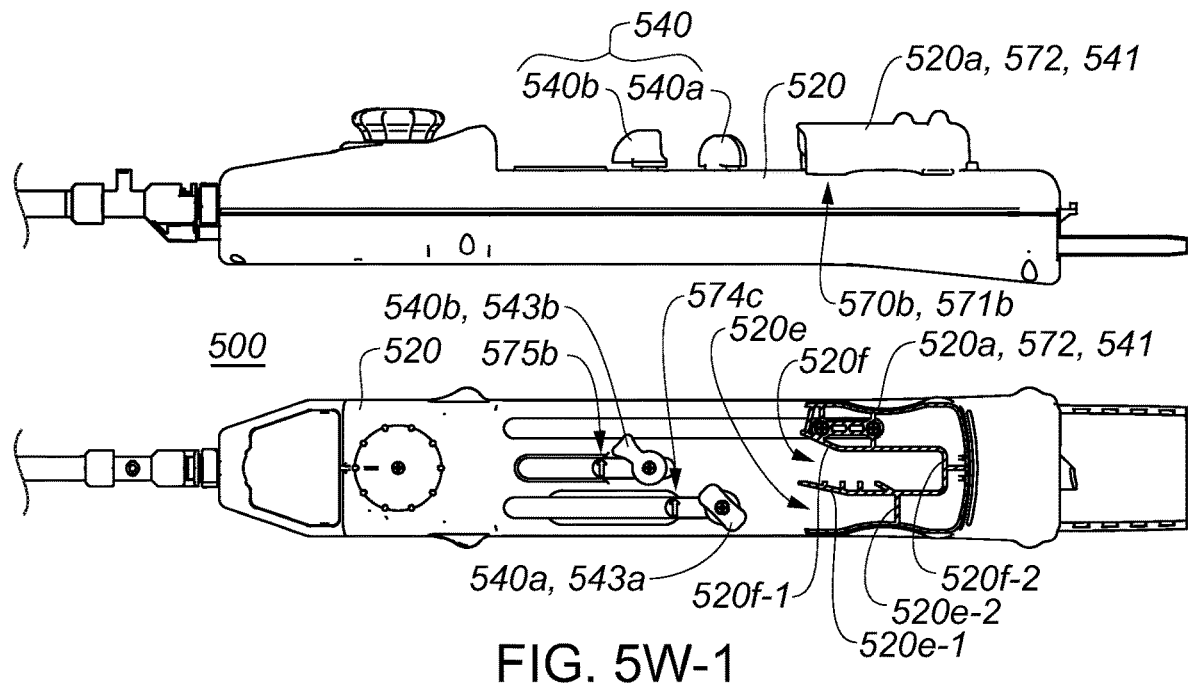
Figures 2, 5W:
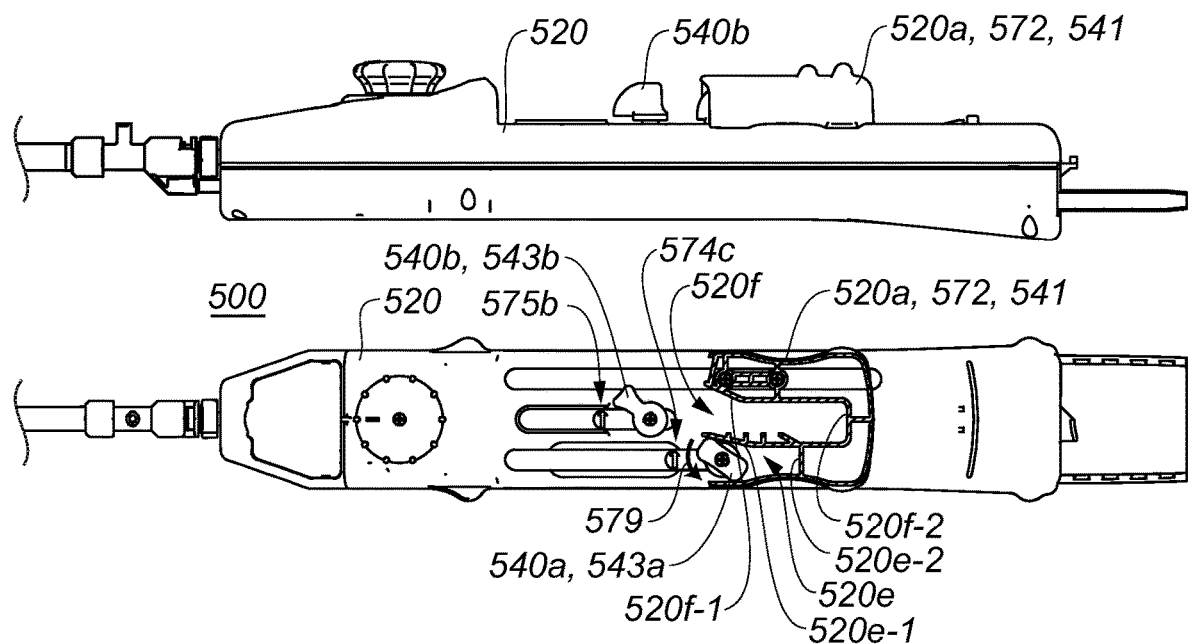
Figures 3, 5W:
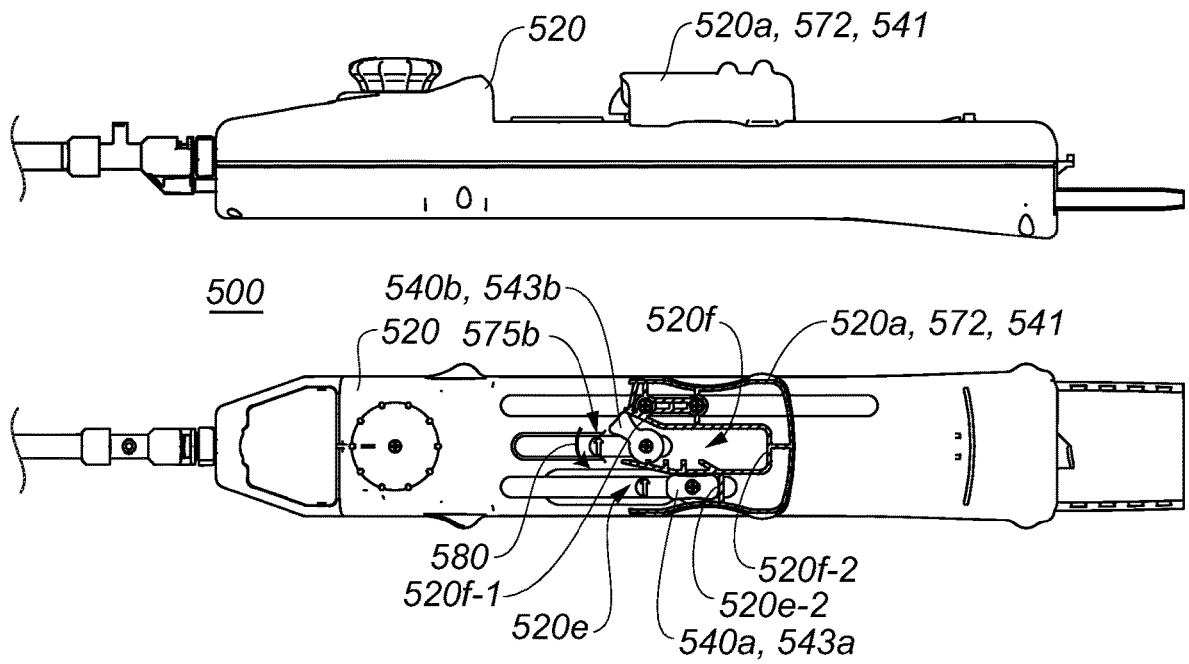
Figures 4, 5W:
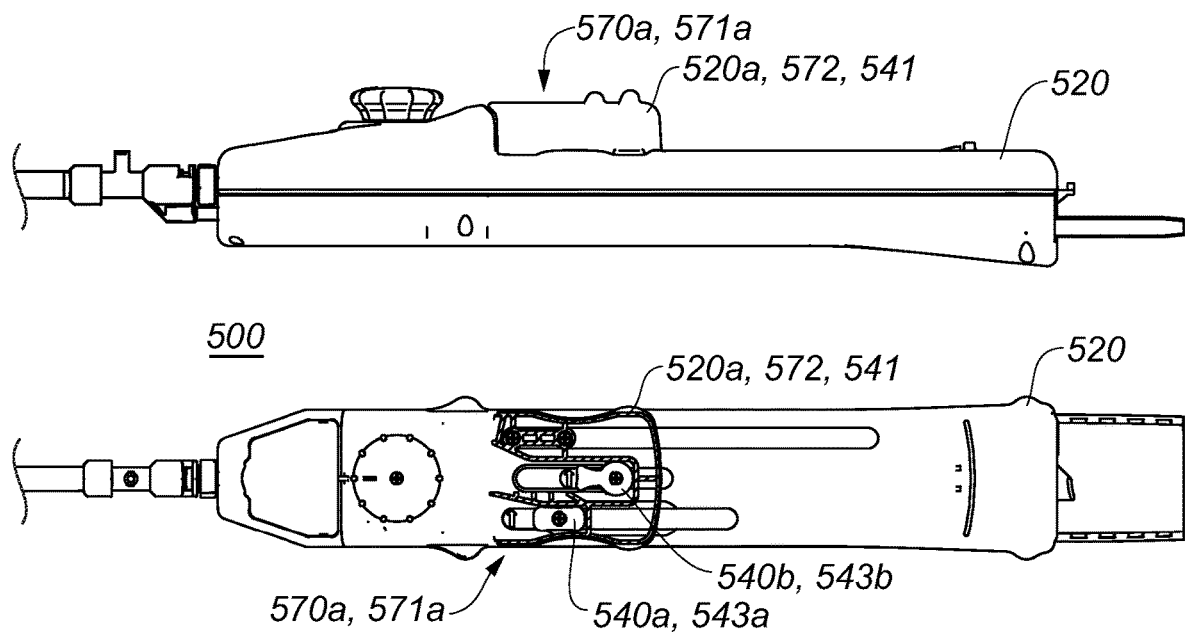
Figure 6:
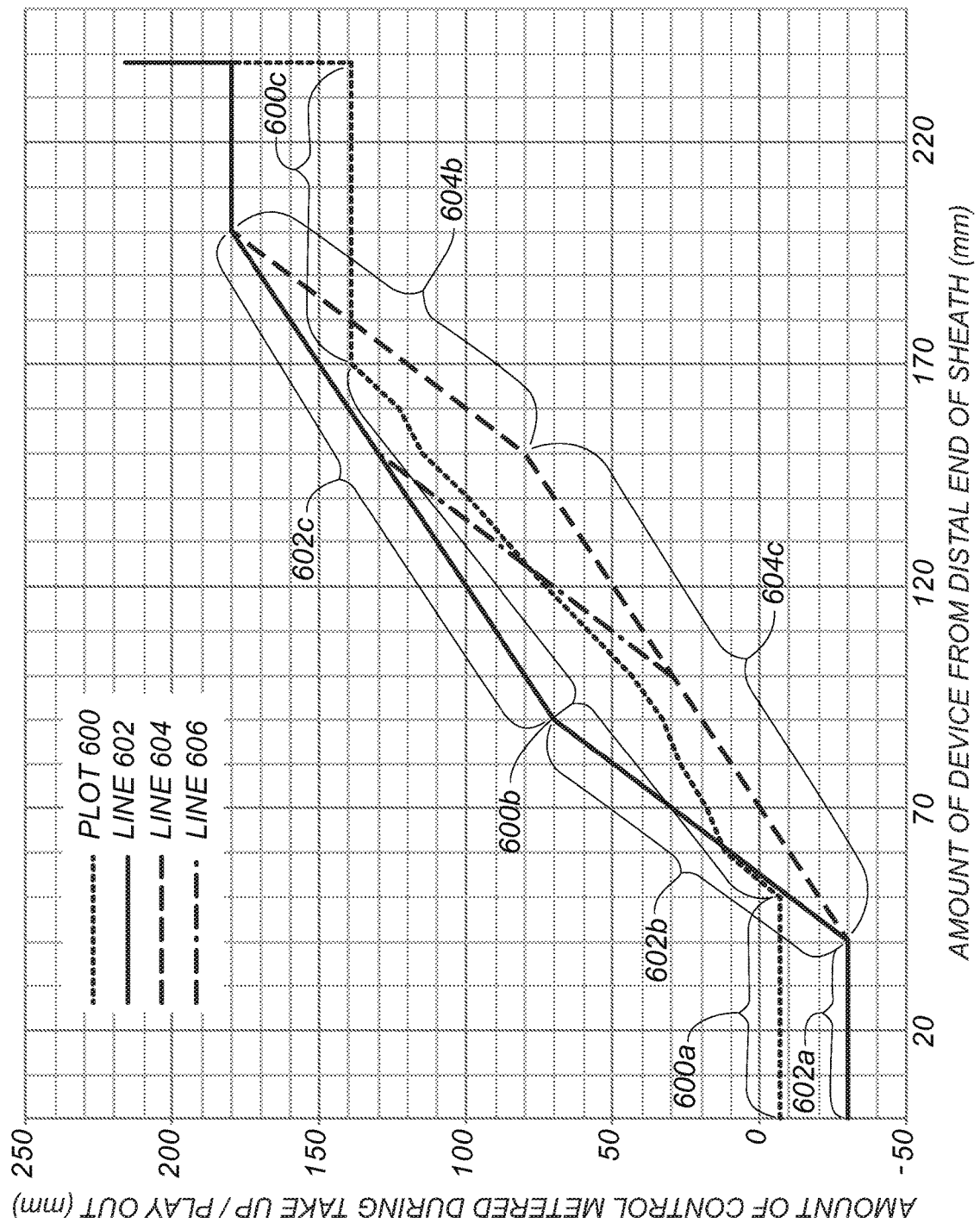

For example, FIGS. 5W-1, 5W-2, 5W-3, and 5W-4 (collectively, FIG. 5W) each respectively show plan and elevation views of a portion of catheter system 500 according to some embodiments. In particular, FIG. 5W-1 shows a positioning of each of various actuators in first actuator set 540 including a positioning of first particular actuator 540a in respective second activation position 574c and a positioning of second particular actuator 540b in respective second activation position 575b. Cover 520a has been moved from its first position 570a (e.g., called out in FIGS. 5S-1 and 5W-4 but not shown in FIG. 5W-1) to its second position 570b to permit user access to actuators 540a and 540b so as to allow movement of actuators 540a and 540b into their respective second activation positions 574c, 575b from their respective first activation positions 574a, 575a (e.g., called out in FIG. 5S-2 but not called out in FIG. 5W-1). Additionally, third particular actuator 572 has been moved (e.g., via manipulation of cover 520a) into its respective second activation position 571b from its first activation position 571a (e.g., called out in FIGS. 5S-1 and 5W-4, but not called out in FIG. 5W-1). (Cover 520a has been sectioned in the respective plan view of each of FIGS. 5W-1, 5W-1, 5W-3 and 5W-4 for clarity of view of various features associated with cover 520a.) Accordingly, the positioning of these actuators into their respective second activation positions collectively changes the size, the shape, or both a size and a shape of the expanded configuration of the manipulable portion 502 into a particular state.

In some embodiments, the particular state of the expanded configuration corresponding to the various actuator positions shown in FIG. 5W-1 is collectively a combination of the flattened expanded configuration exemplified in FIG. 5O and the open clam shell configuration 544a exemplified in FIG. 5P. It is understood that other combinations of expanded configurations are provided in other embodiments. In various embodiments, manipulable portion 502 has a size too large for percutaneous delivery or a size too large to fit in the lumen 512d of catheter sheath 512 when the expanded configuration of the manipulable portion is moved into a particular state in response to the positioning of the various actuators into their respective second activation positions.

In FIG. 5W-1, handle 543a of first particular actuator 540a has been rotated (e.g., by a user manipulation) in rotational direction (e.g., rotational direction 576, not called out in FIG. 5W-1) to cause a locking device (e.g., locking device of FIG. 10) of first particular actuator 540a to move from an unlocked configuration to a locked configuration suitable for maintaining the first particular actuator 540a in its second activation position 574c. In FIG. 5W-1, handle 543b of second particular actuator 540b has been rotated (e.g., by a user manipulation) in a rotational direction (e.g., rotational direction 577, not called out in FIG. 5W-1) to cause a locking device (e.g., locking device of FIG. 10) of second particular actuator 540b to move from an unlocked configuration to a locked configuration suitable for maintaining the second particular actuator 540b in its second activation position 575b. In various embodiments, third particular actuator 572 is also locked in its respective second activation position 572 (for example as described above in this disclosure).

In some embodiments, a second actuator set is employed. The second actuator set may include a particular actuator moveable between two activation positions to cause at least two actuators in the first actuator set that are positioned in their respective second activation positions to move away from their respective second activation positions to cause the collectively changed size, the collectively changed shape, or both the collectively changed size and shape of the expanded configuration of the manipulable portion 502 to move away from a particular state corresponding to the positioning of the at least two actuators in the first actuator set in their respective second activation positions. For example, in various embodiments, actuator 572 is a particular actuator in a second actuator set 541 that is moveable between two activation positions to cause the at least two actuators (e.g., actuators 540a, 540b) in the first actuator set 540 that are positioned in their respective second activation positions (e.g., second activation positions 574c, 575b) to move away from their respective second activation positions to cause the collectively changed size, the collectively changed shape, or both the collectively changed size and shape of the expanded configuration of the manipulable portion 502 to move away from the particular state corresponding to the positioning of the at least two actuators in their respective second activation positions.

In some embodiments, first actuator set 540 does not include any actuator in the second actuator set 541. In some embodiments, the at least two actuators (e.g., actuators 540a, 540b) in the first actuator set 540 do not include any actuator (e.g., actuator 572) in the second actuator set 541. However, a particular actuator (e.g., actuator 572) in the second actuator set 541, in some embodiments, may also form part of the first actuator set 540. For example, recall that the first actuator set 540 may be defined to include one or more actuators (e.g., actuators 540a, 540b) at least operatively coupled to manipulable portion 502 to change or vary a size, a shape, or both a size and a shape of an expanded configuration of the manipulable portion 502. Also recall that the second actuator set 541 may be defined to include a particular actuator (e.g., actuator 572) moveable between two activation positions to cause at least two actuators (e.g., actuators 540a, 540b) in the first actuator set that are positioned in their respective second activation positions to move away from their respective second activation positions to cause the collectively changed size, the collectively changed shape, or both the collectively changed size and shape of the expanded configuration of the manipulable portion 502 to move away from a particular state corresponding to the positioning of the at least two actuators in the first actuator set in their respective second activation positions. In this case, in some embodiments, the particular actuator (e.g., actuator 572) may meet the definition or perform the functionalities of both the first actuator set 540 and the second actuator set 541. In such a case, the particular actuator (e.g., actuator 572) may be considered part of both the first actuator set 540 and the second actuator set 541.

For instance, if actuator 540a is a first particular actuator, actuator 540b is a second particular actuator, and actuator 572 is a third particular actuator 572, the third particular actuator 572: (a) may cause, according to a definition or functionality of the second actuator set 541, according to some embodiments, the first and second particular actuators 540a, 540b to move away from their respective second activation positions (e.g., respective ones of second activation positions 574c, 575b) when actuator 572 moves between its respective activation positions 571a, 571b, and (b) may, according to a definition or functionality of the first actuator set 540, according to some embodiments, be further independently or separately moveable from the other actuators in the first actuator set 540 from a respective first activation position 571a into a respective second activation position 571b to independently change a size, a shape, or both a size and a shape of the expanded configuration of the manipulable portion 502. Regarding (b), for example, the third particular actuator 572 may cause the expanded configuration of the manipulable portion 502 to change between a first fanned configuration 536 exemplified in FIGS. 5L-1 and 5L-2 and a second fanned configuration 537 exemplified in FIGS. 5M-1 and 5M-2. Accordingly, the third particular actuator 572, in some embodiments, may be considered part of both the first actuator set 540 and the second actuator set 541. However, whether or not the first actuator set 540 includes an actuator in the second actuator set 541 depends on the particular embodiment employed.

FIG. 5W show a movement of third particular actuator 572 at four successive points in time during a movement of third particular actuator 572 between two activation positions. In these illustrated embodiments, third particular actuator 572 is moved (e.g., via manipulation of cover 520a) from second activation position 571b (i.e., called out in FIG. 5W-1) toward or to first activation position 571a (i.e., called out in FIG. 5W-4). In some embodiments, a locking device associated with third particular actuator 572 (e.g., the locking device associated with cover 520a described above in this disclosure) is unlocked before the commencement of this movement. In various embodiments, the movement of third particular actuator 572 between the two activation positions 571a and 571b, and, in particular, from the second activation position 571b toward or to first activation position 571a, causes each of the first particular actuator 540a and the second particular actuator 540b to move away from their respective activation positions 574c, 575b as shown in FIGS. 5W-2, 5W-3 and 5W-4. For example, in some embodiments, third particular actuator 572 includes at least a first actuator override 520e and a second actuator override 520f. In various embodiments, first actuator override 520e is configured to override an operative state associated with first particular actuator 540a. In various embodiments, second actuator override 520e is configured to override an operative state associated with second particular actuator 540b. In some embodiments, first actuator override 520e is configured to override an operative positioning of first particular actuator 540a at its respective second activation position (e.g., second activation position 574c) and cause it to move away from its respective second activation position. In some embodiments, second actuator override 520f is configured to override an operative positioning of second particular actuator 540b its respective second activation position (e.g., second activation position 575b) and cause it to move away from its respective second activation position. In some embodiments, the first actuator override 520e, the second actuator override 520f, or each of the first and the second actuator overrides 520e, 520f is operatively coupled (for example via a linkage or other force transmission member or mechanism) to a respective one of first particular actuator 540a and second particular actuator 540b to cause movement thereof. In some embodiments, the first actuator override 520e, the second actuator override 520f, or each of the first and the second actuator overrides 520e, 520f is configured to be selectively brought into engagement or disengagement with a respective one of first particular actuator 540a and second particular actuator 540b. For example, in some embodiments, each of the first and the second actuator overrides 520e, 520f may include a slot, cavity, tunnel, or other receiver or engagement mechanism that includes one or more engagement surfaces that may be selectively brought into contact or engagement with a respective one of the first particular actuator 540a and second particular actuator 540b.

In some embodiments associated with FIG. 5W, each of the first and second overrides 520e, 520f is provided by, or forms part of third particular actuator 572. In some embodiments associated with FIG. 5W, each of the first and second overrides 520e, 520f of third particular actuator 572 is provided by, or forms part of the cover 520a, which may in turn, form part of third particular actuator 572 in some embodiments. In some embodiments, first actuator override 520e includes various engagement surfaces (e.g., engagement surfaces 520e-1 and 520e-2) configured to engage and subsequently manipulate a portion of first particular actuator 540a. In some embodiments, second actuator override 520f includes various engagement surfaces (e.g., engagement surfaces 520f-1 and 520f-2) configured to engage and subsequently manipulate a portion of second particular actuator 540b. It is noted that although surfaces 520e-1 and 520e-2 are called out separately, they may form part of a single or uniform surface in some embodiments. It is noted that although surfaces 520f-1 and 520f-2 are called out separately, they may form part of a single or uniform surface in some embodiments.

As third particular actuator 572 is moved from its second activation position 571b (e.g., FIG. 5W-1) toward or to its first activation position 571a (e.g., FIG. 5W-4), the engagement surface 520e-1 of first actuator override 520e is brought into contact, or otherwise engages with a portion of first particular actuator 540a (e.g., FIG. 5W-2). In some embodiments, the first engagement surface 520e-1 (or other engagement surface of first actuator override 520e) is brought into contact, or otherwise engages, with handle 543a of first particular actuator 540a. In some embodiments, engagement surface 520e forms part of a cam (e.g., a linear cam) that is arranged to act on a cam follower (e.g., handle 543a) to move the cam follower in a desired manner. In some embodiments, engagement surface 520e-1 forms part of a cam that is arranged to act on a cam follower (e.g., handle 543a) to move the cam follower to move a locking device (e.g., locking device of FIG. 10) of first particular actuator 540a between a locked and unlocked configuration. For example, in FIG. 5W-2, handle 543a is oriented in a manner similar to, or the same as in FIGS. 5S-3, 5S-4, 5S-5 and 5S-6 corresponding to a locked configuration or state of a locking device (e.g., locking device of FIG. 10) that restricts movement (e.g., movement away from second activation position 574c) of first particular actuator 540a when handle 543a is positioned in the locked configuration or state. In some embodiments associated with FIG. 5W-2, engagement surface 520e-1 contacts handle 543a to rotate handle 543a in a direction (e.g., rotational direction 579) suitable for moving the locking device associated with first particular actuator 540a from the locked configuration to an unlocked configuration which allows for movement (e.g., movement away from second activation position 574c) of the first particular actuator 540a.

In various embodiments, once the first actuator 540a is free to move from its second activation position 574c, further or subsequent movement of third particular actuator 572 (e.g., by way of manipulation of cover 520a) causes movement of first particular actuator 540a away from its second activation position 574c. In some embodiments, this movement away from the second activation position 574c occurs when engagement surface 520e-2 of first actuator override 520e comes into contact, or otherwise engages, a portion of first actuator 540a (e.g., handle 543a) to cause movement of first actuator 540a away from its second activation position 574c, for example, as shown in FIG. 5W-3.

In some embodiments, the movement of third particular actuator 572 between the two activation positions 571a and 571b, (for example, from the second activation position 571b toward or to first activation position 571a) causes a first actuator (e.g., first particular actuator 540a) in the first actuator set 540 to move away from its respective second activation position (e.g., second activation position 574c) before a second actuator (e.g., second particular actuator 540b) in the first actuator set 540 is caused to move away from its respective second activation position (e.g., second activation position 575b) by the third particular actuator 572. In various embodiments, after the commencement of a movement of the first particular actuator 540a away from its respective second activation position 574c, engagement surface 520f-2 contacts, or otherwise engages a portion of second particular actuator 540b (e.g., handle 543b) to move second particular actuator 540b (e.g., in a direction away from second activation position 575b). For example, in FIG. 5W-3, after the commencement of a movement of the first particular actuator 540a away from its respective second activation position 574c, third particular actuator 572 has moved to a position where an engagement surface 520f-1 of second actuator override 520f contacts, or otherwise engages, a portion of second actuator 540b (e.g., handle 543b) to move (for example, by rotating handle 543b in rotational direction 580) a locking device (e.g., locking device of FIG. 10) from a locked configuration, which restricts movement of the second particular actuator 540b, to an unlocked configuration, which permits movement of second particular actuator 540b.

It is noted, that in some embodiments, the movement of third particular actuator 572 between the two activation positions 571a and 571b (e.g., from the second activation position 571b toward or to first activation position 571a) may cause a first actuator (e.g., first particular actuator 540a) in the first actuator set 540 to move away from its respective second activation position at the same time, or at approximately the same time as a second actuator (e.g., second particular actuator 540b) in the first actuator set 540 is caused to move away from its respective second activation position by the third particular actuator 572. For example, if first particular actuator 540a is positioned at second activation position 574b (i.e., instead of second activation position 574c) while second particular actuator 540b is positioned at second activation position 575b (e.g., in a manner similar to, or the same as that shown in FIG. 5S-5), initial engagement with each of the first and second particular actuators 540a, 540b by the third particular actuator 572 may occur at the same time, or at substantially the same time.

In various embodiments, third particular actuator 572 moves from its second activation position 571b (e.g., FIG. 5W-1) to a location at least proximate its respective first activation position 571a (e.g., FIG. 5W-4). In various embodiments, movement of the third particular actuator 572 between it respective activations positions 571b, 571a causes (a) the first particular actuator 540a to move from its second activation position (e.g., second activation position 574c) to a location at least proximate to its first activation position 574a, (b) the second particular actuator 540b to move from its second activation position (e.g., second activation position 574b) to a location at least proximate to its first activation position 575a, or both (a) and (b) as shown in FIG. 5W-4. In FIG. 5W-4, cover 520a has been moved from it second position 570b to its first position 570a. As described previously in this disclosure, cover 520a restricts access to the first and second actuators 540a, 540b when the cover 520a is in the first position 570a.

In various embodiments, when the third particular actuator 572 moves between its two activation positions (for example, from the second activation position 571b toward or to the first activation position 571a), each of the first and second particular actuators 540a and 540b move away from respective ones of their second activation positions (e.g., second activation positions 574c, 575b) to cause a size, a shape, or both a size and a shape of the expanded configuration of manipulable portion 502 to move away from the particular state that the expanded configuration of the manipulable portion 502 assumed when each of the first and second particular actuators 540a and 540b were in their respective second activation positions. In some of these embodiments, each of the first and second particular actuators 540a and 540b move away from respective ones of their second activation positions (e.g., second activation positions 574c, 575b) to cause the particular state of the expanded configuration of the manipulable portion 502 (i.e., when the first and second particular actuators 540a and 540b were positioned at respective ones of their second activation positions) to move toward or to the delivery configuration.

In various embodiments, associated with FIG. 5W, movement of the third particular actuator 572 from its second activation position 571b toward or to its first activation position 571a causes changes in various states or sub-states of the expanded configuration that were combined to impart the particular collective state or super-state onto the expanded configuration of the manipulable portion 502. For example, the positioning of each particular actuator (e.g., each actuator 540a, 540b, 572) imparts its own sub-state onto the configuration of the manipulable portion 502. For example, positioning of the actuator 540b into its second activation position 575b causes an open-clam shell sub-state effect on the expanded configuration of the manipulable portion 502 as shown, for example, in FIG. 5P, according to some embodiments. Positioning of the actuator 540a into its second activation position 574c causes a flattening sub-state effect on the expanded configuration of the manipulable portion 502 as shown, for example, in FIG. 5O, according to some embodiments. Positioning of the actuator 572 into its second activation position 571b causes a fanning sub-state effect on the expanded configuration of the manipulable portion 502, according to some embodiments. Accordingly, the combination of at least some of these individual sub-states is a collective state or super-state of the configuration of the manipulable portion 502. For instance, positioning of the actuator 540b into its second activation position 575b, positioning of the actuator 540a into its second activation position 574c, and positioning of the actuator 572 into its second activation position 571b cause a collective of super-state of the expanded configuration of the manipulable portion 502 that would appear like a combination of FIGS. 5O and 5P.

Accordingly, in various embodiments associated with FIG. 5W, changes in these collective or super-states may include a departure from the combined FIG. 5O-5P state when third particular actuator 572 moves the first and second particular actuators 540a and 540b away from their respective second activation positions 574c, 575b. For another example, in various embodiments associated with FIG. 5W, changes in these collective or super-states may include a departure from the second fanned configuration 537 (e.g., exemplified in FIGS. 5M-1, 5M-2) as the third particular actuator 572 moves from the second activation position 571b toward or to the first activation position 571a. In some of these embodiments, departure from these various states may cause the expanded configuration of the manipulable portion 502 to move, at least in part, toward or to the delivery configuration.

In this regard, changes in these collective or super-states may cause the collective or super-state of the configuration of the manipulable portion 502 to be changed from one state to another state. For instance, movement of the third particular actuator 572 from the second activation position 571b toward or to the first activation position 571a may cause the manipulable portion 502 to move from an expanded configuration state toward or to a delivery configuration state.

Accordingly, the expanded configuration of the manipulable portion 502 may undergo various changes as it transitions to a targeted or desired particular state (for example, a state suitable for a particular medical procedure having diagnostic aspects, treatment aspects, or combined diagnostic and treatment aspects) or transitions away from a previously targeted or desired particular state (e.g., during a transition toward or to a delivery configuration which may be motivated for various reasons including a desire to remove the manipulable portion 502 from the body upon which the medical procedure is performed). For example, as described above with respect to FIG. 5S, in some embodiments, each of at least two of the particular actuators (e.g., first particular actuator 540a, second particular actuator 540b) is moveable between its respective first activation position (e.g., a respective one of first activation positions 574a, 575a) and its respective second activation position (e.g., a respective one of second activation positions 574c, 575b) to collectively change a size, a shape or both a size and a shape of the expanded configuration of the manipulable portion 502 from a first particular (e.g., collective or super-) state to a second particular (e.g., collective or super-) state. In some embodiments, each actuator of the at least two actuators (e.g., the first actuator 540a or second actuator 540b) may include a user-accessible portion (e.g., a respective one of handles 543a, 543b) that is slideable relative to a surface of housing 520 by a user to move the actuator between its respective first and second activation positions and cause a size, a shape, or both a size and a shape of the expanded configuration of the manipulable portion 502 to be varied. The second particular state may be any of various configurations in various embodiments including the particular state described above in this disclosure in which the expanded configuration includes a combination of the forms shown in FIGS. 5O and 5P. In some embodiments, the first particular state is a preliminary or initial state of the expanded configuration. In other embodiments, the first state results from a transitioning of the expanded configuration from another state (e.g., a third state other than the second state).

In some embodiments, a particular actuator (e.g., actuator 572) in the second actuator set 541 is selectively moveable from one activation position (e.g., first activation position 571a) to another activation position (e.g., second activation position 571b) to independently change a size, a shape, or both a size and a shape of the expanded configuration of the manipulable portion 502 from a third state to the first state. For example, in some embodiments, manipulation of the third particular actuator 572 from first activation position 571a to second activation position 571b changes an expanded configuration of the manipulable portion 502 from a third state (e.g., first fanned configuration 536) to the first state (e.g., second fanned configuration 537) without engagement or coordinated movement of the actuators 540a, 540b in the first actuator set 540. Subsequent manipulation of various actuators in the first actuator set 540 may further transition the expanded configuration from the first state (e.g., second fanned configuration 537) to the second state (e.g., a combination of FIGS. 5O and 5P) as described above in this disclosure. When the collective or super-state of the configuration of the manipulable portion 502 is changed to the second state or some other state (e.g., the first or third states), it may be said that the collective or super-state to which the manipulable portion 502 is changed is a collectively changed size, a collectively changed shape, or both a collectively changed size and shape of the configuration of the manipulable portion 502.

In various embodiments, when the third particular actuator 572 is moved from its second activation position 571b toward or to its first activation position 571a, various actuators (e.g., first and second particular actuators 540a, 540b) in the first actuator set 540 may move from their respective second activation positions (e.g., second activation position 574c, 575b) to cause a size, a shape, or both a size and a shape of the expanded configuration of the manipulable portion 502 to move away from the second state to transition the manipulable portion at least in part toward or to the delivery configuration. In various embodiments, when the third particular actuator 572 is moved from its second activation position 571b toward or to its first activation position 571a, various actuators (e.g., first and second particular actuators 540a, 540b) in the first actuator set 540 may move from their respective second activation positions (e.g., second activation position 574c, 575b) to cause a size, a shape, or both a size and shape of the expanded configuration of the manipulable portion 502 to move away from the second state toward or to the third state (e.g., the first fanned configuration 536).

It is noted, in some embodiments, when the first and second actuators 540a, 540b are moved away from respective ones of their second activation positions (e.g., second activation positions 574c, 575b) to the respective ones of the first activation positions (e.g., first activation positions 574a, 575a), the expanded configuration of the manipulable portion 502 may have a different shape, size, or both size and shape than that possessed by the expanded configuration when the first and second actuators 540a, 540b were positioned at their respective first activation positions during a movement of the first and second actuators 540a, 540b from their respective first activation positions toward or to their respective second activation positions. In other words, the manipulable portion 502 may have a different shape, size, or both size and shape when in the same state (e.g., first activation positions 574a, 575a of first and second actuators 540a, 540b, even when the positioning of the actuator 572 is held constant) at two different times. This situation may happen for various reasons including friction and hysteresis in various portions of the catheter system 500. In some embodiments, the word "state" at least when used in the context of the configuration of the manipulable portion 502 may be understood to be a mode, condition, or characteristic of the configuration of the manipulable portion 502 and is not necessarily limited to an exact positioning, size, or shape of the manipulable portion 502. For example, in some embodiments, a particular collective state of the expanded configuration of the manipulable portion 502 may be a flattened state (e.g., FIG. 5O), as opposed to a precise position, size, and shape of the manipulable portion 502 in the flattened state. In some embodiments, a particular collective state of the expanded configuration of the manipulable portion 502 may be defined to include an absence of a particular sub-state, such as an absence of the flattening effects of FIG. 5O (e.g., due to the actuator 540a not being in its second activation position 574c) or an absence of the open clam shell effects of FIG. 5P (e.g., due to the actuator 540b not being in its second activation position 575b).

In various embodiments, a particular actuator (e.g., third particular actuator 572) in the second actuator set 541 is selectively moveable toward or to one particular activation position (e.g., first activation position 571a) while engaging at least two actuators (e.g., first and second particular actuators 540a, 540b) in first actuator set 540, and, consequently, causing the at least two actuators in the first actuator set 540 to move between their respective second and first activation positions (for example as described above with respect to FIG. 5W). In some of these various embodiments, the particular actuator (e.g., third particular actuator 572) in the second actuator set 541 is selectively moveable toward or to another particular activation position (e.g., second activation position 571b) while not engaging various actuators (e.g., first and second particular actuators 540a, 540b or any respective locking device (e.g., FIG. 10) thereof) in first actuator set 540, and while not causing each of the at least two actuators in the first actuator set 540 to move between their respective second and first activation positions (for example as described above with respect to FIGS. 5S-1 and 5S-2). In various embodiments, movement of the particular actuator (e.g., actuator 572) in the second actuator set 541 toward or to the one particular activation position (e.g., first activation position 571a) is in a different direction than movement of the particular actuator in the second actuator set 541 toward or to the another particular activation position (e.g., second activation position 571b).

In various embodiments, catheter system 500 includes an interlock device configured to restrict at least one actuator (e.g., at least first particular actuator 540a, second particular actuator 540b, or both) in the first actuator set 540 from being moved away from a respective first activation position (e.g., a respective one of first activation positions 574a, 575a) until at least a first actuator (e.g., third particular actuator 572) in the second actuator set 541 is moved in response to a user action. For example, the interlock device may be provided at least by a portion (e.g., the cover 520a) of the third particular actuator 572, such that the first particular actuator 540a and the second particular actuator 540b are restricted from moving away from their respective first activation positions 574a, 575a until the cover 520a is moved (e.g., FIGS. 5S-1 to 5S-2). In some embodiments, catheter system 500 includes an interlock device configured to restrict at least one actuator (e.g., at least one of first particular actuator 540a, second particular actuator 540b) in the first actuator set 540 from being moved between the respective first and second activation positions of the at least one actuator in the first actuator set 540 until at least one other actuator in the first actuator set 540 is moved into the respective second activation position of the at least one other actuator in the first actuator set 540. For example, when third particular actuator 572 forms part of the first actuator set 540, either of first and second particular actuators 540a, 540b is restricted from being moved between its respective first and second activation positions until the third particular actuator 572 is moved away from its first activation position 571a toward or to its second activation position 571b.

The use of an interlock device in various embodiments may be motivated for various reasons. For example, in some embodiments, a particular sequence in the activation of various ones of the actuators is desired. In some embodiments, an interlock device is employed to ensure that one particular actuator is activated to facilitate a subsequent activation of another actuator. For example, in some embodiments, an interlock device (e.g., cover 520a) is used to guide a user to activate actuator 572 to manipulate the expanded configuration of the manipulable portion 502 into the second fanned configuration 537 prior to an activation of any of actuators 540a, 540b. This sequence may be motivated for various reasons including circumventing a condition in which actuator 572, if activated after the activation of one or both of actuators 540a and 540b, could possibly need to apply potentially higher forces (e.g., forces that could damage or render a device of system 500 inoperable) to fan the elongate members 504 of the manipulable portion 502 into the second fanned configuration 537.

In some particular embodiments, cover 520a is configured (e.g., includes one or more suitably positioned engagement surfaces) to engage various ones of the actuators in the first actuation set 540 when the cover 520a is moved in a first direction (e.g., in a direction toward first position 570a) along a path between first and second positions 570a, 570b, but not engage various ones of the actuators in the first actuator set 540 when the cover 520a is moved in a second direction (e.g., in a direction toward second position 570b) along the path between first and second positions 570a, 570b, the second direction being different than the first direction. In some particular embodiments, cover 520a is configured (e.g., includes suitably positioned engagement surfaces) to engage various ones of the actuators in the first actuator set 540 to cause movement thereof when the cover 520a is moved in a first direction (e.g., in a direction toward first position 570a) along a path between first and second positions 570a, 570b, but not engage various ones (or, in some embodiments, any) of the actuators in the first actuation set 540 to cause movement thereof when the cover 520a is moved in a second direction (e.g., in a direction toward second position 570b) along the path between first and second positions 570a, 570b, the second direction being different than the first direction. For example in some embodiments, cover 520a does not engage actuators 540a, 540b and does not move them when the cover 520a moves from first position 570a toward or to second position 570b as described above in this disclosure with respect to various ones of FIG. 5S, but does engage actuators 540a, 540b to cause them to move when the cover 520a moves from second position 570b toward or to first position 570a as described above in this disclosure with respect to various ones of FIG. 5W. Movement of various ones of the actuators in the first actuation set 540 induced by an engagement by the cover 520a may cause, or lead to a change in a size, shape, or both, of an expanded configuration of the manipulable portion 502 away from a particular state. In various embodiments, cover 520a is operatively coupled to manipulable portion 502 to cause the manipulable portion 502 to move, at least partially, from the expanded configuration toward or to the delivery configuration when cover 520a moves from second position 570b toward or to first position 570a.

In various embodiments, catheter system 500 includes an actuator set that includes one or more actuators (e.g., first particular actuator 540a, second particular actuator 540b or both of the first and the second particular actuators 540a, 540b), each actuator in the actuator set selectively moveable into a respective activation position to cause a size, a shape, or both a size and a shape of the expanded configuration of the manipulable portion 502 to be varied. Cover 520a is selectively moveable between a first position (e.g., first position 570a) where user access to at least a respective part (e.g., handle 543a, 543b) of each of at least one actuator in the actuator set is restricted and a second position (e.g., second position 570b) where user access to at least the respective part of each of the at least one actuator in the actuator set is permitted. In some of these various embodiments, when cover 520a is moved from the second position toward or to the first position, the cover 520a engages each particular actuator in the actuator set that is positioned in the respective activation position of the particular actuator to move the particular actuator away from the respective activation position of the particular actuator.

In some embodiments, each actuator in the actuator set is selectively moveable into its respective activation position to cause a size, a shape or both a size and a shape of the expanded configuration of the manipulable portion 502 to be varied from an associated respective first (e.g., sub-) state to an associated respective second (e.g., sub-) state. For example, the actuator 540a is selectively moveable into its respective second activation position 574c to cause the expanded configuration of the manipulable portion 502 to include the flattened sub-state (e.g., characteristics of FIG. 5O), according to some embodiments. When the cover 520a is moved from the second position 570b toward or to the first position 570a, cover 520a engages each particular actuator in the actuator set that is positioned in the respective activation position of the particular actuator to move the particular actuator away from its respective activation position to cause, the size, the shape, or both of the expanded configuration of the manipulable portion to move from the respective second state associated with the particular actuator toward or to the respective first state associated with the particular actuator. For example, if movement of the actuator 540a into its respective second activation position 574c caused the expanded configuration of the manipulable portion 502 to change from a first state associated with the actuator 540a (e.g., a state not including the flattened sub-state effects such as shown in FIG. 5O) to a second state associated with the actuator 540a (e.g., a state including the flattened sub-state effects such as shown in FIG. 5O), the cover 520a may cause movement of the actuator 540b away from its respective second activation position 574c and, consequently, cause the expanded configuration to move from the second state (e.g., a state including the flattened sub-state effects such as shown in FIG. 5O) toward or to the first state (e.g., a state not including the flattened sub-state effects such as shown in FIG. 5O).

In some embodiments, the manipulable portion 502 has a size too large to fit in the lumen 512d of the catheter sheath 512 or a size too large to be percutaneously delivered to a bodily cavity when the expanded configuration of the manipulable portion 502 is in either of the respective first or second respective states associated with each actuator in the actuator set. In some embodiments, the catheter system 500 includes at least a first actuator (e.g., third particular actuator 572) that is selectively moveable into a respective activation position to cause a size, a shape, or both of the expanded configuration of the manipulable portion 502 to be varied, and cover 520a is operable to cause the first actuator to move (e.g., toward or to its respective activation position) when the cover 520a is moved between the first position 570a and the second position 570b (e.g., from the first position 570a toward or to the second position 570b). In some embodiments, the cover 520a is operable to cause the first actuator (e.g., third particular actuator 572) to move away from the respective activation position of the first actuator when the cover 520a is moved from the second position 570b toward or to the first position 570a.

In some embodiments, catheter system 500 includes at least a first actuator and a second actuator, each of the first and the second actuators independently or separately moveable with respect to one another into a respective activation position to cause a size, a shape, or both of the expanded configuration of the manipulable portion 502 to be varied from an associated respective first state to an associated respective second state. For example, in some embodiments, a first actuator 540a is moveable independently or separately with respect to a second actuator 540b into a respective second activation position 574c to cause the manipulable portion to be varied from a first state associated with the first actuator 540a (e.g., a state not including the flattened sub-state effects like FIG. 5O) to a second state associated with the first actuator 540a (e.g., a state including the flattened sub-state effects like FIG. 5O). Similarly, in some embodiments, the second actuator 540b is moveable independently or separately with respect to the first actuator 540a into a respective second activation position 575b to cause the manipulable portion to be varied from a first state associated with the second actuator 540b (e.g., a state not including the open-clam-shell sub-state effects like FIG. 5P) to a second state associated with the second actuator 540b (e.g., a state including the open-clam-shell sub-state effects like FIG. 5P).

In at least embodiments like these, cover 520a is moveable between a first position 570a where user access to at least a part of the second actuator is restricted and a second position 570b where user access to at least the part of the second actuator is permitted. In this regard, in some embodiments, cover 520a is operable to cause the first actuator to move away from the respective activation position of the first actuator when the cover 520a is moved from the second position 570b toward or to the first position 570a to cause the size, the shape, or both of the expanded configuration of the manipulable portion 502 to move from the respective second state associated with the first actuator toward or to the respective first state associated with the first actuator.

For example, in some embodiments, the second actuator is provided by one of the first and second particular actuators 540a and 540b (i.e., access to the one of the first and second particular actuators 540a and 540b being restricted when cover 520a is in first position 570a) and the first actuator is provided by another one of the first and the second particular actuators 540a and 540b, the another one of the first and the second particular actuators 540a and 540b being caused to move away from the respective activation state of the another one of the first and the second particular actuators 540a and 540b when the cover 520a is moved from the second position 570b toward or to the first position 570a to cause the size, the shape, or both of the expanded configuration of the manipulable portion 502 to move from the respective second state associated with the another one of the first and the second particular actuators 540a and 540b toward or to the respective first state associated with the another one of the first and the second particular actuators 540*a* and 540*b*.

In some embodiments, the second actuator is provided by one of the first and the second particular actuators 540*a* and 540*b*, and the first actuator is provided by the third particular actuator 572, the third particular actuator 572 being caused (e.g., by engagement) to move away from the respective activation state of the third particular actuator 572 when the cover 520*a* is moved from the second position 570*b* toward or to the first position 570*a* to cause the size, the shape, or both of the expanded configuration of the manipulable portion 502 to move from the respective second state associated with the third particular actuator 572 toward or to the respective first state associated with the third particular actuator 572. In some embodiments, cover 520*a* is physically coupled to and is a user-accessible portion of the first actuator (e.g., actuator 572) slideable along a surface of the housing 520 to cause the first actuator to move toward or to the respective activation position of the first actuator when the cover 520*a* is moved from the first position 570*a* to the second position 570*b* as described above in this disclosure. In various embodiments, the second actuator (e.g., one of the first and the second particular actuators 540*a* and 540*b*) includes a user-accessible portion (e.g., handle 543*a* or 543*b*) slideable relative to a surface of housing 520 by a user to cause the size, the shape or both of the expanded configuration of the manipulable portion 502 to be varied from the respective first state associated with the second actuator to the respective second state associated with the second actuator. The user-accessible portion (e.g., handle 543*a* or 543*b*) may include a locking device (e.g., locking device of FIG. 10) as described above, at least a portion of which is rotatable by a user to prevent sliding of at least the user-accessible portion of the second actuator relative to the surface of the housing 520.

In various embodiments, the manipulable portion 502 has a size too large to fit in the lumen 512*d* of catheter sheath 512 or a size too large to be percutaneously delivered to a bodily cavity when the expanded configuration of the manipulable portion 502 is in (a) either of the respective first and second states associated with the first actuator, (b) either of the respective first and second states associated with the second actuator, or both (a) and (b). In various embodiments, the manipulable portion 502 is in the expanded configuration when the second actuator (e.g., one of the first and the second particular actuators 540*a* and 540*b*) is in its respective activation position. In various embodiments, the manipulable portion 502 is in the expanded configuration when the second actuator (e.g., one of the first and the second particular actuators 540*a* and 540*b*) is in its respective activation position and when the first actuator (e.g., third particular actuator 572 or another one of the first and the second particular actuators 540*a* and 540*b*) is in its respective activation position.

It should be noted that many of the various descriptions, above, refer to particular actuators in examples, such as actuators 540*a*, 540*b*, 572, etcetera, merely for illustration purposes. In this regard, it should be noted that the present invention is not limited to such particular actuators or their configurations, and different actuator sets or different actuator configurations may be implemented.

A discussion is now made regarding methods of controlling various catheter systems according to various embodiments. Although reference is made to catheter system 500 for ease of discussion, it is understood that the methods may be associated with other catheter devices or systems in other embodiments. In some of these embodiments, a catheter system controlled by various ones of the described methods includes a catheter sheath (e.g., catheter sheath 512) a proximal end (e.g., proximal end 512*a*), a distal end (e.g., distal end 512*b*), and a lumen (e.g., first lumen 512*d*) extending between the proximal end of the catheter sheath and the distal end of the catheter sheath. The catheter system may further include a shaft (e.g., shaft 510) comprising a proximal end (e.g., proximal end 510*a*), a distal end (e.g., distal end 510*b*), and an elongated portion (e.g., elongated portion 510*c*) extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft. The catheter system may further include a manipulable portion (e.g., manipulable portion 502) coupled to the shaft and located at least proximate the distal end of the shaft, the manipulable portion shaped for delivery through the lumen of the catheter sheath. The catheter system may further include a control element (e.g., control element 513) physically coupled to the manipulable portion, the control element receivable in the lumen of the catheter sheath. In some embodiments, the manipulable portion is selectively moveable between a delivery configuration in which the manipulable portion is shaped to be delivered though the lumen of the catheter sheath and an expanded configuration in which the manipulable portion is shaped too large for delivery through the lumen of the catheter sheath, for example as described above with respect to manipulable portion 502.

In some embodiments, each of various ones of the methods described in this disclosure is implemented under the guidance of a control system (e.g., control system 545 described later in this disclosure, or one or more components of system 100 or control system 322, such as controller 324). The control system may be a controller-based control system, a mechanical-based control system or a combination of the two. In some embodiments, each of various ones of the methods described in this disclosure may be implemented at least in part by manual input from an operator or user. It is understood that the methods described in this disclosure are not exhaustive and various aspects from different ones of the described methods may be combined to form at least one other method. Additionally, different sequences of steps or additional or alternate steps may be employed by at least some of the described methods. In some embodiments, each of various ones of the methods is employed to achieve a particular desired outcome of a portion of the catheter system (for example, a required control line tension adjustment that is the same or similar to that described above in this disclosure). In some embodiments, each of various ones of the methods is employed to achieve a particular deployment state of the catheter system operated in a medical treatment or diagnostic procedure.

A flow chart representing a method 900A for controlling the catheter system according to various embodiments is provided in FIG. 9A. In block 902 of method 900A, at least a shape of the manipulable portion is modulated at least in a state where at least a part of the manipulable portion and a part of the control element extend outside the distal end of the catheter sheath. In some embodiments, a portion of shaft is located in a lumen of the sheath. The modulation of the manipulable portion may occur in a manner that is the same or similar to the modulation of the manipulable portion 502 in the sequence depicted in FIGS. 5I and 5J by way of non-limiting example. In various embodiments, the part of the manipulable portion extending outside the distal end of the catheter sheath has a shape during or throughout the modulation that is too large to fit in the lumen of the catheter sheath. In block 904 of method 900A, the control element is manipulated to cause a length of the part of the control element extending outside the distal end of the catheter sheath to increase and subsequently decrease during or throughout the modulation of the manipulable portion. The manipulation of the control element may occur in a manner that is the same or similar to the manipulation of cable 513b in the sequence depicted in FIGS. 5H, 5I and 5J by way of non-limiting example.

A flow chart representing a method 900B for controlling the catheter system according to various embodiments is provided in FIG. 9B. In Block 912 of method 900B, the manipulable portion is transitioned at least partially between the expanded configuration and the delivery configuration. In block 914, a manipulation of the control element causes the control element to have a first amount of length located outside the distal end of the catheter sheath when a particular amount of the manipulable portion is located outside the distal end of the catheter sheath during a transition toward or to the expanded configuration. In block 916, a manipulation of the control element causes the control element to have a second amount of length located outside of the distal end of the catheter sheath, when the same particular amount of the manipulable portion is located outside the distal end of the catheter sheath during a transition toward or to the delivery configuration. In various embodiments, the second amount of length is different than the first amount of length. The transitioning of the manipulable portion at least partially between the expanded configuration and the delivery configuration may occur in a different manner in other embodiments. For example, an exploded view of block 912 is provided in FIG. 9C according to some embodiments. In block 912a the manipulable portion is transitioned toward or to the expanded configuration as the manipulable portion is advanced out of the distal end of the catheter sheath. In block 912b, the manipulable portion is transitioned toward or to the delivery configuration as the manipulable portion is retracted into the distal end of the catheter sheath.

A flow chart representing a method 900C for controlling the catheter system according to various embodiments is provided in FIG. 9D. In block 922 of method 900C, the manipulable portion is transitioned at least partially between the expanded configuration and the delivery configuration. In block 924, a manipulation of the control element causes the control element to have a first amount of length located outside of the distal end of the catheter sheath when a particular relative positioning exists between the catheter sheath and the shaft received in the lumen of the catheter sheath during the transition toward or to the expanded configuration. In block 926, a manipulation of the control element causes the control element to have a second amount of length located outside of the distal end of the catheter sheath when the same particular relative positioning exists between the catheter sheath and the shaft received in the lumen of the catheter sheath during the transition toward or to the delivery configuration. In various embodiments, the second amount of length is different than the first amount of length. In various embodiments, the particular relative positioning between the catheter sheath and the shaft received in the lumen of the catheter sheath is a relative longitudinal positioning.

A flow chart representing a method 900D for controlling the catheter system according to various embodiments is provided in FIG. 9E. In block 928 of method 900D, a first relative movement is provided to cause a distance between a location on the part of the shaft received in the lumen of the catheter sheath and a location on the catheter sheath to decrease. In block 930 of method 900D, a second relative movement is provided to cause a distance between a location on the part of the shaft received in the lumen of the catheter sheath and a location on the catheter sheath to increase. Each of the first or second relative movements may be provided by a manipulation of the shaft, the catheter sheath or both the shaft and the catheter sheath. In block 932, in response to the first relative movement, a shape of at least a part of the manipulable portion extending outside the distal end of the catheter sheath is varied to, at least in part, cause the distal end of the manipulable portion to move along a first trajectory during the first relative movement. In block 934, in response to the second relative movement, a shape of at least a part of the manipulable portion extending outside the distal end of the catheter sheath is varied to, at least in part, cause the distal end of the manipulable portion to move along a second trajectory during the second relative movement. In various embodiments, the second trajectory is different than the first trajectory.

While some of the embodiments disclosed above are suitable for cardiac mapping, the same or similar embodiments may be used for mapping other bodily organs, for example gastric mapping, bladder mapping, arterial mapping and mapping of any bodily lumen, bodily chamber or bodily cavity into which the devices of the present invention may be introduced.

While some of the embodiments disclosed above are suitable for cardiac ablation, the same or similar embodiments may be used for ablating other bodily organs or any bodily lumen, bodily chamber or bodily cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other catheter systems including all medical treatment catheter systems and medical diagnostic catheter systems in accordance with the claims. Accordingly, the invention is not limited by the disclosure, but instead its scope is to be determined entirely by the following claims.

What is claimed is:

1. A method of coupling portions of a catheter system, the method comprising:
    moving a manipulable portion of the catheter system into a flushing portion of the catheter system in a first state in which the flushing portion is detached from a portion of a catheter sheath of the catheter system, the manipulable portion of the catheter system physically coupled to a distal end portion of an elongate shaft member of the catheter system, the distal end portion of the elongate shaft member configured to be advanced percutaneously toward a bodily cavity ahead of a proximal end portion of the elongate shaft member;
    introducing fluid into the flushing portion in the first state in which the flushing portion is detached from the portion of the catheter sheath;
    attaching, after the moving, the flushing portion to the portion of the catheter sheath; and
    advancing, after the attaching, the manipulable portion of the catheter system from the flushing portion into the catheter sheath, wherein the flushing portion comprises an elongate body surrounding a lumen into which the manipulable portion is moved during the moving, the lumen extending between a proximal end portion of the elongate body and a distal end portion of the elongate body, the distal end portion of the elongate body attachable to the portion of the catheter sheath during the attaching, wherein the elongate body comprises a first port located distally from the proximal end portion of the elongate body and a second port located proximally from the distal end portion of the elongate body, each of the first port and the second port in fluid communication with the lumen, wherein the introducing fluid includes introducing fluid, via the first port or the second port as a fluid inlet port, into the flushing portion, and wherein the introducing fluid into the flushing portion causes an egress of fluid from the flushing portion via a fluid outlet port, and wherein the first port or the second port is the fluid outlet port, whichever is not the fluid inlet port.

2. The method of claim 1, wherein the introducing fluid occurs with the manipulable portion of the catheter system positioned in the flushing portion in the first state in which the flushing portion is detached from the portion of the catheter sheath.

3. The method of claim 1, wherein the manipulable portion is configurable between an unexpanded configuration in which the manipulable portion is sized to be deliverable through the flushing portion, and an expanded configuration in which the manipulable portion is sized too large to be deliverable through the flushing portion.

4. The method of claim 3, wherein the catheter system comprises an actuator operatively coupled to the manipulable portion by at least one control element configured to transmit force from the actuator to the manipulable portion to adjust the manipulable portion between the expanded configuration and the unexpanded configuration, and wherein the method comprises operating the actuator to adjust the manipulable portion toward the unexpanded configuration before the moving.

5. The method of claim 1, wherein the manipulable portion is a transducer-based device.

6. The method of claim 1, wherein the manipulable portion is an implant.

7. The method of claim 1, wherein the moving the manipulable portion of the catheter system into the flushing portion of the catheter system in the first state includes retracting the manipulable portion of the catheter system into the flushing portion of the catheter system in the first state.

\* \* \* \* \*